US011298417B2

(12) United States Patent
Duprex et al.

(10) Patent No.: US 11,298,417 B2
(45) Date of Patent: Apr. 12, 2022

(54) MEASLES VIRUS VACCINE EXPRESSING SARS-COV-2 PROTEIN(S)

(71) Applicant: University of Pittsburgh—Of the Commonwealth System of Higher Education, Pittsburgh, PA (US)

(72) Inventors: William Paul Duprex, Pittsburgh, PA (US); Natasha Louise Tilston-Lunel, Pittsburgh, PA (US); Shamkumar Nambulli, Bridgeville, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 17/143,740

(22) Filed: Jan. 7, 2021

(65) Prior Publication Data

US 2021/0386852 A1   Dec. 16, 2021

Related U.S. Application Data

(62) Division of application No. 17/010,591, filed on Sep. 2, 2020, now Pat. No. 11,103,576.

(60) Provisional application No. 63/071,479, filed on Aug. 28, 2020, provisional application No. 63/039,275, filed on Jun. 15, 2020.

(51) Int. Cl.
| | |
|---|---|
| *A61K 39/00* | (2006.01) |
| *C12N 7/00* | (2006.01) |
| *A61K 39/12* | (2006.01) |
| *A61K 39/145* | (2006.01) |
| *C12N 15/67* | (2006.01) |
| *A61K 39/215* | (2006.01) |
| *C07K 14/005* | (2006.01) |

(52) U.S. Cl.
CPC .......... *A61K 39/215* (2013.01); *C07K 14/005* (2013.01); *C12N 7/00* (2013.01); *A61K 2039/5256* (2013.01); *A61K 2039/575* (2013.01); *C12N 2760/18434* (2013.01); *C12N 2760/18443* (2013.01); *C12N 2770/20034* (2013.01)

(58) Field of Classification Search
CPC .... A61K 39/12; A61K 2039/53; A61K 39/00; C12N 7/00; A61P 31/12
See application file for complete search history.

(56) References Cited

FOREIGN PATENT DOCUMENTS

| CN | 111218459 A | 6/2020 |
|---|---|---|
| WO | WO 98/13501 A2 | 4/1998 |
| WO | WO 2009/032954 A1 | 3/2009 |

OTHER PUBLICATIONS

Liniger et al., "Induction of neutralizing antibodies and cellular immune responses against SARS coronavirus by recombinant measles viruses", Vaccine, 2008, 26:2164-2174.*
Padron-Regalado, "Vaccines for SARS-CoV-2: Lessonse from other coronavirus strains", Infect Dis Ther, 2020, 9:255-274.*
Bankamp et al., "Genetic characterization of measles vaccine strains," *J. Infect. Dis.*, 204 Suppl. 1: 5533-5548 (2011).
Case et al., "Neutralizing antibody and soluble ACE2 inhibition of a replication-competent VSV-SARS-CoV-2 and a clinical isolate of SARS-CoV-2," bioRxiv, doi:10.1101/2020.05.18.102038 (2020).
Duckert et al., "Prediction of proprotein convertase cleavage sites," *Protein Engineering, Design & Selection*, 17(1): 107-112 (2004).
Liniger et al., "Induction of neutralising antibodies and cellular immune responses against SARS coronavirus by recombinant measles viruses," Vaccine, 26:2164-2174 (2008).
Padron-Regalado, "Vaccines for SARS-CoV-2: Lessons from Other Coronavirus Strains," *Infect. Dis. Ther.*, 9: 255-274 (2020).
Rennick et al., "Live-attenuated measles virus vaccine targets dendritic cells and macrophages in muscle of nonhuman primates," *J. Virol.* 89(4): 2192-2200 (2015).
Wrapp et al., "Cryo-EM structure of the 2019-nCoV spike in the prefusion conformation," Science, 13: 1260-1263 (2020).
Malczyk et al. "A Highly Immunogenic and Protective Middle East Respiratory Syndrome Coronavirus Vaccine Based on a Recombinant Measles Virus Vaccine Platform," *Journal of Virology*, 89(22): 11654-11667 (2015).
The Native Antigen Company, "An Early Look at Vaccines for COVID-19," Retrieved Online from https://thenativeantigencompany.com/an-early-look-at-vaccines-for-covid-19/ (Apr. 14, 2020).
U.S. Patent and Trademark Office, invitation to Pay Additional Fees in International Patent Application No. PCT/US21/37339, dated Sep. 24, 2021.
UniProtKB-PODTC2 (SPIKE_SARS2), Retrieved on Nov. 8, 2021 from https://www.uniprot.org/uniprot/P0DTC2 (Apr. 2020).
U.S. Patent and Trademark Office, International Search Report in International Patent Application No. PCT/US21/37339, dated Dec. 8, 2021.
U.S. Patent and Trademark Office, Written Opinion in International Patent Application No. PCT/US21/37339, dated Dec. 8, 2021.

* cited by examiner

Primary Examiner — Barry A Chestnut
(74) Attorney, Agent, or Firm — Leydig, Voit & Mayer, Ltd.

(57) ABSTRACT

A recombinant measles viral vector comprising a nucleic acid sequence encoding a Severe Acute Respiratory Syndrome Coronavirus 2 (SARS-CoV-2) spike glycoprotein is provided. Polypeptides comprising the SARS-CoV-2 spike glycoprotein also are provided, as well as related nucleic acids, vectors, and compositions. The polypeptides, nucleic acids, vectors, and compositions can be used in methods of preventing, inhibiting, reducing, eliminating, protecting, or delaying the onset of an infection or an infectious clinical condition caused by coronavirus and methods for inducing an immune response against a coronavirus.

20 Claims, 15 Drawing Sheets
Specification includes a Sequence Listing.

rMV^EZSARSCoV2-S6 rMV^EZSARSCoV2-S6

Fig. 11A vaccine dose: 10^4 to 10^5 | 10^4 to 10^5 | 10^6
challenge dose:

days: 1 — prime
21 — boost
42 — challenge
46* 53* — PET/CT and sampling*
56 — necropsy

Fig. 11B

| | measles virus neutralization (pre-challenge) | | | | | | SARS-CoV-2 neutralization (pre-challenge) | | | | | |
|---|---|---|---|---|---|---|---|---|---|---|---|---|
| | 1:20 | 1:40 | 1:80 | 1:160 | 1:320 | 1:640 | 1:20 | 1:40 | 1:80 | 1:160 | 1:320 | 1:640 |
| rMV$^{EZ}$SARS-CoV-2-S-CO | + | + | + | + | - | - | + | + | +/- | + | - | - |
| rMV$^{EZ}$SARS-CoV-2-S-CO | + | + | + | + | - | - | + | + | + | + | + | + |
| rMV$^{EZ}$SARS-CoV-2-S-CO | + | - | - | - | - | - | + | + | - | - | - | - |
| rMV$^{EZ}$ | + | + | + | + | - | - | - | - | - | - | - | - |
| rMV$^{EZ}$ | + | + | + | + | - | - | - | - | - | - | - | - |

US 11,298,417 B2

MEASLES VIRUS VACCINE EXPRESSING SARS-COV-2 PROTEIN(S)

CROSS-REFERENCE TO RELATED APPLICATIONS

This patent application is a continuation application of copending U.S. patent application Ser. No. 17/010,591, filed Sep. 2, 2020, which claims the benefit of U.S. Provisional Patent Application No. 63/039,275, filed Jun. 15, 2020, and U.S. Provisional Patent Application No. 63/071,479, filed Aug. 28, 2020, each of which is incorporated by reference herein in its entirety.

SEQUENCE LISTING

Incorporated by reference in its entirety herein is a nucleotide/amino acid sequence listing submitted concurrently herewith and identified as follows: One 337,231 Byte ASCII (Text) file named "751552_ST25.TXT," created on Dec. 28, 2020.

BACKGROUND OF THE INVENTION

In December 2019, a novel coronavirus (Severe Acute Respiratory Syndrome Coronavirus 2 or SARS-CoV-2) belonging to the betacoronavirus family emerged. All human betacoronaviruses are unique from one another, however, they do share a certain degree of genetic and structural homology. SARS-CoV-2 genome sequence homology with SARS-CoV and MERS-CoV is 77% and 50%, respectively.

In contrast to the relatively smaller outbreaks of SARS-CoV in 2002 and MERS-CoV in 2012, SARS-CoV-2 is exhibiting an unprecedented scale of infection, resulting in a global pandemic declaration of Coronavirus Infectious Disease (COVID-19) by the World Health Organization (WHO). COVID-19 has a high infection rate and long incubation period. Similar to influenza, COVID-19 has the potential to become a seasonal disease.

Therefore, there is a desire for a COVID-19 vaccine.

BRIEF SUMMARY OF THE INVENTION

An embodiment of the invention provides a recombinant measles viral vector (rMV) (e.g., Edmonston Zagreb (EZ) MV) comprising a nucleic acid sequence encoding a Severe Acute Respiratory Syndrome Coronavirus 2 (SARS-CoV-2) spike (S) glycoprotein.

An embodiment of the invention provides a pharmaceutical composition comprising the recombinant measles viral vector, as well as methods for preventing, inhibiting, reducing, eliminating, protecting, or delaying the onset of an infection or an infectious clinical condition caused by coronavirus in a subject and methods for inducing an immune response against a coronavirus in a subject.

An embodiment of the invention also provides a polypeptide comprising an amino acid sequence selected from the group consisting of the amino acid sequences of SEQ ID NO: 8 (S6), SEQ ID NO: 9 (S-CO), SEQ ID NO: 10 (S-CO-AA), SEQ ID NO: 11 (S), SEQ ID NO: 12 (S-CO-AA-PP), SEQ ID NO: 13 (S-CO-AA-fneg-PP), and SEQ ID NO: 14 (S-CO-AA-fneg), as well as related nucleic acids, recombinant vectors, compositions, and methods.

BRIEF DESCRIPTION OF THE SEVERAL VIEWS OF THE DRAWINGS

FIG. 1A is a schematic representation of parental virus rMV$^{EZ}$EGFP(3), the cDNA clone of which was used to generate cDNA plasmids for viruses rMV$^{EZ}$SARS-CoV-2-S3, rMV$^{EZ}$SARS-CoV-2-S6, rMV$^{EZ}$SARS-CoV-2-S-CO and rMV$^{EZ}$SARS-CoV-2-S-COAA. Amino acid differences in the spike between the four viruses are shown, wherein underlined residues differ from wild-type spike sequence. Residues K and H in the cytoplasmic tail region were altered to A and A to disrupt a endoplasmic reticulum (ER) retention signal (KxHxx) sequence in viruses rMV$^{EZ}$SARS-CoV-2-S3, rMV$^{EZ}$SARS-CoV-2-S6 and rMV$^{EZ}$SARS-CoV-2-S-COAA. RBD; receptor binding domain, TM; transmembrane domain. FIG. 1B is a phase image of Vero cell monolayer infected with rMV$^{EZ}$SARS-CoV-2-S6 (shown as a representative image of a primary rescue). FIG. 1C are images of an immunoplaque assay of Vero cell monolayers infected with a 10-fold dilution of rescued rMV$^{EZ}$SARS-CoV-2-S6. Plaques were stained using anti-SARS-CoV-2-S antibody. Dilutions $10^{-6}$ and $10^{-7}$ are shown as representatives.

FIG. 3A is a schematic describing the experiment. Groups of 5 mice were infected with either rMV$^{EZ}$SARS-CoV-2-S3, rMV$^{EZ}$SARS-CoV-2-S6, rMV$^{EZ}$SARS-CoV-2-S-CO, rMV$^{EZ}$SARS-CoV-2-S-COAA, or rMV$^{EZ}$EGFP(3). Serum was collected on days 21 and 42, and splenocytes were collected on day 42. FIG. 3B is table showing neutralization of SARS-CoV-2 using the harvested mice serum, indicating that SARS-CoV-2 neutralizing antibodies were produced in mice vaccinated with rMV$^{EZ}$SARS-CoV-2-S-CO and rMV$^{EZ}$SARS-CoV-2-S-COAA viruses.

FIGS. 11A-B demonstrates an experimental set-up for non-human primates vaccinated (prime and/or boost) with any of the candidates. FIG. 11A is a schematic describing the experiment. Groups of 2 or 3 African green monkeys (AGMs) were vaccinated with rMV$^{EZ}$SARS-CoV-2-S-CO or rMV$^{EZ}$ and then challenged with SARS-CoV-2. FIG. 11B is a table with neutralization titers of serum against SARS-CoV-2, which were determined as described in Klimstra et al., 2020: PMID: 32821033, and MV as described in de Swart et al., 2017: PMID: 29263877. The results support that primates produce antibodies which neutralize both SARS-CoV-2 and measles virus following vaccination.

DETAILED DESCRIPTION OF THE INVENTION

An embodiment of the invention provides a recombinant measles viral vector that encodes one or more (e.g., two, three, four, or five) SARS-CoV-2 spike glycoproteins, wherein the SARS-CoV-2 spike glycoproteins may be the same or different. The recombinant measles viral vector or a composition thereof can be administered to a subject to prevent, inhibit, reduce, eliminate, protect, or delay the onset of an infection or an infectious clinical condition caused by coronavirus (e.g., SARS-CoV-2) in a subject. The recombinant measles viral vector or a composition thereof also can be administered to a subject to induce an immune response against a coronavirus (e.g., SARS-CoV-2) in a subject.

The recombinant measles viral vector can be any suitable recombinant measles viral vector. For example, the measles viral vector can be an Edmonston wild-type virus or vaccine strains of the Edmonston lineage, such as the AIK-C, Moraten, Rubeovax, Schwarz, or Zagreb strains (Bankamp et al., *J. Infect. Dis.*, 204 Suppl. 1: 5533-5548 (2011)). Alternatively, the measles viral vector can be selected from the group consisting of CAM-70, Changchun-47, Leningrad-4, Shanghai-191 (Bankamp et al., *J. Infect. Dis.*, 204 Suppl. 1: 5533-5548 (2011)), Leningrad-16, Moscow-5 (Sinitsyna et al., *Res. Virol.*, 141(5): 517-31 (1990)), 9301B (Takeda et al., *J. Virol.*, 72(11): 8690-8696 (1998)), ATTENUVAX®, and those described in Schneider-Schaulies et al., PNAS, 92(2): 3943-7 (1995).

Measles viruses and recombinant measles viral vectors are described in WO 98/13501, which provides the sequence of a DNA copy of the positive strand (antigenomic) message sense RNA of various wild-type of vaccine measles strains, including Edmonston wild-type strain, Moraten strain, and Schwarz strain, and WO 97/06270, which discloses the production of recombinant measles vectors.

Figure 4:
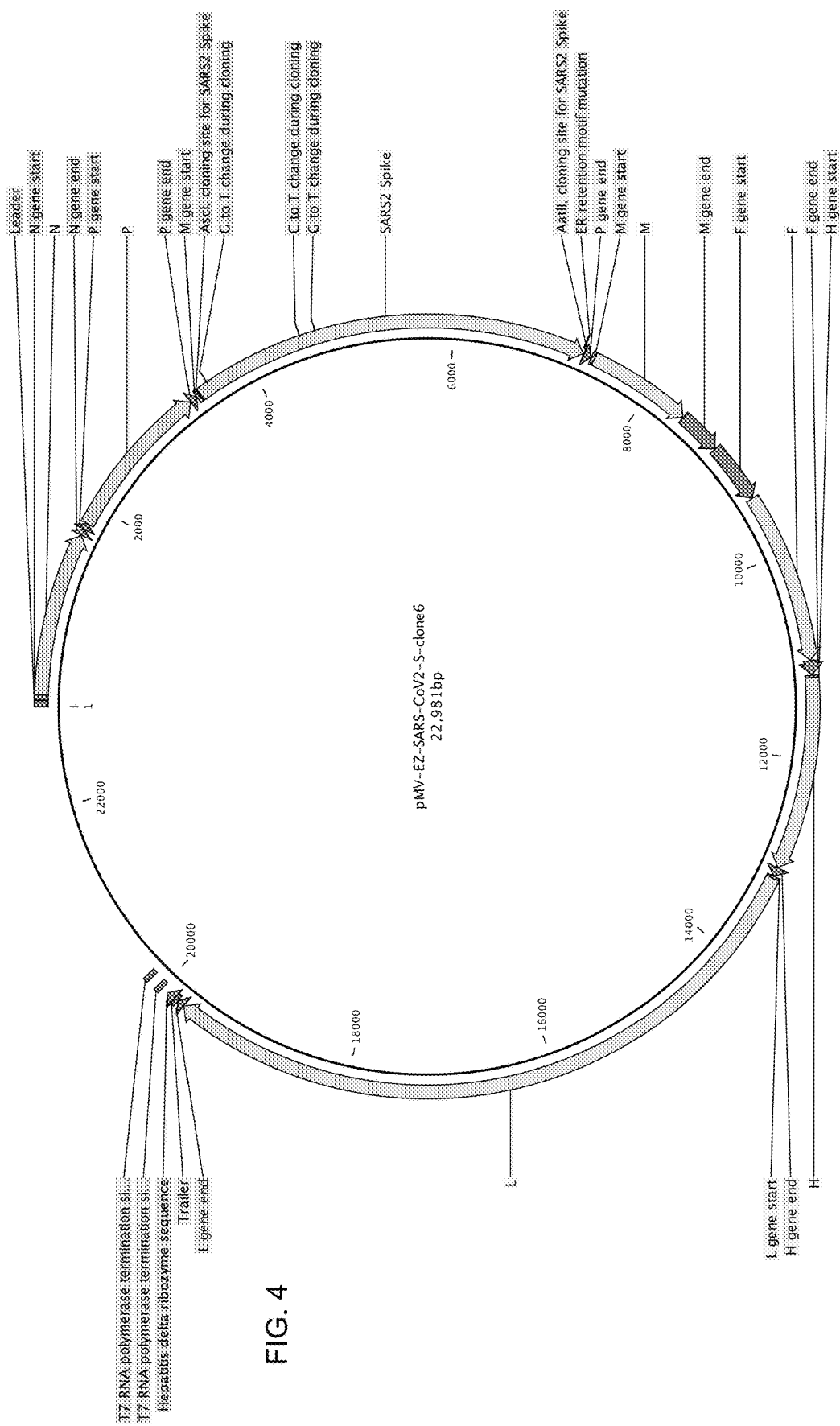
FIG. 4 is a vector map of rMV$^{EZ}$SARS-CoV-2-S6.
Figure 5:
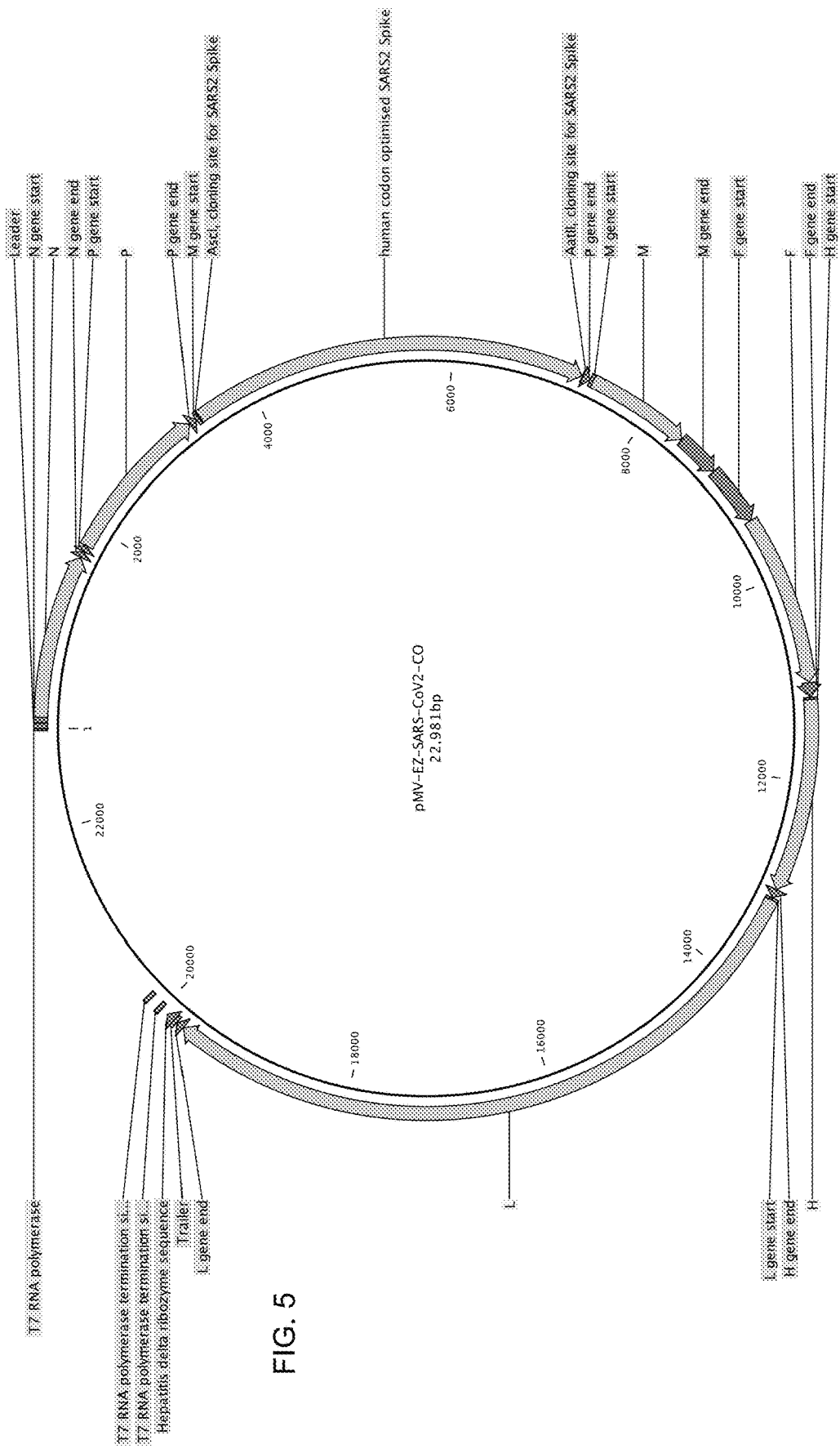
FIG. 5 is a vector map of rMV$^{EZ}$SARS-CoV-2-S-CO.
Figure 6:
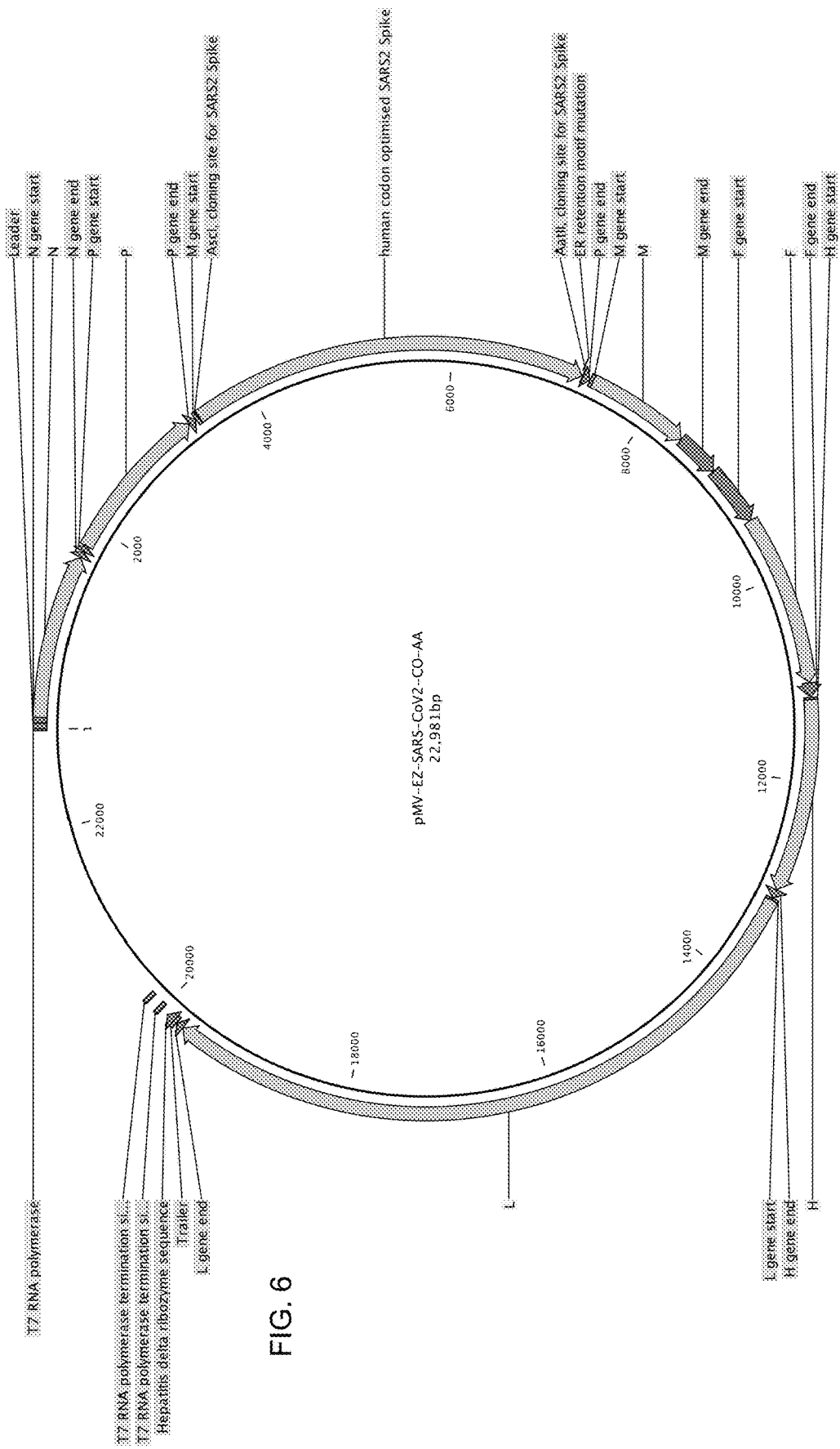
FIG. 6 is a vector map of rMV$^{EZ}$SARS-CoV-2-S-COAA.
Figure 7:
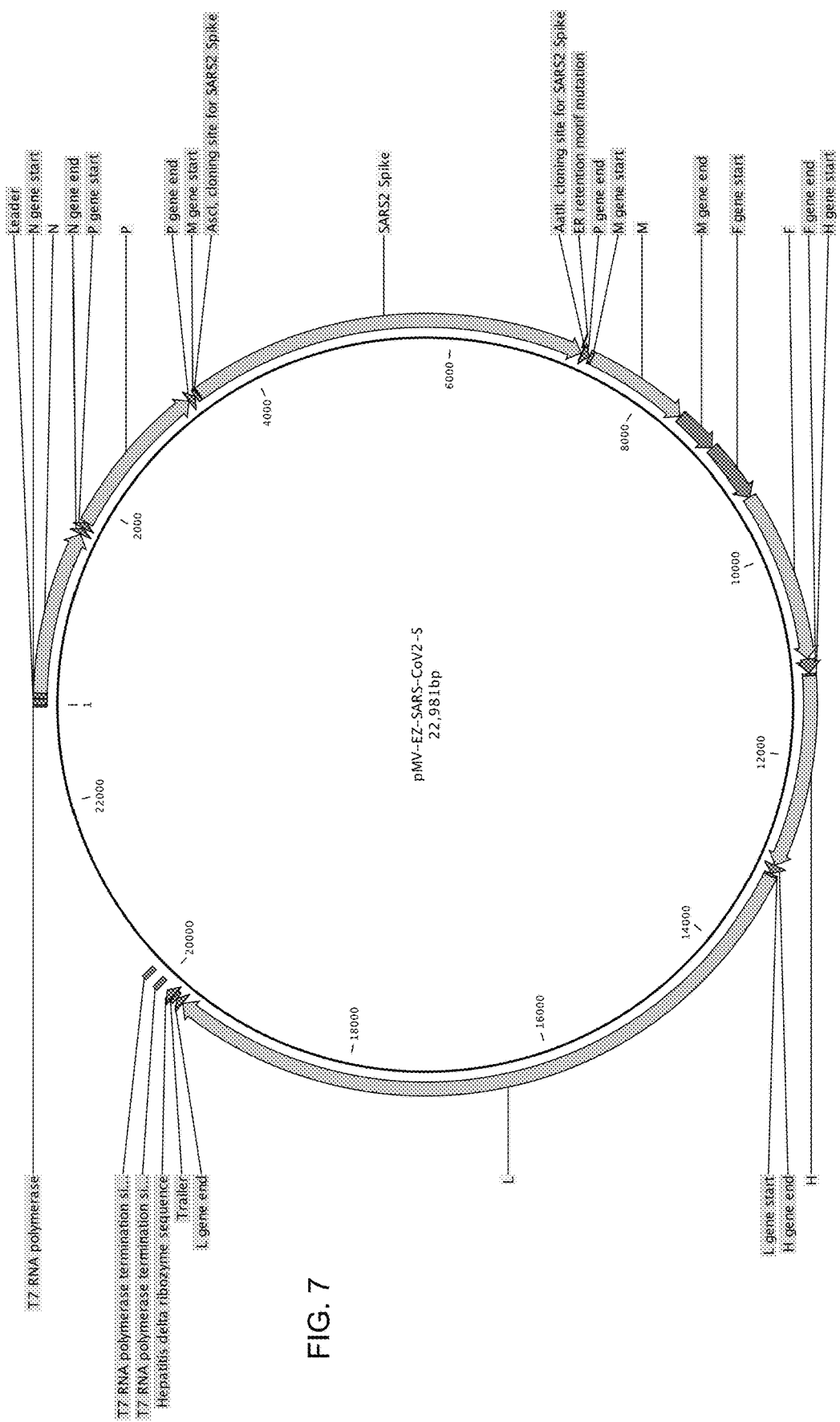
FIG. 7 is a vector map of rMV$^{EZ}$SARS-CoV-2-S.
Figure 8:
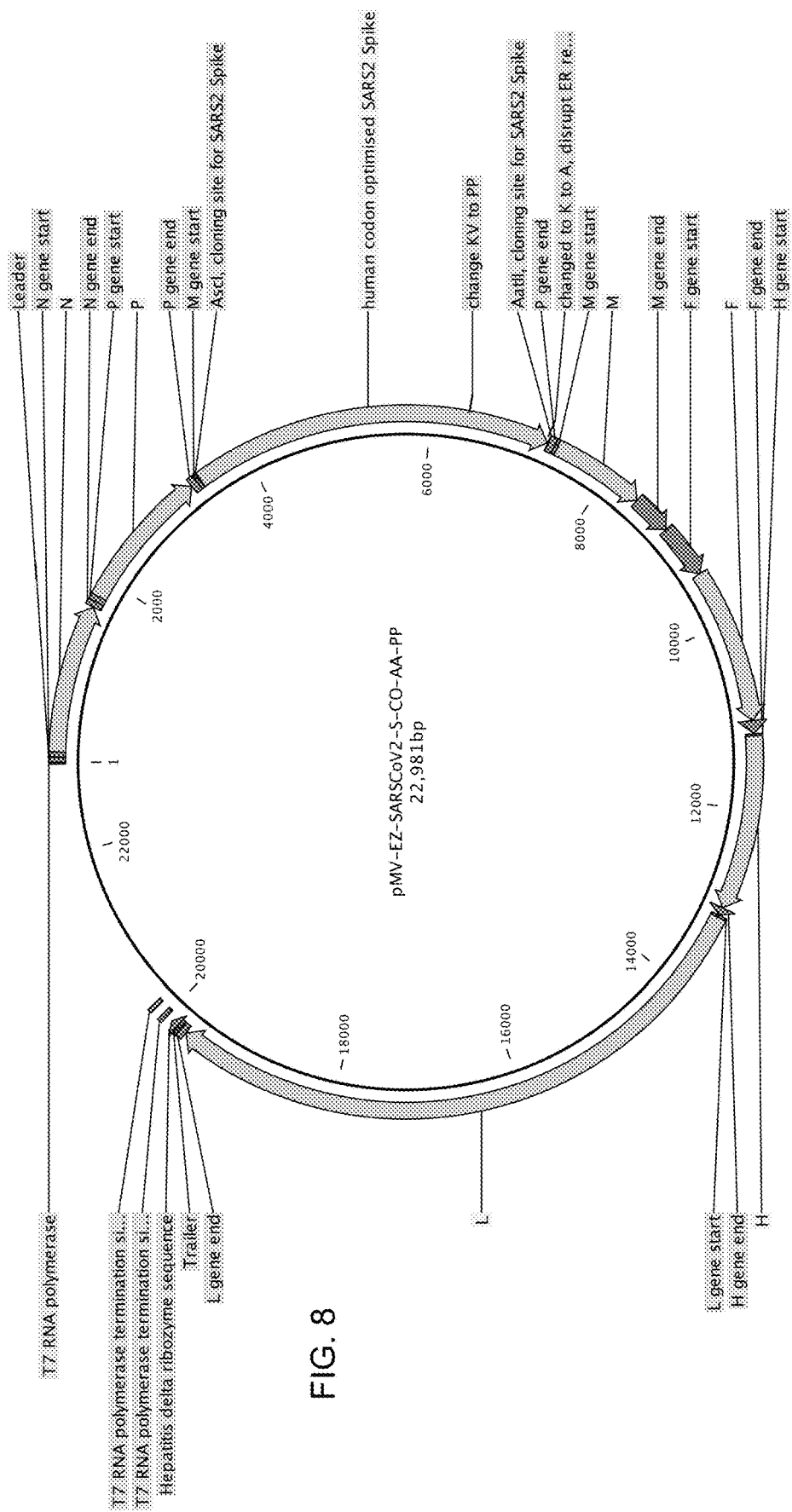
FIG. 8 is a vector map of rMV$^{EZ}$SARS-CoV-2-S-COAA-PP.
Figure 9:
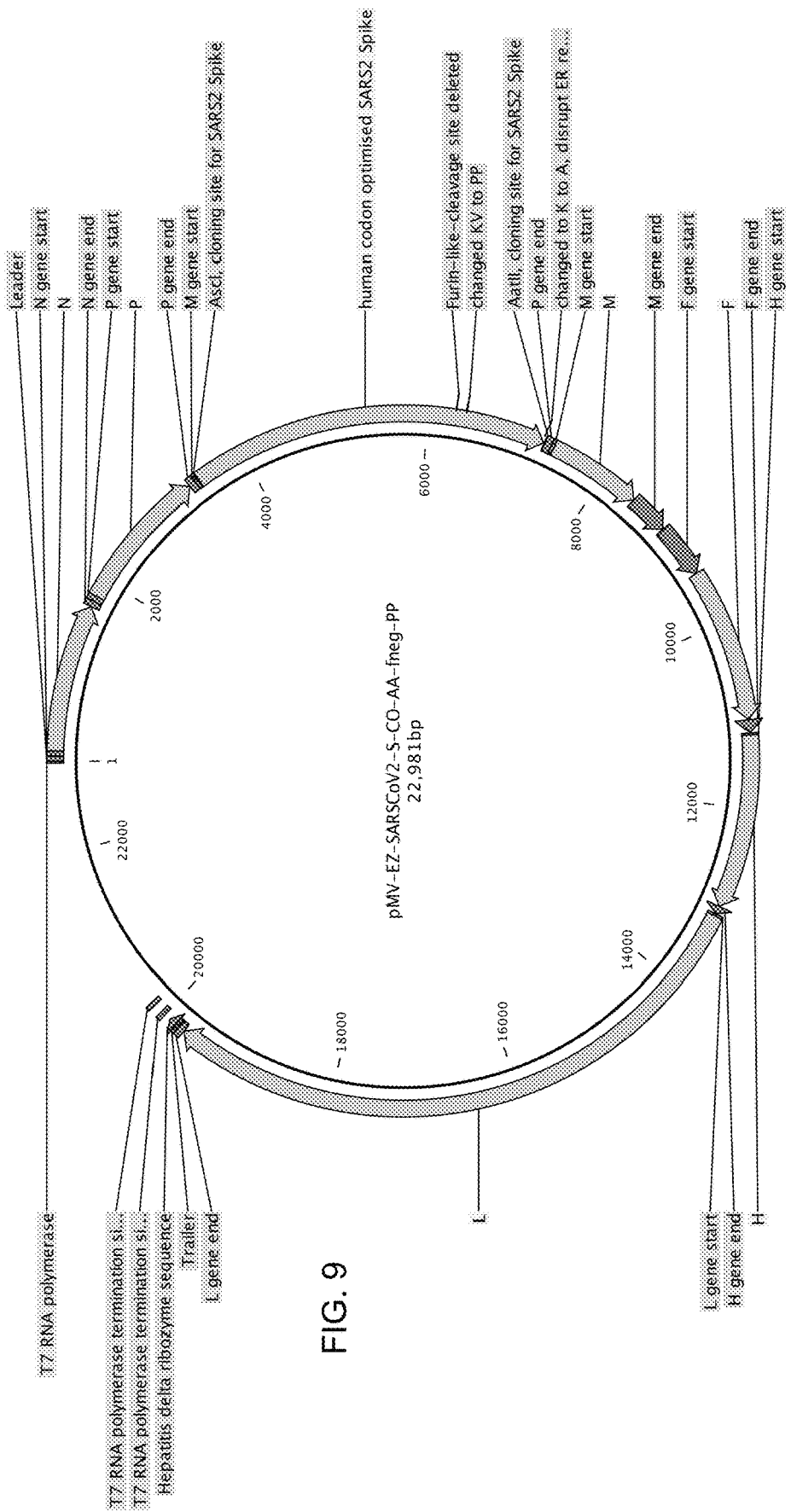
FIG. 9 is a vector map of rMV$^{EZ}$SARS-CoV-2-S-COAA-fneg-PP.
Figure 10:
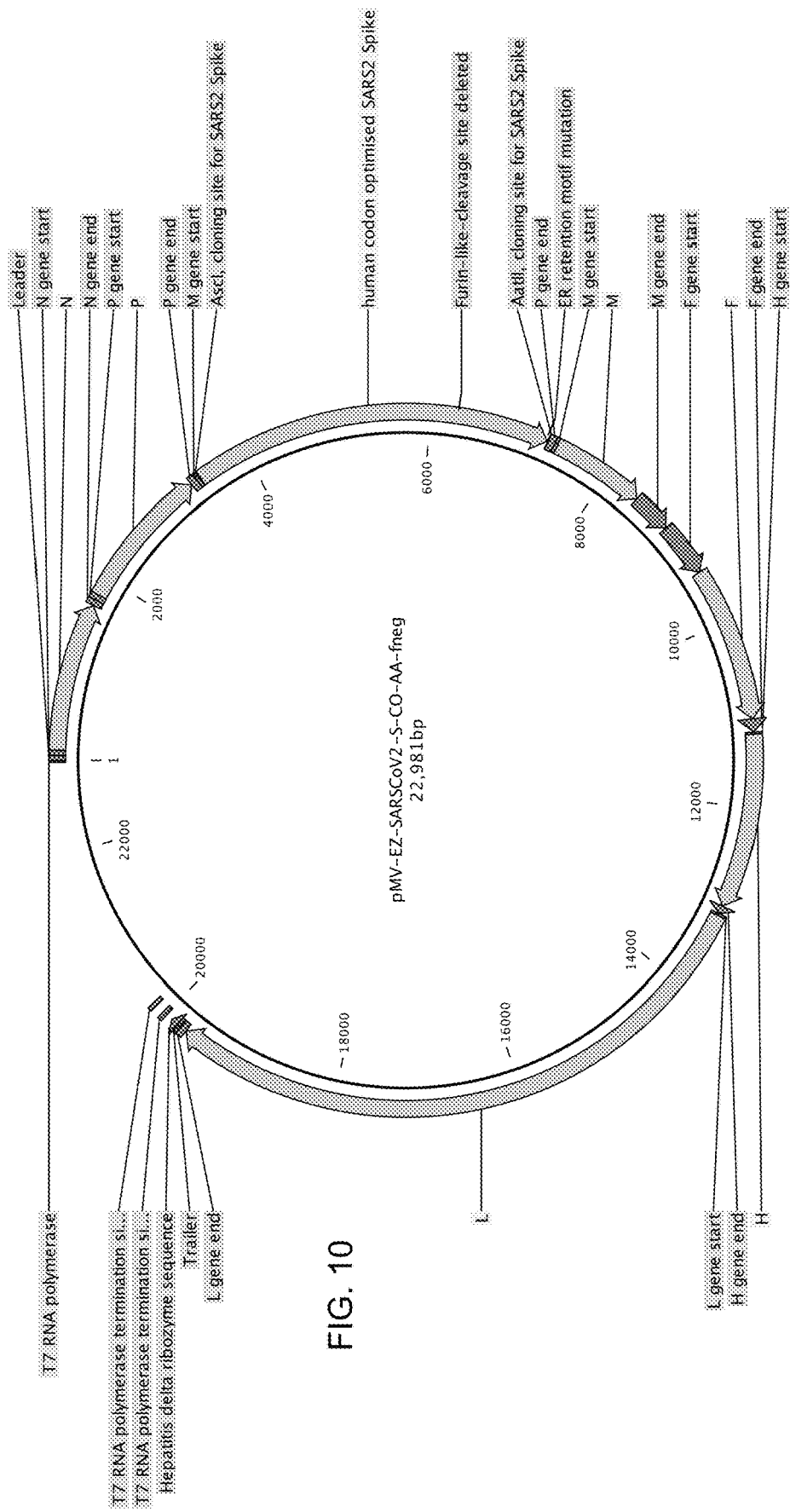
FIG. 10 is a vector map of and rMV$^{EZ}$SARS-CoV-2-S-COAA-fneg.

In one embodiment, the measles viral vector is an Edmonston-Zagreb (EZ) measles viral vector. Particular recombinant measles viral vectors of the Edmonston-Zagreb (EZ) strain include the following: $rMV^{EZ}$SARS-CoV-2-S6 (FIG. 4), $rMV^{EZ}$SARS-CoV-2-S-CO (FIG. 5), $rMV^{EZ}$SARS-CoV-2-S-COAA (FIG. 6), $rMV^{EZ}$SARS-CoV-2-S (FIG. 7), $rMV^{EZ}$SARS-CoV-2-S-COAA-PP (FIG. 8), $rMV^{EZ}$SARS-CoV-2-S-COAA-fneg-PP (FIG. 9), and $rMV^{EZ}$SARS-CoV-2-S-COAA-fneg (FIG. 10).

The recombinant measles vector comprises a nucleic acid encoding the SARS-CoV-2 spike glycoprotein, wherein the nucleic acid sequence encoding the SARS-CoV-2 spike glycoprotein can be any suitable nucleic acid sequence.

In one embodiment, the nucleic acid sequence encoding the SARS-CoV-2 spike glycoprotein is codon optimized. Without being bound to a particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by ribosomes using tRNAs that are more readily available within a cell, thus increasing translation efficiency and overall protein production. Optimization of the nucleotide sequence may also reduce secondary mRNA structures that would interfere with translation, thus increasing translation efficiency. $rMV^{EZ}$SARS-CoV-2-S-CO, $rMV^{EZ}$SARS-CoV-2-S-COAA, $rMV^{EZ}$SARS-CoV-2-S-COAA-PP, $rMV^{EZ}$SARS-CoV-2-S-COAA-fneg-PP, and $rMV^{EZ}$SARS-CoV-2-S-COAA-fneg each contain codon optimized SARS-CoV-2 spike glycoprotein sequences. Techniques for codon optimization are known in the art.

The nucleic acid sequence encoding the SARS-CoV-2 spike glycoprotein can contain at least one modification that disrupts the endoplasmic reticulum (ER) retention sequence of the SARS-CoV-2 spike glycoprotein. For example, the modification can result in an ER retention sequence of the SARS-CoV-2 spike glycoprotein containing AxAxx rather than KxHxx in the cytoplasmic tail (as described in Case et al., *bioRxiv* (2020). doi:10.1101/2020.05.18.102038 and Example 2). $rMV^{EZ}$SARS-CoV2-S6, $rMV^{EZ}$SARS-CoV-2-S, $rMV^{EZ}$SARS-CoV-2-S-COAA, $rMV^{EZ}$SARS-CoV-2-S-COAA-PP, $rMV^{EZ}$SARS-CoV-2-S-COAA-fneg-PP, and $rMV^{EZ}$SARS-CoV-2-S-COAA-fneg each contain modifications to ablate the ER retention signal. In particular, the amino acid sequences of the SARS-CoV-2 spike glycoproteins encoded by $rMV^{EZ}$SARS-CoV2-S6, $rMV^{EZ}$SARS-CoV-2-S, $rMV^{EZ}$SARS-CoV-2-S-COAA, $rMV^{EZ}$SARS-CoV2-S, $rMV^{EZ}$SARS-CoV-2-S-COAA-PP, $rMV^{EZ}$SARS-CoV-2-S-COAA-fneg-PP, and $rMV^{EZ}$SARS-CoV-2-S-COAA-fneg each contain two alanine substitutions at residues 1269 and 1271 of SEQ ID NOs: 8 and 10-14, respectively.

The nucleic acid encoding the SARS-CoV-2 spike glycoprotein can contain at least one modification that locks in the prefusion conformation. The spike (S) glycoprotein is a trimeric class I fusion protein that exists in a metastable prefusion conformation that undergoes a substantial structural rearrangement to fuse the viral membrane with the host cell membrane (Wrapp et al., *Science*, 13: 1260-1263 (2020)). This process is triggered when the 51 subunit binds to a host cell receptor. Receptor binding destabilizes the prefusion trimer, resulting in shedding of the 51 subunit and transition of the S2 subunit to a stable postfusion conformation. To engage a host cell receptor, the receptor-binding domain (RBD) of 51 undergoes hinge-like conformational movements that transiently hide or expose the determinants of receptor binding. The amino acid sequences of the SARS-CoV-2 spike glycoproteins encoded by $rMV^{EZ}$SARS-CoV-2-S-COAA-PP and $rMV^{EZ}$SARS-CoV-2-S-COAA-fneg-PP each contain two proline modifications (PP) at residues 986 and 987 of SEQ ID NOs: 9 and 10, respectively, which lock in the prefusion conformation.

The nucleic acid encoding the SARS-CoV-2 spike glycoprotein can contain at least one modification that ablates the furin cleavage signal, such as by modifying the furin cleavage site so that furin no longer cleaves the sequence. The furin cleavage site can be any polypeptide site cleavable by furin. The minimal cleavage site typically is, in the single letter code for amino acid residues, R-X-X-R, with cleavage occurring after the second "R" (Duckert et al., *Protein Engineering, Design & Selection*, 17(1):107-112 (2004); and WO 2009/032954). Whether or not any particular sequence is cleavable by furin can be determined by methods known in the art. For example, whether or not a sequence is cleavable by furin can be tested by incubating the sequence with furin.

rMV$^{EZ}$SARS-CoV-2-S-COAA-fneg-PP and rMV$^{EZ}$SARS-CoV-2-S-COAA-fneg each contain modifications to ablate the furin cleavage signal. In particular, the amino acid sequences of the SARS-CoV-2 spike glycoproteins encoded by rMV$^{EZ}$SARS-CoV2-S-COAA-fneg-PP and rMV$^{EZ}$SARS-CoV-2-S-COAA-fneg each contain four amino acid changes (ASVG; SEQ ID NO: 23) at residues 682-685 of SEQ ID NOs: 13 and 14, respectively, that ablate the furin cleavage signal.

In one embodiment, the nucleic acid encoding the SARS-CoV-2 spike glycoprotein encodes an amino acid sequence selected from the group consisting of SEQ ID NO: 8 (S6 spike glycoprotein), SEQ ID NO: 9 (S-CO spike glycoprotein), SEQ ID NO: 10 (S-CO-AA spike glycoprotein), SEQ ID NO: 11 (S spike glycoprotein), SEQ ID NO: 12 (S-CO-AA-PP spike glycoprotein), SEQ ID NO: 13 (S-CO-AA-fneg-PP spike glycoprotein), and SEQ ID NO: 14 (S-CO-AA-fneg spike glycoprotein).

In another embodiment, the nucleic acid encoding the SARS-CoV-2 spike glycoprotein is selected from the group consisting of SEQ ID NO: 1 (S6), SEQ ID NO: 2 (S-CO), SEQ ID NO: 3 (S-CO-AA), SEQ ID NO: 4 (S), SEQ ID NO: 5 (S-CO-AA-PP), SEQ ID NO: 6 (S-CO-AA-fneg-PP), and SEQ ID NO: 7 (S-CO-AA-fneg).

The recombinant measles viral vector comprising a nucleic acid sequence encoding a SARS-CoV-2 spike glycoprotein can have any suitable nucleic acid sequence. For example, the recombinant measles viral vector can comprise, consist essentially of, or consist of a nucleic acid sequence selected from the group consisting of SEQ ID NO: 15 (rMV$^{EZ}$SARS-CoV-2-S6), SEQ ID NO: 16 (rMV$^{EZ}$SARS-CoV-2-S-CO), SEQ ID NO: 17 (rMV$^{EZ}$SARS-CoV-2-S-COAA), SEQ ID NO: 18 (rMV$^{EZ}$SARS-CoV-2-S), SEQ ID NO: 19 (rMV$^{EZ}$SARS-CoV-2-S-COAA-PP), SEQ ID NO: 20 (rMV$^{EZ}$SARS-CoV-2-S-COAA-fneg-PP), and SEQ ID NO: 21 (rMV$^{EZ}$SARS-CoV-2-S-COAA-fneg). The vector sequences can comprise one or more nucleic acid sequences encoding the N, P, S, M, F, H, and L genes as described in GenBank Accession Nos. AY486083.1 and AY486084.1.

An embodiment of the invention also provides a polypeptide comprising, consisting essentially of, or consisting of an amino acid sequence selected from the group consisting of SEQ ID NO: 8 (S6), SEQ ID NO: 9 (S-CO), SEQ ID NO: 10 (S-CO-AA), SEQ ID NO: 11 (S), SEQ ID NO: 12 (S-CO-AA-PP), SEQ ID NO: 13 (S-CO-AA-fneg-PP), and SEQ ID NO: 14 (S-CO-AA-fneg), corresponding a SARS-CoV-2 spike glycoprotein.

The polypeptide can be prepared by any of a number of conventional techniques. In this respect, the polypeptide sequence can be synthetic, recombinant, isolated, and/or purified.

The polypeptide can be isolated or purified from a recombinant source. For instance, a DNA fragment encoding a desired polypeptide can be subcloned into an appropriate vector using well-known molecular genetic techniques. The fragment can be transcribed and the polypeptide subsequently translated in vitro. Commercially available kits also can be employed. The polymerase chain reaction optionally can be employed in the manipulation of nucleic acids.

The polypeptide also can be synthesized using an automated peptide synthesizer in accordance with methods known in the art. Alternately, the polypeptide can be synthesized using standard peptide synthesizing techniques well-known to those of skill in the art. In particular, the polypeptide can be synthesized using the procedure of solid-phase synthesis. If desired, this can be done using an automated peptide synthesizer. Removal of the t-butyloxycarbonyl (t-BOC) or 9-fluorenylmethyloxycarbonyl (Fmoc) amino acid blocking groups and separation of the polypeptide from the resin can be accomplished by, for example, acid treatment at reduced temperature. The protein-containing mixture then can be extracted, for instance, with diethyl ether, to remove non-peptidic organic compounds, and the synthesized polypeptide can be extracted from the resin powder (e.g., with about 25% w/v acetic acid). Following the synthesis of the polypeptide, further purification (e.g., using HPLC) optionally can be performed in order to eliminate any incomplete proteins, polypeptides, peptides or free amino acids. Amino acid and/or HPLC analysis can be performed on the synthesized polypeptide to validate its identity. For other applications according to the invention, it may be preferable to produce the polypeptide as part of a larger fusion protein, either by chemical conjugation or through genetic means, such as are known to those skilled in the art. In this regard, an embodiment of the invention also provides a fusion protein comprising the polypeptide and one or more other protein(s) having any desired properties or functions, such as to facilitate isolation, purification, analysis, or stability of the fusion protein.

An embodiment of the invention also provides a nucleic acid encoding the polypeptide. In one embodiment, the nucleic acid comprises, consists essentially of, or consists of a nucleic acid sequence selected from the group consisting of SEQ ID NO: 1 (S6), SEQ ID NO: 2 (S-CO), SEQ ID NO: 3 (S-CO-AA), SEQ ID NO: 4 (SARS-CoV2-S), SEQ ID NO: 5 (S-CO-AA-PP), SEQ ID NO: 6 (S-CO-AA-fneg-PP), and SEQ ID NO: 7 (S-CO-AA-fneg).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

In an embodiment, the nucleic acid is recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acid (e.g., DNA, RNA, cDNA, and the like) can be produced in any suitable matter including, but not limited to recombinant production and commercial synthesis. In this respect, the nucleic acid sequence can be synthetic, recombinant, isolated, and/or purified.

The nucleic acid can be constructed based on chemical synthesis and/or enzymatic ligation reactions using procedures known in the art. See, for example, Green et al. (eds.), *Molecular Cloning, A Laboratory Manual*, $4^{th}$ Edition, Cold Spring Harbor Laboratory Press, New York (2012). For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid encoding the polypeptide can be provided as part of a construct comprising the nucleic acid and elements that enable delivery of the nucleic acid to a cell, and/or expression of the nucleic acid in a cell. For example, the polynucleotide sequence encoding the polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG/AUG) in front of a protein-encoding gene, splicing signal for introns, maintenance of the correct reading frame of that gene to permit proper translation of mRNA, and stop codons.

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, and the RSV promoter. Inducible promoters include, for example, the Tet system, the Ecdysone inducible system, the T-REX™ system (Invitrogen, Carlsbad, Calif.), LACSWITCH™ System (Stratagene, San Diego, Calif.), and the Cre-ERT tamoxifen inducible recombinase system.

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. For example, the nucleic acid encoding the polypeptide can be operably linked to a CMV enhancer/ chicken β-actin promoter (also referred to as a "CAG promoter").

A nucleic acid encoding the polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the polypeptide can be isolated by polymerase chain reaction of cDNA using primers based on the DNA sequence of the molecule. A wide variety of cloning and in vitro amplification methodologies are well known to persons skilled in the art.

An embodiment of the invention also provides a recombinant vector comprising the nucleic acid. Examples of suitable vectors include plasmids (e.g., DNA plasmids), bacterial vectors, and viral vectors, such as poxvirus, retrovirus, adenovirus, adeno-associated virus, herpes virus, poliovirus, alphavirus, baculovirus, measles virus, and Sindbis virus. When the vector is a plasmid (e.g., DNA plasmid), the plasmid can be complexed with chitosan.

The polypeptide, nucleic acid, or vector (e.g., recombinant measles virus vector) can be formulated as a composition (e.g., pharmaceutical composition) comprising the polypeptide, nucleic acid, or vector (e.g., recombinant measles virus vector) and a carrier (e.g., a pharmaceutically or physiologically acceptable carrier). Furthermore, the polypeptide, nucleic acid, vector (e.g., recombinant measles virus vector), or composition can be used in the methods described herein alone or as part of a pharmaceutical formulation.

The composition (e.g., pharmaceutical composition) can comprise more than one polypeptide, nucleic acid, vector (e.g., recombinant measles virus vector), or composition of the invention. Alternatively, or in addition, the composition can comprise one or more (e.g., one, two, three, or more) additional pharmaceutically active agents or drugs, such as corticosteroids, antibiotics, and antivirals.

The carrier can be any of those conventionally used and is limited only by physio-chemical considerations, such as solubility and lack of reactivity with the active compound(s) and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular polypeptide, nucleic acid, vector, or composition thereof of the invention and other active agents or drugs used, as well as by the particular method used to administer the polypeptide, nucleic acid, vector (e.g., recombinant measles virus vector), or composition thereof.

The composition also can be formulated to enhance transduction efficiency. In addition, a person of ordinary skill in the art will appreciate that the one or more of the polypeptides, nucleic acids, or vectors (e.g., recombinant measles virus vectors) can be present in a composition with other therapeutic or biologically-active agents. For example, factors that control inflammation, such as ibuprofen or steroids, can be part of the composition to reduce swelling and inflammation associated with in vivo administration of one or more of the polypeptides, nucleic acids, or vectors (e.g., recombinant measles virus vector). Antibiotics, i.e., microbicides and fungicides, can be present to treat existing infection and/or reduce the risk of future infection.

The invention provides a method for preventing, inhibiting, reducing, eliminating, protecting, or delaying the onset of an infection or an infectious clinical condition caused by coronavirus in a subject comprising administering the polypeptide, nucleic acid, vector (e.g., recombinant measles virus vector), or composition thereof to a subject. The invention also provides a method for inducing an immune response against a coronavirus in a subject comprising administering the polypeptide, nucleic acid, vector (e.g., recombinant measles virus vector), or composition thereof to the subject.

Administration of the polypeptide, nucleic acid, vector (e.g., recombinant measles virus vector), or composition thereof to the subject can be used to protect against one or more strains of coronavirus (e.g., SARS-CoV-2), thereby treating, preventing, and/or protecting against coronavirus-based pathologies.

Administration of the polypeptide, nucleic acid, vector (e.g., recombinant measles virus vector), or composition thereof can significantly induce an immune response of a subject administered the polypeptide, nucleic acid, vector (e.g., recombinant measles virus vector), or composition thereof, thereby protecting against and treating coronavirus (e.g., SARS-CoV-2) infection.

Administration of the polypeptide, nucleic acid, vector (e.g., recombinant measles virus vector), or composition thereof can induce a humoral immune response in a subject. The induced humoral immune response can be specific for the SARS-CoV-2 spike glycoprotein. The humoral immune response can be induced in the subject administered the vaccine by at least about 1.5-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 10.5-fold, at least about 11-fold, at least about 11.5-fold, at least about 12-fold, at least about 12.5-fold, at least about 13-fold, at least about 13.5-fold, at least about 14-fold, at least about 14.5-fold, at least about 15-fold, at least about 15.5-fold, at least about 16-fold, at least about 16.5-fold, at least about 17-fold, at least about 17.5-fold, at least about 18-fold, at least about 18.5-fold, at least about 19-fold, at least about 19.5-fold, at least about 20-fold, or ranges of any combination of these values as compared to a subject not administered the polypeptide, nucleic acid, vector (e.g., recombinant measles virus vector), or composition thereof.

The induced humoral immune response can include an increased level of neutralizing antibodies as compared to a subject not administered the polypeptide, nucleic acid, vector (e.g., recombinant measles virus vector), or composition thereof. The neutralizing antibodies can be specific for the SARS-CoV-2 spike glycoprotein. The neutralizing antibodies can provide protection against and/or treatment of SARS-CoV-2 infection and its associated pathologies in the subject administered the polypeptide, nucleic acid, vector (e.g., recombinant measles virus vector), or composition thereof.

The induced humoral immune response can include an increased level of IgG antibodies as compared to a subject not administered the polypeptide, nucleic acid, vector (e.g., recombinant measles virus vector), or composition thereof. These IgG antibodies can be specific for the SARS-CoV-2 antigens. The level of IgG antibody can be increased by at least about 1.5-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 10.5-fold, at least about 11-fold, at least about 11.5-fold, at least about 12-fold, at least about 12.5-fold, at least about 13-fold, at least about 13.5-fold, at least about 14-fold, at least about 14.5-fold, at least about 15-fold, at least about 15.5-fold, at least about 16-fold, at least about 16.5-fold, at least about 17-fold, at least about 17.5-fold, at least about 18-fold, at least about 18.5-fold, at least about 19-fold, at least about 19.5-fold, at least about 20-fold, or ranges of any combination of these values as compared to a subject not administered the polypeptide, nucleic acid, vector (e.g., recombinant measles virus vector), or composition thereof.

The induced humoral immune response can include an increased level of IgM and/or IgA antibodies as compared to a subject not administered the polypeptide, nucleic acid, vector (e.g., recombinant measles virus vector), or composition thereof. These IgM and or IgA antibodies can be specific for the SARS-CoV-2 antigen. The level of IgM/IgA antibody can be increased by at least about 1.5-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 10.5-fold, at least about 11-fold, at least about 11.5-fold, at least about 12-fold, at least about 12.5-fold, at least about 13-fold, at least about 13.5-fold, at least about 14-fold, at least about 14.5-fold, at least about 15-fold, at least about 15.5-fold, at least about 16-fold, at least about 16.5-fold, at least about 17-fold, at least about 17.5-fold, at least about 18-fold, at least about 18.5-fold, at least about 19-fold, at least about 19.5-fold, at least about 20-fold, or ranges of any combination of these values as compared to a subject not administered the polypeptide, nucleic acid, vector (e.g., recombinant measles virus vector), or composition thereof.

Administration of the polypeptide, nucleic acid, vector (e.g., recombinant measles virus vector), or composition thereof can induce a cellular immune response in the subject. The induced cellular immune response can be specific for the SARS-CoV-2 antigen.

The induced cellular immune response can include eliciting a CD8+ T cell response, which can include eliciting a CD8+ T cell response in which the CD8+ T cells produce interferon-gamma (IFN-γ), tumor necrosis factor alpha (TNF-α), interleukin-2 (IL-2), or a combination thereof (e.g., a combination of IFN-γ and TNF-α).

The CD8+ T cell response can be increased by at least about 1.5-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 10.5-fold, at least about 11-fold, at least about 11.5-fold, at least about 12-fold, at least about 12.5-fold, at least about 13-fold, at least about 13.5-fold, at least about 14-fold, at least about 14.5-fold, at least about 15-fold, at least about 15.5-fold, at least about 16-fold, at least about 17-fold, at least about 18-fold, at least about 19-fold, at least about 20-fold, at least about 21-fold, at least about 22-fold, at least about 23-fold, at least about 24-fold, at least about 25-fold, at least about 26-fold, at least about 27-fold, at least about 28-fold, at least about 29-fold, at least about 30-fold, or ranges of any combination of these values as compared to the subject not administered the polypeptide, nucleic acid, vector (e.g., recombinant measles virus vector), or composition thereof.

Administration of the polypeptide, nucleic acid, vector (e.g., recombinant measles virus vector), or composition thereof can also include eliciting a CD4+ T cell response, which can include eliciting a CD4+ T cell response in which the CD4+ T cells produce IFN-γ, TNF-α, IL-2, or a combination thereof (e.g., a combination of IFN-γ and TNF-α).

The polypeptide, nucleic acid, vector (e.g., recombinant measles virus vector), or composition thereof can be administered to the subject by various routes including, but not limited to, oral, sublingual, buccal, intradermal, topical, parenteral (using single or arrays of dissolvable and hybrid microneedles, in lyophilized or solution), subcutaneous, intravenous, intramuscular, intraarterial, intrathecal, interperitoneal, intranasal, large and/or small particle aerosol, dry-powder aerosols or intratracheal administration, or subretinal injection or intravitreal injection.

The invention includes a prime and boost protocol. In particular, the protocol includes an initial "prime" with the polypeptide, nucleic acid, vector (e.g., recombinant measles virus vector), or composition thereof, followed by one or preferably multiple "boosts" with the polypeptide, nucleic acid, vector (e.g., recombinant measles virus vector), or composition thereof. The boosts can be administered 1-3 times (e.g., 1, 2, or 3 times) at any suitable time period (e.g., every 3-4 weeks, every six months, or once a year) for any suitable length of time.

The polypeptide, nucleic acid, vector (e.g., recombinant measles virus vector), or composition thereof can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The subject can be a mammal, such as a human, a horse, a cow, a pig, a sheep, a cat, a dog, a rat, or a mouse.

The polypeptide, nucleic acid, vector (e.g., recombinant measles virus vector), or composition thereof can be administered prophylactically or therapeutically. In prophylactic administration, the polypeptide, nucleic acid, vector (e.g., recombinant measles virus vector), or composition thereof are administered in an amount sufficient to induce an immune response. In therapeutic applications, the polypeptide, nucleic acid, vector (e.g., recombinant measles virus vector), or composition thereof are administered to a subject in need thereof in an amount sufficient to elicit a therapeutic effect. An amount adequate to accomplish this is defined as "therapeutically effective dose." Amounts effective for this use will depend on, e.g., the particular composition of the polypeptide, nucleic acid, vector (e.g., recombinant measles virus vector), or composition thereof administered to a subject, the manner of administration, the stage and severity of the infection, the general state of health of the patient, and the judgment of the prescribing physician.

The following examples further illustrate the invention but, of course, should not be construed as in any way limiting its scope.

Example 1

This example provides materials and methods for the studies described in Example 2.

Cell Lines, Viruses and Plasmids

Vero cells (African green monkey kidney cells; ATCC CCL-81) purchased from ATCC (Manassas, Va., USA) were grown in advanced Dulbecco's modified Eagle medium (DMEM; Gibco) supplemented with 10% (V/V) fetal bovine serum (HI FBS heat inactivated, Gibco) and GlutaMAX-I (Gibco). Cells were grown and maintained at 37° C. and 5% (V/V) $CO_2$, and tested negative for *mycoplasma* contamination prior to use in virus rescue experiments. MV plasmids expressing N, P and L, rMV$^{EZ}$EGFP(3), as well as rMV$^{EZ}$EGFP(3) virus have been described previously (Rennick et al., *J. Virol.* (2015). doi:10.1128/jvi.02924-14).

Construction of MV$^{EZ}$ cDNA Plasmids Expressing SARS-CoV-2 Spike Glycoprotein As described in Rennick et al., *J. Virol.* (2015). doi: 10.1128/jvi.02924-14), three recombinant viruses were generated that contained the open reading frame encoding enhanced green fluorescent protein (EGFP) within an additional transcriptional unit (ATU) at various positions within the genome. rMV$^{EZ}$EGFP(1), rMV$^{EZ}$EGFP(3), and rMV$^{EZ}$EGFP(6) contained the ATU upstream of the N gene, following the P gene, and following the H gene, respectively. The viruses were compared in vitro by growth curves, which indicated that rMV$^{EZ}$EGFP(1) was over-attenuated. Intratracheal infection of cynomolgus macaques with these recombinant viruses revealed differences in immunogenicity. rMV$^{EZ}$EGFP(1) and rMV$^{EZ}$EGFP(6) did not induce satisfactory serum antibody responses, whereas both in vitro and in vivo rMV$^{EZ}$EGFP(3) was functionally equivalent to the commercial MV$^{EZ}$-containing vaccine. Intramuscular vaccination of macaques with rMV$^{EZ}$EGFP(3) resulted in the identification of EGFP$^+$ cells in the muscle at days 3, 5, and 7 post-vaccination. Therefore, rMV$^{EZ}$EGFP(3) was selected for further experiments.

pMV$^{EZ}$ versions expressing SARS-CoV-2 spike glycoprotein (Accession number MN908947) were generated by replacing the open reading frame of EGFP in rMV$^{EZ}$EGFP (3) (Rennick et al., J. Virol. (2015). doi:10.1128/jvi.02924-14).

Plasmid rMV$^{EZ}$EGFP(3) was linearized using restriction sites Asc I at genome position 3439 and Aat II at genome position 4176. These restriction sites were originally designed into pMV$^{EZ}$EGFP(3) to allow easy replacement of foreign genes in place of EGFP. SARS-CoV-2 spike with mutations in the endoplasmic reticulum (ER) retention signal sequence as previously described (Case et al., bioRxiv (2020). doi:10.1101/2020.05.18.102038) were obtained in two gene fragments. These fragments were ligated into the linearized pMV$^{EZ}$EGFP(3) using Gibson Assembly (NEBuilder® HiFi DNA assembly, NEB). This generated two versions pMV$^{EZ}$SARS-CoV-2-S and pMV$^{EZ}$SARS-CoV-2-S6.

A human codon optimized SARS-CoV-2 spike glycoprotein expressing plasmid was obtained from GenScript (Piscataway, N.J., USA). Spike was amplified from the plasmid using oligonucleotides that contained a 35 nucleotide homology (lower case sequence) to the linearized rMV$^{EZ}$EGFP(3) (Forward primer: 5'caaagtgattgcctcc-caagttccacaggcgcgccATGTTCGTCTTCCTGGTC3' (SEQ ID NO: 24) and reverse primer: 5'gttggcaggtaagtt-gagctgtaggacgtcgcgcgTTAGGTGTAATGCAGCTTCAC3' (SEQ ID NO: 25)). The amplified product was then ligated into linearized rMV$^{EZ}$EGFP(3) using Gibson Assembly (NEBuilder® HiFi DNA assembly, NEB). This generated pMV$^{EZ}$SARSCoV2-S-CO. pMV$^{EZ}$SARS-CoV-2-S-COAA was generated the same way, but using a reverse primer (5'ggttggcaggtaagttgagctgtaggacgtcgcgcgT-TAGGTGTAAGCCAGCGCCACGCC3' (SEQ ID NO: 26) with nucleotide changes (in bold) to disrupt the ER retention signal.

The spike sequence in all plasmids were sequence confirmed via Sanger sequencing (Genewiz, NJ, USA).

Generation of Recombinant rMV$^{EZ}$-SARS-CoV-2-Spike Glycoprotein Viruses

Vero cell monolayers in 6-well trays were infected with a recombinant vaccinia virus expressing T7 polymerase (MVA-T7) in Opti-MEM (Gibco) for 30 mins at 37° C. and then spinoculated at room temperature for another 30 mins. Virus inoculum was removed and 1 ml fresh Opti-MEM was added onto cells. Cells were then transfected with 5 µg of pMV$^{EZ}$SARS-CoV-2-S, pMV$^{EZ}$SARS-CoV-2-S6, pMV$^{EZ}$SARS-CoV-2-S-CO, or pMV$^{EZ}$SARS-CoV-2-S-COAA. MV plasmids expressing nucleoprotein (N), phosphoprotein (P) and polymerase (L) at 1 µg, 0.6 µg and 0.4 µg respectively, were also transfected into the cells. 24 hours post-transfection (h.p.t.), medium was removed from the cells and DMEM/2% (V/V) fetal bovine serum (FBS) was added. Cells were monitored daily for approximately 14 days post-transfection (d.p.t.) for syncytium formation. Plaque picked viruses were then grown in Vero cells and harvested by free-thaw when complete cytopathic effect was visible. Virus titers were determined by endpoint titration and expressed as 50% tissue culture infectious (TCID$_{50}$) units.

Reverse Transcription Polymerase Chain Reaction (RT/PCR) and Sequencing

Total RNA from working virus stocks was extracted using TRIzol LS reagent (ThermoFisher) according to manufacturer's recommendations and RNA pellet resuspended in 40 µl nuclease-free water (Invitrogen). cDNA was generated with 5 µl of resuspended RNA using SuperScript™ III First-strand synthesis system (Thermo Fisher Scientific) and random primers. 3 µl of the resultant cDNA was then used to amplify MV-spike fragments with primers using Phusion high-fidelity DNA polymerase (NEB) in a total volume of 50 µl (using a touch-down PCR amplification protocol). Amplified PCR products were analyzed on a 1% agarose gel and bands gel purified using QIAquick gel extraction kit (Qiagen). Products were sequenced confirmed via Sanger sequencing (Genewiz, NJ, USA).

Immunofluorescence

Confluent Vero cells in 24-well trays were infected with rMV$^{EZ}$SARS-CoV2-S6 or rMV$^{EZ}$SARS-CoV-2-S-CO at a multiplicity of infection (MOI) of 0.01. At 2 days post infection, cells were fixed with 4% paraformaldehyde for 10 minutes at room temperature. Cells were washed twice in PBS and permeabilized (0.1% Triton-X in PBS) at 37° C. for 30 minutes before incubating with primary antibody (Rabbit anti-SARS2-S, Sino biologicals 40150-R007; 1:500) made in PBS with 0.1% (V/V) Triton-X at 37° C. for 1 hour. Cells were then washed three times in PBS before incubating with secondary antibody (Chicken anti-rabbit Alexa Fluor 488, Invitrogen; 1:400) at 37° C. for 1 hour. Cells were washed three times in PBS and stained with DAPI nuclei stain (Invitrogen; 300 nM DAPI stain solution) for 10 minutes at room temperature in the dark. Images were obtained using a fluorescent microscope (Leica).

Virus Growth Kinetics

Vero cell monolayers at 2×10$^5$ cells in 24-well trays were infected with rMV$^{EZ}$EGFP(3), rMV$^{EZ}$SARS-CoV-2-S3, rMV$^{EZ}$SARS-CoV-2-S6, rMV$^{EZ}$SARS-CoV-2-S-CO, or rMV$^{EZ}$SARS-CoV-2-S-COAA at a 0.05 MOI. Cell monolayers were infected for 1 hour at 37° C. after which virus inoculum was removed and cell monolayers washed twice using phosphate-buffered saline (PBS; Gibco). DMEM/2% (V/V) FBS was added onto the cells and at the desired time points cells were scraped into culture medium and placed at −80° C. After freeze-thawing the cells and medium, cell debris were clarified and total virus measured by TCID$_{50}$.

Immunoplaque Assay

Confluent Vero cell monolayers in 6-well trays were infected with a 10-fold serial dilution of virus prepared in Opti-MEM. Cells were incubated for 1 h at 37° C. and then overlaid with 0.6% Avicel (FMC Biopolymer) supplemented with 2×MEM (10×MEM, no glutamine, Gibco) and 2% FBS. Cells were incubated for 5 days and then fixed using 4% paraformaldehyde for 30 minutes at room temperature. Cells were permeabilized (0.5% Triton X-100, 20 mM sucrose in PBS; 1 ml) for 30 minutes at room temperature and then washed (0.1% Tween-20 in PBS; 1 ml) once before incubating with primary antibody (Rabbit anti-SARS2-S, Sino biologicals 40150-R007; 1:1000) in blocking buffer (4% dried milk/0.1% Tween-20 in PBS) for 1 hour at room temperature. Cells were washed three times and incubated with secondary antibody (Goat anti-rabbit HRP, Abcam, ab6721; 1:1000) for 1 hour at room temperature. Plaques were visualized using KPL TrueBlue Peroxidase Substrate solution (Sera Care, 5510-0050). Plates were digitalized using a scanner.

Animal Study Design

All animal experiments were conducted in compliance with all applicable U.S. Federal policies and regulations and AAALAC International standards for the humane care and use of animals. All protocols were approved by the University of Pittsburgh Institutional Animal Care and Use Committee (IACUC).

Twenty-five IFNar1 knockout mice in groups of five were infected with 10$^4$ TCID$_{50}$ of rMV$^{EZ}$EGFP(3), rMV$^{EZ}$SARS- CoV-2-S3, rMV$^{EZ}$SARS-CoV-2-S6, rMV$^{EZ}$SARS-CoV-2-S-CO, or rMV$^{EZ}$SARS-CoV-2-S-COAA viruses via the intraperitoneal (IP) route. 21 days post-infection, mice were bled for serum, and then boosted with $10^5$ TCID$_{50}$ of the respective virus.

African green monkeys were immunized with either measles vaccine or rMV$^{EZ}$SARS-CoV-2-S-CO (in groups of 2 or 3) with $10^5$ TCID$_{50}$ of candidate vaccine. In our proof of principle study we focused on a prime/boost (day 0 and 21 days). Animals were challenged 42 days after immunization with $10^6$ plaque forming units of SARS-CoV-2.

All animals seroconverted generating antibodies to both measles and SARS-CoV-2. These antibodies neutralized both viruses, some at levels higher than what is seen in human convalescent serum.

Statistical Analysis

Statistical analyses were performed using GraphPad Prism software (La Jolla, Calif.).

Vector Maps

Vector maps are provided in FIGS. 4-10 for each of rMV$^{EZ}$SARS-CoV-2-S6, rMV$^{EZ}$SARS-CoV-2-S-CO, rMV$^{EZ}$SARS-CoV-2-S-COAA, rMV$^{EZ}$SARS-CoV-2-S, rMV$^{EZ}$SARS-CoV-2-S-COAA-PP, rMV$^{EZ}$SARS-CoV-2-S-COAA-fneg-PP, and rMV$^{EZ}$SARS-CoV-2-S-COAA-fneg, wherein the spike glycoprotein is inserted after the measles virus N and P genes (in the third (3) position).

Example 2

This example demonstrates the generation and characterization of recombinant MV vaccine strain viruses expressing SARS-CoV-2 spike glycoprotein.

Based on previously generated reverse genetics system for live-attenuated measles virus (MV) vaccine strain Edmonston-Zagreb (EZ) that expresses an enhanced green fluorescent protein (EGFP; rMV$^{EZ}$ EGFP(3)), recombinant MV vaccine viruses encoding SARS-CoV-2 spike glycoprotein were generated and rescued. The open reading frame for the spike glycoprotein lies within an additional transcriptional unit at position 3 in the MV genome in place of EGFP. These viruses were compared in vitro for replication and expression of the spike glycoprotein. The growth kinetics of all tested viruses were equivalent to rMV$^{EZ}$ EGFP(3).

rMV$^{EZ}$EGFP(3) (Rennick et al., *J. Virol.* (2015). doi: 10.1128/jvi.02924-14) was modified to express SARS-CoV-2 spike glycoprotein in place of EGFP. In a manner similar to that described in Case et al, *bioRxiv* (2020). doi:10.1101/2020.05.18.102038, an endoplasmic reticulum (ER) retention signal sequence present in the cytoplasmic tail (CT) of the spike was altered from KxHxx to AxAxx-COOH, and anti-genomic plasmids expressing a non-codon and human codon optimized version (pMV$^{EZ}$SARS-CoV2-S and pMV$^{EZ}$SARS-CoV-2-COAA, respectively) were generated. An additional human codon optimized version with the authentic KxHxx-COOH sequence was also generated (pMV$^{EZ}$SARS-CoV-2-CO).

Recovery of a plasmid with the correct spike sequence proved challenging for the non-codon optimized version, and as a result two plasmids were generated: one with the authentic sequence (pMV$^{EZ}$SARS-CoV-2-S) and one with three nucleotide changes, one of which does not cause an amino acid change (pMV$^{EZ}$SARS-CoV-2-S6).

To recover recombinant viruses, Vero cells were transfected with either pMV$^{EZ}$SARS-CoV-2-S, pMV$^{EZ}$SARS-CoV-2-S6, pMV$^{EZ}$SARS-CoV-2-CO or pMV$^{EZ}$SARS-CoV-2-COAA along with expression plasmids for nucleoprotein (N), phosphoprotein (P) and polymerase (L) proteins. Sequence confirmation of the virus generated from clone pMV$^{EZ}$SARS-CoV-2-S revealed an amino acid change in the CT tail. This virus was subsequently named rMV$^{EZ}$SARS-CoV-2-S3 (FIG. 1A).

Figure 1A:
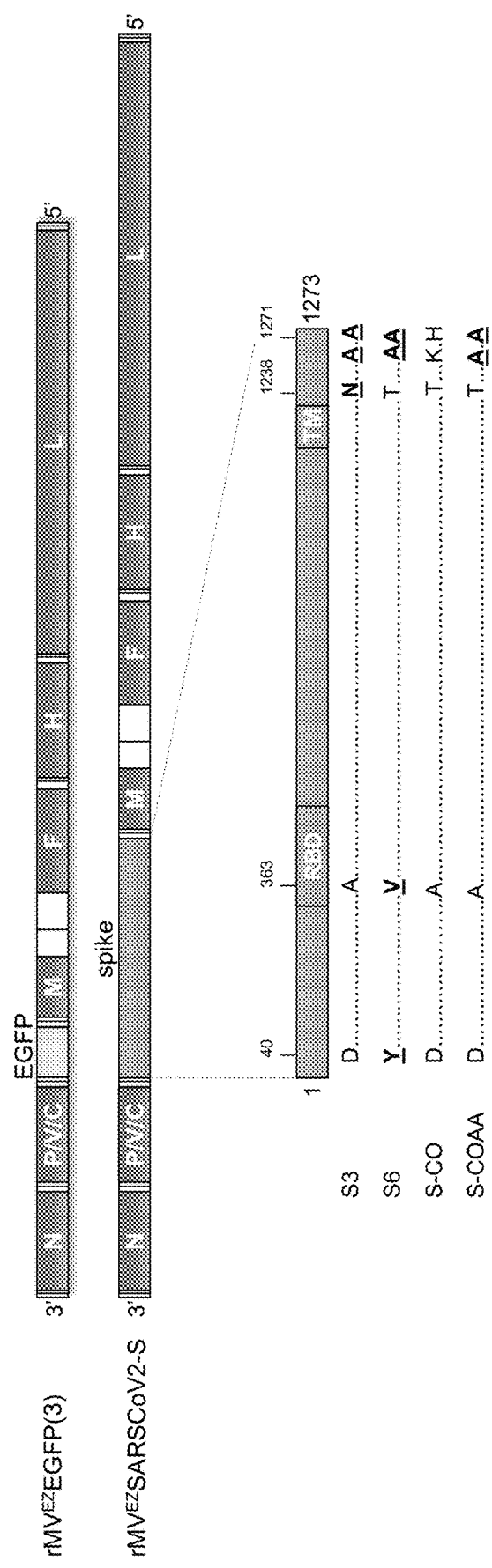
FIGS. 1A-1C demonstrate the generation of rMV$^{EZ}$ viruses expressing SARS-CoV-2 spike glycoprotein.
Figure 1C:
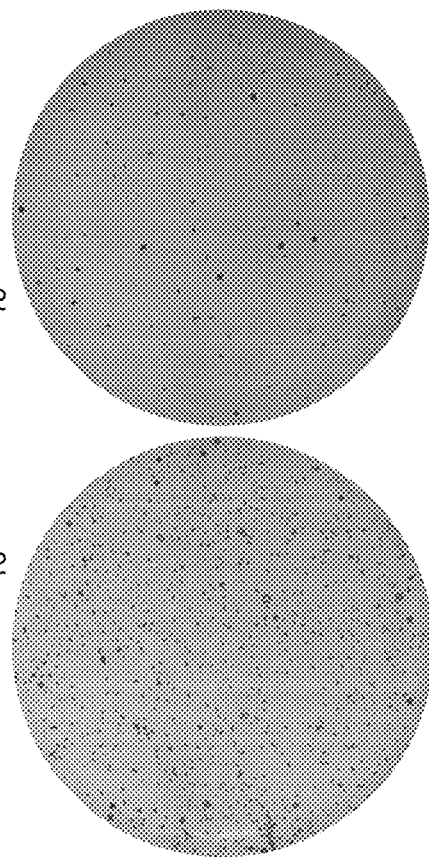
Figure 1B:
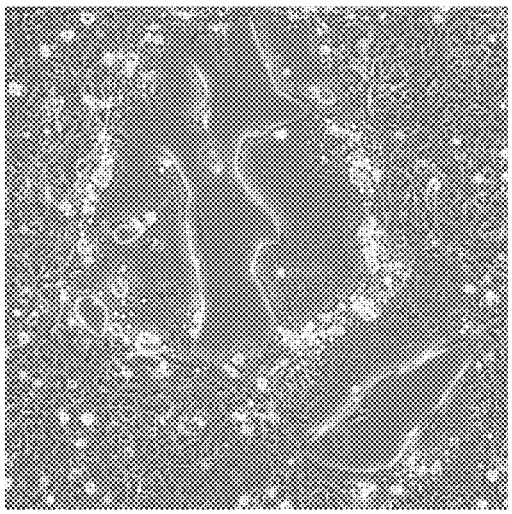

The spike glycoprotein sequences in rMV$^{EZ}$SARS-CoV-2-S6, rMV$^{EZ}$SARS-CoV-2-CO, and rMV$^{EZ}$SARS-CoV-2-COAA correspond to their cDNA clones (FIG. 1A). Rescue experiments were reproducible with syncytium formation about 14 days post transfection (FIG. 1B).

To test if the spike glycoprotein was expressed, Vero cells were infected and fixed and stained at 48 hours post-infection using an anti-SARS2-S antibody. Substantial amounts of spike expression were detectable in the infected cells, especially for rMV$^{EZ}$SARS-CoV-2-CO (FIG. 1C). Expression was further confirmed by staining viral plaques with anti-SARS2-S antibody (FIG. 1D).

Figure 2:
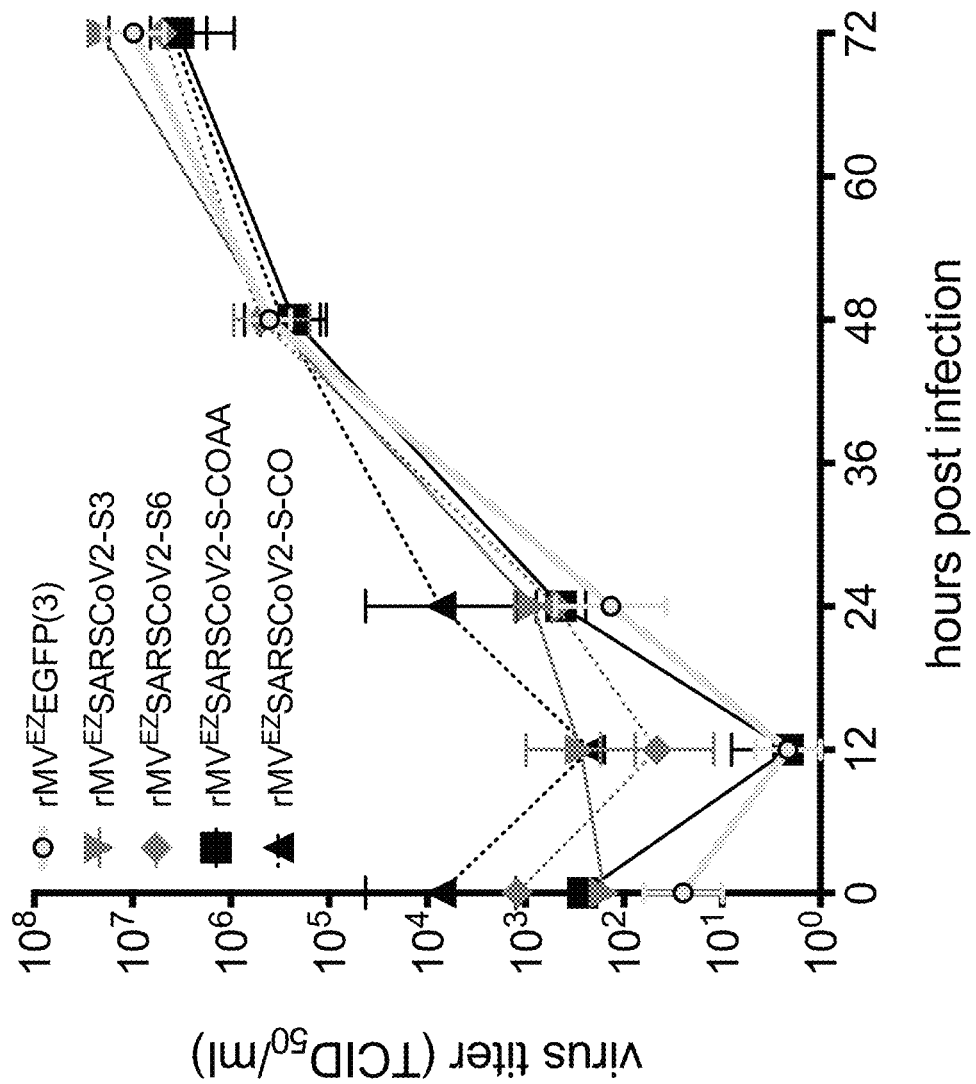
FIG. 2 demonstrates that growth kinetics of rMV$^{EZ}$SARS-CoV-2-S3, rMV$^{EZ}$SARS-CoV-2-S6, rMV$^{EZ}$SARS-CoV-2-S-CO, and rMV$^{EZ}$SARS-CoV-2-S-COAA compared to rMV$^{EZ}$EGFP(3). Vero cells were infected at a multiplicity of infections (MOI) of 0.05. Samples were harvested at the indicated time points and titrated on Vero cells. Error bars indicate standard deviation (n=3).

Growth analysis of rMV$^{EZ}$SARS-CoV-2-S3, rMV$^{EZ}$SARS-CoV-2-S6, rMV$^{EZ}$SARS-CoV-2-CO, and rMV$^{EZ}$SARS-CoV-2-COAA were compared to rMV$^{EZ}$EGFP(3) in Vero cells over a 3 day period. Viruses replicated similar to rMV$^{EZ}$EGFP(3) by reaching a titers close to $10^7$ TCID$_{50}$/ml (FIG. 2).

Additional vectors were generated with modifications to ablate the furin cleavage signal (rMV$^{EZ}$SARS-CoV-2-S-COAA-fneg and rMV$^{EZ}$SARS-CoV-2-S-COAA-fneg-PP), and to lock in the prefusion conformation by substitution of two proline residues (rMV$^{EZ}$SARS-CoV-2-S-COAA-PP and S-CO-AA-fneg-PP).

rMV$^{EZ}$SARS-CoV-2-S3 and rMV$^{EZ}$SARS-CoV-2-S6 encode a spike glycoprotein with nucleotide changes that arose during virus rescue and plasmid generation, respectively.

rMV$^{EZ}$SARS-CoV-2-S-CO, rMV$^{EZ}$SARS-CoV-2-S-COAA, rMV$^{EZ}$SARS-CoV-2-S-COAA-PP, rMV$^{EZ}$SARS-CoV-2-S-COAA-fneg, and rMV$^{EZ}$SARS-CoV-2-S-COAA-fneg-PP encode a human codon optimized spike glycoprotein.

rMV$^{EZ}$SARS-CoV-2-S3, rMV$^{EZ}$SARS-CoV-2-S6, rMV$^{EZ}$SARS-CoV-2-S, rMV$^{EZ}$SARS-CoV-2-S-COAA, rMV$^{EZ}$SARS-CoV-2-S-COAA-PP, rMV$^{EZ}$SARS-CoV-2-S-COAA-fneg-PP, and rMV$^{EZ}$SARS-CoV-2-S-COAA-fneg contain mutations in the spike glycoprotein to disrupt the endoplasmic reticulum (ER) retention sequence that has been described as essential for SARS-CoV-2 virion assembly via the ER-Golgi compartment.

The nucleic acid sequence encoding the spike glycoprotein of rMV$^{EZ}$SARS-CoV-2-S3 corresponds to SEQ ID NO: 22.

The following table summarizes the sequence information for each of the vectors and the corresponding nucleic acid and amino acid sequences of the spike glycoprotein.

| Vector Designation | Nucleic Acid Sequence of Spike Glycoprotein | Amino Acid Sequence of Spike Glycoprotein | Nucleic Acid Sequence of Vector | Modifications |
|---|---|---|---|---|
| rMV$^{EZ}$SARS-CoV-2-S6 | 1 | 8 | 15 | modifications to ablate ER retention signal |
| rMV$^{EZ}$SARS-CoV-2-CO | 2 | 9 | 16 | codon optimized |

| Vector Designation | Nucleic Acid Sequence of Spike Glycoprotein | Amino Acid Sequence of Spike Glycoprotein | Nucleic Acid Sequence of Vector | Modifications |
| --- | --- | --- | --- | --- |
| rMV$^{EZ}$SARS-CoV-2-S-COAA | 3 | 10 | 17 | codon optimized; modifications to ablate ER retention signal |
| rMV$^{EZ}$SARS-CoV-2-S | 4 | 11 | 18 | modifications to ablate ER retention signal |
| rMV$^{EZ}$SARS-CoV-2-S-COAA-PP | 5 | 12 | 19 | codon optimized; modifications to ablate ER retention signal; modifications to lock in prefusion conformation |
| rMV$^{EZ}$SARS-CoV-2-S-COAA-fneg-PP | 6 | 13 | 20 | codon optimized; modifications to ablate ER retention signal; modifications to lock in prefusion conformation; modifications to ablate furin cleavage signal |
| rMV$^{EZ}$SARS-CoV-2-S-COAA-fneg | 7 | 14 | 21 | codon optimized; modifications to ablate ER retention signal; modifications to ablate furin cleavage signal |
| rMV$^{EZ}$SARS-CoV-2-S3 | 22 | | | modifications to ablate ER retention signal |

Example 3

This example describes vaccination/challenge studies with recombinant MV vaccine strain viruses expressing SARS-CoV-2 spike glycoprotein.

Mice

Figures 3A, 3B:
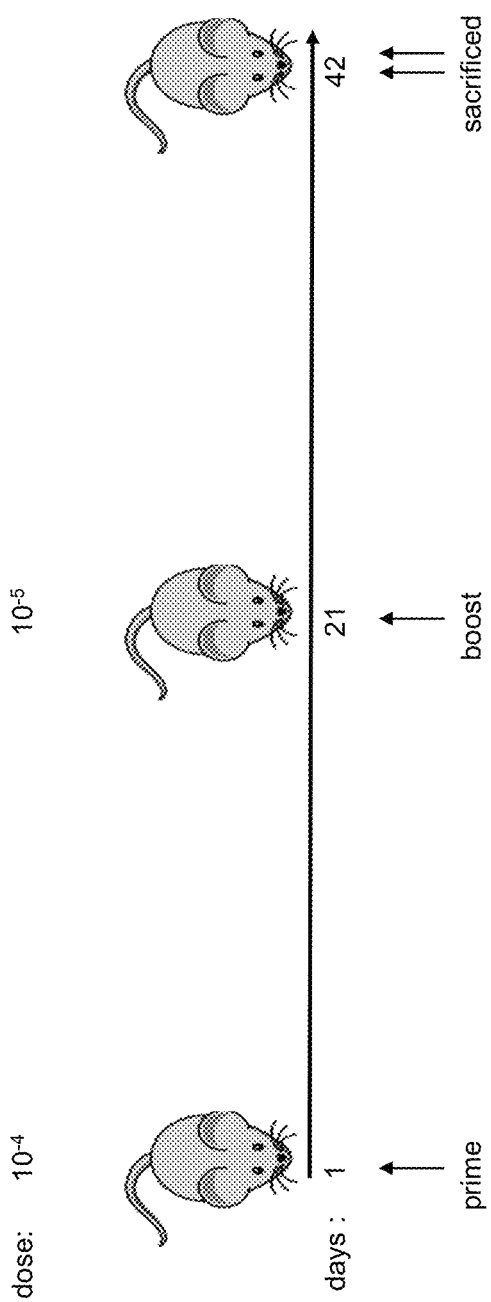
FIGS. 3A-3B demonstrate an experimental set-up for mice immunized with recombinant viruses.

The experimental set-up for mice immunized with recombinant viruses is described in FIG. 3A. Groups of 5 mice were infected with either rMV$^{EZ}$SARS-CoV-2-S3, rMV$^{EZ}$SARS-CoV-2-S6, rMV$^{EZ}$SARS-CoV-2-S-CO, rMV$^{EZ}$SARS-CoV-2-S-COAA, or rMV$^{EZ}$EGFP(3). Serum was collected on days 21 and 42, and splenocytes were collected on day 42. Neutralization of SARS-CoV-2 using the harvested mice serum indicates that SARS-CoV-2 neutralizing antibodies were produced in mice vaccinated with rMV$^{EZ}$SARS-CoV-2-S-CO and rMV$^{EZ}$SARS-CoV-2-S-COAA viruses (FIG. 3B).

Figure 12:
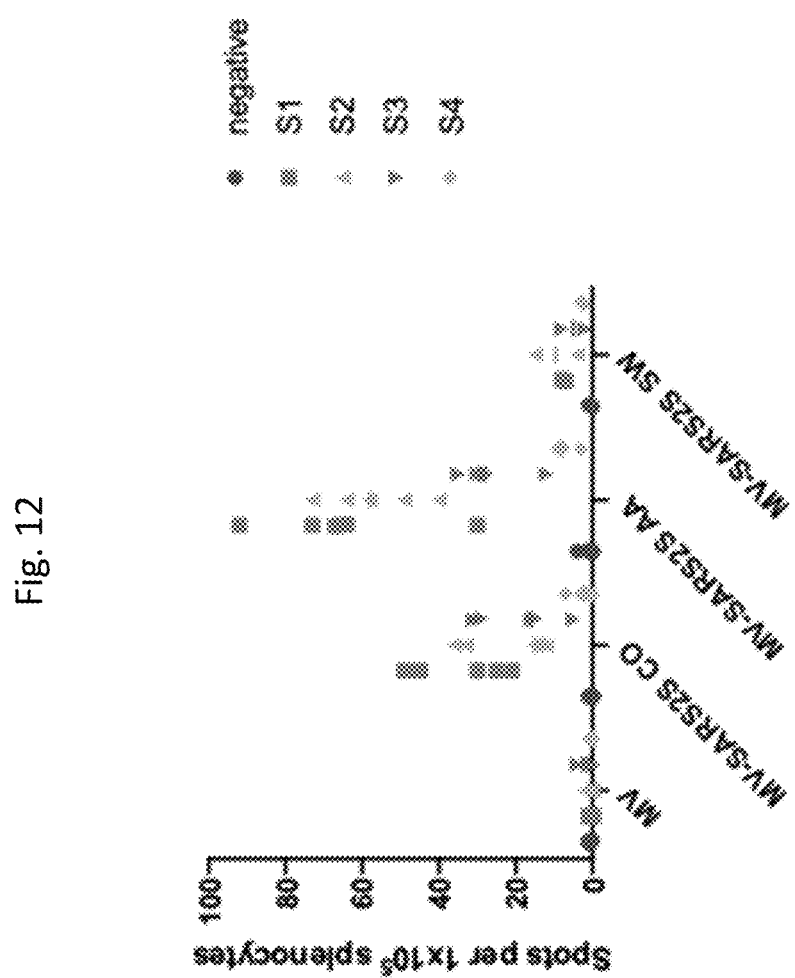
FIG. 12 is a graph demonstrating the secretion of IFN-γ in spleens from mice immunized with recombinant measles virus expressing SARS-CoV-2 codon-optimized spike protein. Splenocytes prepared from rMV$^{EZ}$, rMV$^{EZ}$SARS-CoV-2-CO, rMV$^{EZ}$SARS-CoV-2-S6, and rMV$^{EZ}$SARS-CoV-2-COAA immunized mice were used in an ELISPOT assay to detect the secretion of proinflammatory cytokine IFN-γ. Mice splenocytes were re-stimulated for 24 hours with four pools of synthetic peptides (S1, S2, S3 and S4) designed to span the entire SARS-CoV-2 spike protein. Unstimulated splenocytes (medium) served as negative controls and splenocytes treated with PMA/ionomycin confirmed splenocyte re-stimulation. Dots represent individual animals (n=5) for each vaccinated group. The number of cells expressing IFN-γ after re-stimulation are represented as $1 \times 10^5$ cells.

Splenocytes prepared from rMV$^{EZ}$, rMV$^{EZ}$SARS-CoV-2-CO, rMV$^{EZ}$SARS-CoV-2-S6, and rMV$^{EZ}$SARS-CoV-2-COAA immunized mice were used in an ELISPOT assay to detect the secretion of proinflammatory cytokine IFN-γ. Mice splenocytes were re-stimulated for 24 hours with four pools of synthetic peptides (S1, S2, S3 and S4) designed to span the entire SARS-CoV-2 spike protein. Unstimulated splenocytes (medium) served as negative controls and splenocytes treated with PMA/ionomycin confirmed splenocyte re-stimulation. The number of cells expressing IFN-γ after re-stimulation are represented as 1×10$^5$ cells in FIG. 12. The results demonstrate that IFN-γ is secreted in spleens from mice immunized with recombinant measles virus expressing SARS-CoV-2 codon-optimized spike protein.

Figure 13A:
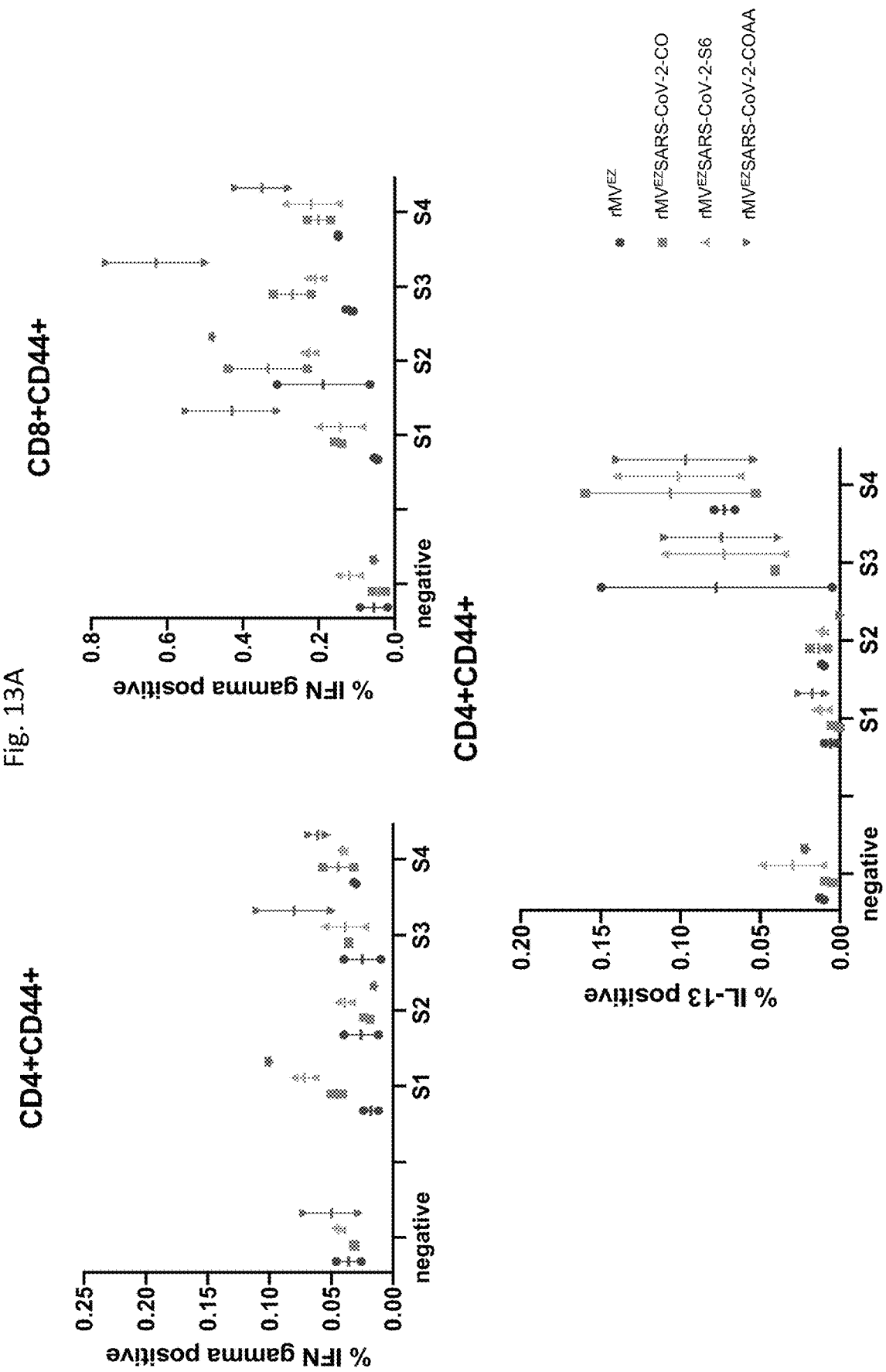
FIGS. 13A and 13B demonstrate the T cell responses in immunized mice. Flow cytometry was used to determine the proportion of $CD4^+/CD44^+$ and $CD8^+/CD44^+$ T cells in the spleens of mice immunized with $rMV^{EZ}$, $rMV^{EZ}$SARS-CoV-2-CO, $rMV^{EZ}$SARS-CoV-2-S6, and $rMV^{EZ}$SARS-CoV-2-COAA. To determine the optimal re-stimulation period splenocytes from two mice from each immunized group were first re-stimulated for 6 hours (FIG. 13A) while the remaining three mice spleens were re-stimulated for 12-hours (FIG. 13B). Cells were re-stimulated with spike specific peptide pools S1, S2, S3 and S4, or left unstimulated (negative control; medium). Re-stimulation was confirmed with a cell activation cocktail containing PMA/ionomycin and brefaldin-A. Intracellular cytokine staining for IFN-γ and IL-13 were then carried out to determine Th1 and Th2 responses, respectively. Dots represent individual animals.
Figure 13B:
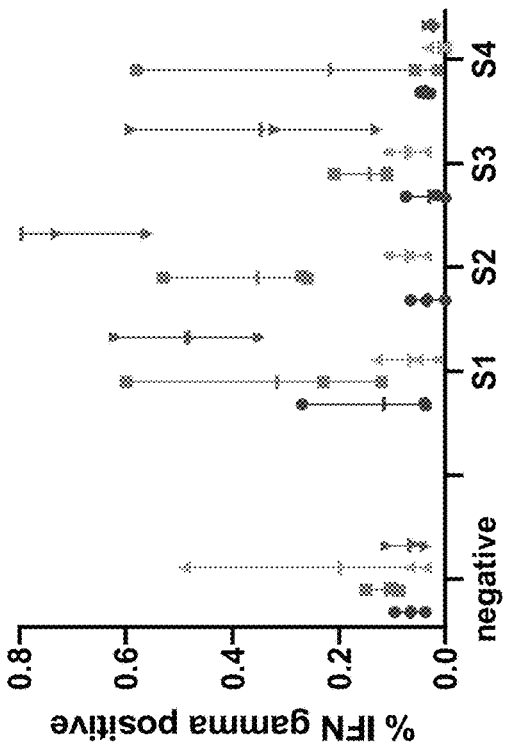
Figure 13B:
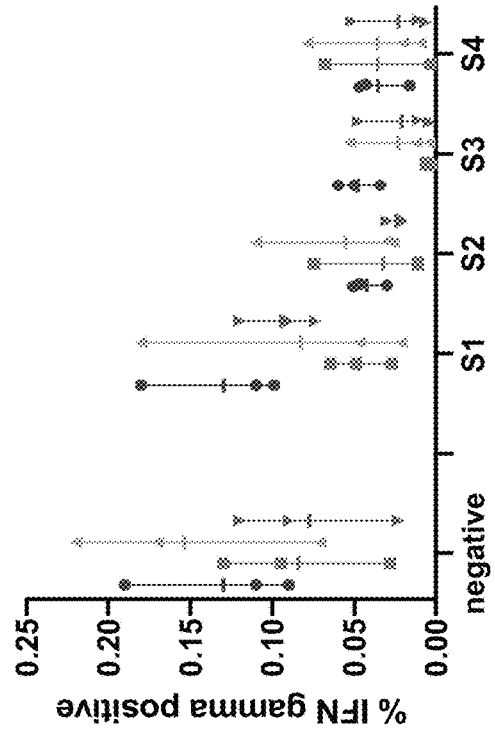
Figure 13B:
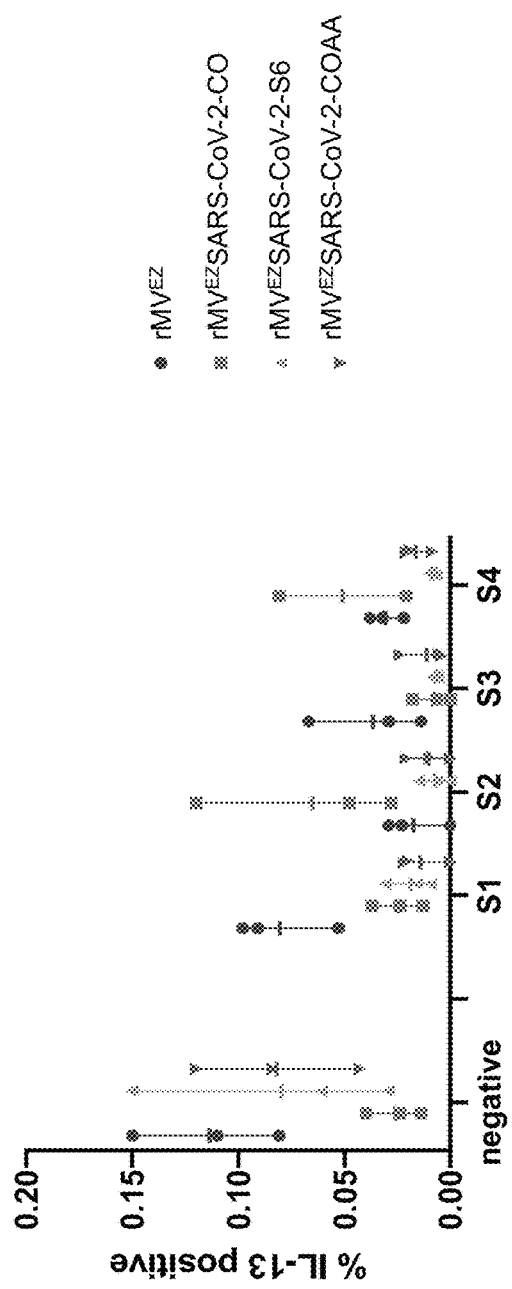
Figure 13B:
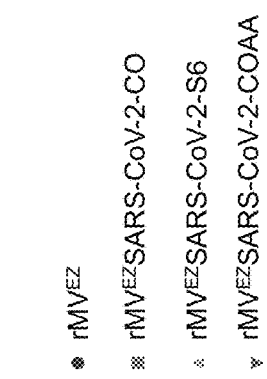

Flow cytometry was used to determine the proportion of CD4$^+$/CD44$^+$ and CD8$^+$/CD44$^+$ T cells in the spleens of mice immunized with rMV$^{EZ}$, rMV$^{EZ}$SARS-CoV-2-CO, rMV$^{EZ}$SARS-CoV-2-S6, and rMV$^{EZ}$SARS-CoV-2-COAA. To determine the optimal re-stimulation period splenocytes from two mice from each immunized group were first re-stimulated for 6 hours (FIG. 13A) while the remaining three mice spleens were re-stimulated for 12-hours (FIG. 13B). Cells were re-stimulated with spike specific peptide pools 51, S2, S3 and S4, or left unstimulated (negative control; medium). Re-stimulation was confirmed with a cell activation cocktail containing PMA/ionomycin and Brefaldin-A. Intracellular cytokine staining for IFN-γ and IL-13 were then carried out to determine Th1 and Th2 responses, respectively. The results in FIGS. 13A and 13B demonstrate the T cell responses in immunized mice.

Non-Human Primates

Multi-route delivery and challenge testing for natural measles is described in de Swart et al., *NPJ vaccines*, 2(1), pp. 1-11 (2017). Specifically, infection of rhesus macaques with rMV$^{EZ}$EGFP(3) vaccine via the intramuscular, intranasal, and aerosol routes, along with the intratracheal route as a control matching the usual experimental inoculation route, has been described. Serum antibody responses were detected by enzyme linked immunosorbent assay (ELISA), virus neutralization, or indirect immunofluorescence for MV fusion (MV-F) or hemagglutinin (MV-H) glycoprotein-specific antibodies. Animals vaccinated by the intramuscular (IM) route produced similar antibody responses to those inoculated via the aerosol route. In all assays, lowest serum antibody levels were consistently observed in animals immunized by intranasal instillation. All animals were protected from challenge after intratracheal instillation of a wild-type strain of MV.

For this study, African green monkeys (AGMs) were used since a SARS-CoV-2 challenge model has been established (Hartman et al., doi: https://doi.org/10.1101/2020.06.20.137687 (2020)—in press *PLoS Pathogens*). In this challenge model, AGMs were inoculated via a multi-route mucosal (oral, nasal, and ocular) exposure with a low passage, clinical isolate of SARS-CoV-2. The experimental design is detailed in FIGS. 11A and 11B.

All AGMs develop mild disease with pulmonary lesions detectable by PET/CT in the acute phase which subsequently resolve. All AGMs exhibit prolonged shedding of infectious virus from oral, nasal, conjunctival, and rectal mucosal surfaces with viral RNA (vRNA) detectable throughout the respiratory and gastrointestinal tissues at later timepoints in the absence of replication-competent virus.

Animals (maximum group size n=6) were vaccinated (IM) with the recombinant measles viral vector of the invention. Two animals were vaccinated with the standard measles virus Edmonston Zagreb vaccine strain. Some animals received a boost at 3 or 4 weeks post-vaccination. Animals were sampled before vaccination and then weekly over 6 or 8 weeks for the development of SARS-CoV-2 and MV serum antibody responses (IgG, IgM, IgA and neutralizing antibodies and T cell responses).

Development of MV-specific immune response will be compared to historical controls using banked samples from the studies analyzing intramuscular, aerosol, intranasal, and intratracheal administration of MV vaccine (de Swart et al., *NPJ vaccines*, 2(1), pp. 1-11 (2017)). EDTA blood samples will be collected in Vacuette tubes containing K$_3$EDTA as an anticoagulant. A sample of whole blood will be used directly for hematology analysis. Plasma will be separated from blood cells by low speed centrifugation and used in a commercial ELISA classic Measles Virus IgG assay (Serion) to assess anti-MV IgG alongside an in house MV-N-specific IgG ELISA.

Development of anti SARS-CoV-2 specific IgG and IgM will be determined using an in house ELISA that detects antibodies against the SARS-CoV-2 spike protein receptor binding domain (RBD). ELISA plates will be coated with 50 ng/well of SARS-CoV-2 RBD and subsequently blocked in 5% (V/V) FBS, 5% (W/V) skim milk in PBS with 0.1% (V/V) Tween-20 (PBS T) for 1 hour at 37° C. Serial dilutions of plasma will be made in block solution and incubated on the blocked plates for 2 h at 37° C. After washing with PBS T, bound antibodies will be detected by incubation with goat-anti-monkey IgM(p)-HRP (Seracare/KPL #5220-0334) or goat-anti-rhesus IgG (H+L)-HRP (Southern Biotech #6200-05), both used at a 1:5,000 dilution in blocking solution for 1 hour at 37° C. After washing with PBS T the assay will be developed by incubation with TMB (Seracare) for 7 min prior to the addition of TMB stop solution (Seracare). Absorbance values will be determined at 450 nm.

PBMC are isolated from the residual blood cell pellet by layering diluted whole blood onto Lymphoprep and subsequent density gradient centrifugation. A sample of PBMC will be used for MV virus isolation by plating dilutions of PBMC with Vero cells expressing human CD150 (Vero hCD150 cells). Assays are incubated at 37° C. for 3-5 days and then scored for cytopathic effect. A portion of PBMC will also be used for RNA extraction and subsequent RT/PCR analysis for detection of viral genome.

Blood samples for serum will be collected in Vacuette tubes (FIG. 11B). After coagulation, low speed centrifugation will be used to remove the clot from the serum supernatant. A sample will be used for serum biochemistry and the rest will be available for neutralizing antibody analysis. Virus neutralizing antibodies will be detected using a fluorescent focus reduction neutralization test (FRNT) for MV and a plaque reduction neutralization test (PRNT) for SARS-CoV-2. The FRNT uses a MV that expresses EGFP during replication; this facilitates rapid screening of assays. Detection of fluorescence indicates virus replication and seronegativity while lack of fluorescence indicates the presence of neutralizing antibodies which prevent virus infection. Serum dilutions will be mixed with 100 plaque forming units (p.f.u.) of MV and incubated at 37° C. for 1 hour. After addition of Vero cells expressing the MV receptor human CD150, assays will be incubated at 37° C. for 3-5 days before screening for fluorescence as a measure of virus replication. For the PRNT, serum dilutions will be mixed with 100 p.f.u. of SARS-CoV-2 and incubated at 37° C. for 1 hour after which they will be added to confluent Vero E6 cell monolayers. After incubation at 37° C. for 1 hour, medium will be replaced by immunodiffusion agarose. After incubation at 37° C. for 72 hours, the agarose overlay will be removed and the cell monolayer fixed and stained with crystal violet. Plaques will be enumerated and the $PRNT_{80}$ calculated. The SARS-CoV-2 molecular, virological and immunological assays are described in Klimstra et al., *J. Gen. Virol.*, doi: 10.1099/jgv.0.001481 (2020).

The vaccinated and sham vaccinated animals will be challenged via multi route mucosal exposure with $10^6$ p.f.u. of SARS-CoV-2. Protection will be assessed by sampling oral, ocular, rectal and nasal swabs for decreases in infectious virus and viral RNA copies following challenge, decreased PET/CT signals in lungs and lymph nodes and secondary immune responses. Brushes will be used to collect throat and rectal samples and swabs will be used to collect nasal and ocular samples into virus transport medium. After vortexing the brush/swab is removed and the remaining liquid is used directly for SARS-CoV-2 virus isolation by adding to VeroE6 cell monolayers, and for RNA isolation for RTqPCR analysis. For virus isolations, after incubation at 37° C. for 1 hour, medium will be replaced by immunodiffusion agarose. After incubation at 37° C. for 72 hours, the agarose overlay will be removed and the cell monolayer fixed and stained with crystal violet to allow visualization of plaques. After RNA isolation, one-step RT-qPCR will be performed using a One-Step Multiplex RT-qPCR Supermix (BioRad), and primers and probe targeting the SARS-CoV-2 N gene sequence. Quantitation of virus genome copies will be determined by comparing the cycle threshold values from the unknown samples to cycle threshold values from a positive-sense SARS-CoV-2 vRNA standard curve generated from 10-fold serial dilutions of in house synthesized template.

Serial PET/CT images will be acquired pre-infection and at 3 or 4 and 10 or 11 dpi. The scans will be performed on a MultiScan LFER 150 (Mediso Medical Imaging Systems). CT acquisition will be performed using the following parameters: Semi-circular single field-of-view, 360 projections, 80 kVp, 670 µA, exposure time 90 ms, binning 1:4, voxel size of final image: 500×500 µm. PET acquisition will be performed 55 min after intravenous injection of 18F-fluoro-2-deoxy-D-glucose (FDG) with the following parameters: 10 min acquisition, single field-of-view, 1-9 coincidence mode, 5 ns coincidence time window. PET images will be reconstructed with the following parameters: Tera-Tomo 3D reconstruction, 400-600 keV energy window, 1-9 coincidence mode, median filter on, spike filter on, voxel size 0.7 mm, 8 iterations, 9 subsets, scatter correction on, attenuation correction based on CT material map segmentation. Images will be analyzed using OsiriX MD or 64-bit (v.11, Pixmeo, Geneva, Switzerland). Before analysis, PET images will be Gaussian smoothed in OsiriX and smoothing will be applied to raw data with a 3×3 matrix size and a matrix normalization value of 24. Whole lung FDG uptake will be measured by first creating a whole lung region-of-interest (ROI) on the lung in the CT scan by creating a 3D growing region highlighting every voxel in the lungs between −1024 and −500 Hounsfield units. This whole lung ROI will be copied and pasted to the PET scan and gaps within the ROI will be filled in using a closing ROI brush tool with a structuring element radius of 3. All voxels within the lung ROI with a standard uptake value (SUV) below 1.5 will be set to zero and the SUVs of the remaining voxels will be summed for a total lung FDG uptake (total inflammation) value. Thoracic lymph nodes will be analyzed by measuring the maximum SUV within each lymph node using an oval drawing tool. Both total FDG uptake and lymph node uptake values will be normalized to back muscle FDG uptake measured by drawing cylinder ROIs on the back muscles adjacent to the spine at the same axial level as the carina (SUVCMR; cylinder-muscle-ratio). PET quantification values will be organized in Microsoft Excel and graphed using GraphPad Prism.

Blood samples will be collected and processed as for the vaccination phase of the study and the secondary immune response to SARS-CoV-2 will be measured as before using the SARS-CoV-2 spike protein receptor binding domain ELISA for detection of IgG and IgM, and the PRNT for detection of neutralizing antibodies and the T cells assays already established in the IFNAR mice (FIGS. 13A and 13B) to assess cellular immune responses.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for preventing, inhibiting, reducing, eliminating, protecting, or delaying the onset of an infection or an infectious clinical condition caused by coronavirus in a subject comprising administering a recombinant measles viral vector comprising a nucleic acid sequence encoding a Severe Acute Respiratory Syndrome Coronavirus 2 (SARS-CoV-2) spike glycoprotein to the subject, wherein the nucleic acid sequence contains at least one modification that disrupts the endoplasmic reticulum (ER) retention sequence of the SARS-CoV-2 spike glycoprotein.

2. The method of claim 1, wherein the recombinant measles viral vector is a recombinant Edmonston-Zagreb (EZ) measles viral vector.

3. The method of claim 1, wherein the nucleic acid sequence has been codon optimized.

4. The method of claim 1, wherein the ER retention sequence of the SARS-CoV-2 spike glycoprotein contains AxAxx rather than KxHxx in the cytoplasmic tail.

5. The method of claim 1, wherein the nucleic acid sequence encoding the SARS-CoV-2 spike glycoprotein is SEQ ID NO: 3 (S-CO-AA).

6. The method of claim 1, wherein the SARS-CoV-2 spike glycoprotein comprises the amino acid sequence of SEQ ID NO: 10 (S-CO-AA).

7. The method of claim 1, wherein the recombinant measles viral vector comprises the nucleic acid sequence of SEQ ID NO: 17 (SARS-CoV-2-S-CO-AA).

8. A method for inducing an immune response against a coronavirus in a subject comprising administering a recombinant measles viral vector comprising a nucleic acid sequence encoding a SARS-CoV-2 spike glycoprotein to the subject, wherein the nucleic acid sequence contains at least one modification that disrupts the endoplasmic reticulum (ER) retention sequence of the SARS-CoV-2 spike glycoprotein.

9. The method of claim 1, wherein the subject is a human subject.

10. The method of claim 1, wherein the recombinant measles viral vector is administered by oral, sublingual, buccal, intradermal, parenteral, subcutaneous, intravenous, intramuscular, intraarterial, intrathecal, or interperitoneal administration.

11. A polypeptide comprising an amino acid sequence selected from the group consisting of SEQ ID NO: 10 (S-CO-AA).

12. A pharmaceutical composition comprising (i) the polypeptide of claim 11, a nucleic acid encoding the polypeptide, or a recombinant vector comprising the nucleic acid and (ii) a pharmaceutically acceptable carrier.

13. A method for preventing, inhibiting, reducing, eliminating, protecting, or delaying the onset of an infection or an infectious clinical condition caused by coronavirus in a subject comprising administering the polypeptide of claim 11, a nucleic acid encoding the polypeptide, a recombinant vector comprising the nucleic acid, or a pharmaceutical composition thereof to the subject.

14. A method for inducing an immune response against a coronavirus in a subject comprising administering the polypeptide of claim 11, a nucleic acid encoding the polypeptide, a recombinant vector comprising the nucleic acid, or a pharmaceutical composition thereof to the subject.

15. The method of claim 8, wherein the recombinant measles viral vector is a recombinant Edmonston-Zagreb (EZ) measles viral vector.

16. The method of claim 8, wherein the nucleic acid sequence has been codon optimized.

17. The method of claim 8, wherein the ER retention sequence of the SARS-CoV-2 spike glycoprotein contains AxAxx rather than KxHxx in the cytoplasmic tail.

18. The method of claim 8, wherein the nucleic acid sequence encoding the SARS-CoV-2 spike glycoprotein is SEQ ID NO: 3 (S-CO-AA).

19. The method of claim 8, wherein the SARS-CoV-2 spike glycoprotein comprises the amino acid sequence of SEQ ID NO: 10 (S-CO-AA).

20. The method of claim 8, wherein the recombinant measles viral vector comprises the nucleic acid sequence of SEQ ID NO: 17 (SARS-CoV-2-S-CO-AA).

* * * * *

SEQUENCE LISTING

```
<160> NUMBER OF SEQ ID NOS: 26

<210> SEQ ID NO 1
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Non-codon optimized SARS-CoV-2 Spike from
      rMV-EZ-SARS-CoV-2-S clone 6
<220> FEATURE:
<221> NAME/KEY: misc_feature
<222> LOCATION: (118)..(118)
<223> OTHER INFORMATION: mutation that arose during cloning
<220> FEATURE:
<221> NAME/KEY: misc_feature
<222> LOCATION: (1088)..(1088)
<223> OTHER INFORMATION: mutation that arose during cloning
<220> FEATURE:
<221> NAME/KEY: misc_feature
<222> LOCATION: (1239)..(1239)
<223> OTHER INFORMATION: mutation that arose during cloning
<220> FEATURE:
<221> NAME/KEY: misc_feature
<222> LOCATION: (3805)..(3807)
<223> OTHER INFORMATION: mutation that disrupts ER retention signal
<220> FEATURE:
<221> NAME/KEY: misc_feature
<222> LOCATION: (3811)..(3813)
<223> OTHER INFORMATION: mutation that disrupts ER retention signal

<400> SEQUENCE: 1
atgtttgttt ttcttgtttt attgccacta gtctctagtc agtgtgttaa tcttacaacc      60
agaactcaat taccccctgc atacactaat tctttcacac gtggtgttta ttacccttac     120
aaagttttca gatcctcagt tttacattca actcaggact tgttcttacc tttctttcc     180 aatgttactt ggttccatgc tatacatgtc tctgggacca atggtactaa gaggtttgat     240
aaccctgtcc taccatttaa tgatggtgtt tattttgctt ccactgagaa gtctaacata     300
ataagaggct ggatttttgg tactacttta gattcgaaga cccagtccct acttattgtt     360
```

```
aataacgcta ctaatgttgt tattaaagtc tgtgaatttc aattttgtaa tgatccattt    420
ttgggtgttt attaccacaa aaacaacaaa agttggatgg aaagtgagtt cagagtttat    480
tctagtgcga ataattgcac ttttgaatat gtctctcagc cttttcttat ggaccttgaa    540
ggaaaacagg gtaatttcaa aaatcttagg gaatttgtgt ttaagaatat tgatggttat    600
tttaaaatat attctaagca cacgcctatt aatttagtgc gtgatctccc tcagggtttt    660
tcggctttag aaccattggt agatttgcca ataggtatta acatcactag gtttcaaact    720
ttacttgctt tacatagaag ttatttgact cctggtgatt cttcttcagg ttggacagct    780
ggtgctgcag cttattatgt gggttatctt caacctagga cttttctatt aaaatataat    840
gaaaatggaa ccattacaga tgctgtagac tgtgcacttg accctctctc agaaacaaag    900
tgtacgttga atccttcac tgtagaaaaa ggaatctatc aaacttctaa ctttagagtc    960
caaccaacag aatctattgt tagatttcct aatattacaa acttgtgccc ttttggtgaa   1020
gtttttaacg ccaccagatt tgcatctgtt tatgcttgga acaggaagag aatcagcaac   1080
tgtgttgttg attattctgt cctatataat tccgcatcat tttccacttt taagtgttat   1140
ggagtgtctc ctactaaatt aaatgatctc tgctttacta atgtctatgc agattcattt   1200
gtaattagag gtgatgaagt cagacaaatc gctccaggtc aaactggaaa gattgctgat   1260
tataattata aattaccaga tgattttaca ggctgcgtta tagcttggaa ttctaacaat   1320
cttgattcta aggttggtgg taattataat tacctgtata gattgtttag aagtctaat    1380 ctcaaaccttt tgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg atgttaactg cacagaagtc   1860
cctgttgcta ttcatgcaga tcaacttact cctacttggc gtgtttattc tacaggttct   1920 aatgttttc aaaacacgtgc aggctgttta ataggggctg aacatgtcaa caactcatat   1980
gagtgtgaca tacccattgg tgcaggtata tgcgctagtt atcagactca gactaattct   2040
cctcggcggg cacgtagtgt agctagtcaa tccatcattg cctacactat gtcacttggt   2100
gcagaaaatt cagttgctta ctctaataac tctattgcca tacccacaaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagttttgt   2280 acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcatt tattgaagat   2460
ctacttttca caaagtgac acttgcagat gctggcttca tcaaacaata tggtgattgc   2520
cttggtgata ttgctgctag agacctcatt tgtgcacaaa agtttaacgg ccttactgtt   2580
ttgccacctt tgctcacaga tgaaatgatt gctcaataca cttctgcact gttagcgggt   2640
acaatcactt ctggttggac ctttggtgca ggtgctgcat tacaaatacc atttgctatg   2700
```

-continued

```
caaatggctt ataggtttaa tggtattgga gttacacaga atgttctcta tgagaaccaa    2760
aaattgattg ccaaccaatt taatagtgct attggcaaaa ttcaagactc actttcttcc    2820
acagcaagtg cacttggaaa acttcaagat gtggtcaacc aaaatgcaca agctttaaac    2880
acgcttgtta aacaacttag ctccaatttt ggtgcaattt caagtgtttt aaatgatatc    2940
ctttcacgtc ttgacaaagt tgaggctgaa gtgcaaattg ataggttgat cacaggcaga    3000
cttcaaagtt tgcagacata tgtgactcaa caattaatta gagctgcaga aatcagagct    3060
tctgctaatc ttgctgctac taaaatgtca gagtgtgtac ttggacaatc aaaaagagtt    3120
gatttttgtg gaaagggcta tcatcttatg tccttccctc agtcagcacc tcatggtgta    3180
gtcttcttgc atgtgactta tgtccctgca caagaaaaga acttcacaac tgctcctgcc    3240
atttgtcatg atggaaaagc acactttcct cgtgaaggtg tctttgtttc aaatggcaca    3300
cactggtttg taacacaaag gaattttat gaaccacaaa tcattactac agacaacaca    3360
tttgtgtctg gtaactgtga tgttgtaata ggaattgtca acaacacagt ttatgatcct    3420
ttgcaacctg aattagactc attcaaggag gagttagata aatattttaa gaatcataca    3480
tcaccagatg ttgatttagg tgacatctct ggcattaatg cttcagttgt aaacattcaa    3540
aaagaaattg accgcctcaa tgaggttgcc aagaatttaa atgaatctct catcgatctc    3600
caagaacttg gaaagtatga gcagtatata aaatggccat ggtacatttg gctaggtttt    3660
atagctggct tgattgccat agtaatggtg acaattatgc tttgctgtat gaccagttgc    3720
tgtagttgtc tcaagggctg ttgttcttgt ggatcctgct gcaaatttga tgaagacgac    3780
tctgagccag tgctcaaagg agtcgcatta gcttacacat aa    3822
```

<210> SEQ ID NO 2
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3822)
<223> OTHER INFORMATION: Human codon optimized SARS-CoV-2 Spike from
      rMV-EZ-SARS-CoV-2-S-CO

<400> SEQUENCE: 2

```
atgttcgtct tcctggtcct gctgcctctg gtctcctcac agtgcgtcaa tctgacaact     60
cggactcagc tgccacctgc ttatactaat agcttcacca gaggcgtgta ctatcctgac    120
aaggtgttta aagctccgt gctgcactct acacaggatc tgtttctgcc attctttagc    180
aacgtgacct ggttccacgc catccacgtg agcggcacca atggcacaaa gcggttcgac    240
aatcccgtgc tgccttttaa cgatggcgtg tacttcgcct ctaccgagaa gagcaacatc    300
atcagaggct ggatctttgg caccacactg gactccaaga cacagtctct gctgatcgtg    360
aacaatgcca ccaacgtggt catcaaggtg tgcgagttcc agttttgtaa tgatcccttc    420
ctgggcgtgt actatcacaa gaacaataag agctggatgg agtccgagtt tagagtgtat    480
tctagcgcca caactgcac atttgagtac gtgagccagc ctttcctgat ggacctggag    540
ggcaagcagg gcaatttcaa gaacctgagg gagttcgtgt ttaagaatat cgacggctac    600
ttcaaaatct actctaagca cacccccatc aacctggtgc gcgacctgcc tcagggcttc    660
agcgccctgg agcccctggt ggatctgcct atcggcatca acatcacccg gtttcagaca    720
ctgctggccc tgcacagaag ctacctgaca cccggcgact cctctagcgg atggaccgcc    780
```

```
ggcgctgccg cctactatgt gggctacctc cagccccgga ccttcctgct gaagtacaac    840
gagaatggca ccatcacaga cgcagtggat tgcgccctgg accccctgag cgagacaaag    900
tgtacactga agtcctttac cgtggagaag ggcatctatc agacatccaa tttcagggtg    960
cagccaaccg agtctatcgt gcgctttcct aatatcacaa acctgtgccc atttggcgag   1020
gtgttcaacg caacccgctt cgccagcgtg tacgcctgga taggaagcg atcagcaac    1080 tgcgtggccg actatagcgt gctgtacaac tccgcctctt tcagcacctt taagtgctat   1140
ggcgtgtccc ccacaaagct gaatgacctg tgctttacca acgtctacgc cgattctttc   1200
gtgatcaggg cgacgaggt cgccagatc gccccggcc agacaggcaa gatcgcagac    1260
tacaattata agctgccaga cgatttcacc ggctgcgtga tcgcctggaa cagcaacaat   1320
ctggattcca agtgggcgg caactacaat tatctgtacc ggctgtttag aaagagcaat   1380
ctgaagccct tcgagaggga catctctaca gaaatctacc aggccggcag caccccttgc   1440
aatggcgtgg agggctttaa ctgttatttc ccactccagt cctacggctt ccagcccaca   1500
aacggcgtgg gctatcagcc ttaccgcgtg gtggtgctga gctttgagct gctgcacgcc   1560
ccagcaacag tgtgcggccc caagaagtcc accaatctgg tgaagaacaa gtgcgtgaac   1620
ttcaacttca acggcctgac cggcacaggc gtgctgaccg agtccaacaa gaagttcctg   1680 ccattcagc agttcggcag ggacatcgca gataccacag acgccgtgcg cgacccacag   1740
accctggaga tcctggacat cacaccctgc tcttcggcg gcgtgagcgt gatcacaccc    1800
ggcaccaata caagcaacca ggtggccgtg ctgtatcagg acgtgaattg taccgaggtg   1860
cccgtggcta tccacgccga tcagctgacc ccaacatggc gggtgtacag caccggctcc   1920
aacgtcttcc agacaagagc cggatgcctg atcggagcag agcacgtgaa caattcctat   1980
gagtgcgaca tcccaatcgg cgccggcatc tgtgcctctt accagaccca gacaaactct   2040
cccagaagag cccggagcgt ggcctcccag tctatcatcg cctataccat gtccctgggc   2100
gccgagaaca gcgtggccta ctctaacaat agcatcgcca tcccaaccaa cttcacaatc   2160
tctgtgacca cagagatcct gcccgtgtcc atgaccaaga catctgtgga ctgcacaatg   2220
tatatctgtg gcgattctac cgagtgcagc aacctgctgc tccagtacgg cagcttttgt   2280
acccagctga atagagccct gacaggcatc gccgtggagc aggataagaa cacacaggag   2340
gtgttcgccc aggtgaagca aatctacaag acccccccta tcaaggactt tggcggcttc   2400
aattttttcc agatcctgcc tgatccatcc aagccttcta gcggagctt tatcgaggac   2460 ctgctgttca acaaggtgac cctggccgat gccggcttca tcaagcagta tggcgattgc   2520
ctgggcgaca tcgcagccag ggacctgatc tgcgcccaga gtttaatgg cctgaccgtg   2580 ctgccacccc tgctgacaga tgagatgatc gcacagtaca aagcgccct gctgccggc    2640 accatcacat ccggatggac cttcggcgca ggagccgccc tccagatccc ctttgccatg   2700
cagatggcct ataggttcaa cggcatcggc gtgacccaga atgtgctgta cgagaaccag   2760
aagctgatcg ccaatcagtt taactccgcc atcggcaaga tccaggacag cctgtcctct   2820
acagccagcg ccctgggcaa gctccaggat gtggtgaatc agaacgccca ggccctgaat   2880
accctggtga gcagctgag cagcaacttc ggcgccatct ctagcgtgct gaatgacatc   2940
ctgagccggc tggacaaggt ggaggcagag gtgcagatcg accggctgat caccggccgg   3000
ctccagagcc tccagaccta tgtgacacag cagctgatca gggccgccga tcagggcc    3060 agcgccaatc tggcagcaac caagatgtcc gagtgcgtgc tgggccagtc taagagagtg   3120
gacttttgtg gcaagggcta tcacctgatg tccttcccctc agtctgcccc acacggcgtg   3180
```

```
gtgtttctgc acgtgaccta cgtgcccgcc caggagaaga acttcaccac agcccctgcc    3240
atctgccacg atggcaaggc ccactttcca agggagggcg tgttcgtgtc aacggcacc     3300 cactggtttg tgacacagcg caatttctac gagccccaga tcatcaccac agacaacacc    3360
ttcgtgagcg gcaactgtga cgtggtcatc ggcatcgtga acaataccgt gtatgatcca    3420
ctccagcccg agctggacag cttttaaggag gagctggata agtatttcaa gaatcacacc   3480
tcccctgacg tggatctggg cgacatcagc ggcatcaatg cctccgtggt gaacatccag    3540
aaggagatcg accgcctgaa cgaggtggct aagaatctga cgagagcct gatcgacctc     3600 caggagctgg gcaagtatga gcagtacatc aagtggccct ggtacatctg gctgggcttc    3660
atcgccggcc tgatcgccat cgtgatggtg accatcatgc tgtgctgtat gacatcctgc    3720
tgttcttgcc tgaagggctg ctgtagctgt ggctcctgct gtaagtttga cgaggatgac    3780
tctgaacctg tgctgaaggg cgtgaagctg cattacacct aa                       3822

<210> SEQ ID NO 3
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Human codon optimized SARS-CoV-2 Spike from
      rMV-EZ-SARS-CoV-2-S-CO-AA
<220> FEATURE:
<221> NAME/KEY: misc_feature
<222> LOCATION: (3805)..(3806)
<223> OTHER INFORMATION: mutation that disrupts ER retention signal
<220> FEATURE:
<221> NAME/KEY: misc_feature
<222> LOCATION: (3811)..(3812)
<223> OTHER INFORMATION: mutation that disrupts ER retention signal

<400> SEQUENCE: 3
atgttcgtct tcctggtcct gctgcctctg gtctcctcac agtgcgtcaa tctgacaact     60
cggactcagc tgccacctgc ttatactaat agcttcacca gaggcgtgta ctatcctgac    120
aaggtgttta aagctccgt gctgcactct acacaggatc tgtttctgcc attctttagc     180
aacgtgacct ggttccacgc catccacgtg agcggcacca atggcacaaa gcggttcgac    240
aatcccgtgc tgccttttaa cgatggcgtg tacttcgcct ctaccgagaa gagcaacatc    300
atcagaggct ggatctttgg caccacactg gactccaaga cacagtctct gctgatcgtg    360
aacaatgcca ccaacgtggt catcaaggtg tgcgagttcc agttttgtaa tgatcccttc    420
ctgggcgtgt actatcacaa gaacaataag agctggatgg agtccgagtt tagagtgtat    480
tctagcgcca caactgcac atttgagtac gtgagccagc cttcctgat ggacctggag     540 ggcaagcagg gcaatttcaa gaacctgagg gagttcgtgt ttaagaatat cgacggctac    600
ttcaaaatct actctaagca cacccccatc aacctggtgc gcgacctgcc tcagggcttc    660
agcgccctgg agcccctggt ggatctgcct atcggcatca acatcacccg gtttcagaca    720
ctgctggccc tgcacagaag ctacctgaca cccggcgact cctctagcgg atggaccgcc    780
ggcgctgccg cctactatgt gggctacctc cagcccggga ccttcctgct gaagtacaac    840
gagaatggca ccatcacaga cgcagtggat tgcgccctgg acccctgag cgagacaaag    900 tgtacactga agtcctttac cgtggagaag ggcatctatc agacatccaa tttcagggtg    960
cagccaaccg agtctatcgt gcgcttctcct aatatcacaa acctgtgccc atttggcgag   1020
```

-continued

```
gtgttcaacg caacccgctt cgccagcgtg tacgcctgga ataggaagcg gatcagcaac    1080
tgcgtggccg actatagcgt gctgtacaac tccgcctctt tcagcacctt taagtgctat    1140
ggcgtgtccc ccacaaagct gaatgacctg tgctttacca acgtctacgc cgattctttc    1200
gtgatcaggg gcgacgaggt gcgccagatc gcccccggcc agacaggcaa gatcgcagac    1260
tacaattata agctgccaga cgatttcacc ggctgcgtga tcgcctggaa cagcaacaat    1320
ctggattcca agtgggcgg caactacaat tatctgtacc ggctgtttag aaagagcaat    1380
ctgaagccct tcgagaggga catctctaca gaaatctacc aggccggcag cacccccttgc   1440
aatggcgtgg agggctttaa ctgttatttc ccactccagt cctacggctt ccagcccaca    1500
aacggcgtgg gctatcagcc ttaccgcgtg gtggtgctga gctttgagct gctgcacgcc    1560
ccagcaacag tgtgcggccc caagaagtcc accaatctgg tgaagaacaa gtgcgtgaac    1620
ttcaacttca acggcctgac cggcacaggc gtgctgaccg agtccaacaa gaagttcctg    1680
ccatttcagc agttcggcag ggacatcgca gataccacag acgccgtgcg cgacccacag    1740
accctggaga tcctggacat cacaccctgc tctttcggcg cgtgagcgt gatcacaccc     1800
ggcaccaata caagcaacca ggtggccgtg ctgtatcagg acgtgaattg taccgaggtg    1860
cccgtggcta tccacgccga tcagctgacc ccaacatggc gggtgtacag caccggctcc    1920
aacgtcttcc agacaagagc cggatgcctg atcggagcag agcacgtgaa caattcctat    1980
gagtgcgaca tcccaatcgg cgccggcatc tgtgcctctt accagaccca gacaaactct    2040
cccagaagag cccggagcgt ggcctcccag tctatcatcg cctataccat gtccctgggc    2100
gccgagaaca gcgtggccta ctctaacaat agcatcgcca tcccaaccaa cttcacaatc    2160
tctgtgacca cagagatcct gcccgtgtcc atgaccaaga catctgtgga ctgcacaatg    2220
tatatctgtg gcgattctac cgagtgcagc aacctgctgc tccagtacgg cagcttttgt    2280
acccagctga atagagccct gacaggcatc gccgtggagc aggataagaa cacacaggag    2340
gtgttcgccc aggtgaagca aatctacaag acccccccta tcaaggactt tggcggcttc    2400
aattttttccc agatcctgcc tgatccatcc aagccttcta agcggagctt tatcgaggac    2460
ctgctgttca acaaggtgac cctggccgat gccggcttca tcaagcagta tggcgattgc    2520
ctgggcgaca tcgcagccag ggacctgatc tgcgcccaga gtttaatgg cctgaccgtg    2580
ctgccacccc tgctgacaga tgagatgatc gcacagtaca aagcgccct gctgccggc    2640
accatcacat ccggatggac cttcggcgca ggagccgccc tccagatccc ctttgccatg    2700
cagatggcct ataggttcaa cggcatcggc gtgacccaga atgtgctgta cgagaaccag    2760
aagctgatcg ccaatcagtt taactccgcc atcggcaaga tccaggacag cctgtcctct    2820
acagccagcg ccctgggcaa gctccaggat gtggtgaatc agaacgccca ggcccctgaat    2880
accctggtga agcagctgag cagcaacttc ggcgccatct ctagcgtgct gaatgacatc    2940
ctgagccggc tggacaaggt ggaggcagag gtgcagatcg accggctgat caccggccgg    3000
ctccagagcc tccagaccta tgtgacacag cagctgatca gggccgccga gatcagggcc    3060
agcgccaatc tggcagcaac caagatgtcc gagtgcgtgc tgggccagtc taagagagtg    3120
gacttttgtg gcaagggcta tcacctgatg tccttccctc agtctgcccc acacggcgtg    3180
gtgtttctgc acgtgaccta cgtgcccgcc caggagaaga acttcaccac agcccctgcc    3240
atctgccacg atggcaaggc ccactttcca agggagggcg tgttcgtgtc caacggcacc    3300
cactggttg tgacacagcg caatttctac gagccccaga tcatcaccac agacaacacc    3360
ttcgtgagcg gcaactgtga cgtggtcatc ggcatcgtga acaataccgt gtatgatcca    3420
```

-continued

```
ctccagcccg agctggacag ctttaaggag gagctggata agtatttcaa gaatcacacc    3480
tcccctgacg tggatctggg cgacatcagc ggcatcaatg cctccgtggt gaacatccag    3540
aaggagatcg accgcctgaa cgaggtggct aagaatctga cgagagcct gatcgacctc     3600 caggagctgg gcaagtatga gcagtacatc aagtggccct ggtacatctg ctgggcttc     3660 atcgccggcc tgatcgccat cgtgatggtg accatcatgc tgtgctgtat gacatcctgc    3720
tgttcttgcc tgaagggctg ctgtagctgt ggctcctgct gtaagtttga cgaggatgac    3780
tctgaacctg tgctgaaggg cgtggcgctg gcttacacct aa                       3822
```

<210> SEQ ID NO 4
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Non-codon optimized SARS-CoV-2 Spike from
      rMV-EZ-SARS-CoV-2-S
<220> FEATURE:
<221> NAME/KEY: misc_feature
<222> LOCATION: (3805)..(3807)
<223> OTHER INFORMATION: mutation that disrupts ER retention signal
<220> FEATURE:
<221> NAME/KEY: misc_feature
<222> LOCATION: (3811)..(3813)
<223> OTHER INFORMATION: mutation that disrupts ER retention signal

<400> SEQUENCE: 4

```
atgtttgttt tcttgttttt attgccacta gtctctagtc agtgtgttaa tcttacaacc    60
agaactcaat accccctgc atacactaat tctttcacac gtggtgttta ttaccctgac     120
aaagttttca gatcctcagt tttacattca actcaggact tgttcttacc tttcttttcc    180
aatgttactt ggttccatgc tatacatgtc tctgggacca atggtactaa gaggtttgat    240
aaccctgtcc taccatttaa tgatggtgtt tatttttgctt ccactgagaa gtctaacata    300
ataagaggct ggatttttgg tactacttta gattcgaaga cccagtccct acttattgtt    360
aataacgcta ctaatgttgt tattaaagtc tgtgaatttc aattttgtaa tgatccattt    420
ttgggtgttt attaccacaa aaacaacaaa agttggatgg aaagtgagtt cagagtttat    480
tctagtgcga ataattgcac ttttgaatat gtctctcagc cttttcttat ggaccttgaa    540
ggaaaacagg gtaatttcaa aaatcttagg gaatttgtgt ttaagaatat tgatggttat    600
tttaaaatat attctaagca cacgcctatt aattagtgc gtgatctccc tcagggtttt    660
tcggctttag aaccattggt agatttgcca ataggtatta acatcactag gtttcaaact    720
ttacttgctt tacatagaag ttatttgact cctggtgatt cttcttcagg ttggacagct    780
ggtgctgcag cttattatgt gggttatctt caacctagga cttttctatt aaaatataat    840
gaaaatggaa ccattacaga tgctgtagac tgtgcacttg accctctctc agaaacaaag    900
tgtacgttga atccttcac tgtagaaaaa ggaatctatc aaacttctaa ctttagagtc    960
caaccaacag aatctattgt tagatttcct aatattacaa acttgtgccc ttttggtgaa    1020
gtttttaacg ccaccagatt tgcatctgtt tatgcttgga caggaagag atcagcaac     1080 tgtgttgctg attattctgt cctatataat tccgcatcat tttccacttt taagtgttat    1140
ggagtgtctc ctactaaatt aaatgatctc tgctttacta atgtctatgc agattcattt    1200
gtaattagag gtgatgaagt cagacaaatc gctccagggc aaactggaaa gattgctgat    1260
```

```
tataattata aattaccaga tgattttaca ggctgcgtta tagcttggaa ttctaacaat    1320
cttgattcta aggttggtgg taattataat tacctgtata gattgtttag gaagtctaat    1380
ctcaaacctt ttgagagaga tatttcaact gaaatctatc aggccggtag cacaccttgt    1440
aatggtgttg aaggttttaa ttgttacttt cctttacaat catatggttt ccaacccact    1500
aatggtgttg gttaccaacc atacagagta gtagtacttt cttttgaact tctacatgca    1560
ccagcaactg tttgtggacc taaaaagtct actaatttgg ttaaaaacaa atgtgtcaat    1620
ttcaacttca atggtttaac aggcacaggt gttcttactg agtctaacaa aaagtttctg    1680
cctttccaac aatttggcag agacattgct gacactactg atgctgtccg tgatccacag    1740
acacttgaga ttcttgacat taccatgt tcttttggtg gtgtcagtgt tataacacca    1800
ggaacaaata cttctaacca ggttgctgtt ctttatcagg atgttaactg cacagaagtc    1860
cctgttgcta ttcatgcaga tcaacttact cctacttggc gtgtttattc tacaggttct    1920 aatgttttc aaaacacgtgc aggctgttta taggggctg aacatgtcaa caactcatat    1980
gagtgtgaca tacccattgg tgcaggtata tgcgctagtt atcagactca gactaattct    2040
cctcggcggg cacgtagtgt agctagtcaa tccatcattg cctacactat gtcacttggt    2100
gcagaaaatt cagttgctta ctctaataac tctattgcca tacccacaaa ttttactatt    2160
agtgttacca cagaaattct accagtgtct atgaccaaga catcagtaga ttgtacaatg    2220
tacatttgtg gtgattcaac tgaatgcagc aatcttttgt tgcaatatgg cagttttgt    2280 acacaattaa accgtgcttt aactggaata gctgttgaac aagacaaaaa cacccaagaa    2340
gtttttgcac aagtcaaaca aatttacaaa acaccaccaa ttaaagattt tggtggtttt    2400 aattttttcac aaatattacc agatccatca aaaccaagca gaggtcatt tattgaagat    2460 ctactttca acaaagtgac acttgcagat gctggcttca tcaaacaata tggtgattgc    2520
cttggtgata ttgctgctag agacctcatt tgtgcacaaa agtttaacgg ccttactgtt    2580 ttgccaccttt tgctcacaga tgaaatgatt gctcaataca cttctgcact gttagcgggt    2640
acaatcactt ctggttggac ctttggtgca ggtgctgcat tacaaatacc atttgctatg    2700
caaatggctt ataggtttaa tggtattgga gttacacaga tgttctctaa tgagaaccaa    2760
aaattgattg ccaaccaatt taatagtgct attggcaaaa ttcaagactc actttcttcc    2820
acagcaagtg cacttggaaa acttcaagat gtggtcaacc aaaatgcaca agcttttaaac    2880 acgcttgtta acaacttag ctccaatttt ggtgcaattt caagtgtttt aaatgatatc    2940
ctttcacgtc ttgacaaagt tgaggctgaa gtgcaaattg ataggttgat cacaggcaga    3000
cttcaaagtt tgcagacata tgtgactcaa caattaatta gagctgcaga aatcagagct    3060
tctgctaatc ttgctgctac taaaatgtca gagtgtgtac ttggacaatc aaaaagagtt    3120 gattttgtg aaagggcta tcatcttatg tccttccctc agtcagcacc tcatggtgta    3180
gtcttcttgc atgtgactta tgtccctgca caagaaaaga cttcacaac tgctcctgcc    3240 atttgtcatg atggaaaagc acactttcct cgtgaaggtg tctttgtttc aaatggcaca    3300
cactggtttg taacacaaag gaattttat gaaccacaaa tcattactac agacaacaca    3360
tttgtgtctg gtaactgtga tgttgtaata ggaattgtca acaacacagt ttatgatcct    3420
ttgcaacctg aattagactc attcaaggag gagttagata aatatttaa gaatcataca    3480 tcaccagatg ttgatttagg tgacatctct ggcattaatg cttcagttgt aaacattcaa    3540
aaagaaattg accgcctcaa tgaggttgcc aagaattaa atgaatctct catcgatctc    3600
caagaacttg gaaagtatga gcagtatata aaatggccat ggtacatttg ctaggtttt    3660
```

```
atagctggct tgattgccat agtaatggtg acaattatgc tttgctgtat gaccagttgc    3720
tgtagttgtc tcaagggctg ttgttcttgt ggatcctgct gcaaatttga tgaagacgac    3780
tctgagccag tgctcaaagg agtcgcatta gcttacacat aa                      3822
```

<210> SEQ ID NO 5
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3822)
<223> OTHER INFORMATION: codon optimized SARS-CoV-2 S sequence from
      rMV-EZ-SARS-CoV-2-S-CO-AA-PPP
<220> FEATURE:
<221> NAME/KEY: misc_feature
<222> LOCATION: (2956)..(2961)
<223> OTHER INFORMATION: mutation to lock in the prefusion conformation
<220> FEATURE:
<221> NAME/KEY: misc_feature
<222> LOCATION: (3805)..(3806)
<223> OTHER INFORMATION: mutation that disrupts ER retention signal
<220> FEATURE:
<221> NAME/KEY: misc_feature
<222> LOCATION: (3811)..(3812)
<223> OTHER INFORMATION: mutation that disrupts ER retention signal

<400> SEQUENCE: 5

```
atgttcgtct tcctggtcct gctgcctctg gtctcctcac agtgcgtcaa tctgacaact      60
cggactcagc tgccacctgc ttatactaat agcttcacca gaggcgtgta ctatcctgac     120
aaggtgttta gaagctccgt gctgcactct acacaggatc tgtttctgcc attctttagc     180
aacgtgacct ggttccacgc catccacgtg agcggcacca tggcacaaa  gcggttcgac     240 aatcccgtgc tgccttttaa cgatggcgtg tacttcgcct ctaccgagaa gagcaacatc     300
atcagaggct ggatctttgg caccacactg gactccaaga cacagtctct gctgatcgtg     360
aacaatgcca ccaacgtggt catcaaggtg tgcgagttcc agttttgtaa tgatcccttc     420
ctgggcgtgt actatcacaa gaacaataag agctggatgg agtccgagtt tagagtgtat     480
tctagcgcca caactgcac  atttgagtac gtgagccagc ctttcctgat ggacctggag     540
ggcaagcagg gcaatttcaa gaacctgagg gagttcgtgt ttaagaatat cgacggctac     600
ttcaaaatct actctaagca caccccatc  aacctggtgc gcgacctgcc tcagggcttc     660
agcgccctgg agcccctggt ggatctgcct atcggcatca acatcacccg gtttcagaca     720
ctgctggccc tgcacagaag ctacctgaca cccggcgact cctctagcgg atggaccgcc     780
ggcgctgccg cctactatgt gggctacctc cagccccgga ccttcctgct gaagtacaac     840
gagaatggca ccatcacaga cgcagtggat tgcgccctgg acccctgag  cgagacaaag     900 tgtacactga gtcctttac  cgtggagaag gcatctatc  agacatccaa tttcagggtg     960
cagccaaccg agtctatcgt cgcctttcct aatatcacaa acctgtgccc atttggcgag    1020
gtgttcaacg caacccgctt cgccagcgtg tacgcctgga taggaagcg  atcagcaac    1080 tgcgtggccg actatagcgt gctgtacaac tccgcctctt tcagcacctt taagtgctat    1140
ggcgtgtccc ccacaaagct gaatgacctg tgctttacca acgtctacgc cgattctttc    1200
gtgatcaggg cgacgaggt gcgccagatc gcccccggcc agacaggcaa gatcgcagac    1260
tacaattata gctgccaga  cgatttcacc ggctgcgtga tcgcctggaa cagcaacaat    1320
ctggattcca agtgggcgg  caactacaat tatctgtacc ggctgtttag aaagagcaat    1380
```

```
ctgaagccct tcgagaggga catctctaca gaaatctacc aggccggcag cacccttgc    1440 aatggcgtgg agggctttaa ctgttatttc ccactccagt cctacggctt ccagcccaca   1500
aacggcgtgg gctatcagcc ttaccgcgtg gtggtgctga gctttgagct gctgcacgcc   1560
ccagcaacag tgtgcggccc caagaagtcc accaatctgg tgaagaacaa gtgcgtgaac   1620
ttcaacttca acggcctgac cggcacaggc gtgctgaccg agtccaacaa gaagttcctg   1680
ccatttcagc agttcggcag ggacatcgca gataccacag acgccgtgcg cgacccacag   1740
accctggaga tcctggacat cacaccctgc tctttcggcg gcgtgagcgt gatcacaccc   1800
ggcaccaata caagcaacca ggtggccgtg ctgtatcagg acgtgaattg taccgaggtg   1860
cccgtggcta tccacgccga tcagctgacc ccaacatggc gggtgtacag caccggctcc   1920
aacgtcttcc agacaagagc cggatgcctg atcggagcag agcacgtgaa caattcctat   1980
gagtgcgaca tcccaatcgg cgccggcatc tgtgcctctt accagaccca gacaaactct   2040
cccagaagag cccggagcgt ggcctcccag tctatcatcg cctataccat gtccctgggc   2100
gccgagaaca gcgtggccta ctctaacaat agcatcgcca tcccaaccaa cttcacaatc   2160
tctgtgacca cagagatcct gcccgtgtcc atgaccaaga catctgtgga ctgcacaatg   2220
tatatctgtg gcgattctac cgagtgcagc aacctgctgc tccagtacgg cagcttttgt   2280
acccagctga atagcccct gacaggcatc gccgtggagc aggataagaa cacacaggag   2340
gtgttcgccc aggtgaagca aatctacaag accccccta tcaaggactt tggcggcttc   2400
aatttttccc agatcctgcc tgatccatcc aagccttcta gcggagctt tatcgaggac   2460 ctgctgttca acaaggtgac cctggccgat gccggcttca tcaagcagta tggcgattgc   2520
ctgggcgaca tcgcagccag ggacctgatc tgcgcccaga gtttaatgg cctgaccgtg   2580 ctgccacccc tgctgacaga tgagatgatc gcacagtaca aagcgccct gctggccggc   2640 accatcacat ccggatggac cttcggcgca ggagccgccc tccagatccc ctttgccatg   2700
cagatggcct ataggttcaa cggcatcggc gtgacccaga atgtgctgta cgagaaccag   2760
aagctgatcg ccaatcagtt taactccgcc atcggcaaga tccaggacag cctgtcctct   2820
acagccagcg ccctgggcaa gctccaggat gtggtgaatc agaacgccca ggccctgaat   2880
accctggtga gcagctgag cagcaacttc ggcgccatct ctagcgtgct gaatgacatc   2940
ctgagccggc tggaccctcc tgaggcagag gtgcagatcg accggctgat caccggccgg   3000
ctccagagcc tccagaccta tgtgacacag cagctgatca gggccgccga tcagggcc   3060 agcgccaatc tggcagcaac caagatgtcc gagtgcgtgc tgggccagtc taagagagtg   3120
gacttttgtg caagggcta tcacctgatg tccttccctc agtctgcccc acacggcgtg   3180
gtgtttctgc acgtgaccta cgtgcccgcc aggagaagac ttcaccac agcccctgcc   3240 atctgccacg atggcaaggc ccactttcca agggagggcg tgttcgtgtc aacggcacc   3300 cactggtttg tgacacagcg caatttctac gagcccagat catcaccac agacaacacc   3360 ttcgtgagcg gcaactgtga cgtggtcatc ggcatcgtga caataccgt gtatgatcca   3420 ctccagcccg agctgacag ctttaaggag gagctggata gtatttcaa gaatcacacc   3480 tcccctgacg tggatctggg cgacatcagc ggcatcaatg cctccgtggt gaacatccag   3540
aaggagatcg accgcctgaa cgaggtggct aagaatctga acgagagcct gatcgacctc   3600
caggagctgg gcaagtatga gcagtacatc aagtggccct ggtacatctg gctgggcttc   3660
atcgccggcc tgatcgccat cgtgatggtg accatcatgc tgtgctgtat gacatcctgc   3720
```

```
tgttcttgcc tgaagggctg ctgtagctgt ggctcctgct gtaagtttga cgaggatgac    3780
tctgaacctg tgctgaaggg cgtggcgctg gcttacacct aa                        3822

<210> SEQ ID NO 6
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3822)
<223> OTHER INFORMATION: codon optimized SARS-CoV-2 S sequence from
      rMV-EZ-SARS-CoV-2-S-CO-AA-fneg-PP
<220> FEATURE:
<221> NAME/KEY: misc_feature
<222> LOCATION: (2044)..(2045)
<223> OTHER INFORMATION: mutation to ablate the furin cleavage signal
<220> FEATURE:
<221> NAME/KEY: misc_feature
<222> LOCATION: (2047)..(2049)
<223> OTHER INFORMATION: mutation to ablate the furin cleavage signal
<220> FEATURE:
<221> NAME/KEY: misc_feature
<222> LOCATION: (2051)..(2053)
<223> OTHER INFORMATION: mutation to ablate the furin cleavage signal
<220> FEATURE:
<221> NAME/KEY: misc_feature
<222> LOCATION: (2055)..(2055)
<223> OTHER INFORMATION: mutation to ablate the furin cleavage signal
<220> FEATURE:
<221> NAME/KEY: misc_feature
<222> LOCATION: (2956)..(2961)
<223> OTHER INFORMATION: mutation to lock in the prefusion conformation
<220> FEATURE:
<221> NAME/KEY: misc_feature
<222> LOCATION: (3805)..(3806)
<223> OTHER INFORMATION: mutation that disrupts ER retention signal
<220> FEATURE:
<221> NAME/KEY: misc_feature
<222> LOCATION: (3811)..(3812)
<223> OTHER INFORMATION: mutation that disrupts ER retention signal

<400> SEQUENCE: 6
atgttcgtct tcctggtcct gctgcctctg gtctcctcac agtgcgtcaa tctgacaact      60
cggactcagc tgccacctgc ttatactaat agcttcacca gaggcgtgta ctatcctgac     120
aaggtgttta aagctccgt gctgcactct acacaggatc tgtttctgcc attctttagc     180
aacgtgacct ggttccacgc catccacgtg agcggcacca tggcacaaa gcggttcgac     240 aatcccgtgc tgccttttaa cgatggcgtg tacttcgcct ctaccgagaa gagcaacatc     300
atcagaggct ggatctttgg caccacactg gactccaaga cacagtctct gctgatcgtg     360
aacaatgcca ccaacgtggt catcaaggtg tgcgagttcc agttttgtaa tgatcccttc     420
ctgggcgtgt actatcacaa gaacaataag agctggatgg agtccgagtt tagagtgtat     480
tctagcgcca caactgcac atttgagtac gtgagccagc ctttcctgat ggacctggag     540
ggcaagcagg gcaatttcaa gaacctgagg gagttcgtgt ttaagaatat cgacggctac     600
ttcaaaatct actctaagca cacccccatc aacctggtgc gcgacctgcc tcagggcttc     660 agcgcccctgg agcccctggt ggatctgcct atcggcatca acatcacccg gtttcagaca     720
ctgctggccc tgcacagaag ctacctgaca cccggcgact cctctagcgg atggaccgcc     780
ggcgctgccg cctactatgt gggctaccctc cagccccgga ccttcctgct gaagtacaac     840
gagaatggca ccatcacaga cgcagtggat tgcgccctgg accccctgag cgagacaaag     900
tgtacactga agtcctttac cgtggagaag ggcatctatc agacatccaa tttcagggtg     960
```

```
cagccaaccg agtctatcgt gcgctttcct aatatcacaa acctgtgccc atttggcgag    1020
gtgttcaacg caacccgctt cgccagcgtg tacgcctgga ataggaagcg gatcagcaac    1080
tgcgtggccg actatagcgt gctgtacaac tccgcctctt tcagcacctt taagtgctat    1140
ggcgtgtccc ccacaaagct gaatgacctg tgctttacca acgtctacgc cgattctttc    1200
gtgatcaggg gcgacgaggt gcgccagatc gcccccggcc agacaggcaa gatcgcagac    1260
tacaattata agctgccaga cgatttcacc ggctgcgtga tcgcctggaa cagcaacaat    1320
ctggattcca aagtgggcgg caactacaat tatctgtacc ggctgtttag aaagagcaat    1380
ctgaagccct tcgagaggga catctctaca gaaatctacc aggccggcag cacccccttgc   1440 aatggcgtgg agggctttaa ctgttatttc ccactccagt cctacggctt ccagcccaca    1500
aacggcgtgg gctatcagcc ttaccgcgtg gtggtgctga gctttgagct gctgcacgcc    1560
ccagcaacag tgtgcggccc caagaagtcc accaatctgg tgaagaacaa gtgcgtgaac    1620
ttcaacttca acggcctgac cggcacaggc gtgctgaccg agtccaacaa gaagttcctg    1680
ccatttcagc agttcggcag ggacatcgca gataccacac acgccgtgcg cgacccacag    1740
accctggaga tcctggacat cacaccctgc tctttcggcg gcgtgagcgt gatcacaccc    1800
ggcaccaata caagcaacca ggtggccgtg ctgtatcagg acgtgaattg taccgaggtg    1860
cccgtggcta tccacgccga tcagctgacc ccaacatggc gggtgtacag caccggctcc    1920
aacgtcttcc agacaagagc cggatgcctg atcggagcag agcacgtgaa caattcctat    1980
gagtgcgaca tcccaatcgg cgccggcatc tgtgcctctt accagcccca gacaaactct    2040
cccgcatctg tgggcagcgt ggcctcccag tctatcatcg cctataccat gtccctgggc    2100
gccgagaaca gcgtggccta ctctaacaat agcatcgcca tcccaaccaa cttcacaatc    2160
tctgtgacca cagagatcct gcccgtgtcc atgaccaaga catctgtgga ctgcacaatg    2220
tatatctgtg gcgattctac cgagtgcagc aacctgctgc tccagtacgg cagcttttgt    2280
acccagctga atagagccct gacaggcatc gccgtggagc aggataagaa cacacaggag    2340
gtgttcgccc aggtgaagca aatctacaag acccccccta tcaaggactt tggcggcttc    2400
aatttttccc agatcctgcc tgatccatcc aagccttcta gcggagctt tatcgaggac    2460 ctgctgttca acaaggtgac cctggccgat gccggcttca tcaagcagta tggcgattgc    2520
ctgggcgaca tcgcagccag ggacctgatc tgcgcccaga gtttaatgg cctgaccgtg    2580 ctgccacccc tgctgacaga tgagatgatc gcacagtaca agcgccct gctggccggc    2640 accatcacat ccggatggac cttcggcgca ggagccgccc tccagatccc ctttgccatg    2700
cagatggcct ataggttcaa cggcatcggc gtgacccaga atgtgctgta cgagaaccag    2760
aagctgatcg ccaatcagtt taactccgcc atcggcaaga tccaggacag cctgtcctct    2820
acagccagcg ccctgggcaa gctccaggat gtggtgaatc agaacgccca ggccctgaat    2880
accctggtga gcagctgag cagcaacttc ggcgccatct ctagcgtgct gaatgacatc    2940
ctgagccggc tggaccctcc tgaggcagag gtgcagatcg accggctgat caccggccgg    3000
ctccagagcc tccagaccta tgtgacacag cagctgatca gggccgccga tcagggcc    3060 agcgccaatc tggcagcaac caagatgtcc gagtgcgtgc tgggccagtc taagagagtg    3120
gacttttgtg gcaagggcta tcacctgatg tccttccctc agtctgcccc acacggcgtg    3180
gtgtttctgc acgtgaccta cgtgcccgcc caggagaaga acttcaccac agcccctgcc    3240
atctgccacg atggcaaggc ccactttcca agggagggcg tgttcgtgtc caacggcacc    3300
cactggtttg tgacacagcg caatttctac gagccccaga tcatcaccac agacaacacc    3360
```

```
ttcgtgagcg gcaactgtga cgtggtcatc ggcatcgtga acaataccgt gtatgatcca      3420
ctccagcccg agctggacag ctttaaggag gagctggata agtatttcaa gaatcacacc      3480
tcccctgacg tggatctggg cgacatcagc ggcatcaatg cctccgtggt gaacatccag      3540
aaggagatcg accgcctgaa cgaggtggct aagaatctga cgagagcct gatcgacctc       3600 caggagctgg gcaagtatga gcagtacatc aagtggccct ggtacatctg gctgggcttc      3660
atcgccggcc tgatcgccat cgtgatggtg accatcatgc tgtgctgtat gacatcctgc      3720
tgttcttgcc tgaagggctg ctgtagctgt ggctcctgct gtaagtttga cgaggatgac      3780
tctgaacctg tgctgaaggg cgtggcgctg gcttacacct aa                         3822
```

```
<210> SEQ ID NO 7
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3822)
<223> OTHER INFORMATION: codon optimized SARS-CoV-2 S from
      rMV-EZ-SARS-CoV-2-S-CO-AA-fneg
<220> FEATURE:
<221> NAME/KEY: misc_feature
<222> LOCATION: (2044)..(2045)
<223> OTHER INFORMATION: mutation to ablate the furin cleavage signal
<220> FEATURE:
<221> NAME/KEY: misc_feature
<222> LOCATION: (2047)..(2049)
<223> OTHER INFORMATION: mutation to ablate the furin cleavage signal
<220> FEATURE:
<221> NAME/KEY: misc_feature
<222> LOCATION: (2051)..(2053)
<223> OTHER INFORMATION: mutation to ablate the furin cleavage signal
<220> FEATURE:
<221> NAME/KEY: misc_feature
<222> LOCATION: (2055)..(2055)
<223> OTHER INFORMATION: mutation to ablate the furin cleavage signal
<220> FEATURE:
<221> NAME/KEY: misc_feature
<222> LOCATION: (3805)..(3806)
<223> OTHER INFORMATION: mutation that disrupts ER retention signal
<220> FEATURE:
<221> NAME/KEY: misc_feature
<222> LOCATION: (3811)..(3812)
<223> OTHER INFORMATION: mutation that disrupts ER retention signal

<400> SEQUENCE: 7
```

```
atgttcgtct tcctggtcct gctgcctctg gtctcctcac agtgcgtcaa tctgacaact       60
cggactcagc tgccacctgc ttatactaat agcttcacca gaggcgtgta ctatcctgac      120
aaggtgttta aagctccgt gctgcactct acacaggatc tgtttctgcc attctttagc       180
aacgtgacct ggttccacgc catccacgtg agcggcacca atggcacaaa gcggttcgac      240
aatcccgtgc tgccttttaa cgatggcgtg tacttcgcct ctaccgagaa gagcaacatc      300
atcagaggct ggatctttgg caccacactg gactccaaga cagtctctct gctgatcgtg      360
aacaatgcca ccaacgtggt catcaaggtg tgcgagttcc agttttgtaa tgatcccttc      420
ctgggcgtgt actatcacaa gaacaataag agctggatgg agtccgagtt tagagtgtat      480
tctagcgcca acaactgcac atttgagtac gtgagccagc ctttcctgat ggacctggag      540
ggcaagcagg gcaatttcaa gaacctgagg gagttcgtgt taagaatat cgacggctac       600 ttcaaaatct actctaagca cacccccatc aacctggtgc gcgacctgcc tcagggcttc      660
agcgccctgg agcccctggt ggatctgcct atcggcatca acatcacccg gtttcagaca      720
```

```
ctgctggccc tgcacagaag ctacctgaca cccggcgact cctctagcgg atggaccgcc    780
ggcgctgccg cctactatgt gggctacctc cagccccgga ccttcctgct gaagtacaac    840
gagaatggca ccatcacaga cgcagtggat tgcgccctgg accccctgag cgagacaaag    900
tgtacactga agtcctttac cgtggagaag ggcatctatc agacatccaa tttcagggtg    960
cagccaaccg agtctatcgt gcgctttcct aatatcacaa acctgtgccc atttggcgag   1020
gtgttcaacg caacccgctt cgccagcgtg tacgcctgga ataggaagcg gatcagcaac   1080
tgcgtggccg actatagcgt gctgtacaac tccgcctctt tcagcacctt taagtgctat   1140
ggcgtgtccc ccacaaagct gaatgacctg tgctttacca acgtctacgc cgattctttc   1200
gtgatcaggg gcgacgaggt gcgccagatc gcccccggcc agacaggcaa gatcgcagac   1260
tacaattata gctgccaga cgatttcacc ggctgcgtga tcgcctggaa cagcaacaat   1320
ctggattcca agtgggcgg caactacaat tatctgtacc ggctgtttag aaagagcaat   1380
ctgaagccct tcgagaggga catctctaca gaaatctacc aggccggcag cacccccttgc   1440
aatggcgtgg agggctttaa ctgttatttc ccactccagt cctacggctt ccagcccaca   1500
aacggcgtgg gctatcagcc ttaccgcgtg gtggtgctga gctttgagct gctgcacgcc   1560
ccagcaacag tgtgcggccc caagaagtcc accaatctgg tgaagaacaa gtgcgtgaac   1620
ttcaacttca acggcctgac cggcacaggc gtgctgaccg agtccaacaa gaagttcctg   1680
ccatttcagc agttcggcag ggacatcgca gataccacag acgccgtgcg cgacccacag   1740
accctggaga tcctggacat cacaccctgc tctttcggcg gcgtgagcgt gatcacaccc   1800
ggcaccaata caagcaacca ggtggccgtg ctgtatcagg acgtgaattg taccgaggtg   1860
cccgtggcta tccacgccga tcagctgacc ccaacatggc gggtgtacag caccggctcc   1920
aacgtcttcc agacaagagc cggatgcctg atcggagcag agcacgtgaa caattcctat   1980
gagtgcgaca tcccaatcgg cgccggcatc tgtgcctctt accagaccca gacaaactct   2040
cccgcatctg tgggcagcgt ggcctcccag tctatcatcg cctataccat gtccctgggc   2100
gccgagaaca gcgtggccta ctctaacaat agcatcgcca tcccaaccaa cttcacaatc   2160
tctgtgacca cagagatcct gcccgtgtcc atgaccaaga catctgtgga ctgcacaatg   2220
tatatctgtg gcgattctac cgagtgcagc aacctgctgc tccagtacgg cagcttttgt   2280
acccagctga atagagccct gacaggcatc gccgtggagc aggataagaa cacacaggag   2340
gtgttcgccc aggtgaagca aatctacaag accccccta tcaaggactt tggcggcttc   2400
aattttttccc agatcctgcc tgatccatcc aagccttcta gcggagctt tatcgaggac   2460
ctgctgttca caaggtgac cctggccgat gccggcttca tcaagcagta tggcgattgc   2520
ctgggcgaca tcgcagccag ggacctgatc tgcgcccaga gtttaatgg cctgaccgtg   2580
ctgccacccc tgctgacaga tgagatgatc gcacagtaca agcgccct gctggccggc   2640
accatcacat ccggatggac cttcggcgca ggagccgccc tccagatccc ctttgccatg   2700
cagatggcct ataggttcaa cggcatcggc gtgacccaga atgtgctgta cgagaaccag   2760
aagctgatcg ccaatcagtt taactccgcc atcggcaaga tccaggacag cctgtcctct   2820
acagccagcg ccctgggcaa gctccaggat gtggtgaatc agaacgccca ggccctgaat   2880
accctggtga agcagctgag cagcaacttc ggcgccatct ctagcgtgct gaatgacatc   2940
ctgagccggc tggacaaggt ggaggcagag gtgcagatcg accggctgat caccggccgg   3000
ctccagagcc tccagaccta tgtgacacag cagctgatca gggccgccga gatcagggcc   3060
```

```
agcgccaatc tggcagcaac caagatgtcc gagtgcgtgc tgggccagtc taagagagtg   3120
gactttgtgt gcaagggcta tcacctgatg tccttccctc agtctgcccc acacggcgtg   3180
gtgtttctgc acgtgaccta cgtgcccgcc caggagaaga acttcaccac agcccctgcc   3240
atctgccacg atggcaaggc ccactttcca agggagggcg tgttcgtgtc caacggcacc   3300
cactggtttg tgacacagcg caatttctac gagccccaga tcatcaccac agacaacacc   3360
ttcgtgagcg gcaactgtga cgtggtcatc ggcatcgtga acaataccgt gtatgatcca   3420
ctccagcccg agctggacag ctttaaggag gagctggata agtatttcaa gaatcacacc   3480
tcccctgacg tggatctggg cgacatcagc ggcatcaatg cctccgtggt gaacatccag   3540
aaggagatcg accgcctgaa cgaggtggct aagaatctga cgagagcct gatcgacctc    3600 caggagctgg gcaagtatga gcagtacatc aagtggccct ggtacatctg gctgggcttc   3660
atcgccggcc tgatcgccat cgtgatggtg accatcatgc tgtgctgtat gacatcctgc   3720
tgttcttgcc tgaagggctg ctgtagctgt ggctcctgct gtaagtttga cgaggatgac   3780
tctgaacctg tgctgaaggg cgtggcgctg gcttacacct aa                      3822
```

<210> SEQ ID NO 8
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3822)
<223> OTHER INFORMATION: Non-codon optimized SARS-CoV-2 Spike from
      rMV-EZ-SARS-CoV-2-S clone 6
<220> FEATURE:
<221> NAME/KEY: MISC_FEATURE
<222> LOCATION: (40)..(40)
<223> OTHER INFORMATION: residue differs from designed sequence
<220> FEATURE:
<221> NAME/KEY: MISC_FEATURE
<222> LOCATION: (363)..(363)
<223> OTHER INFORMATION: residue differs from designed sequence
<220> FEATURE:
<221> NAME/KEY: MISC_FEATURE
<222> LOCATION: (1269)..(1269)
<223> OTHER INFORMATION: mutation that disrupts ER retention signal
<220> FEATURE:
<221> NAME/KEY: MISC_FEATURE
<222> LOCATION: (1271)..(1271)
<223> OTHER INFORMATION: mutation that disrupts ER retention signal

<400> SEQUENCE: 8

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Tyr Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile

```
            115                 120                 125
Lys Val Cys Glu Phe Gln Phe Cys Asn Asp Pro Phe Leu Gly Val Tyr
130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Val Asp Tyr Ser Val Leu
        355                 360                 365

Tyr Asn Ser Ala Ser Phe Ser Thr Phe Lys Cys Tyr Gly Val Ser Pro
370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
530                 535                 540
```

```
Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
930                 935                 940

Leu Gly Lys Leu Gln Asp Val Val Asn Gln Asn Ala Gln Ala Leu Asn
945                 950                 955                 960
```

Thr Leu Val Lys Gln Leu Ser Ser Asn Phe Gly Ala Ile Ser Ser Val
            965                 970                 975

Leu Asn Asp Ile Leu Ser Arg Leu Asp Lys Val Glu Ala Glu Val Gln
        980                 985                 990

Ile Asp Arg Leu Ile Thr Gly Arg Leu Gln Ser Leu Gln Thr Tyr Val
        995                1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Ser Glu Pro
    1250                1255                1260

Val Leu Lys Gly Val Ala Leu Ala Tyr Thr
    1265                1270

<210> SEQ ID NO 9
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1273)
<223> OTHER INFORMATION: Human codon optimized SARS-CoV-2 Spike from
    rMV-EZ-SARS-CoV-2-S-CO

<400> SEQUENCE: 9

Met Phe Val Phe Leu Val Leu Leu Pro Leu Val Ser Ser Gln Cys Val

```
1               5                   10                  15
Asn Leu Thr Thr Arg Thr Gln Leu Pro Pro Ala Tyr Thr Asn Ser Phe
            20                  25                  30
Thr Arg Gly Val Tyr Tyr Pro Asp Lys Val Phe Arg Ser Ser Val Leu
            35                  40                  45
His Ser Thr Gln Asp Leu Phe Leu Pro Phe Phe Ser Asn Val Thr Trp
        50                  55                  60
Phe His Ala Ile His Val Ser Gly Thr Asn Gly Thr Lys Arg Phe Asp
65                  70                  75                  80
Asn Pro Val Leu Pro Phe Asn Asp Gly Val Tyr Phe Ala Ser Thr Glu
                85                  90                  95
Lys Ser Asn Ile Ile Arg Gly Trp Ile Phe Gly Thr Thr Leu Asp Ser
                100                 105                 110
Lys Thr Gln Ser Leu Leu Ile Val Asn Asn Ala Thr Asn Val Val Ile
            115                 120                 125
Lys Val Cys Glu Phe Gln Phe Cys Asn Asp Pro Phe Leu Gly Val Tyr
        130                 135                 140
Tyr His Lys Asn Asn Lys Ser Trp Met Glu Ser Glu Phe Arg Val Tyr
145                 150                 155                 160
Ser Ser Ala Asn Asn Cys Thr Phe Glu Tyr Val Ser Gln Pro Phe Leu
                165                 170                 175
Met Asp Leu Glu Gly Lys Gln Gly Asn Phe Lys Asn Leu Arg Glu Phe
                180                 185                 190
Val Phe Lys Asn Ile Asp Gly Tyr Phe Lys Ile Tyr Ser Lys His Thr
            195                 200                 205
Pro Ile Asn Leu Val Arg Asp Leu Pro Gln Gly Phe Ser Ala Leu Glu
210                 215                 220
Pro Leu Val Asp Leu Pro Ile Gly Ile Asn Ile Thr Arg Phe Gln Thr
225                 230                 235                 240
Leu Leu Ala Leu His Arg Ser Tyr Leu Thr Pro Gly Asp Ser Ser Ser
                245                 250                 255
Gly Trp Thr Ala Gly Ala Ala Ala Tyr Tyr Val Gly Tyr Leu Gln Pro
            260                 265                 270
Arg Thr Phe Leu Leu Lys Tyr Asn Glu Asn Gly Thr Ile Thr Asp Ala
            275                 280                 285
Val Asp Cys Ala Leu Asp Pro Leu Ser Glu Thr Lys Cys Thr Leu Lys
            290                 295                 300
Ser Phe Thr Val Glu Lys Gly Ile Tyr Gln Thr Ser Asn Phe Arg Val
305                 310                 315                 320
Gln Pro Thr Glu Ser Ile Val Arg Phe Pro Asn Ile Thr Asn Leu Cys
                325                 330                 335
Pro Phe Gly Glu Val Phe Asn Ala Thr Arg Phe Ala Ser Val Tyr Ala
            340                 345                 350
Trp Asn Arg Lys Arg Ile Ser Asn Cys Val Ala Asp Tyr Ser Val Leu
            355                 360                 365
Tyr Asn Ser Ala Ser Phe Ser Thr Phe Lys Cys Tyr Gly Val Ser Pro
        370                 375                 380
Thr Lys Leu Asn Asp Leu Cys Phe Thr Asn Val Tyr Ala Asp Ser Phe
385                 390                 395                 400
Val Ile Arg Gly Asp Glu Val Arg Gln Ile Ala Pro Gly Gln Thr Gly
                405                 410                 415
Lys Ile Ala Asp Tyr Asn Tyr Lys Leu Pro Asp Asp Phe Thr Gly Cys
            420                 425                 430
```

Val Ile Ala Trp Asn Ser Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

-continued

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
                915                 920                 925

Ser Ala Ile Gly Lys Ile Gln Asp Ser Leu Ser Ser Thr Ala Ser Ala
930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
            995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro

-continued

```
              1250                1255                1260

Val Leu Lys Gly Val Lys Leu His Tyr Thr
        1265                1270

<210> SEQ ID NO 10
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1273)
<223> OTHER INFORMATION: Human codon optimized SARS-CoV-2 Spike from
      rMV-EZ-SARS-CoV-2-S-CO-AA
<220> FEATURE:
<221> NAME/KEY: MISC_FEATURE
<222> LOCATION: (1269)..(1269)
<223> OTHER INFORMATION: mutation that disrupts ER retention signal
<220> FEATURE:
<221> NAME/KEY: MISC_FEATURE
<222> LOCATION: (1271)..(1271)
<223> OTHER INFORMATION: mutation that disrupts ER retention signal

<400> SEQUENCE: 10

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Tyr Tyr Val Gly Tyr Leu Gln Pro
            260                 265                 270
```

```
Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
```

-continued

```
            690             695             700
Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
                725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
                755             760             765

Gly Ile Ala Val Glu Gln Asp Lys Asn Thr Gln Glu Val Phe Ala Gln
            770             775             780

Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
                805             810             815

Phe Ile Glu Asp Leu Leu Phe Asn Lys Val Thr Leu Ala Asp Ala Gly
            820             825             830

Phe Ile Lys Gln Tyr Gly Asp Cys Leu Gly Asp Ile Ala Ala Arg Asp
                835             840             845

Leu Ile Cys Ala Gln Lys Phe Asn Gly Leu Thr Val Leu Pro Pro Leu
850             855             860

Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Ala Ala Leu Gln Ile
                885             890             895

Pro Phe Ala Met Gln Met Ala Tyr Arg Phe Asn Gly Ile Gly Val Thr
            900             905             910

Gln Asn Val Leu Tyr Glu Asn Gln Lys Leu Ile Ala Asn Gln Phe Asn
                915             920             925

Ser Ala Ile Gly Lys Ile Gln Asp Ser Leu Ser Ser Thr Ala Ser Ala
            930             935             940

Leu Gly Lys Leu Gln Asp Val Val Asn Gln Asn Ala Gln Ala Leu Asn
945             950             955             960

Thr Leu Val Lys Gln Leu Ser Ser Asn Phe Gly Ala Ile Ser Ser Val
                965             970             975

Leu Asn Asp Ile Leu Ser Arg Leu Asp Lys Val Glu Ala Glu Val Gln
            980             985             990

Ile Asp Arg Leu Ile Thr Gly Arg Leu Gln Ser Leu Gln Thr Tyr Val
            995            1000            1005

Thr Gln Gln Leu Ile Arg Ala Ala Glu Ile Arg Ala Ser Ala Asn
       1010            1015            1020

Leu Ala Ala Thr Lys Met Ser Glu Cys Val Leu Gly Gln Ser Lys
       1025            1030            1035

Arg Val Asp Phe Cys Gly Lys Gly Tyr His Leu Met Ser Phe Pro
       1040            1045            1050

Gln Ser Ala Pro His Gly Val Val Phe Leu His Val Thr Tyr Val
       1055            1060            1065

Pro Ala Gln Glu Lys Asn Phe Thr Thr Ala Pro Ala Ile Cys His
       1070            1075            1080

Asp Gly Lys Ala His Phe Pro Arg Glu Gly Val Phe Val Ser Asn
       1085            1090            1095

Gly Thr His Trp Phe Val Thr Gln Arg Asn Phe Tyr Glu Pro Gln
       1100            1105            1110
```

```
Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Ala Leu Ala Tyr Thr
    1265                1270

<210> SEQ ID NO 11
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1273)
<223> OTHER INFORMATION: SARS-CoV-2 Spike from rMV-EZ-SARS-CoV-2-S-CO-S
<220> FEATURE:
<221> NAME/KEY: MISC_FEATURE
<222> LOCATION: (1269)..(1269)
<223> OTHER INFORMATION: mutation that disrupts ER retention signal
<220> FEATURE:
<221> NAME/KEY: MISC_FEATURE
<222> LOCATION: (1271)..(1271)
<223> OTHER INFORMATION: mutation that disrupts ER retention signal

<400> SEQUENCE: 11

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Ser Asn Val Thr Trp
    50                  55                  60

Phe His Ala Ile His Val Ser Gly Thr Asn Gly Thr Lys Arg Phe Asp
65              70                  75                  80

Asn Pro Val Leu Pro Phe Asn Asp Gly Val Tyr Phe Ala Ser Thr Glu
            85                  90                  95

Lys Ser Asn Ile Ile Arg Gly Trp Ile Phe Gly Thr Thr Leu Asp Ser
        100                 105                 110

Lys Thr Gln Ser Leu Leu Ile Val Asn Asn Ala Thr Asn Val Val Ile
    115                 120                 125
```

```
Lys Val Cys Glu Phe Gln Phe Cys Asn Asp Pro Phe Leu Gly Val Tyr
130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
            165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
            245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
            405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
            485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
530                 535                 540
```

-continued

```
Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
```

```
                     965                 970                 975
Leu Asn Asp Ile Leu Ser Arg Leu Asp Lys Val Glu Ala Glu Val Gln
                980                 985                 990

Ile Asp Arg Leu Ile Thr Gly Arg Leu Gln Ser Leu Gln Thr Tyr Val
                995                 1000                1005

Thr Gln Gln Leu Ile Arg Ala Ala Glu Ile Arg Ala Ser Ala Asn
        1010                1015                1020

Leu Ala Ala Thr Lys Met Ser Glu Cys Val Leu Gly Gln Ser Lys
        1025                1030                1035

Arg Val Asp Phe Cys Gly Lys Gly Tyr His Leu Met Ser Phe Pro
        1040                1045                1050

Gln Ser Ala Pro His Gly Val Val Phe Leu His Val Thr Tyr Val
        1055                1060                1065

Pro Ala Gln Glu Lys Asn Phe Thr Thr Ala Pro Ala Ile Cys His
        1070                1075                1080

Asp Gly Lys Ala His Phe Pro Arg Glu Gly Val Phe Val Ser Asn
        1085                1090                1095

Gly Thr His Trp Phe Val Thr Gln Arg Asn Phe Tyr Glu Pro Gln
        1100                1105                1110

Ile Ile Thr Thr Asp Asn Thr Phe Val Ser Gly Asn Cys Asp Val
        1115                1120                1125

Val Ile Gly Ile Val Asn Asn Thr Val Tyr Asp Pro Leu Gln Pro
        1130                1135                1140

Glu Leu Asp Ser Phe Lys Glu Glu Leu Asp Lys Tyr Phe Lys Asn
        1145                1150                1155

His Thr Ser Pro Asp Val Asp Leu Gly Asp Ile Ser Gly Ile Asn
        1160                1165                1170

Ala Ser Val Val Asn Ile Gln Lys Glu Ile Asp Arg Leu Asn Glu
        1175                1180                1185

Val Ala Lys Asn Leu Asn Glu Ser Leu Ile Asp Leu Gln Glu Leu
        1190                1195                1200

Gly Lys Tyr Glu Gln Tyr Ile Lys Trp Pro Trp Tyr Ile Trp Leu
        1205                1210                1215

Gly Phe Ile Ala Gly Leu Ile Ala Ile Val Met Val Thr Ile Met
        1220                1225                1230

Leu Cys Cys Met Thr Ser Cys Cys Ser Cys Leu Lys Gly Cys Cys
        1235                1240                1245

Ser Cys Gly Ser Cys Cys Lys Phe Asp Glu Asp Asp Ser Glu Pro
        1250                1255                1260

Val Leu Lys Gly Val Ala Leu Ala Tyr Thr
        1265                1270

<210> SEQ ID NO 12
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1273)
<223> OTHER INFORMATION: codon optimized SARS-CoV-2 S sequence from
      rMV-EZ-SARS-CoV-2-S-CO-AA-PP
<220> FEATURE:
<221> NAME/KEY: MISC_FEATURE
<222> LOCATION: (986)..(987)
<223> OTHER INFORMATION: mutation to lock in the prefusion conformation
<220> FEATURE:
```

-continued

```
<221> NAME/KEY: MISC_FEATURE
<222> LOCATION: (1269)..(1269)
<223> OTHER INFORMATION: mutation that disrupts ER retention signal
<220> FEATURE:
<221> NAME/KEY: MISC_FEATURE
<222> LOCATION: (1271)..(1271)
<223> OTHER INFORMATION: mutation that disrupts ER retention signal

<400> SEQUENCE: 12
```

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

-continued

```
Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
```

```
                785                 790                 795                 800
Asn Phe Ser Gln Ile Leu Pro Asp Pro Ser Lys Pro Ser Lys Arg Ser
                805                 810                 815
Phe Ile Glu Asp Leu Leu Phe Asn Lys Val Thr Leu Ala Asp Ala Gly
                820                 825                 830
Phe Ile Lys Gln Tyr Gly Asp Cys Leu Gly Asp Ile Ala Ala Arg Asp
                835                 840                 845
Leu Ile Cys Ala Gln Lys Phe Asn Gly Leu Thr Val Leu Pro Pro Leu
                850                 855                 860
Leu Thr Asp Glu Met Ile Ala Gln Tyr Thr Ser Ala Leu Leu Ala Gly
            865                 870                 875                 880
Thr Ile Thr Ser Gly Trp Thr Phe Gly Ala Gly Ala Ala Leu Gln Ile
                885                 890                 895
Pro Phe Ala Met Gln Met Ala Tyr Arg Phe Asn Gly Ile Gly Val Thr
                900                 905                 910
Gln Asn Val Leu Tyr Glu Asn Gln Lys Leu Ile Ala Asn Gln Phe Asn
                915                 920                 925
Ser Ala Ile Gly Lys Ile Gln Asp Ser Leu Ser Ser Thr Ala Ser Ala
            930                 935                 940
Leu Gly Lys Leu Gln Asp Val Val Asn Gln Asn Ala Gln Ala Leu Asn
945                 950                 955                 960
Thr Leu Val Lys Gln Leu Ser Ser Asn Phe Gly Ala Ile Ser Ser Val
                965                 970                 975
Leu Asn Asp Ile Leu Ser Arg Leu Asp Pro Pro Glu Ala Glu Val Gln
                980                 985                 990
Ile Asp Arg Leu Ile Thr Gly Arg Leu Gln Ser Leu Gln Thr Tyr Val
                995                 1000                1005
Thr Gln Gln Leu Ile Arg Ala Ala Glu Ile Arg Ala Ser Ala Asn
                1010                1015                1020
Leu Ala Ala Thr Lys Met Ser Glu Cys Val Leu Gly Gln Ser Lys
                1025                1030                1035
Arg Val Asp Phe Cys Gly Lys Gly Tyr His Leu Met Ser Phe Pro
                1040                1045                1050
Gln Ser Ala Pro His Gly Val Val Phe Leu His Val Thr Tyr Val
                1055                1060                1065
Pro Ala Gln Glu Lys Asn Phe Thr Thr Ala Pro Ala Ile Cys His
                1070                1075                1080
Asp Gly Lys Ala His Phe Pro Arg Glu Gly Val Phe Val Ser Asn
                1085                1090                1095
Gly Thr His Trp Phe Val Thr Gln Arg Asn Phe Tyr Glu Pro Gln
                1100                1105                1110
Ile Ile Thr Thr Asp Asn Thr Phe Val Ser Gly Asn Cys Asp Val
                1115                1120                1125
Val Ile Gly Ile Val Asn Asn Thr Val Tyr Asp Pro Leu Gln Pro
                1130                1135                1140
Glu Leu Asp Ser Phe Lys Glu Glu Leu Asp Lys Tyr Phe Lys Asn
                1145                1150                1155
His Thr Ser Pro Asp Val Asp Leu Gly Asp Ile Ser Gly Ile Asn
                1160                1165                1170
Ala Ser Val Val Asn Ile Gln Lys Glu Ile Asp Arg Leu Asn Glu
                1175                1180                1185
Val Ala Lys Asn Leu Asn Glu Ser Leu Ile Asp Leu Gln Glu Leu
                1190                1195                1200
```

```
Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Ala Leu Ala Tyr Thr
    1265                1270

<210> SEQ ID NO 13
<211> LENGTH: 1281
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1273)
<223> OTHER INFORMATION: codon optimized SARS-CoV-2 S sequence from
      rMV-EZ-SARS-CoV-2-S-CO-AA-fneg-PP
<220> FEATURE:
<221> NAME/KEY: MISC_FEATURE
<222> LOCATION: (682)..(685)
<223> OTHER INFORMATION: mutation to ablate the furin cleavage signal
<220> FEATURE:
<221> NAME/KEY: MISC_FEATURE
<222> LOCATION: (986)..(987)
<223> OTHER INFORMATION: mutation to lock in the prefusion conformation
<220> FEATURE:
<221> NAME/KEY: MISC_FEATURE
<222> LOCATION: (1269)..(1269)
<223> OTHER INFORMATION: mutation that disrupts ER retention signal
<220> FEATURE:
<221> NAME/KEY: MISC_FEATURE
<222> LOCATION: (1271)..(1271)
<223> OTHER INFORMATION: mutation that disrupts ER retention signal

<400> SEQUENCE: 13

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175
```

```
Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590
```

-continued

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Ala Ser Val Gly Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn

|      |      |      |      |      | 1010 |      |      |      |      | 1015 |      |      |      |      | 1020 |      |      |      |      |

Leu Ala Ala Thr Lys Met Ser Glu Cys Val Leu Gly Gln Ser Lys
         1025              1030              1035

Arg Val Asp Phe Cys Gly Lys Gly Tyr His Leu Met Ser Phe Pro
         1040              1045              1050

Gln Ser Ala Pro His Gly Val Val Phe Leu His Val Thr Tyr Val
         1055              1060              1065

Pro Ala Gln Glu Lys Asn Phe Thr Thr Ala Pro Ala Ile Cys His
         1070              1075              1080

Asp Gly Lys Ala His Phe Pro Arg Glu Gly Val Phe Val Ser Asn
         1085              1090              1095

Gly Thr His Trp Phe Val Thr Gln Arg Asn Phe Tyr Glu Pro Gln
         1100              1105              1110

Ile Ile Thr Thr Asp Asn Thr Phe Val Ser Gly Asn Cys Asp Val
         1115              1120              1125

Val Ile Gly Ile Val Asn Asn Thr Val Tyr Asp Pro Leu Gln Pro
         1130              1135              1140

Glu Leu Asp Ser Phe Lys Glu Glu Leu Asp Lys Tyr Phe Lys Asn
         1145              1150              1155

His Thr Ser Pro Asp Val Asp Leu Gly Asp Ile Ser Gly Ile Asn
         1160              1165              1170

Ala Ser Val Val Asn Ile Gln Lys Glu Ile Asp Arg Leu Asn Glu
         1175              1180              1185

Val Ala Lys Asn Leu Asn Glu Ser Leu Ile Asp Leu Gln Glu Leu
         1190              1195              1200

Gly Lys Tyr Glu Gln Tyr Ile Lys Trp Pro Trp Tyr Ile Trp Leu
         1205              1210              1215

Gly Phe Ile Ala Gly Leu Ile Ala Ile Val Met Val Thr Ile Met
         1220              1225              1230

Leu Cys Cys Met Thr Ser Cys Cys Ser Cys Leu Lys Gly Cys Cys
         1235              1240              1245

Ser Cys Gly Ser Cys Cys Lys Phe Asp Glu Asp Asp Ser Glu Pro
         1250              1255              1260

Val Leu Lys Gly Val Ala Leu Ala Tyr Thr Arg Arg Ala Arg Ser
         1265              1270              1275

Val Ala Ser
         1280

```
<210> SEQ ID NO 14
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1273)
<223> OTHER INFORMATION: codon optimized SARS-CoV-2 S from
      rMV-EZ-SARS-CoV-2-S-CO-AA-fneg
<220> FEATURE:
<221> NAME/KEY: MISC_FEATURE
<222> LOCATION: (682)..(685)
<223> OTHER INFORMATION: mutation to ablate the furin cleavage signal
<220> FEATURE:
<221> NAME/KEY: MISC_FEATURE
<222> LOCATION: (1269)..(1269)
<223> OTHER INFORMATION: mutation that disrupts ER retention signal
<220> FEATURE:
<221> NAME/KEY: MISC_FEATURE
<222> LOCATION: (1271)..(1271)
```

<223> OTHER INFORMATION: mutation that disrupts ER retention signal

<400> SEQUENCE: 14

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400
```

-continued

```
Val Ile Arg Gly Asp Glu Val Arg Gln Ile Ala Pro Gly Gln Thr Gly
                405                 410                 415
Lys Ile Ala Asp Tyr Asn Tyr Lys Leu Pro Asp Asp Phe Thr Gly Cys
            420                 425                 430
Val Ile Ala Trp Asn Ser Asn Asn Leu Asp Ser Lys Val Gly Gly Asn
            435                 440                 445
Tyr Asn Tyr Leu Tyr Arg Leu Phe Arg Lys Ser Asn Leu Lys Pro Phe
450                 455                 460
Glu Arg Asp Ile Ser Thr Glu Ile Tyr Gln Ala Gly Ser Thr Pro Cys
465                 470                 475                 480
Asn Gly Val Glu Gly Phe Asn Cys Tyr Phe Pro Leu Gln Ser Tyr Gly
            485                 490                 495
Phe Gln Pro Thr Asn Gly Val Gly Tyr Gln Pro Tyr Arg Val Val Val
            500                 505                 510
Leu Ser Phe Glu Leu Leu His Ala Pro Ala Thr Val Cys Gly Pro Lys
            515                 520                 525
Lys Ser Thr Asn Leu Val Lys Asn Lys Cys Val Asn Phe Asn Phe Asn
            530                 535                 540
Gly Leu Thr Gly Thr Gly Val Leu Thr Glu Ser Asn Lys Lys Phe Leu
545                 550                 555                 560
Pro Phe Gln Gln Phe Gly Arg Asp Ile Ala Asp Thr Thr Asp Ala Val
            565                 570                 575
Arg Asp Pro Gln Thr Leu Glu Ile Leu Asp Ile Thr Pro Cys Ser Phe
            580                 585                 590
Gly Gly Val Ser Val Ile Thr Pro Gly Thr Asn Thr Ser Asn Gln Val
            595                 600                 605
Ala Val Leu Tyr Gln Asp Val Asn Cys Thr Glu Val Pro Val Ala Ile
            610                 615                 620
His Ala Asp Gln Leu Thr Pro Thr Trp Arg Val Tyr Ser Thr Gly Ser
625                 630                 635                 640
Asn Val Phe Gln Thr Arg Ala Gly Cys Leu Ile Gly Ala Glu His Val
            645                 650                 655
Asn Asn Ser Tyr Glu Cys Asp Ile Pro Ile Gly Ala Gly Ile Cys Ala
            660                 665                 670
Ser Tyr Gln Thr Gln Thr Asn Ser Pro Ala Ser Val Gly Ser Val Ala
            675                 680                 685
Ser Gln Ser Ile Ile Ala Tyr Thr Met Ser Leu Gly Ala Glu Asn Ser
            690                 695                 700
Val Ala Tyr Ser Asn Asn Ser Ile Ala Ile Pro Thr Asn Phe Thr Ile
705                 710                 715                 720
Ser Val Thr Thr Glu Ile Leu Pro Val Ser Met Thr Lys Thr Ser Val
            725                 730                 735
Asp Cys Thr Met Tyr Ile Cys Gly Asp Ser Thr Glu Cys Ser Asn Leu
            740                 745                 750
Leu Leu Gln Tyr Gly Ser Phe Cys Thr Gln Leu Asn Arg Ala Leu Thr
            755                 760                 765
Gly Ile Ala Val Glu Gln Asp Lys Asn Thr Gln Glu Val Phe Ala Gln
            770                 775                 780
Val Lys Gln Ile Tyr Lys Thr Pro Pro Ile Lys Asp Phe Gly Gly Phe
785                 790                 795                 800
Asn Phe Ser Gln Ile Leu Pro Asp Pro Ser Lys Pro Ser Lys Arg Ser
            805                 810                 815
Phe Ile Glu Asp Leu Leu Phe Asn Lys Val Thr Leu Ala Asp Ala Gly
```

```
                820                 825                 830
Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
            930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
            995                1000                1005

Thr Gln Gln Leu Ile Arg Ala  Ala Glu Ile Arg Ala  Ser Ala Asn
    1010                1015                1020

Leu Ala Ala Thr Lys Met Ser  Glu Cys Val Leu Gly  Gln Ser Lys
    1025                1030                1035

Arg Val Asp Phe Cys Gly Lys  Gly Tyr His Leu Met  Ser Phe Pro
    1040                1045                1050

Gln Ser Ala Pro His Gly Val  Val Phe Leu His Val  Thr Tyr Val
    1055                1060                1065

Pro Ala Gln Glu Lys Asn Phe  Thr Thr Ala Pro Ala  Ile Cys His
    1070                1075                1080

Asp Gly Lys Ala His Phe Pro  Arg Glu Gly Val Phe  Val Ser Asn
    1085                1090                1095

Gly Thr His Trp Phe Val Thr  Gln Arg Asn Phe Tyr  Glu Pro Gln
    1100                1105                1110

Ile Ile Thr Thr Asp Asn Thr  Phe Val Ser Gly Asn  Cys Asp Val
    1115                1120                1125

Val Ile Gly Ile Val Asn Asn  Thr Val Tyr Asp Pro  Leu Gln Pro
    1130                1135                1140

Glu Leu Asp Ser Phe Lys Glu  Glu Leu Asp Lys Tyr  Phe Lys Asn
    1145                1150                1155

His Thr Ser Pro Asp Val Asp  Leu Gly Asp Ile Ser  Gly Ile Asn
    1160                1165                1170

Ala Ser Val Val Asn Ile Gln  Lys Glu Ile Asp Arg  Leu Asn Glu
    1175                1180                1185

Val Ala Lys Asn Leu Asn Glu  Ser Leu Ile Asp Leu  Gln Glu Leu
    1190                1195                1200

Gly Lys Tyr Glu Gln Tyr Ile  Lys Trp Pro Trp Tyr  Ile Trp Leu
    1205                1210                1215

Gly Phe Ile Ala Gly Leu Ile  Ala Ile Val Met Val  Thr Ile Met
    1220                1225                1230
```

Leu Cys Cys Met Thr Ser Cys Cys Ser Cys Leu Lys Gly Cys Cys
    1235            1240            1245

Ser Cys Gly Ser Cys Cys Lys Phe Asp Glu Asp Asp Ser Glu Pro
    1250            1255            1260

Val Leu Lys Gly Val Ala Leu Ala Tyr Thr
    1265            1270

<210> SEQ ID NO 15
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S-clone 6

<400> SEQUENCE: 15

| | | | | | |
|---|---|---|---|---|---|
| accaaacaaa | gttgggtaag | gatagttcaa | tcaatgatca | ttttctagtg | cacttaggat | 60 |
| tcaagatcct | attatcaggg | acaagagcag | gattaaggat | atccgagatg | gccacacttt | 120 |
| taaggagctt | agcattgttc | aaaagaaaca | aggacaaacc | acccattaca | tcaggatccg | 180 |
| gtggagccat | cagaggaatc | aaacacatta | ttatagtacc | aatccctgga | gattcctcaa | 240 |
| ttaccactcg | atccagactt | ctggaccggt | tggtcaggtt | aattggaaac | ccggatgtga | 300 |
| gcgggcccaa | actaacaggg | gcactaatag | gtatattatc | cttatttgtg | gagtctccag | 360 |
| gtcaattgat | tcagaggatc | accgatgacc | ctgacgttag | cataaggctg | ttagaggttg | 420 |
| tccagagtga | ccagtcacaa | tctggcctta | ccttcgcatc | aagaggtacc | aacatggagg | 480 |
| atgaggcgga | ccaatacttt | tcacatgatg | atccaattag | tagtgatcaa | tccaggttcg | 540 |
| gatggttcga | gaacaaggaa | atctcagata | ttgaagtgca | agaccctgag | ggattcaaca | 600 |
| tgattctggg | taccatccta | gctcaaattt | gggtcttgct | cgcaaaggcg | ttacggccc | 660 |
| cagacacggc | agctgattcg | gagctaagaa | ggtggataaa | gtacacccaa | caagaaggg | 720 |
| tagttggtga | atttagattg | gagagaaaat | ggttggatgt | ggtgaggaac | aggattgccg | 780 |
| aggacctctc | cttacgccga | ttcatggtcg | ctctaatcct | ggatatcaag | agaacacccg | 840 |
| gaaacaaacc | caggattgct | gaaatgatat | gtgacattga | tacatatatc | gtagaggcag | 900 |
| gattagccag | tttatcctg | actattaagt | ttgggataga | aactatgtat | cctgctcttg | 960 |
| gactgcatga | atttgctggt | gagttatcca | cacttgagtc | cttgatgaac | ctttaccagc | 1020 |
| aaatgggga | aactgcaccc | tacatggtaa | tcctggagaa | ctcaattcag | aacaagttca | 1080 |
| gtgcaggatc | ataccctctg | ctctggagct | atgccatggg | agtaggagtg | gaacttgaaa | 1140 |
| actccatggg | aggtttgaac | tttggccgat | cttactttga | tccagcatat | tttagattag | 1200 |
| ggcaagagat | ggtaaggagg | tcagctggaa | aggtcagttc | cacattggca | tctgaactcg | 1260 |
| gtatcactgc | cgaggatgca | aggcttgttt | cagagattgc | aatgcatact | actgaggaca | 1320 |
| agatcagtag | agcggttgga | cccagacaag | cccaagtatc | atttctacac | ggtgatcaaa | 1380 |
| gtgagaatga | gctaccgaga | ttgggggca | aggaagatag | gagggtcaaa | cagagtcgag | 1440 |
| gagaagccag | ggagagctac | agagaaaccg | ggcccagcag | agcaagtgat | gcgagagctg | 1500 |
| cccatcttcc | aaccggcaca | cccctagaca | ttgacactgc | atcggagtcc | agccaagatc | 1560 |
| cgcaggacag | tcgaaggtca | gctgacgccc | tgcttaggct | gcaagccatg | caggaatct | 1620 |
| cggaagaaca | aggctcagac | acggacaccc | ctatagtgta | caatgacaga | aatcttctag | 1680 |

```
actaggtgcg agaggccgag gaccagaaca acatccgcct accctccatc attgttataa    1740
aaaacttagg aaccaggtcc acacagccgc cagcccatca accatccact cccacgattg    1800
gagccgatgg cagaagagca ggcacgccat gtcaaaaacg gactggaatg catccgggct    1860
ctcaaggccg agcccatcgg ctcactggcc atcgaggaag ctatggcagc atggtcagaa    1920
atatcagaca acccaggaca ggagcgagcc acctgcaggg aagagaaggc aggcagttcg    1980
ggtctcagca aaccatgcct ctcagcaatt ggatcaactg aaggcggtgc acctcgcatc    2040
cgcggtcagg gacctggaga gagcgatgac gacgctgaaa ctttgggaat cccccaaga    2100 aatctccagg catcaagcac tgggttacag tgttattatg tttatgatca cagcggtgaa    2160
gcggttaagg gaatccaaga tgctgactct atcatggttc aatcaggcct tgatggtgat    2220
agcaccctct caggaggaga caatgaatct gaaaacagcg atgtggatat tggcgaacct    2280
gataccgagg gatatgctat cactgaccgg ggatctgctc ccatctctat ggggttcagg    2340
gcttctgatg ttgaaactgc agaaggaggg gagatccacg agctcctgag actccaatcc    2400
agaggcaaca actttccgaa gcttgggaaa actctcaatg ttcctccgcc tccggacccc    2460
ggtagggcca gcacttccgg gacacccatt aaaaagggca cagacgcgag attagcctca    2520
tttggaacgg agatcgcgtc tttattgaca ggtggtgcaa cccaatgtgc tcgaaagtca    2580
ccctcggaac catcagggcc aggtgcacct gcggggaatg tccccgagtg tgtgagcaat    2640
gccgcactga tacaggagtg gacacccgaa tctggtacca caatctcccc gagatcccag    2700
aataatgaag aaggggggaga ctattatgat gatgagctgt tctctgatgt ccaagatatt    2760
aaaacagcct tggccaaaat acacgaggat aatcagaaga taatctccaa gctagaatca    2820
ctgctgttat tgaagggaga agttgagtca attaagaagc agatcaacag gcaaaatatc    2880
agcatatcca ccctggaagg acacctctca agcatcatga tcgccattcc tggacttggg    2940
aaggatccca acgaccccac tgcagatgtc gaaatcaatc ccgacttgaa acccatcata    3000
ggcagagatt caggccgagc actggccgaa gttctcaaga aacccgttgc cagccgacaa    3060
ctccaaggaa tgacaaatgg acggaccagt tccagaggac agctgctgaa ggaatttcag    3120
ctaaagccga tcgggaaaaa gatgagctca gccgtcgggt ttgttcctga caccggcccct    3180 gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc caaccccatg    3360
ccagtcgacc caactagtac aacctaaatc cattataaaa aacttaggag caaagtgatt    3420
gcctcccaag ttccacaggc gcgccatgtt tgttttttctt gttttattgc cactagtctc    3480
tagtcagtgt gttaatctta caaccagaac tcaattaccc cctgcataca ctaattcttt    3540
cacacgtggt gtttattacc cttacaaagt tttcagatcc tcagttttac attcaactca    3600
ggacttgttc ttacctttct tttccaatgt tacttggttc catgctatac atgtctctgg    3660
gaccaatggt actaagaggt ttgataaccc tgtcctacca tttaatgatg gtgtttattt    3720
tgcttccact gagaagtcta acataataag aggctggatt tttggtacta ctttagattc    3780
gaagacccag tccctactta tgttaataac cgctactaat gttgttatta agtctgtga    3840 atttcaattt tgtaatgatc cattttttggg tgtttattac cacaaaaaaca acaaaagttg    3900 gatggaaagt gagttcagag tttattctag tgcgaataat tgcactttg aatatgtctc    3960 tcagcctttt cttatggacc ttgaaggaaa acagggtaat ttcaaaaatc ttagggaatt    4020
```

-continued

```
tgtgtttaag aatattgatg gttatttaa aatatattct aagcacacgc ctattaattt    4080
agtgcgtgat ctccctcagg ttttttcggc tttagaacca ttggtagatt tgccaatagg    4140
tattaacatc actaggtttc aaactttact tgctttacat agaagttatt tgactcctgg    4200
tgattcttct tcaggttgga cagctggtgc tgcagcttat tatgtgggtt atcttcaacc    4260
taggactttt ctattaaaat ataatgaaaa tggaaccatt acagatgctg tagactgtgc    4320
acttgaccct ctctcagaaa caaagtgtac gttgaaatcc ttcactgtag aaaaaggaat    4380
ctatcaaact tctaacttta gagtccaacc aacagaatct attgttagat ttcctaatat    4440
tacaaacttg tgccctttg gtgaagtttt taacgccacc agatttgcat ctgtttatgc    4500
ttggaacagg aagagaatca gcaactgtgt tgttgattat tctgtcctat ataattccgc    4560
atcattttcc acttttaagt gttatggagt gtctcctact aaattaaatg atctctgctt    4620
tactaatgtc tatgcagatt catttgtaat tagaggtgat gaagtcagac aaatcgctcc    4680
aggtcaaact ggaaagattg ctgattataa ttataaatta ccagatgatt ttacaggctg    4740
cgttatagct tggaattcta caatcttga ttctaaggtt ggtggtaatt ataattacct    4800
gtatagattg tttaggaagt ctaatctcaa acctttgag agagatattt caactgaaat    4860
ctatcaggcc ggtagcacac cttgtaatgg tgttgaaggt tttaattgtt actttccttt    4920
acaatcatat ggtttccaac ccactaatgg tgttggttac caaccataca gagtagtagt    4980
actttctttt gaacttctac atgcaccagc aactgtttgt ggacctaaaa agtctactaa    5040
tttggttaaa acaaatgtg tcaatttcaa cttcaatggt ttaacaggca caggtgttct    5100
tactgagtct aacaaaaagt ttctgccttt ccaacaattt ggcagagaca ttgctgacac    5160
tactgatgct gtccgtgatc cacagacact tgagattctt gacattacac catgttcttt    5220
tggtggtgtc agtgttataa caccaggaac aaatacttct aaccaggttg ctgttcttta    5280
tcaggatgtt aactgcacag aagtccctgt tgctattcat gcagatcaac ttactcctac    5340
ttggcgtgtt tattctacag gttctaatgt ttttcaaaca cgtgcaggct gtttaatagg    5400
ggctgaacat gtcaacaact catatgagtg tgacatacc attggtgcag gtatatgcgc    5460
tagttatcag actcagacta attctcctcg gcgggcacgt agtgtagcta gtcaatccat    5520
cattgcctac actatgtcac ttggtgcaga aaattcagtt gcttactcta ataactctat    5580
tgccataccc acaaatttta ctattagtgt taccacagaa attctaccag tgtctatgac    5640
caagacatca gtagattgta caatgtacat tgtggtgat tcaactgaat gcagcaatct    5700
tttgttgcaa tatggcagtt tttgtacaca attaaaccgt gctttaactg gaatagctgt    5760
tgaacaagac aaaaacaccc aagaagtttt tgcacaagtc aaacaatttt acaaaacacc    5820
accaattaaa gatttggtg gttttaattt ttcacaaata ttaccagatc catcaaaacc    5880
aagcaagagg tcatttattg aagatctact tttcaacaaa gtgacacttg cagatgctgg    5940
cttcatcaaa caatatggtg attgccttgg tgatattgct gctagagacc tcatttgtgc    6000
acaaaagttt aacggcctta ctgttttgcc accttttgctc acagatgaaa tgattgctca    6060
atacactttc tgcactgttag cgggtacaat cacttctggt tggaccctttg gtgcaggtgc    6120
tgcattacaa ataccatttg ctatgcaaat ggcttatagg tttaatggta ttggagttac    6180
acagaatgtt ctctatgaga accaaaaatt gattgccaac caatttaata gtgctattgg    6240
caaaattcaa gactcacttt cttccacagc aagtgcactt ggaaaacttc aagatgtggt    6300
caaccaaaat gcacaagctt taaacacgct tgttaaacaa cttagctcca ttttggtgc    6360
aatttcaagt gttttaaatg atatcctttc acgtcttgac aaagttgagg ctgaagtgca    6420
```

```
aattgatagg ttgatcacag gcagacttca aagtttgcag acatatgtga ctcaacaatt    6480
aattagagct gcagaaatca gagcttctgc taatcttgct gctactaaaa tgtcagagtg    6540
tgtacttgga caatcaaaaa gagttgattt ttgtggaaag ggctatcatc ttatgtcctt    6600
ccctcagtca gcacctcatg gtgtagtctt cttgcatgtg acttatgtcc ctgcacaaga    6660
aaagaacttc acaactgctc ctgccatttg tcatgatgga aaagcacact ttcctcgtga    6720
aggtgtcttt gtttcaaatg gcacacactg gtttgtaaca caaggaatt tttatgaacc     6780 acaaatcatt actacagaca acacatttgt gtctggtaac tgtgatgttg taataggaat    6840
tgtcaacaac acagtttatg atcctttgca acctgaatta gactcattca aggaggagtt    6900
agataaatat tttaagaatc atacatcacc agatgttgat ttaggtgaca tctctggcat    6960
taatgcttca gttgtaaaca ttcaaaaaga aattgaccgc tcaatgagg ttgccaagaa     7020 tttaaatgaa tctctcatcg atctccaaga acttggaaag tatgagcagt atataaaatg    7080
gccatggtac atttggctag gttttatagc tggcttgatt gccatagtaa tggtgacaat    7140
tatgctttgc tgtatgacca gttgctgtag ttgtctcaag ggctgttgtt cttgtggatc    7200
ctgctgcaaa tttgatgaag acgactctga gccagtgctc aaaggagtcg cattagctta    7260
cacataacgc gcgacgtcct acagctcaac ttacctgcca accccatgcc agtcgaccca    7320
actagtacaa cctaaatcca ttataaaaaa cttaggagca aagtgattgc ctcccaagtt    7380
ccacaatgac agagatctac gacttcgaca agtcggcatg gacatcaaa gggttgatcg     7440 ctccgataca acccaccacc tacagtgatg gcaggctggt gccccaggtc agagtcatag    7500
atcctggtct aggcgacagg aaggatgaat gctttatgta catgtttctg ctgggggttg    7560
ttgaggacag cgatccccta gggcctccaa tcgggcgagc atttgggtcc ctgcccttag    7620
gtgttggcag atccacagca aagcccgaaa aactcctcaa agaggccact gagcttgaca    7680
tagttgttag acgtacagca gggctcaatg aaaaactggt gttctacaac aacacccac     7740 taactctcct cacaccttgg agaaaggtcc taacaacagg gagtgtcttc aacgcaaacc    7800
aagtgtgcaa tgcggttaat ctgataccgc tcgataccc gcagaggttc cgtgttgttt      7860
atatgagcat cacccgtctt tcggataacg ggtattacac cgttcctaga agaatgctgg    7920
aattcagatc ggtcaatgca gtggccttca acctgctggt gacccttagg attgacaagg    7980
cgataggccc tgggaagatc atcgacaata cagagcaact tcctgaggca acatttatgg    8040
tccacatcgg gaacttcagg agaaagaaga gtgaagtcta ctctgccgat tattgcaaaa    8100
tgaaaatcga aagatgggc ctggtttttg cacttggtgg datagggggc accagtcttc      8160
acattagaag cacaggcaaa atgagcaaga ctctccatgc acaactcggg ttcaagaaga    8220
ccttatgtta cccgctgata gatatcaatg aagaccttaa tcgattactc tggaggagca    8280
gatgcaagat agtaagaatc caggcagttt tgcagccatc agttcctcaa gaattccgca    8340
tttacgacga cgtgatcata aatgatgacc aaggactatt caaagttctg tagaccgtag    8400
tgcccagcaa tgcccgaaaa cgacccccct cacaatgaca gccagaaggc ccggacaaaa    8460 aagcccctc cgaaagactc cacggaccaa gcgagaggcc agccagcagc cgacggcaag      8520
cgcgaacacc aggcggcccc agcacagaac agccctgata caaggccacc accagccacc    8580
ccaatctgca tcctcctcgt gggaccccg aggaccaacc cccaaggctg cccccgatcc      8640
aaaccaccaa ccgcatcccc accaccccg ggaaagaaac cccagcaat tggaaggccc       8700 ctcccccctct tcctcaacac aagaactcca caaccgaacc gcacaagcga ccgaggtgac    8760
```

```
ccaaccgcag gcatccgact ccctagacag atcctctctc cccggcaaac taaacaaaac   8820
ttagggccaa ggaacataca cacccaacag aacccagacc ccggcccacg gcgccgcgcc   8880
cccaaccccc gacaaccaga gggagccccc aaccaatccc gccggctccc ccggtgccca   8940
caggcaggga caccaccccc gaacagacc cagcacccaa ccatcgacaa tccaagacgg    9000
gggggccccc ccaaaaaaag gccccaggg gccgacagcc agcaccgcga ggaagcccac    9060
ccaccccaca cacgaccacg gcaaccaaac cagaacccag accaccctgg gccaccagct   9120
cccagactcg gccatcaccc cgcagaaagg aaaggccaca acccgcgcac cccagccccg   9180
atccggcggg gagccaccca acccgaacca gcacccaaga gcgatccccg aaggacccc    9240
gaaccgcaaa ggacatcagt atcccacagc ctctccaagt cccccggtct cctccccttc   9300
tcgaagggac caaagatca atccaccaca cccgacgaca ctcaactccc cacccctaaa    9360
ggagacaccg ggaatcccag aatcaagact catccaatgt ccatcatggg tctcaaggtg   9420
aacgtctctg ccatattcat ggcagtactt ttaactctcc aaacacccac cggtcaaatc   9480
cattgggca atctctctaa gataggggtg gtaggaatag gaagtgcaag ctacaaagtt    9540
atgactcgtt ccagccatca atcattagtc ataaaattaa tgcccaatat aactctcctc   9600
aataactgca cgagggtaga gattgcagaa tacaggagac tactgagaac agttttggaa   9660
ccaattagag atgcacttaa tgcaatgacc cagaatataa gaccggttca gagtgtagct   9720
tcaagtagga gacacaagag atttgcggga gtagtcctgg caggtgcggc cctaggcgtc   9780
gccacagctg ctcagataac agccggcatt gcacttcacc agtccatgct gaactctcaa   9840
gccatcgaca atctgagagc gagcctggaa actactaatc aggcaattga ggcaatcaga   9900
caagcagggc aggagatgat attggctgtt cagggtgtcc aagactacat caataatgag   9960
ctgataccgt ctatgaacca actatcttgt gatttaatcg ccagaagct cgggctcaaa   10020
ttgctcagat actatacaga aatcctgtca ttatttggcc ccagcttacg ggaccccata   10080
tctgcggaga tatctatcca ggctttgagc tatgcgcttg gaggagacat caataaggtg   10140
ttagaaaagc tcggatacag tggaggtgat ttactgggca tcttagagag cagaggaata  10200
aaggcccgga taactcacgt cgacacagag tcctacttca ttgtcctcag tatagcctat  10260
ccgacgctgt ccgagattaa gggggtgatt gtccaccggc tagagggggt ctcgtacaac  10320
ataggctctc aagagtggta taccactgtg cccaagtatg ttgcaaccca agggtacctt  10380
atctcgaatt ttgatgagtc atcgtgtact ttcatgccag aggggactgt gtgcagccaa  10440
aatgccttgt acccgatgag tcctctgctc caagaatgcc tccgggggtc caccaagtcc  10500
tgtgctcgta cactcgtatc cgggtctttt gggaaccggt tcattttatc acaagggaac  10560
ctaatagcca attgtgcatc aatcctttgc aagtgttaca caacaggaac gatcattaat  10620
caagaccctg acaagatcct aacatacatt gctgccgatc actgcccggt agtcgaggtg  10680
aacgcgtga ccatccaagt cgggagcagg aggtatccag atgctgtgta cttgcacaga  10740
attgacctcg gtcctcccat atcattggag aggttggacg tagggacaaa tctgggaat   10800
gcaattgcta agttggagga tgccaaggaa ttgttggagt catcggacca gatattgagg  10860
agtatgaaag gtatcgag cactagcata gtctacatcc tgattgcagt gtgtcttgga    10920
gggttgatag ggatccccgc tttaatatgt tgctgcaggg ggcgttgtaa caaaaaggga  10980
gaacaagttg gtatgtcaag accaggccta aagcctgatc ttacgggaac atcaaaatcc  11040
tatgtaaggt cgctctgatc ctctacaact cttgaaacac aaatgtccca caagtctcct  11100
cttcgtcatc aagcaaccac cgcacccagc atcaagccca cctgaaatta tctccggctt  11160
```

-continued

```
ccctctggcc gaacaatatc ggtagttaat taaaacttag ggtgcaagat catccacaat   11220
gtcaccacaa cgagaccgga taaatgcctt ctacaaagat aaccccccatc ccaagggaag   11280
taggatagtc attaacagag aacatcttat gattgataga ccttatgttt tgctggctgt   11340
tctgtttgtc atgtttctga gcttgatcgg gttgctagcc attgcaggca ttagacttca   11400
tcgggcagcc atctacaccg cagagatcca taaaagcctc agcaccaatc tagatgtaac   11460
taactcaatc gagcatcagg tcaaggacgt gctgacacca ctcttcaaaa tcatcggtga   11520
tgaagtgggc ctgaggacac ctcagagatt cactgaccta gtgaaattca tctctgacaa   11580
gattaaattc cttaatccgg ataggagta cgacttcaga gatctcactt ggtgtatcaa   11640
cccgccagag agaatcaaat tggattatga tcaatactgt gcagatgtgg ctgctgaaga   11700
gctcatgaat gcattggtga actcaactct actggagacc agaacaacca atcagttcct   11760
agctgtctca aagggaaact gctcagggcc cactacaatc agaggtcaat tctcaaacat   11820
gtcgctgtcc ctgttagact tgtatttagg tcgaggttac aatgtgtcat ctatagtcac   11880
tatgacatcc cagggaatgt atgggggaac ttacctagtg gaaaagccta atctgagcag   11940
caaaaggtca gagttgtcac aactgagcat gtaccgagtg tttgaagtag gtgttatcag   12000
aaatccgggt ttgggggctc cggtgttcca tatgacaaac tatcttgagc aaccagccag   12060
taatgatctc agcaactgta tggtggcttt gggggagctc aaactcgcag cccttgtca   12120
cggggaagat tctatcacaa ttccctatca gggatcaggg aaaggtgtca gcttccagct   12180
cgtcaagcta ggtgtctgga atccccaac cgacatgcaa tcctgggtcc ccttatcaac   12240
ggatgatcca gtgatagaca ggctttacct ctcatctcac agaggtgtta tcgctgacaa   12300
tcaagcaaaa tgggctgtcc cgacaacacg aacagatgac aagttgcgaa tggagacatg   12360
cttccaacag gcgtgtaagg gtaaaatcca agcactctgc gagaatcccg agtgggcacc   12420
attgaaggat aacaggattc cttcatacgg ggtcttgtct gttgatctga gtctgacagt   12480
tgagcttaaa atcaaaattg cttcgggatt cgggccattg atcacacacg gttcagggat   12540
ggacctatac aaatccaacc acaacaatgt gtattggctg actatcccgc caatgaagaa   12600
cctagcctta ggtgtaatca acacattgga gtggataccg agattcaagg ttagtcccta   12660
cctcttcaat gtcccaatta aggaagcagg cgaagactgc catgccccaa catacctacc   12720
tgcggaggtg gatggtgatg tcaaactcag ttccaatctg gtgattctac ctggtcaaga   12780
tctccaatat gttttggcaa cctacgatac ttccagggtt gaacatgctg tggtttatta   12840
cgtttacagc ccaggccgct catttttctta ctttttatcct tttaggttgc ctataaaggg   12900
ggtccccatc gaattacaag tggaatgctt cacatgggac caaaaactct ggtgccgtca   12960
cttctgtgtg cttgcggact cagaatctgg tggacatatc actcactctg ggatggtggg   13020
catgggagtc agctgcacag tcacccggga agatggaacc aatcgcagat agggctgcta   13080
gtgaaccaat ctcatgatgt cacccagaca tcaggcatac ccactagtgt gaaatagaca   13140
tcagaattaa gaaaaacgta gggtccaagt ggttccccgt tatggactcg ctatctgtca   13200
accagatctt ataccctgaa gttcacctag atagcccgat agttaccaat aagatagtag   13260
ccatcctgga gtatgctcga gtccctcacg cttacagcct ggaggaccct acactgtgtc   13320
agaacatcaa gcaccgccta aaaacggat tttccaacca aatgattata aacaatgtgg   13380
aagttgggaa tgtcatcaag tccaagctta ggagttatcc ggcccactct catattccat   13440
atccaaattg taatcaggat ttatttaaca tagaagacaa agagtcaacg aggaagatcc   13500
```

```
gtgaactcct caaaaagggg aattcgctgt actccaaagt cagtgataag gttttccaat   13560
gcttaaggga cactaactca cggcttggcc taggctccga attgagggag acatcaagg    13620 agaaagttat taacttggga gtttacatgc acagctccca gtggtttgag ccctttctgt   13680
tttggtttac agtcaagact gagatgaggt cagtgattaa atcacaaacc catacttgcc   13740
ataggaggag acacacacct gtattcttca ctggtagttc agttgagttg ctaatctctc   13800
gtgaccttgt tgctataatc agtaaagagt ctcaacatgt atattacctg acatttgaac   13860
tggttttgat gtattgtgat gtcatagagg ggaggttaat gacagagacc gctatgacta   13920
ttgatgctag gtatacagag cttctaggaa gagtcagata catgtggaaa ctgatagatg   13980
gtttcttccc tgcactcggg aatccaactt atcaaattgt agccatgctg gagcctcttt   14040
cacttgctta cctgcagctg agggatataa cagtagaact cagaggtgct ttccttaacc   14100
actgctttac tgaaatacat gatgttcttg accaaaacgg gttttctgat gaaggtactt   14160
atcatgagtt aattgaagct ctagattaca ttttcataac tgatgacata catctgacag   14220
gggagatttt ctcatttttc agaagtttcg gccaccccag acttgaagca gtaacggctg   14280
ctgaaaatgt taggaaatac atgaatcagc ctaaagtcat tgtgtatgag actctgatga   14340
aaggtcatgc catattttgt ggaatcataa tcaacggcta tcgtgacagg cacggaggca   14400
gttggccacc gctgaccctc ccctgcatg ctgcagacac aatccggaat gctcaagctt    14460
caggtgaagg gttaacacat gagcagtgcg ttgataactg gagatctttt gctggagtga   14520
aatttggctg ctttatgcct cttagcctgg atagtgatct gacaatgtac ctaaaggaca   14580
aggcacttgc tgctctccaa agggaatggg attcagttta cccgaaagag ttcctgcgtt   14640
acgaccctcc caagggaacc gggtcacgga ggcttgtaga tgttttcctt aatgattcga   14700
gctttgaccc atatgatgtg ataatgtatg ttgtaagtgg agcttacctc catgaccctg   14760
agttcaacct gtcttacagc ctgaaagaaa aggagatcaa ggaaacaggt agacttttg    14820 ctaaaatgac ttacaaaatg agggcatgcc aagtgattgc tgaaaatcta atctcaaacg   14880
ggattggcaa atattttaag gacaatggga tggccaagga tgagcacgat ttgactaagg   14940
cactccacac tctagctgtc tcaggagtcc ccaaagatct caaagaaagt cacaggggg    15000 ggccagtctt aaaaacctac tcccgaagcc cagtccacac aagtaccagg aacgtgagag   15060
cagcaaaagg gtttataggg ttccctcaag taattcggca ggaccaagac actgatcatc   15120
cggagaatat ggaagcttac gagacagtca gtgcatttat cacgactgat ctcaagaagt   15180
actgccttaa ttggagatat gagaccatca gcttgtttgc acagaggcta aatgagattt   15240
acggattgcc ctcatttttc cagtggctgc ataagaggct tgagacctct gtcctgtatg   15300
taagtgaccc tcattgcccc cccgaccttg acgcccatat cccgttatat aaagtcccca   15360
atgatcaaat cttcattaag taccctatgg gaggtataga agggtattgt cagaagctgt   15420
ggaccatcag caccattccc tatctatacc tggctgctta tgagagcgga gtaaggattg   15480
cttcgttagt gcaaggggac aatcagacca tagccgtaac aaaaagggta cccagcacat   15540
ggccctacaa ccttaagaaa cgggaagctg ctagagtaac tagagattac tttgtaattc   15600
ttaggcaaag gctacatgat attggccatc acctcaaggc aaatgagaca attgttttcat   15660 cacattttt tgtctattca aaaggaatat attatgatgg gctacttgtg tcccaatcac   15720
tcaagagcat cgcaagatgt gtattctggt cagagactat agttgatgaa acaagggcag   15780
catgcagtaa tattgctaca acaatggcta aaagcatcga gagaggttat gaccgttacc   15840
ttgcatattc cctgaacgtc ctaaaagtga tacagcaaat tctgatctct cttggcttca   15900
```

```
caatcaattc aaccatgacc cgggatgtag tcatacccct cctcacgaac aacgacctct   15960
taataaggat ggcactgttg cccgctccta ttgggggggat gaattatctg aatatgagca   16020
ggctgtttgt cagaaacatc ggtgatccag taacatcatc aattgctgat ctcaagagaa   16080
tgattctcgc ctcactaatg cctgaagaga ccctccatca agtaatgaca caacaaccgg   16140
gggactcttc attcctagac tgggctagcg acccttactc agcaaatctt gtatgtgtcc   16200
agagcatcac tagactcctc aagaacataa ctgcaaggtt tgtcctgatc catagtccaa   16260
acccaatgtt aaaaggatta ttccatgatg acagtaaaga gaggacgag ggactggcgg    16320 cattcctcat ggacaggcat attatagtac ctagggcagc tcatgaaatc ctggatcata   16380
gtgtcacagg ggcaagagag tctattgcag gcatgctgga taccacaaaa ggcctgattc   16440
gagccagcat gaggaagggg gggttaacct ctcgagtgat aaccagattg tccaattatg   16500
actatgaaca attcagagca gggatggtgc tattgacagg aagaaagaga aatgtcctca   16560
ttgacaaaga gtcatgttca gtgcagctgg cgagagctct aagaagccat atgtgggcga   16620
ggctagctcg aggacggcct atttacggcc ttgaggtccc tgatgtacta gaatctatgc   16680
gaggccacct tattcggcgt catgagacat gtgtcatctg cgagtgtgga tcagtcaact   16740
acggatggtt ttttgtcccc tcgggttgcc aactggatga tattgacaag gaaacatcat   16800
ccttgagagt cccatatatt ggttctacca ctgatgagag aacagacatg aagcttgcct   16860
tcgtaagagc cccaagtcga tccttgcgat ctgctgttag aatagcaaca gtgtactcat   16920
gggcttacgg tgatgatgat agctcttgga acgaagcctg gttgttggct aggcaaaggg   16980
ccaatgtgag cctggaggag ctaagggtga tcactcccat ctcaacttcg actaatttag   17040
cgcataggtt gagggatcgt agcactcaag tgaaatactc aggtacatcc cttgtccgag   17100
tggcgaggta taccacaatc tccaacgaca atctctcatt tgtcatatca gataagaagg   17160
ttgatactaa ctttatatac caacaaggaa tgcttctagg gttgggtgtt ttagaaacat   17220
tgtttcgact cgagaaagat accggatcat ctaacacggt attacatctt cacgtcgaaa   17280
cagattgttg cgtgatcccg atgatagatc atcccaggat acccagctcc cgcaagctag   17340
agctgagggc agagctatgt accaacccat tgatatatga taatgcacct ttaattgaca   17400
gagatacaac aaggctatac acccagagcc ataggaggca ccttgtggaa tttgttacat   17460
ggtccacacc ccaactatat cacatttag ctaagtccac agcactatct atgattgacc    17520
tggtaacaaa atttgagaag gaccatatga atgaaatttc agctctcata ggggatgacg   17580
atatcaatag tttcataact gagtttctgc tcatagagcc aagattattc actatctact   17640
tgggccagtg tgcggccatc aattgggcat ttgatgtaca ttatcataga ccatcaggga   17700
aatatcagat gggtgagctg ttgtcatcgt tcctttctag aatgagcaaa ggagtgttta   17760
aggtgcttgt caatgctcta agccacccaa agatctacaa gaaattctgg cattgtggta   17820
ttatagagcc tatccatggt ccttcacttg atgctcaaaa cttgcacaca actgtgtgca   17880
acatggttta cacatgctat atgacctacc tcgacctgtt gttgaatgaa gagttagaag   17940
agttcacatt tctcttgtgt gaaagcgacg aggatgtagt accggacaga ttcgacaaca   18000
tccaggcaaa acacttatgt gttctggcag atttgtactg tcaaccaggg acctgcccac   18060
caattcgagg tctaagaccg gtagagaaat gtgcagttct aaccgaccat atcaaggcag   18120
aggctaggtt atctccagca ggatcttcgt ggaacataaa tccaattatt gtagaccatt   18180
actcatgctc tctgacttat ctccggcgag atcgatcaa acagataaga ttgagagttg    18240
```

```
atccaggatt catttcgac gccctcgctg aggtaaatgt cagtcagcca agatcggca      18300 gcaacaacat ctcaaatatg agcatcaagg ctttcagacc cccacacgat gatgttgcaa      18360
aattgctcaa agatatcaac acaagcaagc acaatcttcc catttcaggg ggcaatctcg      18420
ccaattatga aatccatgct ttccgcagaa tcggttgaa ctcatctgct tgctacaaag       18480
ctgttgagat atcaacatta attaggagat gccttgagcc aggggaggac ggcttgttct      18540
tgggtgaggg atcgggttcc atgttgatca cttataagga gatacttaaa ctaaacaagt      18600
gcttctataa tagtggggtt tccgccaatt ctagatctgg tcaaagggaa ttagcaccct      18660
atccctccga agttggcctt gtcgaacaca gaatgggagt aggtaatatt gtcaaagtgc      18720
tctttaacgg gaggcccgaa gtcacgtggg taggcagtgt agattgcttc aatttcatag      18780
ttagtaatat ccctacctct agtgtggggt ttatccattc agatatagag accttgccta      18840
acaaagatac tatagagaag ctagaggaat tggcagccat cttatcgatg gctctgctcc      18900
tgggcaaaat aggatcaata ctggtgatta agcttatgcc tttcagcggg gattttgttc      18960 agggattat aagttatgta gggtcccatt atagagaagt gaaccttgta taccctagat       19020
acagcaactt catatctact gaatcttatt tggttatgac agatctcaag gctaaccggc      19080
taatgaatcc tgaaaagatt aagcagcaga taattgaatc atctgtgagg acttcacctg      19140
gacttatagg tcacatccta tccattaagc aactaagctg catacaagca attgtgggag      19200
acgcagttag tagaggtgat atcaatccta ctctgaaaaa acttacacct atagagcagg      19260
tgctgatcaa ttgcgggttg gcaattaacg gacctaagct gtgcaaagaa ttgatccacc      19320
atgatgttgc ctcagggcaa gatggattgc ttaattctat actcatcctc tacagggagt      19380
tggcaagatt caaagacaac caaagaagtc aacaagggat gttccacgct tacccgtat       19440 tggtaagtag caggcaacga gaacttatat ctaggatcac ccgcaaattt tggggggcaca     19500 ttcttcttta ctccgggaac agaaagttga taaataagtt tatccagaat ctcaagtccg      19560
gctatctgat actagactta caccagaata tcttcgttaa gaatctatcc aagtcagaga      19620
aacagattat tatgacgggg ggtttgaaac gtgagtgggt tttaaggta acagtcaagg       19680 agaccaaaga atggtataag ttagtcggat acagtgccct gattaaggac taattggttg      19740
aactccggaa ccctaatcct gccctaggtg gttaggcatt atttgcaata gattaaagaa      19800
aactttgaaa atacgaagtt tctattccca gctttgtctg gtggccggca tggtcccagc      19860
ctcctcgctg gcgccggctg ggcaacattc cgaggggacc gtccctcgg taatggcgaa       19920 tgggacgcgg ccgatccggc tgctaacaaa gcccgaaagg aagctgagtt ggctgctgcc      19980
accgctgagc aataactagc ataaccccct ggggcctcta acgggtctt gagggggtttt     20040 ttgctgaaag gaggaactat atccggatgc ggccgatccg gctgctaaca aagcccgaaa      20100
ggaagctgag ttggctgctg ccaccgctga gcaataacta gcataacccc ttggggcctc      20160
taaacgggtc ttgagggggtt ttttgctgaa aggaggaact atatccggat ggccgccacc      20220
ggccggtggg ccttgcagca catcccccett tcgccagctg gcgtaatagc gaagaggccc      20280
gcaccgatcg cccttcccaa cagttgcgca gcctgaatgg cgaatgggac gcgccctgta      20340
gcggcgcatt aagcgcggcg ggtgtggtgg ttacgcgcag cgtgaccgct acacttgcca      20400
gcgccctagc gcccgctcct ttcgctttct tcccttcctt tctcgccacg ttcgccggct      20460
ttccccgtca agctctaaat cggggctc ctttagggtt ccgatttagt gctttacggc         20520
acctcgaccc caaaaaactt gattagggtg atggttcacg tgggcatcg ccctgataga         20580 cggtttttcg ccctttgacg ttggagtcca cgttctttaa tagtggactc ttgttccaaa      20640
```

```
ctggaacaac actcaaccct atctcggtct attcttttga tttataaggg attttgccga   20700
tttcggccta ttggttaaaa aatgagctga tttaacaaaa atttaacgcg aatttttaaca   20760 aaatattaac gcttacaatt taggtggcac ttttcgggga aatgtgcgcg gaaccccctat   20820 ttgtttattt ttctaaatac attcaaatat gtatccgctc atgagacaat aaccctgata   20880
aatgcttcaa taatattgaa aaaggaagag tatgagtatt caacatttcc gtgtcgccct   20940
tattcccttt tttgcggcat tttgccttcc tgttttttgct cacccagaaa cgctggtgaa   21000
agtaaaagat gctgaagatc agttgggtgc acgagtgggt tacatcgaac tggatctcaa   21060
cagcggtaag atccttgaga gttttcgccc cgaagaacgt tttccaatga tgagcacttt   21120
taaagttctg ctatgtggcg cggtattatc ccgtattgac gccgggcaag agcaactcgg   21180
tcgccgcata cactattctc agaatgactt ggttgagtac tcaccagtca cagaaaagca   21240
tcttacggat ggcatgacag taagagaatt atgcagtgct gccataacca tgagtgataa   21300
cactgcggcc aacttacttc tgacaacgat cggaggaccg aaggagctaa ccgcttttt   21360 gcacaacatg ggggatcatg taactcgcct tgatcgttgg gaaccggagc tgaatgaagc   21420
cataccaaac gacgagcgtg acaccacgat gcctgtagca atggcaacaa cgttgcgcaa   21480
actattaact ggcgaactac ttacactagc ttcccggcaa caattaatag actggatgga   21540
ggcggataaa gttgcaggac cacttctgcg ctcggccctt ccggctggct ggtttattgc   21600
tgataaatct ggagccggtg agcgtgggtc tcgcggtatc attgcagcac tggggccaga   21660
tggtaagccc tcccgtatcg tagttatcta cacgacgggg agtcaggcaa ctatggatga   21720
acgaaataga cagatcgctg agataggtgc ctcactgatt aagcattggt aactgtcaga   21780
ccaagtttac tcatatatac tttagattga tttaaaactt catttttaat ttaaaaggat   21840
ctaggtgaag atcctttttg ataatctcat gaccaaaatc ccttaacgtg agttttcgtt   21900
ccactgagcg tcagaccccg tagaaaagat caaaggatct tcttgagatc ctttttttct   21960
gcgcgtaatc tgctgcttgc aaacaaaaaa accaccgcta ccagcggtgg tttgtttgcc   22020
ggatcaagag ctaccaactc tttttccgaa ggtaactggc ttcagcagag cgcagatacc   22080
aaatactgtt cttctagtgt agccgtagtt aggccaccac ttcaagaact ctgtagcacc   22140
gcctacatac ctcgctctgc taatcctgtt accagtggct gctgccagtg gcgataagtc   22200
gtgtcttacc gggttggact caagacgata gttaccggat aaggcgcagc ggtcgggctg   22260
aacggggggt tcgtgcacac agcccagctt ggagcgaacg acctacaccg aactgagata   22320
cctacagcgt gagctatgag aaagcgccac gcttcccgaa gggagaaagg cggacaggta   22380
tccggtaagc ggcagggtcg gaacaggaga gcgcacgagg gagcttccag ggggaaacgc   22440
ctggtatctt tatagtcctg tcgggtttcg ccacctctga cttgagcgtc gatttttgtg   22500
atgctcgtca ggggggcgga gcctatggaa aaacgccagc aacgcggcct ttttacggtt   22560
cctggccttt tgctggcctt ttgctcacat gttctttcct gcgttatccc ctgattctgt   22620
ggataaccgt attaccgcct ttgagtgagc tgataccgct cgccgcagcc gaacgaccga   22680
gcgcagcgag tcagtgagcg aggaagcgga agagcgccca atacgcaaac cgcctctccc   22740
cgcgcgttgg ccgattcatt aatgcagctg gcacgacagg tttcccgact ggaaagcggg   22800
cagtgagcgc aacgcaatta atgtgagtta gctcactcat taggcacccc aggctttaca   22860
ctttatgctt ccggctcgta tgttgtgtgg aattgtgagc ggacaacaat ttcacacagg   22920
aaacagctat gaccatgatt acgccaagct cgggcggccg cttgtaatac gactcactat   22980
``` a                                                                           22981

<210> SEQ ID NO 16
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S-CO

<400> SEQUENCE: 16

```
accaaacaaa gttgggtaag gatagttcaa tcaatgatca ttttctagtg cacttaggat     60
tcaagatcct attatcaggg acaagagcag gattaaggat atccgagatg cccacacttt    120
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtcaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcga gaacaaggaa atctcagata ttgaagtgca agaccctgag ggattcaaca    600
tgattctggg taccatccta gctcaaattt gggtcttgct cgcaaaggcg ttacggcccc    660 agacacggc agctgattcg gagctaagaa ggtggataaa gtacacccaa caagaaggg     720 tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc ataccctctg ctctggagct atgccatggg agtaggagtg aacttgaaa    1140 actccatggg aggtttgaac tttggccgat cttactttga tccagcatat tttagattag   1200
ggcaagagat ggtaaggagg tcagctgaaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttgggggca aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc atcggagtcc agccaagatc   1560
cgcaggacag tcgaaggtca gctgacgccc tgcttaggct gcaagccatg cagga atct   1620 cggaagaaca aggctcagac acggacaccc tatagtgta caatgacaga atcttctag    1680 actaggtgcg agaggccgag gaccagaaca acatccgcct accctccatc attgttataa   1740
aaaacttagg aaccaggtcc acacagccgc cagcccatca accatccact cccacgattg   1800
gagccgatgg cagaagagca ggcacgccat gtcaaaaacg gactgaatg catccgggct    1860 ctcaaggccg agcccatcgg ctcactggcc atcgaggaag ctatggcagc atggtcagaa   1920
```

| | |
|---|---|
| atatcagaca acccaggaca ggagcgagcc acctgcaggg aagagaaggc aggcagttcg | 1980 |
| ggtctcagca aaccatgcct ctcagcaatt ggatcaactg aaggcggtgc acctcgcatc | 2040 |
| cgcggtcagg gacctggaga gagcgatgac gacgctgaaa ctttgggaat cccccccaaga | 2100 |
| aatctccagg catcaagcac tgggttacag tgttattatg tttatgatca cagcggtgaa | 2160 |
| gcggttaagg gaatccaaga tgctgactct atcatggttc aatcaggcct tgatggtgat | 2220 |
| agcaccctct caggaggaga caatgaatct gaaaacagcg atgtggatat tggcgaacct | 2280 |
| gataccgagg gatatgctat cactgaccgg ggatctgctc ccatctctat ggggttcagg | 2340 |
| gcttctgatg ttgaaactgc agaaggaggg gagatccacg agctcctgag actccaatcc | 2400 |
| agaggcaaca actttccgaa gcttgggaaa actctcaatg ttcctccgcc tccggacccc | 2460 |
| ggtagggcca gcacttccgg gacacccatt aaaaagggca cagacgcgag attagcctca | 2520 |
| tttggaacgg agatcgcgtc tttattgaca ggtggtgcaa cccaatgtgc tcgaaagtca | 2580 |
| ccctcggaac catcagggcc aggtgcacct gcggggaatg tccccgagtg tgtgagcaat | 2640 |
| gccgcactga tacaggagtg gacacccgaa tctggtacca caatctcccc gagatcccag | 2700 |
| aataatgaag aaggggggaga ctattatgat gatgagctgt tctctgatgt ccaagatatt | 2760 |
| aaaacagcct tggccaaaat acacgaggat aatcagaaga taatctccaa gctagaatca | 2820 |
| ctgctgttat tgaagggaga agttgagtca attaagaagc agatcaacag gcaaaatatc | 2880 |
| agcatatcca ccctggaagg cacctctca agcatcatga tcgccattcc tggacttggg | 2940 |
| aaggatccca cgaccccac tgcagatgtc gaaatcaatc ccgacttgaa acccatcata | 3000 |
| ggcagagatt caggccgagc actggccgaa gttctcaaga aacccgttgc cagccgacaa | 3060 |
| ctccaaggaa tgacaaatgg acggaccagt tccagaggac agctgctgaa ggaatttcag | 3120 |
| ctaaagccga tcgggaaaaa gatgagctca gccgtcgggt tgttcctga caccggccct | 3180 |
| gcatcacgca gtgtaatccg ctccattata aaatccagcc ggctagagga ggatcggaag | 3240 |
| cgttacctga tgactctcct tgatgatatc aaaggagcca atgatcttgc caagttccac | 3300 |
| cagatgctga tgaagataat aatgaagtag ctacagctca acttacctgc caaccccatg | 3360 |
| ccagtcgacc caactagtac aacctaaatc cattataaaa aacttaggag caaagtgatt | 3420 |
| gcctcccaag ttccacaggc gcgccatgtt cgtcttcctg gtcctgctgc ctctggtctc | 3480 |
| ctcacagtgc gtcaatctga caactcggac tcagctgcca cctgcttata ctaatagctt | 3540 |
| caccagaggc gtgtactatc ctgacaaggt gtttagaagc tccgtgctgc actctacaca | 3600 |
| ggatctgttt ctgccattct ttagcaacgt gacctggttc cacgccatcc acgtgagcgg | 3660 |
| caccaatggc acaaagcggt tcgacaatcc cgtgctgcct tttaacgatg gcgtgtactt | 3720 |
| cgcctctacc gagaagagca acatcatcag aggctgatc tttggcacca cactggactc | 3780 |
| caagacacag tctctgctga tcgtgaacaa tgccaccaac gtggtcatca aggtgtgcga | 3840 |
| gttccagttt tgtaatgatc ccttcctggg cgtgtactat cacaagaaca taagagctg | 3900 |
| gatggagtcc gagtttagag tgtattctag cgccaacaac tgcacatttg agtacgtgag | 3960 |
| ccagccttc ctgatggacc tggagggcaa gcagggcaat ttcaagaacc tgagggagtt | 4020 |
| cgtgtttaag aatatcgacg gctacttcaa aatctactct aagcacaccc ccatcaacct | 4080 |
| ggtgcgcgac ctgcctcagg gcttcagcgc cctggagccc ctggtggatc tgcctatcgg | 4140 |
| catcaacatc acccggtttc agacactgct ggccctgcac agaagctacc tgacacccgg | 4200 |
| cgactcctct agcggatgga ccgccggcgc tgccgcctac tatgtgggct acctccagcc | 4260 |

```
ccggaccttc ctgctgaagt acaacgagaa tggcaccatc acagacgcag tggattgcgc    4320
cctggacccc ctgagcgaga caaagtgtac actgaagtcc tttaccgtgg agaagggcat    4380
ctatcagaca tccaatttca gggtgcagcc aaccgagtct atcgtgcgct ttcctaatat    4440
cacaaacctg tgcccatttg gcgaggtgtt caacgcaacc cgcttcgcca gcgtgtacgc    4500
ctggaatagg aagcggatca gcaactgcgt ggccgactat agcgtgctgt acaactccgc    4560
ctctttcagc acctttaagt gctatggcgt gtcccccaca aagctgaatg acctgtgctt    4620
taccaacgtc tacgccgatt ctttcgtgat caggggcgac gaggtgcgcc agatcgcccc    4680
cggccagaca ggcaagatcg cagactacaa ttataagctg ccagacgatt tcaccggctg    4740
cgtgatcgcc tggaacagca caatctggga ttccaaagtg ggcggcaact acaattatct    4800
gtaccggctg tttagaaaga gcaatctgaa gcccttcgag agggacatct ctacagaaat    4860
ctaccaggcc ggcagcaccc cttgcaatgg cgtggagggc tttaactgtt atttcccact    4920
ccagtcctac ggcttccagc ccacaaacgg cgtgggctat cagccttacc gcgtggtggt    4980
gctgagcttt gagctgctgc acgccccagc aacagtgtgc ggcccaaaga agtccaccaa    5040
tctggtgaag aacaagtgcg tgaacttcaa cttcaacggc ctgaccggca caggcgtgct    5100
gaccgagtcc aacaagaagt tcctgccatt tcagcagttc ggcagggaca tcgcagatac    5160
cacagacgcc gtgcgcgacc cacagaccct ggagatcctg acatcacac cctgctcttt    5220 cggcggcgtg agcgtgatca cacccggcac caatacaagc aaccaggtgg ccgtgctgta    5280
tcaggacgtg aattgtaccg aggtgcccgt ggctatccac gccgatcagc tgacccccaac   5340 atggcgggtg tacagcaccg gctccaacgt cttccagaca agagccggat gcctgatcgg    5400
agcagagcac gtgaacaatt cctatgagtg cgacatccca atcggcgccg gcatctgtgc    5460
ctcttaccag acccagacaa actctcccag aagagcccgg agcgtggcct cccagtctat    5520
catcgcctat accatgtccc tgggcgccga aacagcgtg gcctactcta caatagcat    5580 cgccatccca accaacttca caatctctgt gaccacagag atcctgcccg tgtccatgac    5640
caagacatct gtggactgca caatgtatat ctgtggcgat tctaccgagt gcagcaacct    5700
gctgctccag tacggcagct tttgtaccca gctgaataga gccctgacag gcatcgccgt    5760
ggagcaggat aagaacacac aggaggtgtt cgcccaggtg aagcaaatct acaagacccc    5820
ccctatcaag gactttggcg gcttcaattt ttcccagatc ctgcctgatc catccaagcc    5880
ttctaagcgg agctttatcg aggacctgct gttcaacaag gtgaccctgg ccgatgccgg    5940
cttcatcaag cagtatggcg attgcctggg cgacatcgca gccagggacc tgatctgcgc    6000
ccagaagttt aatggcctga ccgtgctgcc accctgctg acagatgaga tgatcgcaca    6060
gtacacaagc gccctgctgg ccggcaccat cacatccgga tggaccttcg gcgcaggagc    6120
cgccctccag atcccctttg ccatgcagat ggcctatagg ttcaacggca tcggcgtgac    6180
ccagaatgtg ctgtacgaga accagaagct gatcgccaat cagtttaact ccgccatcgg    6240
caagatccag gacagcctgt cctctacagc cagcgccctg ggcaagctcc aggatgtggt    6300
gaatcagaac gcccaggccc tgaatacct ggtgaagcag ctgagcagca acttcggcgc    6360
catctctagc gtgctgaatg acatcctgag ccggctggac aaggtggagg cagaggtgca    6420
gatcgaccgg ctgatcaccg gccggctcca gagcctccag acctatgtga cacagcagct    6480
gatcagggcc gccgagatca gggccagcgc caatctggca gcaaccaaga tgtccgagtg    6540
cgtgctgggc cagtctaaga gagtggactt ttgtggcaag ggctatcacc tgatgtcctt    6600
ccctcagtct gccccacacg gcgtggtgtt tctgcacgtg acctacgtgc cgcccagga    6660
```

```
gaagaacttc accacagccc ctgccatctg ccacgatggc aaggcccact ttccaaggga      6720
gggcgtgttc gtgtccaacg gcacccactg gtttgtgaca cagcgcaatt tctacgagcc      6780
ccagatcatc accacagaca acaccttcgt gagcggcaac tgtgacgtgg tcatcggcat      6840
cgtgaacaat accgtgtatg atccactcca gcccgagctg acagcttta aggaggagct       6900 ggataagtat ttcaagaatc acacctcccc tgacgtggat ctgggcgaca tcagcggcat      6960
caatgcctcc gtggtgaaca tccagaagga gatcgaccgc ctgaacgagg tggctaagaa      7020
tctgaacgag agcctgatcg acctccagga gctgggcaag tatgagcagt acatcaagtg      7080
gccctggtac atctggctgg gcttcatcgc cggcctgatc gccatcgtga tggtgaccat      7140
catgctgtgc tgtatgacat cctgctgttc ttgcctgaag ggctgctgta gctgtggctc      7200
ctgctgtaag tttgacgagg atgactctga acctgtgctg aagggcgtga agctgcatta      7260
cacctaacgc gcgacgtcct acagctcaac ttacctgcca accccatgcc agtcgaccca      7320
actagtacaa cctaaatcca ttataaaaaa cttaggagca aagtgattgc ctcccaagtt      7380
ccacaatgac agagatctac gacttcgaca agtcggcatg gacatcaaa gggttgatcg       7440 ctccgataca acccaccacc tacagtgatg gcaggctggt gccccaggtc agagtcatag      7500
atcctggtct aggcgacagg aaggatgaat gctttatgta catgtttctg ctgggggttg      7560
ttgaggacag cgatcccta gggcctccaa tcgggcgagc atttgggtcc ctgcccttag       7620
gtgttggcag atccacagca aagcccgaaa aactcctcaa agaggccact gagcttgaca      7680
tagttgttag acgtacagca gggctcaatg aaaaactggt gttctacaac aacaccccac      7740
taactctcct cacaccttgg agaaaggtcc taacaacagg gagtgtcttc aacgcaaacc      7800
aagtgtgcaa tgcggttaat ctgataccgc tcgataccc gcagaggttc cgtgttgttt       7860
atatgagcat cacccgtctt tcggataacg ggtattacac cgttcctaga agaatgctgg      7920
aattcagatc ggtcaatgca gtggccttca acctgctggt gacccttagg attgacaagg      7980
cgataggccc tgggaagatc atcgacaata cagagcaact tcctgaggca acatttatgg      8040
tccacatcgg gaacttcagg agaaagaaga gtgaagtcta ctctgccgat tattgcaaaa      8100
tgaaaatcga aagatgggc ctggttttg cacttggtgg datagggggc accagtcttc        8160
acattagaag cacaggcaaa atgagcaaga ctctccatgc acaactcggg ttcaagaaga      8220
ccttatgtta cccgctgata gatatcaatg aagaccttaa tcgattactc tggaggagca      8280
gatgcaagat agtaagaatc caggcagttt tgcagccatc agttcctcaa gaattccgca      8340
tttacgacga cgtgatcata aatgatgacc aaggactatt caaagttctg tagaccgtag      8400
tgcccagcaa tgcccgaaaa cgaccccct cacaatgaca gccagaaggc ccggacaaaa       8460 aagcccctc cgaaagactc cacgaccaa gcgagaggcc agccagcagc cgacggcaag        8520
cgcgaacacc aggcggcccc agcacagaac agccctgata caaggccacc accagccacc      8580
ccaatctgca tcctcctcgt gggaccccg aggaccaacc cccaaggctg ccccgatcc        8640 aaaccaccaa ccgcatcccc accaccccg ggaaagaaac cccagcaat tggaaggccc       8700 ctccccctct tcctcaacac aagaactcca caaccgaacc gcacaagcga ccgaggtgac      8760
ccaaccgcag gcatccgact ccctagacag atcctctctc cccggcaaac taaacaaaac      8820
ttagggccaa ggaacataca cacccaacag aacccagacc ccggcccacg gcgccgcgcc      8880 cccaacccc gacaaccaga gggagccccc aaccaatccc gccggctccc ccggtgccca       8940
caggcaggga caccaacccc cgaacagacc cagcacccaa ccatcgacaa tccaagacgg      9000
```

```
gggggccccc ccaaaaaaag gccccagggg gccgacagcc agcaccgcga ggaagcccac    9060 ccacccaca cacgaccacg gcaaccaaac cagaacccag accaccctgg gccaccagct     9120
cccagactcg gccatcaccc cgcagaaagg aaaggccaca acccgcgcac cccagccccg    9180
atccggcggg gagccaccca acccgaacca gcacccaaga gcgatccccg aaggacccca    9240
gaaccgcaaa ggacatcagt atcccacagc ctctccaagt cccccggtct cctccccttc    9300
tcgaagggac caaagatca atccaccaca cccgacgaca ctcaactccc cacccctaaa     9360
ggagacaccg ggaatcccag aatcaagact catccaatgt ccatcatggg tctcaaggtg    9420
aacgtctctg ccatattcat ggcagtactg ttaactctcc aaacacccac cggtcaaatc    9480 cattgggca atctctctaa gataggggtg gtaggaatag gaagtgcaag ctacaaagtt     9540
atgactcgtt ccagccatca atcattagtc ataaaattaa tgcccaatat aactctcctc    9600
aataactgca cgagggtaga gattgcagaa tacaggagac tactgagaac agttttggaa    9660
ccaattagag atgcacttaa tgcaatgacc cagaatataa gaccggttca gagtgtagct    9720
tcaagtagga gacacaagag atttgcggga gtagtcctgg caggtgcggc cctaggcgtc    9780
gccacagctg ctcagataac agccggcatt gcacttcacc agtccatgct gaactctcaa    9840
gccatcgaca atctgagagc gagcctggaa actactaatc aggcaattga ggcaatcaga    9900
caagcagggc aggagatgat attggctgtt cagggtgtcc aagactacat caataatgag    9960
ctgataccgt ctatgaacca actatcttgt gatttaatcg gccagaagct cgggctcaaa    10020
ttgctcagat actatacaga aatcctgtca ttatttggcc ccagcttacg ggaccccata    10080
tctgcggaga tatctatcca ggctttgagc tatgcgcttg gaggagacat caataaggtg    10140
ttagaaaagc tcggatacag tggaggtgat ttactgggca tcttagagag cagaggaata    10200
aaggcccgga taactcacgt cgacacagag tcctacttca ttgtcctcag tatagcctat    10260
ccgacgctgt ccgagattaa gggggtgatt gtccaccggc tagaggggt ctcgtacaac     10320 ataggctctc aagagtggta taccactgtg cccaagtatg ttgcaaccca agggtacctt    10380
atctcgaatt ttgatgagtc atcgtgtact ttcatgccag aggggactgt gtgcagccaa    10440 aatgcccttgt acccgatgag tcctctgctc caagaatgcc tccgggggtc caccaagtcc    10500
tgtgctcgta cactcgtatc cgggtctttt gggaaccggt tcattttatc acaagggaac   10560
ctaatagcca attgtgcatc aatcctttgc aagtgttaca caacaggaac gatcattaat   10620
caagaccctg acaagatcct aacatacatt gctgccgatc actgcccggt agtcgaggtg   10680 aacgcgtga ccatccaagt cgggagcagg aggtatccag atgctgtgta cttgcacaga    10740
attgacctcg gtcctcccat atcattggag aggttggacg tagggacaaa tctggggaat   10800
gcaattgcta agttggagga tgccaaggaa ttgttggagt catcggacca gatattgagg   10860
agtatgaaag gtttatcgag cactagcata gtctacatcc tgattgcagt gtgtcttgga   10920
gggttgatag ggatcccgc tttaatatgt tgctgcaggg gcgttgtaa caaaaaggga      10980 gaacaagttg gtatgtcaag accaggccta agcctgatc ttacgggaac atcaaaatcc    11040
tatgtaaggt cgctctgatc ctctacaact cttgaaacac aaatgtccca caagtctcct   11100
cttcgtcatc aagcaaccac cgcacccagc atcaagccca cctgaaatta tctccggctt   11160
ccctctggcc gaacaatatc ggtagttaat taaaacttag ggtgcaagat catccacaat   11220
gtcaccacaa cgagaccgga taatgccctt ctacaaagat aaccccatc ccaagggaag    11280 taggatagtc attaacagag aacatctat gattgataga ccttatgttt tgctggctgt    11340
tctgtttgtc atgtttctga gcttgatcgg gttgctagcc attgcaggca ttagacttca    11400
```

```
tcgggcagcc atctacaccg cagagatcca taaaagcctc agcaccaatc tagatgtaac    11460
taactcaatc gagcatcagg tcaaggacgt gctgacacca ctcttcaaaa tcatcggtga    11520
tgaagtgggc ctgaggacac ctcagagatt cactgaccta gtgaaattca tctctgacaa    11580
gattaaattc cttaatccgg ataggagta cgacttcaga gatctcactt ggtgtatcaa     11640
cccgccagag agaatcaaat tggattatga tcaatactgt gcagatgtgg ctgctgaaga    11700
gctcatgaat gcattggtga actcaactct actggagacc agaacaacca atcagttcct    11760
agctgtctca aagggaaact gctcagggcc cactacaatc agaggtcaat tctcaaacat    11820
gtcgctgtcc ctgttagact tgtatttagg tcgaggttac aatgtgtcat ctatagtcac    11880
tatgacatcc cagggaatgt atgggggaac ttacctagtg aaaagccta atctgagcag     11940 caaaaggtca gagttgtcac aactgagcat gtaccgagtg tttgaagtag gtgttatcag    12000
aaatccgggt ttgggggctc cggtgttcca tatgacaaac tatcttgagc aaccagccag    12060
taatgatctc agcaactgta tggtggcttt ggggagctc aaactcgcag ccctttgtca     12120
cggggaagat tctatcacaa ttccctatca gggatcaggg aaaggtgtca gcttccagct    12180
cgtcaagcta ggtgtctgga atccccaac cgacatgcaa tcctgggtcc ccttatcaac     12240
ggatgatcca gtgatagaca ggctttacct ctcatctcac agaggtgtta tcgctgacaa    12300
tcaagcaaaa tgggctgtcc cgacaacacg aacagatgac aagttgcgaa tggagacatg    12360
cttccaacag gcgtgtaagg gtaaaatcca agcactctgc gagaatcccg agtgggcacc    12420
attgaaggat aacaggattc cttcatacgg ggtcttgtct gttgatctga gtctgacagt    12480
tgagcttaaa atcaaaattg cttcgggatt cgggccattg atcacacacg gttcagggat    12540
ggacctatac aaatccaacc acaacaatgt gtattggctg actatcccgc caatgaagaa    12600
cctagcctta ggtgtaatca acacattgga gtggataccg agattcaagg ttagtcccta    12660
cctcttcaat gtcccaatta aggaagcagg cgaagactgc catgcccaa catacctacc     12720 tgcggaggtg gatggtgatg tcaaactcag ttccaatctg gtgattctac ctggtcaaga    12780
tctccaatat gttttggcaa cctacgatac ttccagggtt gaacatgctg tggtttatta    12840
cgtttacagc ccaggccgct catttttctta cttttatcct tttaggttgc ctataaaggg    12900
ggtccccatc gaattacaag tggaatgctt cacatgggac caaaaactct ggtgccgtca    12960
cttctgtgtg cttgcggact cagaatctgg tggacatatc actcactctg ggatggtggg    13020
catgggagtc agctgcacag tcacccggga agatggaacc aatcgcagat agggctgcta    13080
gtgaaccaat ctcatgatgt cacccagaca tcaggcatac ccactagtgt gaaatagaca    13140
tcagaattaa gaaaaacgta gggtccaagt ggttccccgt tatggactcg ctatctgtca    13200
accagatctt atacctgaa gttcacctag atagcccgat agttaccaat aagatagtag     13260
ccatcctgga gtatgctcga gtccctcacg cttacagcct ggaggaccct acactgtgtc    13320
agaacatcaa gcaccgccta aaaacggat tttccaacca aatgattata acaatgtgg      13380 aagttgggaa tgtcatcaag tccaagctta ggagttatcc ggcccactct catattccat    13440
atccaaattg taatcaggat ttatttaaca tagaagacaa agagtcaacg aggaagatcc    13500
gtgaactcct caaaaagggg aattcgctgt actccaaagt cagtgataag gttttccaat    13560
gcttaaggga cactaactca cggcttggcc taggctccga attgagggag gacatcaagg    13620
agaaagttat taacttggga gtttacatgc acagctccca gtggtttgag ccctttctgt    13680
tttggtttac agtcaagact gagatgaggt cagtgattaa atcacaaacc catacttgcc    13740
```

```
ataggaggag acacacacct gtattcttca ctggtagttc agttgagttg ctaatctctc  13800
gtgaccttgt tgctataatc agtaaagagt ctcaacatgt atattacctg acatttgaac  13860
tggttttgat gtattgtgat gtcatagagg ggaggttaat gacagagacc gctatgacta  13920
ttgatgctag gtatacagag cttctaggaa gagtcagata catgtggaaa ctgatagatg  13980
gtttcttccc tgcactcggg aatccaactt atcaaattgt agccatgctg gagcctcttt  14040
cacttgctta cctgcagctg agggatataa cagtagaact cagaggtgct ttccttaacc  14100
actgctttac tgaaatacat gatgttcttg accaaaacgg gttttctgat gaaggtactt  14160
atcatgagtt aattgaagct ctagattaca ttttcataac tgatgacata catctgacag  14220
gggagatttt ctcattttc agaagtttcg gccaccccag acttgaagca gtaacggctg  14280
ctgaaaatgt taggaaatac atgaatcagc ctaaagtcat tgtgtatgag actctgatga  14340
aaggtcatgc catattttgt ggaatcataa tcaacggcta tcgtgacagg cacggaggca  14400
gttggccacc gctgaccctc cccctgcatg ctgcagacac aatccggaat gctcaagctt  14460
caggtgaagg gttaacacat gagcagtgcg ttgataactg gagatctttt gctggagtga  14520
aatttggctg ctttatgcct cttagcctgg atagtgatct gacaatgtac ctaaaggaca  14580
aggcacttgc tgctctccaa agggaatggg attcagttta cccgaaagag ttcctgcgtt  14640
acgaccctcc caagggaacc gggtcacgga ggcttgtaga tgttttcctt aatgattcga  14700
gctttgaccc atatgatgtg ataatgtatg ttgtaagtgg agcttacctc catgaccctg  14760
agttcaacct gtcttacagc ctgaaagaaa aggagatcaa ggaaacaggt agacttttg  14820 ctaaaatgac ttacaaaatg agggcatgcc aagtgattgc tgaaaatcta atctcaaacg  14880
ggattggcaa atattttaag gacaatggga tggccaagga tgagcacgat ttgactaagg  14940
cactccacac tctagctgtc tcaggagtcc ccaaagatct caaagaaagt cacagggggg  15000
ggccagtctt aaaaacctac tcccgaagcc cagtccacac aagtaccagg aacgtgagag  15060
cagcaaaagg gtttataggg ttccctcaag taattcggca ggaccaagac actgatcatc  15120
cggagaatat ggaagcttac gagacagtca gtgcattat cacgactgat ctcaagaagt  15180
actgccttaa ttggagatat gagaccatca gcttgtttgc acagaggcta aatgagattt  15240
acggattgcc ctcattttc cagtggctgc ataagaggct tgagacctct gtcctgtatg  15300
taagtgaccc tcattgcccc cccgaccttg acgcccatat cccgttatat aaagtcccca  15360
atgatcaaat cttcattaag taccctatgg gaggtataga agggtattgt cagaagctgt  15420
ggaccatcag caccattccc tatctatacc tggctgctta tgagagcgga gtaaggattg  15480
cttcgttagt gcaaggggac aatcagacca tagccgtaac aaaaagggta cccagcacat  15540 ggcctacaa ccttaagaaa cgggaagctg ctagagtaac tagagattac tttgtaattc  15600
ttaggcaaag gctacatgat attggccatc acctcaaggc aaatgagaca attgtttcat  15660
cacatttttt tgtctattca aaaggaatat attatgatgg gctacttgtg tcccaatcac  15720
tcaagagcat cgcaagatgt gtattctggt cagagactat agttgatgaa caagggcag  15780 catgcagtaa tattgctaca acaatggcta aaagcatcga gagaggttat gaccgttacc  15840
ttgcatattc cctgaacgtc ctaaaagtga tacagcaaat tctgatctct cttggcttca  15900
caatcaattc aaccatgacc cgggatgtag tcatacccct cctcacgaac aacgacctct  15960
taataaggat ggcactgttg cccgctccta ttgggggat gaattatctg aatatgcaca  16020
ggctgtttgt cagaaacatc ggtgatccag taacatcatc aattgctgat ctcaagaaa  16080 tgattctcgc ctcactaatg cctgaagaga ccctccatca gtaatgaca caacaaccgg  16140
```

```
gggactcttc attcctagac tgggctagcg acccttactc agcaaatctt gtatgtgtcc    16200
agagcatcac tagactcctc aagaacataa ctgcaaggtt tgtcctgatc catagtccaa    16260
acccaatgtt aaaaggatta ttccatgatg acagtaaaga agaggacgag ggactggcgg    16320
cattcctcat ggacaggcat attatagtac ctagggcagc tcatgaaatc ctggatcata    16380
gtgtcacagg ggcaagagag tctattgcag gcatgctgga taccacaaaa ggcctgattc    16440
gagccagcat gaggaagggg gggttaacct ctcgagtgat aaccagattg tccaattatg    16500
actatgaaca attcagagca gggatggtgc tattgacagg aagaaagaga aatgtcctca    16560
ttgacaaaga gtcatgttca gtgcagctgg cgagagctct aagaagccat atgtgggcga    16620
ggctagctcg aggacggcct atttacggcc ttgaggtccc tgatgtacta aatctatgc    16680 gaggccacct tattcggcgt catgagacat gtgtcatctg cgagtgtgga tcagtcaact    16740
acggatggtt ttttgtcccc tcgggttgcc aactggatga tattgacaag gaaacatcat    16800
ccttgagagt cccatatatt ggttctacca ctgatgagag aacagacatg aagcttgcct    16860
tcgtaagagc cccaagtcga tccttgcgat ctgctgttag aatagcaaca gtgtactcat    16920
gggcttacgg tgatgatgat agctcttgga acgaagcctg gttgttggct aggcaaaggg    16980
ccaatgtgag cctggaggag ctaagggtga tcactcccat ctcaacttcg actaatttag    17040
cgcataggtt gagggatcgt agcactcaag tgaaatactc aggtacatcc cttgtccgag    17100
tggcgaggta taccacaatc tccaacgaca atctctcatt tgtcatatca gataagaagg    17160
ttgatactaa ctttatatac caacaaggaa tgcttctagg gttgggtgtt ttagaaacat    17220
tgtttcgact cgagaaagat accggatcat ctaacacggt attacatctt cacgtcgaaa    17280
cagattgttg cgtgatcccg atgatagatc atcccaggat acccagctcc cgcaagctag    17340
agctgagggc agagctatgt accaacccat tgatatatga taatgcacct ttaattgaca    17400
gagatacaac aaggctatac acccagagcc ataggaggca ccttgtggaa tttgttacat    17460
ggtccacacc ccaactatat cacatttag ctaagtccac agcactatct atgattgacc    17520
tggtaacaaa atttgagaag gaccatatga atgaaatttc agctctcata ggggatgacg    17580
atatcaatag tttcataact gagtttctgc tcatagagcc aagattattc actatctact    17640
tgggccagtg tgcggccatc aattgggcat tgatgtaca ttatcataga ccatcaggga    17700
aatatcagat gggtgagctg ttgtcatcgt tcctttctag aatgagcaaa ggagtgttta    17760
aggtgcttgt caatgctcta agccaccccaa agatctacaa gaaattctgg cattgtggta    17820
ttatagagcc tatccatggt ccttcacttg atgctcaaaa cttgcacaca actgtgtgca    17880
acatggttta cacatgctat atgacctacc tcgacctgtt gttgaatgaa gagttagaag    17940
agttcacatt tctcttgtgt gaaagcgacg aggatgtagt accggacaga ttcgacaaca    18000
tccaggcaaa acacttatgt gttctggcag atttgtactg tcaaccaggg acctgcccac    18060
caattcgagg tctaagaccg gtagagaaat gtgcagttct aaccgaccat atcaaggcag    18120
aggctaggtt atctccagca ggatcttcgt ggaacataaa tccaattatt gtagaccatt    18180
actcatgctc tctgacttat ctccggcgag gatcgatcaa acagataaga ttgagagttg    18240
atccaggatt cattttcgac gccctcgctg aggtaaatgt cagtcagcca aagatcggca    18300
gcaacaacat ctcaaatatg agcatcaagg ctttcagacc cccacacgat gatgttgcaa    18360
aattgctcaa agatatcaac acaagcaagc acaatcttcc catttcaggg ggcaatctcg    18420
ccaattatga aatccatgct ttccgcagaa tcgggttgaa ctcatctgct tgctacaaag    18480
```

```
ctgttgagat atcaacatta attaggagat gccttgagcc aggggaggac ggcttgttct   18540
tgggtgaggg atcggttcc atgttgatca cttataagga gatacttaaa ctaaacaagt    18600
gcttctataa tagtggggtt tccgccaatt ctagatctgg tcaaagggaa ttagcaccct   18660
atccctccga agttggcctt gtcgaacaca gaatgggagt aggtaatatt gtcaaagtgc   18720
tctttaacgg gaggcccgaa gtcacgtggg taggcagtgt agattgcttc aatttcatag   18780
ttagtaatat ccctacctct agtgtggggt ttatccattc agatatagag accttgccta   18840
acaaagatac tatagagaag ctagaggaat tggcagccat cttatcgatg gctctgctcc   18900
tgggcaaaat aggatcaata ctggtgatta agcttatgcc tttcagcggg gattttgttc   18960
agggatttat aagttatgta gggtcccatt atagagaagt gaaccttgta taccctagat   19020
acagcaactt catatctact gaatcttatt tggttatgac agatctcaag gctaaccggc   19080
taatgaatcc tgaaaagatt aagcagcaga taattgaatc atctgtgagg acttcacctg   19140
gacttatagg tcacatccta tccattaagc aactaagctg catacaagca attgtgggag   19200
acgcagttag tagaggtgat atcaatccta ctctgaaaaa acttacacct atagagcagg   19260
tgctgatcaa ttgcggggttg gcaattaacg gacctaagct gtgcaaagaa ttgatccacc   19320
atgatgttgc ctcagggcaa gatggattgc ttaattctat actcatcctc tacagggagt   19380
tggcaagatt caaagacaac caaagaagtc aacagggat gttccacgct taccccgtat    19440
tggtaagtag caggcaacga gaacttatat ctaggatcac ccgcaaattt tgggggcaca   19500
ttcttcttta ctccgggaac agaaagttga taaataagtt tatccagaat ctcaagtccg   19560
gctatctgat actagactta caccagaata tcttcgttaa gaatctatcc aagtcagaga   19620
aacagattat tatgacgggg ggtttgaaac gtgagtgggt ttttaaggta acagtcaagg   19680
agaccaaaga atggtataag ttagtcggat acagtgccct gattaaggac taattggttg   19740
aactccggaa ccctaatcct gccctaggtg gttaggcatt atttgcaata gattaaagaa   19800
aactttgaaa atacgaagtt tctattccca gctttgtctg gtggccggca tggtcccagc   19860
ctcctcgctg gcgccggctg ggcaacattc cgaggggacc gtcccctcgg taatggcgaa   19920
tgggacgcgg ccgatccggc tgctaacaaa gcccgaaagg aagctgagtt ggctgctgcc   19980
accgctgagc aataactagc ataaccccctt ggggcctcta acgggtctt gaggggtttt   20040 ttgctgaaag gaggaactat atccggatgc ggccgatccg gctgctaaca aagcccgaaa   20100
ggaagctgag ttggctgctg ccaccgctga gcaataacta gcataacccc ttggggcctc   20160
taaacgggtc ttgagggtt ttttgctgaa aggaggaact atatccggat ggccgccacc    20220
ggccggtggg ccttgcagca catccccctt tcgccagctg gcgtaatagc gaagaggccc   20280
gcaccgatcg ccccttccaa cagttgcgca gcctgaatgg cgaatgggac gcgccctgta   20340
gcggcgcatt aagcgcggcg ggtgtggtgg ttacgcgcag cgtgaccgct acacttgcca   20400
gcgccctagc gcccgctcct ttcgctttct cccttcctt tctcgccacg ttcgccggct    20460
tcccccgtca gctctaaat cgggggctcc ctttagggtt ccgatttagt gctttacggc    20520
acctcgaccc caaaaaactt gattagggtg atggttcacg tgggccatcg ccctgataga   20580
cggtttttcg ccctttgacg ttggagtcca cgttctttaa tagtggactc ttgttccaaa   20640
ctggaacaac actcaacccct atctcggtct attctttga tttataaggg attttgccga   20700
tttcggccta ttggttaaaa atgagctga tttaacaaaa atttaacgcg aattttaaca    20760
aaatattaac gcttacaatt taggtggcac ttttcgggga aatgtgcgcg gaaccccctat   20820 ttgtttattt ttctaaatac attcaaatat gtatccgctc atgagacaat aaccctgata   20880
```

```
aatgcttcaa taatattgaa aaaggaagag tatgagtatt caacatttcc gtgtcgccct   20940
tattcccttt tttgcggcat tttgccttcc tgttttttgct cacccagaaa cgctggtgaa   21000
agtaaaagat gctgaagatc agttgggtgc acgagtgggt tacatcgaac tggatctcaa   21060
cagcggtaag atccttgaga gttttcgccc gaagaacgt tttccaatga tgagcacttt   21120
taaagttctg ctatgtggcg cggtattatc ccgtattgac gccgggcaag agcaactcgg   21180
tcgccgcata cactattctc agaatgactt ggttgagtac tcaccagtca cagaaaagca   21240
tcttacggat ggcatgacag taagagaatt atgcagtgct gccataacca tgagtgataa   21300
cactgcggcc aacttacttc tgacaacgat cggaggaccg aaggagctaa ccgctttttt   21360
gcacaacatg ggggatcatg taactcgcct tgatcgttgg gaaccggagc tgaatgaagc   21420
cataccaaac gacgagcgtg acaccacgat gcctgtagca atggcaacaa cgttgcgcaa   21480
actattaact ggcgaactac ttacactagc ttcccggcaa caattaatag actggatgga   21540
ggcggataaa gttgcaggac cacttctgcg ctcggccctt ccggctggct ggtttattgc   21600
tgataaatct ggagccggtg agcgtgggtc tcgcggtatc attgcagcac tggggccaga   21660
tggtaagccc tcccgtatcg tagttatcta cacgacgggg agtcaggcaa ctatggatga   21720
acgaaataga cagatcgctg agataggtgc ctcactgatt aagcattggt aactgtcaga   21780
ccaagtttac tcatatatac tttagattga tttaaaactt cattttttaat ttaaaaggat   21840 ctaggtgaag atccttttttg ataatctcat gaccaaaatc ccttaacgtg agttttcgtt   21900
ccactgagcg tcagaccccg tagaaaagat caaaggatct tcttgagatc ctttttttct   21960
gcgcgtaatc tgctgcttgc aaacaaaaaa accaccgcta ccagcggtgg tttgtttgcc   22020
ggatcaagag ctaccaactc tttttccgaa ggtaactggc ttcagcagag cgcagatacc   22080
aaatactgtt cttctagtgt agccgtagtt aggccaccac ttcaagaact ctgtagcacc   22140
gcctacatac ctcgctctgc taatcctgtt accagtggct gctgccagtg gcgataagtc   22200
gtgtcttacc gggttggact caagacgata gttaccggat aaggcgcagc ggtcgggctg   22260
aacggggggt tcgtgcacac agcccagctt ggagcgaacg acctacaccg aactgagata   22320
cctacagcgt gagctatgag aaagcgccac gcttcccgaa gggagaaagg cggacaggta   22380
tccggtaagc ggcagggtcg gaacaggaga gcgcacgagg gagcttccag ggggaaacgc   22440
ctggtatctt tatagtcctg tcgggtttcg ccacctctga cttgagcgtc gatttttgtg   22500
atgctcgtca gggggggcgga gcctatggaa aaacgccagc aacgcggcct ttttacggtt   22560
cctggccttt tgctggcctt ttgctcacat gttctttcct gcgttatccc ctgattctgt   22620
ggataaccgt attaccgcct ttgagtgagc tgataccgct cgccgcagcc gaacgaccga   22680
gcgcagcgag tcagtgagcg aggaagcgga agagcgccca atacgcaaac cgcctctccc   22740
cgcgcgttgg ccgattcatt aatgcagctg gcacgacagg tttcccgact ggaaagcggg   22800
cagtgagcgc aacgcaatta atgtgagtta gctcactcat taggcacccc aggctttaca   22860
ctttatgctt ccggctcgta tgttgtgtgg aattgtgagc ggacaacaat ttcacacagg   22920
aaacagctat gaccatgatt acgccaagct cgggcggccg cttgtaatac gactcactat   22980
a                                                                  22981
```

<210> SEQ ID NO 17
<211> LENGTH: 22981
<212> TYPE: DNA
<213> ORGANISM: Artificial Sequence
<220> FEATURE:

<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S-CO-AA

<400> SEQUENCE: 17

```
accaaacaaa gttgggtaag gatagttcaa tcaatgatca ttttctagtg cacttaggat      60
tcaagatcct attatcaggg acaagagcag gattaaggat atccgagatg gccacacttt     120
taaggagctt agcattgttc aaaagaaaca aggacaaacc acccattaca tcaggatccg     180
gtggagccat cagaggaatc aaacacatta ttatagtacc aatccctgga gattcctcaa     240
ttaccactcg atccagactt ctggaccggt tggtcaggtt aattggaaac ccggatgtga     300
gcgggcccaa actaacaggg gcactaatag gtatattatc cttatttgtg gagtctccag     360
gtcaattgat tcagaggatc accgatgacc ctgacgttag cataaggctg ttagaggttg     420
tccagagtga ccagtcacaa tctggcctta ccttcgcatc aagaggtacc aacatggagg     480
atgaggcgga ccaatacttt tcacatgatg atccaattag tagtgatcaa tccaggttcg     540
gatggttcga gaacaaggaa atctcagata ttgaagtgca agaccctgag ggattcaaca     600
tgattctggg taccatccta gctcaaattt gggtcttgct cgcaaaggcg ttacggccc      660
cagacacggc agctgattcg gagctaagaa ggtggataaa gtacacccaa caaagaaggg     720
tagttggtga atttagattg gagagaaaat ggttggatgt ggtgaggaac aggattgccg     780
aggacctctc cttacgccga ttcatggtcg ctctaatcct ggatatcaag gaacacccg      840
gaaacaaacc caggattgct gaaatgatat gtgacattga tacatatatc gtagaggcag     900
gattagccag ttttatcctg actattaagt ttgggataga aactatgtat cctgctcttg     960
gactgcatga atttgctggt gagttatcca cacttgagtc cttgatgaac ctttaccagc    1020
aaatggggga aactgcaccc tacatggtaa tcctggagaa ctcaattcag aacaagttca    1080
gtgcaggatc atacccctctg ctctggagct atgccatggg agtaggagtg aacttgaaa    1140
actccatggg aggtttgaac tttggccgat cttactttga tccagcatat tttagattag    1200
ggcaagagat ggtaaggagg tcagctggaa aggtcagttc cacattggca tctgaactcg    1260
gtatcactgc cgaggatgca aggcttgttt cagagattgc aatgcatact actgaggaca    1320
agatcagtag agcggttgga cccagacaag cccaagtatc atttctacac ggtgatcaaa    1380
gtgagaatga gctaccgaga ttgggggggca aggaagatag gagggtcaaa cagagtcgag    1440
gagaagccag ggagagctac agagaaaccg ggcccagcag agcaagtgat gcgagagctg    1500
cccatcttcc aaccggcaca cccctagaca ttgacactgc atcggagtcc agccaagatc    1560
cgcaggacag tcgaaggtca gctgacgccc tgcttaggct gcaagccatg gcaggaatct    1620
cggaagaaca aggctcagac acggacaccc ctatagtgta caatgacaga aatcttctag    1680
actaggtgcg agaggccgag gaccagaaca acatccgcct accctccatc attgttataa    1740
aaaacttagg aaccaggtcc acacagccgc cagcccatca accatccact cccacgattg    1800
gagccgatgg cagaagagca ggcacgccat gtcaaaaacg gactggaatg catccgggct    1860
ctcaaggccg agcccatcgg ctcactggcc atcgaggaag ctatggcagc atggtcagaa    1920
atatcagaca acccaggaca ggagcgagcc acctgcaggg aagagaaggc aggcagttcg    1980
ggtctcagca aaccatgcct ctcagcaatt ggatcaactg aaggcggtgc acctcgcatc    2040
cgcggtcagg gacctggaga gagcgatgac gacgctgaaa ctttgggaat cccccaaga    2100
aatctccagg catcaagcac tgggttacag tgttattatg tttatgatca cagcggtgaa    2160
```

```
gcggttaagg gaatccaaga tgctgactct atcatggttc aatcaggcct tgatggtgat    2220
agcaccctct caggaggaga caatgaatct gaaaacagcg atgtggatat tggcgaacct    2280
gataccgagg gatatgctat cactgaccgg ggatctgctc ccatctctat ggggttcagg    2340
gcttctgatg ttgaaactgc agaaggaggg gagatccacg agctcctgag actccaatcc    2400
agaggcaaca actttccgaa gcttgggaaa actctcaatg ttcctccgcc tccggacccc    2460
ggtagggcca gcacttccgg gacacccatt aaaaagggca cagacgcgag attagcctca    2520
tttggaacgg agatcgcgtc tttattgaca ggtggtgcaa cccaatgtgc tcgaaagtca    2580
ccctcggaac catcagggcc aggtgcacct gcgggaatg tccccgagtg tgtgagcaat     2640
gccgcactga tacaggagtg gacacccgaa tctggtacca caatctcccc gagatcccag    2700
aataatgaag aaggggagag ctattatgat gatgagctgt tctctgatgt ccaagatatt    2760
aaaacagcct tggccaaaat acacgaggat aatcagaaga taatctccaa gctagaatca    2820
ctgctgttat tgaagggaga agttgagtca attaagaagc agatcaacag gcaaaatatc    2880
agcatatcca ccctggaagg acacctctca agcatcatga tcgccattcc tggacttggg    2940
aaggatccca cgaccccac tgcagatgtc gaaatcaatc ccgacttgaa acccatcata     3000
ggcagagatt caggccgagc actggccgaa gttctcaaga aacccgttgc cagccgacaa    3060
ctccaaggaa tgacaaatgg acggaccagt tccagaggac agctgctgaa ggaatttcag    3120
ctaaagccga tcgggaaaaa gatgagctca gccgtcgggt tgttcctga caccggccct     3180 gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc aacccccatg    3360
ccagtcgacc caactagtac aacctaaatc cattataaaa aacttaggag caaagtgatt    3420
gcctcccaag ttccacaggc gcgccatgtt cgtcttcctg gtcctgctgc ctctggtctc    3480
ctcacagtgc gtcaatctga caactcggac tcagctgcca cctgcttata ctaatagctt    3540
caccagaggc gtgtactatc ctgacaaggt gtttagaagc tccgtgctgc actctacaca    3600
ggatctgttt ctgccattct ttagcaacgt gacctggttc cacgccatcc acgtgagcgg    3660
caccaatggc acaaagcggt tcgacaatcc cgtgctgcct tttaacgatg cgtgtacttt     3720
cgcctctacc gagaagagca acatcatcag aggctggatc tttggcacca cactggactc    3780
caagacacag tctctgctga tcgtgaacaa tgccaccaac gtggtcatca aggtgtgcga    3840
gttccagttt tgtaatgatc ccttcctggg cgtgtactat cacaagaaca ataagagctg    3900
gatggagtcc gagtttagag tgtattctag cgccaacaac tgcacatttg agtacgtgag    3960 ccagccttc ctgatggacc tggagggcaa gcagggcaat ttcaagaacc tgagggagtt     4020
cgtgtttaag aatatcgacg gctacttcaa aatctactct aagcacaccc ccatcaacct    4080
ggtgcgcgac ctgcctcagg gcttcagcgc cctggagccc ctggtggatc tgcctatcgg    4140
catcaacatc acccggttc agacactgct ggccctgcac agaagctacc tgacacccgg     4200
cgactcctct agcggatgga ccgccggcgc tgccgcctac tatgtgggct acctccagcc    4260
ccggaccttc ctgctgaagt acaacgagaa tggcaccatc acagacgcag tggattgcgc    4320
cctggacccc ctgagcgaga caaagtgtac actgaagtcc tttaccgtgg agaagggcat    4380
ctatcagaca tccaatttca gggtgcagcc aaccgagtct atcgtgcgct ttcctaatat    4440
cacaaacctg tgcccatttg gcgaggtgtt caacgcaacc cgcttcgcca gcgtgtacgc    4500
```

```
ctggaatagg aagcggatca gcaactgcgt ggccgactat agcgtgctgt acaactccgc   4560
ctctttcagc acctttaagt gctatggcgt gtcccccaca aagctgaatg acctgtgctt   4620
taccaacgtc tacgccgatt ctttcgtgat caggggcgac gaggtgcgcc agatcgcccc   4680
cggccagaca ggcaagatcg cagactacaa ttataagctg ccagacgatt tcaccggctg   4740
cgtgatcgcc tggaacagca acaatctgga ttccaaagtg ggcggcaact acaattatct   4800
gtaccggctg tttagaaaga gcaatctgaa gcccttcgag agggacatct ctacagaaat   4860
ctaccaggcc ggcagcaccc cttgcaatgg cgtggagggc tttaactgtt atttcccact   4920
ccagtcctac ggcttccagc ccacaaacgg cgtgggctat cagccttacc gcgtggtggt   4980
gctgagcttt gagctgctgc acgccccagc aacagtgtgc ggccccaaga agtccaccaa   5040
tctggtgaag aacaagtgcg tgaacttcaa cttcaacggc ctgaccggca caggcgtgct   5100
gaccgagtcc aacaagaagt tcctgccatt tcagcagttc ggcagggaca tcgcagatac   5160
cacagacgcc gtgcgcgacc acagaccct ggagatcctg gacatcacac cctgctcttt   5220
cggcggcgtg agcgtgatca cacccggcac caatacaagc aaccaggtgg ccgtgctgta   5280
tcaggacgtg aattgtaccg aggtgcccgt ggctatccac gccgatcagc tgaccccaac   5340
atggcgggtg tacagcaccg gctccaacgt cttccagaca agagccggat gcctgatcgg   5400
agcagagcac gtgaacaatt cctatgagtg cgacatccca atcggcgccg gcatctgtgc   5460
ctcttaccag acccagacaa actctcccag aagagcccgg agcgtggcct ccagtctat   5520
catcgcctat accatgtccc tgggcgccga aacagcgtg cctactcta acaatagcat   5580
cgccatccca accaacttca caatctctgt gaccacagag atcctgcccg tgtccatgac   5640
caagacatct gtggactgca caatgtatat ctgtggcgat tctaccgagt gcagcaacct   5700
gctgctccag tacggcagct tttgtaccca gctgaataga gccctgacag gcatcgccgt   5760
ggagcaggat aagaacacac aggaggtgtt cgcccaggtg aagcaaatct acaagacccc   5820
ccctatcaag gactttggcg gcttcaattt ttccccagatc ctgcctgatc catccaagcc   5880
ttctaagcgg agctttatcg aggacctgct gttcaacaag gtgaccctgg ccgatgccgg   5940
cttcatcaag cagtatggcg attgcctggg cgacatcgca gccagggacc tgatctcgc   6000
ccagaagttt aatggcctga ccgtgctgcc accctgctg acagatgaga tgatcgcaca   6060
gtacacaagc gccctgctgg ccggcaccat cacatccgga tggaccttcg gcgcaggagc   6120
cgccctccag atccccttg ccatgcagat ggcctatagg ttcaacggca tcggcgtgac   6180
ccagaatgtg ctgtacgaga accagaagct gatcgccaat cagtttaact ccgccatcgg   6240
caagatccag acagcctgt cctctacagc cagcgccctg ggcaagctcc aggatgtggt   6300
gaatcagaac gcccaggccc tgaataccct ggtgaagcag ctgagcagca acttcggcgc   6360
catctctagc gtgctgaatg acatcctgag ccggctggac aaggtggagg cagaggtgca   6420
gatcgaccgg ctgatcaccg gccggctcca gagcctccag acctatgtga cacagcagct   6480
gatcagggcc gccgagatca gggccagcgc caatctggca gcaaccaaga tgtccgagtg   6540
cgtgctgggc cagtctaaga gagtggactt tgtggcaag ggctatcacc tgatgtcctt   6600
ccctcagtct gccccacacg gcgtggtgtt tctgcacgtg acctacgtgc cgcccagga   6660
gaagaacttc accacagccc tgccatctg ccacgatggc aaggcccact tccaaggga   6720
gggcgtgttc gtgtccaacg gcacccactg gtttgtgaca cagcgcaatt tctacgagcc   6780
ccagatcatc accacagaca acaccttcgt gagcggcaac tgtgacgtgg tcatcggcat   6840
cgtgaacaat accgtgtatg atccactcca gcccgagctg gacagcttta aggaggagct   6900
```

```
ggataagtat tcaagaatc acacctcccc tgacgtggat ctgggcgaca tcagcggcat   6960
caatgcctcc gtggtgaaca tccagaagga gatcgaccgc ctgaacgagg tggctaagaa   7020
tctgaacgag agcctgatcg acctccagga gctgggcaag tatgagcagt acatcaagtg   7080
gccctggtac atctggctgg gcttcatcgc cggcctgatc gccatcgtga tggtgaccat   7140
catgctgtgc tgtatgacat cctgctgttc ttgcctgaag ggctgctgta gctgtggctc   7200
ctgctgtaag tttgacgagg atgactctga acctgtgctg aagggcgtgg cgctggctta   7260
cacctaacgc gcgacgtcct acagctcaac ttacctgcca accccatgcc agtcgaccca   7320
actagtacaa cctaaatcca ttataaaaaa cttaggagca aagtgattgc ctcccaagtt   7380
ccacaatgac agagatctac gacttcgaca gtcggcatg gacatcaaa gggttgatcg     7440 ctccgataca acccaccacc tacagtgatg gcaggctggt gccccaggtc agagtcatag   7500
atcctggtct aggcgacagg aaggatgaat gctttatgta catgtttctg ctgggggttg   7560
ttgaggacag cgatccccta gggcctccaa tcgggcgagc atttgggtcc ctgcccttag   7620
gtgttggcag atccacagca aagcccgaaa aactcctcaa agaggccact gagcttgaca   7680
tagttgttag acgtacagca gggctcaatg aaaaactggt gttctacaac aacaccccac   7740
taactctcct cacaccttgg agaaaggtcc taacaacagg gagtgtcttc aacgcaaacc   7800
aagtgtgcaa tgcggttaat ctgataccgc tcgataccc gcagaggttc cgtgttgttt     7860
atatgagcat cacccgtctt tcggataacg ggtattacac cgttcctaga agaatgctgg   7920
aattcagatc ggtcaatgca gtggccttca acctgctggt gacccttagg attgacaagg   7980
cgataggccc tgggaagatc atcgacaata cagagcaact tcctgaggca acatttatgg   8040
tccacatcgg gaacttcagg agaaagaaga gtgaagtcta ctctgccgat tattgcaaaa   8100
tgaaaatcga aagatgggc ctggtttttg cacttggtgg gatagggggc accagtcttc     8160
acattagaag cacaggcaaa atgagcaaga ctctccatgc acaactcggg ttcaagaaga   8220
ccttatgtta cccgctgata gatatcaatg aagaccttaa tcgattactc tggaggagca   8280
gatgcaagat agtaagaatc caggcagttt tgcagccatc agttcctcaa gaattccgca   8340
tttacgacga cgtgatcata aatgatgacc aaggactatt caaagttctg tagaccgtag   8400
tgcccagcaa tgcccgaaaa cgaccccct cacaatgaca gccagaaggc ccggacaaaa     8460 aagcccctc cgaaagactc cacggaccaa gcgagaggcc agccagcagc cgacggcaag   8520
cgcgaacacc aggcggcccc agcacagaac agccctgata caaggccacc accagccacc   8580
ccaatctgca tcctcctcgt gggaccccg aggaccaacc cccaaggctg ccccgatcc     8640 aaaccaccaa ccgcatcccc accacccccg ggaaagaaac cccagcaat tggaaggccc     8700 ctcccctct tcctcaacac aagaactcca caaccgaacc gcacaagcga ccgaggtgac     8760
ccaaccgcag gcatccgact ccctagacag atcctctctc cccggcaaac taaacaaaac   8820
ttagggccaa ggaacataca cacccaacag aacccagacc ccggcccacg gcgccgcgcc   8880 cccaacccc gacaaccaga gggagccccc aaccaatccc gccggctccc ccggtgccca     8940
caggcaggga caccaacccc gaacagacc cagcacccaa ccatcgacaa tccaagacgg     9000 ggggccccc ccaaaaaaag gccccaggg gccgacagca agcaccgcga ggaagcccac       9060
ccaccccaca cacgaccacg gcaaccaaac cagaacccag accaccctgg gccaccagct   9120
cccagactcg gccatcaccc cgcagaaagg aaaggccaca acccgcgcac cccagccccg   9180
atccggcggg gagccaccca acccgaacca gcacccaaga gcgatccccg aaggacccc     9240
```

```
gaaccgcaaa ggacatcagt atcccacagc ctctccaagt cccccggtct cctcccttc      9300 tcgaagggac caaaagatca atccaccaca cccgacgaca ctcaactccc caccccctaaa    9360 ggagacaccg ggaatcccag aatcaagact catccaatgt ccatcatggg tctcaaggtg    9420
aacgtctctg ccatattcat ggcagtactg ttaactctcc aaacacccac cggtcaaatc    9480
cattggggca atctctctaa gataggggtg gtaggaatag gaagtgcaag ctacaaagtt    9540
atgactcgtt ccagccatca atcattagtc ataaaattaa tgcccaatat aactctcctc    9600
aataactgca cgagggtaga gattgcagaa tacaggagac tactgagaac agttttggaa    9660
ccaattagag atgcacttaa tgcaatgacc cagaatataa gaccggttca gagtgtagct    9720
tcaagtagga gacacaagag atttgcggga gtagtcctgg caggtgcggc cctaggcgtc    9780
gccacagctg ctcagataac agccggcatt gcacttcacc agtccatgct gaactctcaa    9840
gccatcgaca atctgagagc gagcctggaa actactaatc aggcaattga ggcaatcaga    9900
caagcagggc aggagatgat attggctgtt cagggtgtcc aagactacat caataatgag    9960
ctgataccgt ctatgaacca actatcttgt gatttaatcg ccagaagct cgggctcaaa    10020 ttgctcagat actatacaga aatcctgtca ttatttggcc ccagcttacg ggaccccata    10080
tctgcggaga tatctatcca ggctttgagc tatgcgcttg gaggagacat caataaggtg    10140
ttagaaaagc tcggatacag tggaggtgat ttactgggca tcttagagag cagaggaata    10200
aaggcccgga taactcacgt cgacacagag tcctacttca ttgtcctcag tatagcctat    10260
ccgacgctgt ccgagattaa gggggtgatt gtccaccggc tagaggggt ctcgtacaac    10320 ataggctctc aagagtggta taccactgtg cccaagtatg ttgcaaccca agggtacctt    10380
atctcgaatt ttgatgagtc atcgtgtact ttcatgccag aggggactgt gtgcagccaa    10440
aatgccttgt acccgatgag tcctctgctc aagaatgcc tccggggtc caccaagtcc    10500 tgtgctcgta cactcgtatc cgggtctttt gggaaccggt tcattttatc acaagggaac    10560
ctaatagcca attgtgcatc aatcctttgc aagtgttaca caacaggaac gatcattaat    10620
caagaccctg acaagatcct aacatacatt gctgccgatc actgcccggt agtcgaggtg    10680
aacggcgtga ccatccaagt cgggagcagg aggtatccag atgctgtgta cttgcacaga    10740
attgacctcg gtcctcccat atcattggag aggttggacg tagggacaaa tctggggaat    10800
gcaattgcta agttggagga tgccaaggaa ttgttggagt catcggacca gatattgagg    10860
agtatgaaag gtttatcgag cactagcata gtctacatcc tgattgcagt gtgtcttgga    10920
gggttgatag ggatcccgc tttaatatgt tgctgcaggg ggcgttgtaa caaaaaggga    10980
gaacaagttg gtatgtcaag accaggccta agcctgatc ttacgggaac atcaaaatcc    11040
tatgtaaggt cgctctgatc ctctacaact cttgaaacac aaatgtccca caagtctcct    11100
cttcgtcatc aagcaaccac cgcacccagc atcaagccca cctgaaatta tctccggctt    11160
ccctctggcc gaacaatatc ggtagttaat taaaacttag ggtgcaagat catccacaat    11220
gtcaccacaa cgagaccgga taaatgcctt ctacaaagat aaccccatc caagggaag    11280 taggatagtc attaacagag aacatcttat gattgataga ccttatgttt tgctggctgt    11340
tctgtttgtc atgtttctga gcttgatcgg gttgctagcc attgcaggca ttagacttca    11400
tcgggcagcc atctacaccg cagagatcca taaaagcctc agcaccaatc tagatgtaac    11460
taactcaatc gagcatcagg tcaaggacgt gctgacacca ctcttcaaaa tcatcggtga    11520
tgaagtgggc ctgaggacac ctcagagatt cactgaccta gtgaaattca tctctgacaa    11580
gattaaattc cttaatccgg ataggagta cgacttcaga gatctcactt ggtgtatcaa    11640
```

```
cccgccagag agaatcaaat tggattatga tcaatactgt gcagatgtgg ctgctgaaga   11700
gctcatgaat gcattggtga actcaactct actggagacc agaacaacca atcagttcct   11760
agctgtctca aagggaaact gctcagggcc cactacaatc agaggtcaat tctcaaacat   11820
gtcgctgtcc ctgttagact tgtatttagg tcgaggttac aatgtgtcat ctatagtcac   11880
tatgacatcc cagggaatgt atgggggaac ttacctagtg gaaaagccta atctgagcag   11940
caaaaggtca gagttgtcac aactgagcat gtaccgagtg tttgaagtag gtgttatcag   12000
aaatccgggt ttgggggctc cggtgttcca tatgacaaac tatcttgagc aaccagccag   12060
taatgatctc agcaactgta tggtggcttt gggggagctc aaactcgcag ccctttgtca   12120
cggggaagat tctatcacaa ttccctatca gggatcaggg aaaggtgtca gcttccagct   12180
cgtcaagcta ggtgtctgga aatccccaac cgacatgcaa tcctgggtcc ccttatcaac   12240
ggatgatcca gtgatagaca ggctttacct ctcatctcac agaggtgtta tcgctgacaa   12300
tcaagcaaaa tgggctgtcc cgacaacacg aacagatgac aagttgcgaa tggagacatg   12360
cttccaacag gcgtgtaagg gtaaaatcca agcactctgc gagaatcccg agtgggcacc   12420
attgaaggat aacaggattc cttcatacgg ggtcttgtct gttgatctga gtctgacagt   12480
tgagcttaaa atcaaaattg cttcgggatt cgggccattg atcacacacg gttcagggat   12540
ggacctatac aaatccaacc acaacaatgt gtattggctg actatcccgc caatgaagaa   12600
cctagcctta ggtgtaatca acacattgga gtggataccg agattcaagg ttagtcccta   12660
cctcttcaat gtcccaatta aggaagcagg cgaagactgc catgccccaa catacctacc   12720
tgcggaggtg gatggtgatg tcaaactcag ttccaatctg gtgattctac ctggtcaaga   12780
tctccaatat gttttggcaa cctacgatac ttccagggtt gaacatgctg tggtttatta   12840
cgtttacagc ccaggccgct cattttctta cttttatcct tttaggttgc ctataaaggg   12900
ggtccccatc gaattacaag tggaatgctt cacatgggac caaaaactct ggtgccgtca   12960
cttctgtgtg cttgcggact cagaatctgg tggacatatc actcactctg ggatggtggg   13020
catgggagtc agctgcacag tcacccggga agatggaacc aatcgcagat agggctgcta   13080
gtgaaccaat ctcatgatgt cacccagaca tcaggcatac ccactagtgt gaaatagaca   13140
tcagaattaa gaaaaacgta gggtccaagt ggttccccgt tatggactcg ctatctgtca   13200
accagatctt ataccctgaa gttcacctag atagcccgat agttaccaat aagatagtag   13260
ccatcctgga gtatgctcga gtccctcacg cttacagcct ggaggaccct acactgtgtc   13320
agaacatcaa gcaccgccta aaaaacggat tttccaacca aatgattata acaatgtgg    13380 aagttgggaa tgtcatcaag tccaagctta ggagttatcc ggcccactct catattccat   13440
atccaaattg taatcaggat ttatttaaca tagaagacaa agagtcaacg aggaagatcc   13500
gtgaactcct caaaaggggg aattcgctgt actccaaagt cagtgataag gttttccaat   13560
gcttaaggga cactaactca cggcttggcc taggctccga attgagggag gacatcaagg   13620
agaaagttat taacttggga gtttacatgc acagctccca gtggtttgag ccctttctgt   13680 tttggttac agtcaagact gagatgaggt cagtgattaa atcacaaacc catacttgcc    13740
ataggaggag acacacacct gtattcttca ctggtagttc agttgagttg ctaatctctc   13800
gtgaccttgt tgctataatc agtaaagagt ctcaacatgt atattacctg acatttgaac   13860
tggttttgat gtattgtgat gtcatagagg ggaggttaat gacagagacc gctatgacta   13920
ttgatgctag gtatacagag cttctaggaa gagtcagata catgtggaaa ctgatagatg   13980
```

```
gtttcttccc tgcactcggg aatccaactt atcaaattgt agccatgctg gagcctcttt    14040
cacttgctta cctgcagctg agggatataa cagtagaact cagaggtgct ttccttaacc    14100
actgctttac tgaaatacat gatgttcttg accaaaacgg gttttctgat gaaggtactt    14160
atcatgagtt aattgaagct ctagattaca ttttcataac tgatgacata catctgacag    14220
gggagatttt ctcattttc agaagtttcg gccaccccag acttgaagca gtaacggctg    14280
ctgaaaatgt taggaaatac atgaatcagc ctaaagtcat tgtgtatgag actctgatga    14340
aaggtcatgc catattttgt ggaatcataa tcaacggcta tcgtgacagg cacggaggca    14400
gttggccacc gctgaccctc ccctgcatg ctgcagacac aatccggaat gctcaagctt    14460
caggtgaagg gttaacacat gagcagtgcg ttgataactg gagatctttt gctggagtga    14520
aatttggctg ctttatgcct cttagcctgg atagtgatct gacaatgtac ctaaaggaca    14580
aggcacttgc tgctctccaa agggaatggg attcagttta cccgaaagag ttcctgcgtt    14640
acgaccctcc caagggaacc gggtcacgga ggcttgtaga tgttttcctt aatgattcga    14700
gctttgaccc atatgatgtg ataatgtatg ttgtaagtgg agcttacctc catgaccctg    14760
agttcaacct gtcttacagc ctgaaagaaa aggagatcaa ggaaacaggt agactttttg    14820
ctaaaatgac ttacaaaatg agggcatgcc aagtgattgc tgaaaatcta atctcaaacg    14880
ggattggcaa atattttaag gacaatggga tggccaagga tgagcacgat ttgactaagg    14940
cactccacac tctagctgtc tcaggagtcc ccaaagatct caaagaaagt cacagggggg    15000
ggccagtctt aaaaacctac tcccgaagcc cagtccacac aagtaccagg aacgtgagag    15060
cagcaaaagg gtttataggg ttccctcaag taattcggca ggaccaagac actgatcatc    15120
cggagaatat ggaagcttac gagacagtca gtgcatttat cacgactgat ctcaagaagt    15180
actgccttaa ttggagatat gagaccatca gcttgtttgc acagaggcta aatgagattt    15240
acggattgcc ctcattttc cagtggctgc ataagaggct tgagacctct gtcctgtatg    15300
taagtgaccc tcattgcccc cccgaccttg acgcccatat cccgttatat aaagtcccca    15360
atgatcaaat cttcattaag taccctatgg gaggtatga agggtattgt cagaagctgt    15420
ggaccatcag caccattccc tatctatacc tggctgctta tgagagcgga gtaaggattg    15480
cttcgttagt gcaaggggac aatcagacca tagccgtaac aaaaagggta cccagcacat    15540 ggcccctacaa ccttaagaaa cgggaagctg ctagagtaac tagagattac tttgtaattc    15600
ttaggcaaag gctacatgat attggccatc acctcaaggc aaatgagaca attgtttcat    15660
cacatttttt tgtctattca aaaggaatat attatgatgg gctacttgtg tcccaatcac    15720
tcaagagcat cgcaagatgt gtattctggt cagagactat agttgatgaa acaagggcag    15780
catgcagtaa tattgctaca acaatggcta aaagcatcga gagaggttat gaccgttacc    15840
ttgcatattc cctgaacgtc ctaaaagtga tacagcaaat tctgatctct cttggcttca    15900
caatcaattc aaccatgacc cgggatgtag tcatacccct cctcacgaac aacgacctct    15960
taataaggat ggcactgttg cccgctccta ttgggggat gaattatctg aatatgagca    16020
ggctgtttgt cagaaacatc ggtgatccag taacatcatc aattgctgat ctcaagagaa    16080
tgattctcgc ctcactaatg cctgaagaga ccctccatca agtaatgaca caacaaccgg    16140
gggactcttc attcctagac tgggctagcg acccttactc agcaaatctt gtatgtgtcc    16200
agagcatcac tagactcctc aagaacataa ctgcaaggtt tgtcctgatc catagtccaa    16260
acccaatgtt aaaaggatta ttccatgatg acagtaaaga gaggacgag ggactggcgg    16320 cattcctcat ggacaggcat attatagtac ctagggcagc tcatgaaatc ctggatcata    16380
```

```
gtgtcacagg ggcaagagag tctattgcag gcatgctgga taccacaaaa ggcctgattc   16440
gagccagcat gaggaagggg gggttaacct ctcgagtgat aaccagattg tccaattatg   16500
actatgaaca attcagagca gggatggtgc tattgacagg aagaaagaga aatgtcctca   16560
ttgacaaaga gtcatgttca gtgcagctgg cgagagctct aagaagccat atgtgggcga   16620
ggctagctcg aggacggcct atttacggcc ttgaggtccc tgatgtacta gaatctatgc   16680
gaggccacct tattcggcgt catgagacat gtgtcatctg cgagtgtgga tcagtcaact   16740
acggatggtt ttttgtcccc tcgggttgcc aactggatga tattgacaag gaaacatcat   16800
ccttgagagt cccatatatt ggttctacca ctgatgagag aacagacatg aagcttgcct   16860
tcgtaagagc cccaagtcga tccttgcgat ctgctgttag aatagcaaca gtgtactcat   16920
gggcttacgg tgatgatgat agctcttgga acgaagcctg gttgttggct aggcaaaggg   16980
ccaatgtgag cctggaggag ctaagggtga tcactcccat ctcaacttcg actaatttag   17040
cgcataggtt gagggatcgt agcactcaag tgaaatactc aggtacatcc cttgtccgag   17100
tggcgaggta taccacaatc tccaacgaca atctctcatt tgtcatatca gataagaagg   17160
ttgatactaa cttttatatac caacaaggaa tgcttctagg gttgggtgtt ttagaaacat   17220
tgtttcgact cgagaaagat accggatcat ctaacacggt attacatctt cacgtcgaaa   17280
cagattgttg cgtgatcccg atgatagatc atcccaggat acccagctcc cgcaagctag   17340
agctgagggc agagctatgt accaacccat tgatatatga taatgcacct ttaattgaca   17400
gagatacaac aaggctatac acccagagcc ataggaggca ccttgtggaa tttgttacat   17460
ggtccacacc ccaactatat cacattttag ctaagtccac agcactatct atgattgacc   17520
tggtaacaaa atttgagaag gaccatatga atgaaatttc agctctcata ggggatgacg   17580
atatcaatag tttcataact gagtttctgc tcatagagcc aagattattc actatctact   17640
tgggccagtg tgcggccatc aattgggcat ttgatgtaca ttatcataga ccatcaggga   17700
aatatcagat gggtgagctg ttgtcatcgt tcctttctag aatgagcaaa ggagtgttta   17760
aggtgcttgt caatgctcta agccacccaa agatctacaa gaaattctgg cattgtggta   17820
ttatagagcc tatccatggt ccttcacttg atgctcaaaa cttgcacaca actgtgtgca   17880
acatggttta cacatgctat atgacctacc tcgacctgtt gttgaatgaa gagttagaag   17940
agttcacatt tctcttgtgt gaaagcgacg aggatgtagt accggacaga ttcgacaaca   18000
tccaggcaaa acacttatgt gttctggcag atttgtactg tcaaccaggg acctgcccac   18060
caattcgagg tctaagaccg gtagagaaat gtgcagttct aaccgaccat atcaaggcag   18120
aggctaggtt atctccagca ggatcttcgt ggaacataaa tccaattatt gtagaccatt   18180
actcatgctc tctgacttat ctccggcgag gatcgatcaa acagataaga ttgagagttg   18240
atccaggatt cattttcgac gccctcgctg aggtaaatgt cagtcagcca aagatcggca   18300
gcaacaacat ctcaaatatg agcatcaagg ctttcagacc cccacacgat gatgttgcaa   18360
aattgctcaa agatatcaac acaagcaagc acaatcttcc catttcaggg ggcaatctcg   18420
ccaattatga aatccatgct ttccgcagaa tcgggttgaa ctcatctgct tgctacaaag   18480
ctgttgagat atcaacatta attaggagat gccttgagcc aggggaggac ggcttgttct   18540
tgggtgaggg atcgggttcc atgttgatca cttataagga gatacttaaa ctaaacaagt   18600
gcttctataa tagtgggggtt tccgccaatt ctagatctgg tcaaagggaa ttagcaccct   18660
atccctccga agttggcctt gtcgaacaca gaatgggagt aggtaatatt gtcaaagtgc   18720
```

```
tctttaacgg gaggcccgaa gtcacgtggg taggcagtgt agattgcttc aatttcatag   18780
ttagtaatat ccctacctct agtgtggggt ttatccattc agatatagag accttgccta   18840
acaaagatac tatagagaag ctagaggaat tggcagccat cttatcgatg gctctgctcc   18900
tgggcaaaat aggatcaata ctggtgatta agcttatgcc tttcagcggg gattttgttc   18960
agggatttat aagttatgta gggtcccatt atagagaagt gaaccttgta taccctagat   19020
acagcaactt catatctact gaatcttatt tggttatgac agatctcaag gctaaccggc   19080
taatgaatcc tgaaaagatt aagcagcaga taattgaatc atctgtgagg acttcacctg   19140
gacttatagg tcacatccta tccattaagc aactaagctg catacaagca attgtgggag   19200
acgcagttag tagaggtgat atcaatccta ctctgaaaaa acttacacct atagagcagg   19260
tgctgatcaa ttgcgggttg gcaattaacg gacctaagct gtgcaaagaa ttgatccacc   19320
atgatgttgc ctcagggcaa gatggattgc ttaattctat actcatcctc tacagggagt   19380
tggcaagatt caaagacaac caaagaagtc aacaagggat gttccacgct taccccgtat   19440
tggtaagtag caggcaacga gaacttatat ctaggatcac ccgcaaattt tgggggcaca   19500
ttcttcttta ctccgggaac agaaagttga taaataagtt tatccagaat ctcaagtccg   19560
gctatctgat actagactta caccagaata tcttcgttaa gaatctatcc aagtcagaga   19620
aacagattat tatgacgggg ggtttgaaac gtgagtgggt ttttaaggta acagtcaagg   19680
agaccaaaga atggtataag ttagtcggat acagtgccct gattaaggac taattggttg   19740
aactccggaa ccctaatcct gccctaggtg gttaggcatt atttgcaata gattaaagaa   19800
aactttgaaa atacgaagtt tctattccca gctttgtctg gtggccggca tggtcccagc   19860
ctcctcgctg gcgccggctg ggcaacattc cgagggggacc gtcccctcgg taatggcgaa   19920
tgggacgcgc ccgatccggc tgctaacaaa gcccgaaagg aagctgagtt ggctgctgcc   19980
accgctgagc aataactagc ataacccctt ggggcctcta aacgggtctt gaggggtttt   20040
ttgctgaaag gaggaactat atccggatgc ggccgatccg gctgctaaca aagcccgaaa   20100
ggaagctgag ttggctgctg ccaccgctga gcaataacta gcataacccc ttggggcctc   20160
taaacgggtc ttgaggggtt ttttgctgaa aggaggaact atatccggat ggccgccacc   20220
ggccggtggg ccttgcagca catccccctt tcgccagctg gcgtaatagc gaagaggccc   20280
gcaccgatcg cccttcccaa cagttgcgca gcctgaatgg cgaatgggac gcgcccgta   20340
gcggcgcatt aagcgcggcg ggtgtggtgg ttacgcgcag cgtgaccgct acacttgcca   20400
gcgccctagc gcccgctcct ttcgctttct tcccttcctt tctcgccacg ttcgccggct   20460
ttccccgtca gctctaaat cggggggctcc ctttagggtt ccgatttagt gctttacggc   20520
acctcgaccc caaaaaactt gattagggtg atggttcacg tgggccatcg ccctgataga   20580
cggttttttcg ccctttgacg ttggagtcca cgttctttaa tagtggactc ttgttccaaa   20640
ctggaacaac actcaaccct atctcggtct attcttttga tttataaggg attttgccga   20700
tttcggccta ttggttaaaa aatgagctga tttaacaaaa atttaacgcg aattttaaca   20760
aaatattaac gcttacaatt taggtggcac ttttcgggga aatgtgcgcg gaacccctat   20820
ttgtttattt ttctaaatac attcaaatat gtatccgctc atgagacaat aaccctgata   20880
aatgcttcaa taatattgaa aaaggaagag tatgagtatt caacatttcc gtgtcgccct   20940
tattcccttt tttgcggcat tttgccttcc tgttttttgct cacccagaaa cgctggtgaa   21000
agtaaaagat gctgaagatc agttgggtgc acgagtgggt tacatcgaac tggatctcaa   21060
cagcggtaag atccttgaga gttttcgccc cgaagaacgt tttccaatga tgagcacttt   21120
```

```
taaagttctg ctatgtggcg cggtattatc ccgtattgac gccgggcaag agcaactcgg   21180
tcgccgcata cactattctc agaatgactt ggttgagtac tcaccagtca cagaaaagca   21240
tcttacggat ggcatgacag taagagaatt atgcagtgct gccataacca tgagtgataa   21300
cactgcggcc aacttacttc tgacaacgat cggaggaccg aaggagctaa ccgctttttt   21360
gcacaacatg ggggatcatg taactcgcct tgatcgttgg aaccggagc tgaatgaagc    21420
cataccaaac gacgagcgtg acaccacgat gcctgtagca atggcaacaa cgttgcgcaa   21480
actattaact ggcgaactac ttacactagc ttcccggcaa caattaatag actggatgga   21540
ggcggataaa gttgcaggac cacttctgcg ctcggccctt ccggctggct ggtttattgc   21600
tgataaatct ggagccggtg agcgtgggtc tcgcggtatc attgcagcac tggggccaga   21660
tggtaagccc tcccgtatcg tagttatcta cacgacgggg agtcaggcaa ctatggatga   21720
acgaaataga cagatcgctg agataggtgc ctcactgatt aagcattggt aactgtcaga   21780
ccaagtttac tcatatatac tttagattga tttaaaactt catttttaat ttaaaaggat   21840
ctaggtgaag atcctttttg ataatctcat gaccaaaatc ccttaacgtg agttttcgtt   21900
ccactgagcg tcagaccccg tagaaaagat caaaggatct cttgagatc ctttttttct    21960
gcgcgtaatc tgctgcttgc aaacaaaaaa accaccgcta ccagcggtgg tttgtttgcc   22020
ggatcaagag ctaccaactc ttttttccgaa ggtaactggc ttcagcagag cgcagatacc   22080
aaatactgtt cttctagtgt agccgtagtt aggccaccac ttcaagaact ctgtagcacc   22140
gcctacatac ctcgctctgc taatcctgtt accagtggct gctgccagtg gcgataagtc   22200
gtgtcttacc gggttggact caagacgata gttaccggat aaggcgcagc ggtcgggctg   22260
aacggggggt tcgtgcacac agcccagctt ggagcgaacg acctacaccg aactgagata   22320
cctacagcgt gagctatgag aaagcgccac gcttcccgaa gggagaaagg cggacaggta   22380
tccggtaagc ggcagggtcg gaacaggaga gcgcacgagg gagcttccag ggggaaacgc   22440
ctggtatctt tatagtcctg tcgggtttcg ccacctctga cttgagcgtc gatttttgtg   22500
atgctcgtca gggggggcgga gcctatggaa aaacgccagc aacgcggcct ttttacggtt   22560
cctggccttt tgctggcctt ttgctcacat gttctttcct gcgttatccc ctgattctgt   22620
ggataaccgt attaccgcct ttgagtgagc tgataccgct cgccgcagcc gaacgaccga   22680
gcgcagcgag tcagtgagcg aggaagcgga agagcgccca atacgcaaac cgcctctccc   22740
cgcgcgttgg ccgattcatt aatgcagctg gcacgacagg tttcccgact ggaaagcggg   22800
cagtgagcgc aacgcaatta atgtgagtta gctcactcat taggcacccc aggctttaca   22860
ctttatgctt ccggctcgta tgttgtgtgg aattgtgagc ggacaacaat ttcacacagg   22920
aaacagctat gaccatgatt acgccaagct cgggcggccg cttgtaatac gactcactat   22980
a                                                                   22981
```

<210> SEQ ID NO 18
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S

<400> SEQUENCE: 18

| | |
|---|---:|
| accaaacaaa gttgggtaag gatagttcaa tcaatgatca ttttctagtg cacttaggat | 60 |
| tcaagatcct attatcaggg acaagagcag gattaaggat atccgagatg gccacacttt | 120 |
| taaggagctt agcattgttc aaaagaaaca aggacaaacc acccattaca tcaggatccg | 180 |
| gtggagccat cagaggaatc aaacacatta ttatagtacc aatccctgga gattcctcaa | 240 |
| ttaccactcg atccagactt ctggaccggt tggtcaggtt aattggaaac ccggatgtga | 300 |
| gcgggcccaa actaacaggg gcactaatag gtatattatc cttatttgtg gagtctccag | 360 |
| gtcaattgat tcagaggatc accgatgacc ctgacgttag cataaggctg ttagaggttg | 420 |
| tccagagtga ccagtcacaa tctggcctta ccttcgcatc aagaggtacc aacatggagg | 480 |
| atgaggcgga ccaatacttt tcacatgatg atccaattag tagtgatcaa tccaggttcg | 540 |
| gatggttcga gaacaaggaa atctcagata ttgaagtgca agaccctgag ggattcaaca | 600 |
| tgattctggg taccatccta gctcaaattt gggtcttgct cgcaaaggcg gttacggccc | 660 |
| cagacacggc agctgattcg gagctaagaa ggtggataaa gtacacccaa caaagaaggg | 720 |
| tagttggtga atttagattg gagagaaaat ggttggatgt ggtgaggaac aggattgccg | 780 |
| aggacctctc cttacgccga ttcatggtcg ctctaatcct ggatatcaag gaacacccg | 840 |
| gaaacaaacc caggattgct gaaatgatat gtgacattga tacatatatc gtagaggcag | 900 |
| gattagccag ttttatcctg actattaagt ttgggataga aactatgtat cctgctcttg | 960 |
| gactgcatga atttgctggt gagttatcca cacttgagtc cttgatgaac ctttaccagc | 1020 |
| aaatggggga aactgcaccc tacatggtaa tcctggagaa ctcaattcag aacaagttca | 1080 |
| gtgcaggatc ataccctctg ctctggagct atgccatggg agtaggagtg gaacttgaaa | 1140 |
| actccatggg aggtttgaac tttggccgat cttactttga tccagcatat tttagattag | 1200 |
| ggcaagagat ggtaaggagg tcagctggaa aggtcagttc cacattggca tctgaactcg | 1260 |
| gtatcactgc cgaggatgca aggcttgttt cagagattgc aatgcatact actgaggaca | 1320 |
| agatcagtag agcggttgga cccagacaag cccaagtatc atttctacac ggtgatcaaa | 1380 |
| gtgagaatga gctaccgaga ttgggggggca aggaagatag gagggtcaaa cagagtcgag | 1440 |
| gagaagccag ggagagctac agagaaaccg ggcccagcag agcaagtgat gcgagagctg | 1500 |
| cccatcttcc aaccggcaca cccctagaca ttgacactgc atcggagtcc agccaagatc | 1560 |
| cgcaggacag tcgaaggtca gctgacgccc tgcttaggct gcaagccatg gcaggaatct | 1620 |
| cggaagaaca aggctcagac acggacaccc ctatagtgta caatgacaga aatcttctag | 1680 |
| actaggtgcg agaggccgag gaccagaaca acatccgcct accctccatc attgttataa | 1740 |
| aaaacttagg aaccaggtcc acacagccgc cagcccatca accatccact cccacgattg | 1800 |
| gagccgatgg cagaagagca ggcacgccat gtcaaaaacg gactggaatg catccgggct | 1860 |
| ctcaaggccg agcccatcgg ctcactggcc atcgaggaag ctatggcagc atggtcagaa | 1920 |
| atatcagaca acccaggaca ggagcgagcc acctgcaggg aagagaaggc aggcagttcg | 1980 |
| ggtctcagca aaccatgcct ctcagcaatt ggatcaactg aaggcggtgc acctcgcatc | 2040 |
| cgcggtcagg gacctggaga gagcgatgac gacgctgaaa cttgggaat cccccaaga | 2100 |
| aatctccagg catcaagcac tgggttacag tgttattatg tttatgatca cagcggtgaa | 2160 |
| gcggttaagg gaatccaaga tgctgactct atcatggttc aatcaggcct tgatggtgat | 2220 |
| agcaccctct caggaggaga caatgaatct gaaaacagcg atgtggatat ggcgaacct | 2280 |
| gataccgagg gatatgctat cactgaccgg ggatctgctc ccatctctat ggggttcagg | 2340 |
| gcttctgatg ttgaaactgc agaaggaggg gagatccacg agctcctgag actccaatcc | 2400 |

```
agaggcaaca actttccgaa gcttgggaaa actctcaatg ttcctccgcc tccggacccc    2460
ggtagggcca gcacttccgg gacacccatt aaaaagggca cagacgcgag attagcctca    2520
tttggaacgg agatcgcgtc tttattgaca ggtggtgcaa cccaatgtgc tcgaaagtca    2580
ccctcggaac catcagggcc aggtgcacct gcggggaatg tccccgagtg tgtgagcaat    2640
gccgcactga tacaggagtg gacacccgaa tctggtacca caatctcccc gagatcccag    2700
aataatgaag aagggggaga ctattatgat gatgagctgt tctctgatgt ccaagatatt    2760
aaaacagcct tggccaaaat acacgaggat aatcagaaga taatctccaa gctagaatca    2820
ctgctgttat tgaagggaga agttgagtca attaagaagc agatcaacag gcaaaatatc    2880
agcatatcca ccctggaagg acacctctca agcatcatga tcgccattcc tggacttggg    2940
aaggatccca acgaccccac tgcagatgtc gaaatcaatc ccgacttgaa acccatcata    3000
ggcagagatt caggccgagc actggccgaa gttctcaaga aacccgttgc cagccgacaa    3060
ctccaaggaa tgacaaatgg acggaccagt tccagaggac agctgctgaa ggaatttcag    3120
ctaaagccga tcgggaaaaa gatgagctca gccgtcgggt tgttcctga caccggccct    3180 gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc caaccccatg    3360
ccagtcgacc caactagtac aacctaaatc cattataaaa aacttaggag caaagtgatt    3420
gcctcccaag ttccacaggc gcgccatgtt tgtttttctt gttttattgc cactagtctc    3480
tagtcagtgt gttaatctta caaccagaac tcaattaccc cctgcataca ctaattcttt    3540
cacacgtggt gtttattacc ctgacaaagt tttcagatcc tcagttttac attcaactca    3600
ggacttgttc ttacctttct tttccaatgt tacttggttc catgctatac atgtctctgg    3660
gaccaatggt actaagaggt ttgataaccc tgtcctacca tttaatgatg gtgtttattt    3720
tgcttccact gagaagtcta acataataag aggctggatt tttggtacta ctttagattc    3780
gaagacccag tccctactta ttgttaataa cgctactaat gttgttatta agtctgtga    3840 atttcaattt tgtaatgatc catttttggg tgtttattac cacaaaaaca caaaagttg    3900 gatggaaagt gagttcagag tttattctag tgcgaataat tgcacttttg aatatgtctc    3960
tcagcctttt cttatggacc ttgaaggaaa acagggtaat ttcaaaaatc ttagggaatt    4020
tgtgtttaag aatattgatg gttattttaa aatatattct aagcacacgc ctattaattt    4080
agtgcgtgat ctccctcagg gttttcggc tttagaacca ttggtagatt tgccaatagg    4140
tattaacatc actaggtttc aaacttact tgctttacat agaagttatt tgactcctgg    4200
tgattcttct tcaggttgga cagctggtgc tgcagcttat tatgtgggtt atcttcaacc    4260
taggactttt ctattaaaat ataatgaaaa tggaaccatt acagatgctg tagactgtgc    4320 acttgacccct ctctcagaaa caaagtgtac gttgaaatcc ttcactgtag aaaaaggaat    4380
ctatcaaact tctaacttta gagtccaacc aacagaatct attgttagat tcctaatat    4440 tacaaacttg tgccctttg tgaagttttt aacgccacc agatttgcat ctgtttatgc    4500
ttggaacagg aagagaatca gcaactgtgt tgctgattat tctgtcctat ataattccgc    4560 atcatttcc actttaagt gttatggagt gtctcctact aaattaaatg atctctgctt    4620
tactaatgtc tatgcagatt catttgtaat tagaggtgat gaagtcagac aaatcgctcc    4680
agggcaaact ggaaagattg ctgattataa ttataaatta ccagatgatt ttacaggctg    4740
```

```
cgttatagct tggaattcta acaatcttga ttctaaggtt ggtggtaatt ataattacct    4800
gtatagattg tttaggaagt ctaatctcaa acctttgag agagatattt caactgaaat     4860
ctatcaggcc ggtagcacac cttgtaatgg tgttgaaggt tttaattgtt actttccttt   4920
acaatcatat ggtttccaac ccactaatgg tgttggttac caaccataca gagtagtagt   4980
actttctttt gaacttctac atgcaccagc aactgtttgt ggacctaaaa agtctactaa   5040
tttggttaaa acaaatgtg tcaatttcaa cttcaatggt ttaacaggca caggtgttct    5100
tactgagtct aacaaaaagt ttctgccttt ccaacaattt ggcagagaca ttgctgacac   5160
tactgatgct gtccgtgatc cacagacact tgagattctt gacattacac catgttcttt   5220
tggtggtgtc agtgttataa caccaggaac aaatacttct aaccaggttg ctgttcttta   5280
tcaggatgtt aactgcacag aagtccctgt tgctattcat gcagatcaac ttactcctac   5340
ttggcgtgtt tattctacag gttctaatgt ttttcaaaca cgtgcaggct gtttaatagg   5400
ggctgaacat gtcaacaact catatgagtg tgacataccc attggtgcag gtatatgcgc   5460
tagttatcag actcagacta attctcctcg gcgggcacgt agtgtagcta gtcaatccat   5520
cattgcctac actatgtcac ttggtgcaga aaattcagtt gcttactcta ataactctat   5580
tgccatacc acaaatttta ctattagtgt taccacagaa attctaccag tgtctatgac    5640
caagacatca gtagattgta caatgtacat ttgtggtgat tcaactgaat gcagcaatct   5700
tttgttgcaa tatggcagtt tttgtacaca attaaaccgt gctttaactg aatagctgt    5760
tgaacaagac aaaaacaccc aagaagtttt tgcacaagtc aaacaaattt acaaaacacc   5820
accaattaaa gattttggtg gttttaattt ttcacaaata ttaccagatc catcaaaacc   5880
aagcaagagg tcatttattg aagatctact tttcaacaaa gtgacacttg cagatgctgg   5940
cttcatcaaa caatatggtg attgccttgg tgatattgct gctagagacc tcatttgtgc   6000
acaaaagttt aacggcctta ctgttttgcc acctttgctc acagatgaaa tgattgctca   6060
atacacttct gcactgttag cgggtacaat cacttctggt tggaccttg gtgcaggtgc   6120
tgcattacaa ataccatttg ctatgcaaat ggcttatagg tttaatggta ttggagttac   6180
acagaatgtt ctctatgaga accaaaaaatt gattgccaac caatttaata gtgctattgg   6240
caaaattcaa gactcacttt cttccacagc aagtgcactt ggaaaacttc aagatgtggt   6300
caaccaaaat gcacaagctt taaacacgct tgttaaacaa cttagctcca attttggtgc   6360
aatttcaagt gttttaaatg atatccttc acgtcttgac aaagttgagg ctgaagtgca    6420
aattgatagg ttgatcacag gcagacttca aagtttgcag acatatgtga ctcaacaatt   6480
aattagagct gcagaaatca gagcttctgc taatcttgct gctactaaaa tgtcagagtg   6540
tgtacttgga caatcaaaaa gagttgattt ttgtggaaag ggctatcatc ttatgtcctt   6600
ccctcagtca gcacctcatg gtgtagtctt cttgcatgtg acttatgtcc ctgcacaaga   6660
aaagaacttc acaactgctc ctgccatttg tcatgatgga aaagcacact ttcctcgtga   6720
aggtgtcttt gtttcaaatg gcacacactg gtttgtaaca caaaggaatt tttatgaacc   6780
acaaatcatt actacagaca acacatttgt gtctggtaac tgtgatgttg taataggaat   6840
tgtcaacaac acagtttatg atccttttgca acctgaatta gactcattca aggaggagtt   6900
agataaatat tttaagaatc atacatcacc agatgttgat ttaggtgaca tctctggcat   6960
taatgcttca gttgtaaaca ttcaaaaaga aattgaccgc ctcaatgagg ttgccaagaa   7020
tttaaatgaa tctctcatcg atctccaaga acttggaaag tatgagcagt atataaaatg   7080
gccatggtac atttggctag gttttatagc tggcttgatt gccatagtaa tggtgacaat   7140
```

```
tatgctttgc tgtatgacca gttgctgtag ttgtctcaag ggctgttgtt cttgtggatc    7200
ctgctgcaaa tttgatgaag acgactctga gccagtgctc aaaggagtcg cattagctta    7260
cacataacgc gcgacgtcct acagctcaac ttacctgcca accccatgcc agtcgaccca    7320
actagtacaa cctaaatcca ttataaaaaa cttaggagca aagtgattgc ctcccaagtt    7380
ccacaatgac agagatctac gacttcgaca agtcggcatg ggacatcaaa gggttgatcg    7440
ctccgataca acccaccacc tacagtgatg gcaggctggt gccccaggtc agagtcatag    7500
atcctggtct aggcgacagg aaggatgaat gctttatgta catgtttctg ctgggggttg    7560
ttgaggacag cgatccccta gggcctccaa tcgggcgagc atttgggtcc ctgcccttag    7620
gtgttggcag atccacagca aagcccgaaa aactcctcaa agaggccact gagcttgaca    7680
tagttgttag acgtacagca gggctcaatg aaaaactggt gttctacaac aacaccccac    7740
taactctcct cacaccttgg agaaaggtcc taacaacagg gagtgtcttc aacgcaaacc    7800
aagtgtgcaa tgcggttaat ctgataccgc tcgataccc gcagaggttc cgtgttgttt    7860
atatgagcat caccgtctct tcggataacg ggtattacac cgttcctaga agaatgctgg    7920
aattcagatc ggtcaatgca gtggccttca acctgctggt gacccttagg attgacaagg    7980
cgataggccc tgggaagatc atcgacaata cagagcaact tcctgaggca acatttatgg    8040
tccacatcgg gaacttcagg agaaagaaga gtgaagtcta ctctgccgat tattgcaaaa    8100
tgaaaatcga aagatgggc ctggttttg cacttggtgg atagggggc accagtcttc    8160 acattagaag cacaggcaaa atgagcaaga ctctccatgc acaactcggg ttcaagaaga    8220
ccttatgtta cccgctgata gatatcaatg aagaccttaa tcgattactc tggaggagca    8280
gatgcaagat agtaagaatc caggcagttt tgcagccatc agttcctcaa gaattccgca    8340
tttacgacga cgtgatcata aatgatgacc aaggactatt caaagttctg tagaccgtag    8400
tgcccagcaa tgcccgaaaa cgacccccct cacaatgaca gccagaaggc ccggacaaaa    8460 aagcccctc cgaaagactc cacggaccaa gcgagaggcc agccagcagc cgacggcaag    8520
cgcgaacacc aggcggcccc agcacagaac agccctgata caaggccacc accagccacc    8580
ccaatctgca tcctcctcgt gggaccccg aggaccaacc cccaaggctg cccccgatcc    8640
aaaccaccaa ccgcatcccc accaccccg ggaaagaaac cccagcaat tggaaggccc    8700 ctccccctct tcctcaacac aagaactcca caaccgaacc gcacaagcga ccgaggtgac    8760
ccaaccgcag gcatccgact ccctagacag atcctctctc cccggcaaac taaacaaaac    8820
ttagggccaa ggaacataca cacccaacag aacccagacc ccggcccacg gcgccgcgcc    8880
cccaaccccc gacaaccaga gggagccccc aaccaatccc gccggctccc ccggtgccca    8940
caggcaggga caccaacccc gaacagacc cagcacccaa ccatcgacaa tccaagacgg    9000
gggggccccc ccaaaaaag gccccaggg gccgacagcc agcaccgcga ggaagcccac    9060
ccaccccaca cacgaccacg gcaaccaaac cagaacccag accaccctgg gccaccagct    9120
cccagactcg gccatcaccc cgcagaaagg aaaggccaca accgcgcac cccagccccg    9180 atccggcggg gagccacca acccgaacca gcacccaaga gcgatccccg aaggaccccc    9240
gaaccgcaaa ggacatcagt atcccacagc ctctccaagt ccccggtct cctcccttc    9300 tcgaagggac caaaagatca atccaccaca cccgacgaca ctcaactccc cacccctaaa    9360
ggagacaccg ggaatcccag aatcaagact catccaatgt ccatcatggg tctcaaggtg    9420
aacgtctctg ccatattcat ggcagtactg ttaactctcc aaacacccac cggtcaaatc    9480
```

```
cattggggca atctctctaa gatagggtg gtaggaatag gaagtgcaag ctacaaagtt    9540
atgactcgtt ccagccatca atcattagtc ataaaattaa tgcccaatat aactctcctc   9600
aataactgca cgagggtaga gattgcagaa tacaggagac tactgagaac agttttggaa   9660
ccaattagag atgcacttaa tgcaatgacc cagaatataa daccggttca gagtgtagct   9720
tcaagtagga gacacaagag atttgcggga gtagtcctgg caggtgcggc cctaggcgtc   9780
gccacagctg ctcagataac agccggcatt gcacttcacc agtccatgct gaactctcaa   9840
gccatcgaca atctgagagc gagcctggaa actactaatc aggcaattga ggcaatcaga   9900
caagcagggc aggagatgat attggctgtt cagggtgtcc aagactacat caataatgag   9960
ctgataccgt ctatgaacca actatcttgt gatttaatcg gccagaagct cgggctcaaa  10020
ttgctcagat actatacaga aatcctgtca ttatttggcc ccagcttacg ggaccccata  10080
tctgcggaga tatctatcca ggctttgagc tatgcgcttg gaggagacat caataaggtg  10140
ttagaaaagc tcggatacag tggaggtgat ttactgggca tcttagagag cagaggaata  10200
aaggcccgga taactcacgt cgacacagag tcctacttca ttgtcctcag tatagcctat  10260
ccgacgctgt ccgagattaa gggggtgatt gtccaccggc tagaggggt ctcgtacaac  10320
ataggctctc aagagtggta taccactgtg cccaagtatg ttgcaaccca agggtacctt  10380
atctcgaatt ttgatgagtc atcgtgtact ttcatgccag aggggactgt gtgcagccaa  10440
aatgccttgt acccgatgag tcctctgctc aagaatgcc tccgggggtc caccaagtcc   10500
tgtgctcgta cactcgtatc cgggtctttt gggaaccggt tcattttatc acaagggaac  10560
ctaatagcca attgtgcatc aatcctttgc aagtgttaca caacaggaac gatcattaat  10620
caagaccctg acaagatcct aacatacatt gctgccgatc actgcccggt agtcgaggtg  10680
aacggcgtga ccatccaagt cgggagcagg aggtatccag atgctgtgta cttgcacaga  10740
attgacctcg gtcctcccat atcattggag aggttggacg tagggacaaa tctggggaat  10800
gcaattgcta agttggagga tgccaaggaa ttgttggagt catcggacca gatattgagg  10860
agtatgaaag gtttatcgag cactagcata gtctacatcc tgattgcagt gtgtcttgga  10920
gggttgatag ggatccccgc tttaatatgt tgctgcaggg ggcgttgtaa caaaaaggga  10980
gaacaagttg gtatgtcaag accaggccta aagcctgatc ttacgggaac atcaaaatcc  11040
tatgtaaggt cgctctgatc ctctacaact cttgaaacac aaatgtccca caagtctcct  11100
cttcgtcatc aagcaaccac cgcacccagc atcaagccca cctgaaatta ctccggctt   11160
ccctctggcc gaacaatatc ggtagttaat taaaacttag ggtgcaagat catccacaat  11220
gtcaccacaa cgagaccgga taaatgcctt ctacaaagat aacccccatc ccaagggaag  11280
taggatagtc attaacagag aacatcttat gattgataga cctttatgttt tgctggctgt  11340
tctgtttgtc atgtttctga gcttgatcgg gttgctagcc attgcaggca ttagacttca  11400
tcgggcagcc atctacaccg cagagatcca taaaagcctc agcaccaatc tagatgtaac  11460
taactcaatc gagcatcagg tcaaggacgt gctgacacca ctcttcaaaa tcatcggtga  11520
tgaagtgggc ctgaggacac ctcagagatt cactgaccta gtgaaattca tctctgacaa  11580
gattaaattc cttaatccgg ataggagta cgacttcaga gatctcactt ggtgtatcaa  11640
cccgccagag agaatcaaat tggattatga tcaatactgt gcagatgtgg ctgctgaaga  11700
gctcatgaat gcattggtga actcaactct actggagacc agaacaacca atcagttcct  11760
agctgtctca aagggaaact gctcagggcc cactacaatc agaggtcaat tctcaaacat  11820
gtcgctgtcc ctgttagact tgtatttagg tcgaggttac aatgtgtcat ctatagtcac  11880
```

```
tatgacatcc cagggaatgt atgggggaac ttacctagtg gaaaagccta atctgagcag   11940
caaaaggtca gagttgtcac aactgagcat gtaccgagtg tttgaagtag gtgttatcag   12000
aaatccgggt ttgggggctc cggtgttcca tatgacaaac tatcttgagc aaccagccag   12060
taatgatctc agcaactgta tggtggcttt gggggagctc aaactcgcag ccctttgtca   12120
cggggaagat tctatcacaa ttccctatca gggatcaggg aaaggtgtca gcttccagct   12180
cgtcaagcta ggtgtctgga aatccccaac cgacatgcaa tcctgggtcc ccttatcaac   12240
ggatgatcca gtgatagaca ggctttacct ctcatctcac agaggtgtta tcgctgacaa   12300
tcaagcaaaa tgggctgtcc cgacaacacg aacagatgac aagttgcgaa tggagacatg   12360
cttccaacag gcgtgtaagg gtaaaatcca agcactctgc gagaatcccg agtgggcacc   12420
attgaaggat aacaggattc cttcatacgg ggtcttgtct gttgatctga gtctgacagt   12480
tgagcttaaa atcaaaattg cttcgggatt cgggccattg atcacacacg gttcagggat   12540
ggacctatac aaatccaacc acaacaatgt gtattggctg actatcccgc caatgaagaa   12600
cctagcctta ggtgtaatca acacattgga gtggataccg agattcaagg ttagtcccta   12660
cctcttcaat gtcccaatta aggaagcagg cgaagactgc catgccccaa catacctacc   12720
tgcggaggtg gatggtgatg tcaaactcag ttccaatctg gtgattctac ctggtcaaga   12780
tctccaatat gttttggcaa cctacgatac ttccagggtt gaacatgctg tggtttatta   12840
cgtttacagc ccaggccgct catttttctta cttttatcct tttaggttgc ctataaaggg   12900
ggtccccatc gaattacaag tggaatgctt cacatgggac caaaaactct ggtgccgtca   12960
cttctgtgtg cttgcggact cagaatctgg tggacatatc actcactctg ggatggtggg   13020
catgggagtc agctgcacag tcacccggga agatggaacc aatcgcagat agggctgcta   13080
gtgaaccaat ctcatgatgt cacccagaca tcaggcatac ccactagtgt gaaatagaca   13140
tcagaattaa gaaaaacgta gggtccaagt ggttccccgt tatggactcg ctatctgtca   13200
accagatctt ataccctgaa gttcacctag atagcccgat agttaccaat aagatagtag   13260
ccatcctgga gtatgctcga gtccctcacg cttacagcct ggaggaccct acactgtgtc   13320
agaacatcaa gcaccgccta aaaaacggat tttccaacca aatgattata aacaatgtgg   13380
aagttgggaa tgtcatcaag tccaagctta ggagttatcc ggcccactct catattccat   13440
atccaaattg taatcaggat ttatttaaca tagaagacaa agagtcaacg aggaagatcc   13500
gtgaactcct caaaaagggg aattcgctgt actccaaagt cagtgataag gttttccaat   13560
gcttaaggga cactaactca cggcttggcc taggctccga attgagggag gacatcaagg   13620
agaaagttat taacttggga gtttacatgc acagctccca gtggtttgag ccctttctgt   13680
tttggtttac agtcaagact gagatgaggt cagtgattaa atcacaaacc catacttgcc   13740
ataggaggag acacacacct gtattcttca ctggtagttc agttgagttg ctaatctctc   13800
gtgaccttgt tgctataatc agtaaagagt ctcaacatgt atattacctg acatttgaac   13860
tggttttgat gtattgtgat gtcatagagg ggaggttaat gacagagacc gctatgacta   13920
ttgatgctag gtatacagag cttctaggaa gagtcagata catgtggaaa ctgatagatg   13980
gtttcttccc tgcactcggg aatccaactt atcaaattgt agccatgctg gagcctcttt   14040
cacttgctta cctgcagctg agggatataa cagtagaact cagaggtgct ttccttaacc   14100
actgctttac tgaaatacat gatgttcttg accaaaacgg gttttctgat gaaggtactt   14160
atcatgagtt aattgaagct ctagattaca tttttcataac tgatgacata catctgacag   14220
```

```
gggagatttt ctcattttc agaagtttcg gccacccag acttgaagca gtaacggctg    14280
ctgaaaatgt taggaaatac atgaatcagc ctaaagtcat tgtgtatgag actctgatga    14340
aaggtcatgc catattttgt ggaatcataa tcaacggcta tcgtgacagg cacggaggca    14400
gttggccacc gctgaccctc ccctgcatg ctgcagacac aatccggaat gctcaagctt    14460
caggtgaagg gttaacacat gagcagtgcg ttgataactg gagatctttt gctggagtga    14520
aatttggctg ctttatgcct cttagcctgg atagtgatct gacaatgtac ctaaaggaca    14580
aggcacttgc tgctctccaa agggaatggg attcagttta cccgaaagag ttcctgcgtt    14640
acgaccctcc caagggaacc gggtcacgga ggcttgtaga tgttttcctt aatgattcga    14700
gctttgaccc atatgatgtg ataatgtatg ttgtaagtgg agcttacctc catgaccctg    14760
agttcaacct gtcttacagc ctgaaagaaa aggagatcaa ggaaacaggt agactttttg    14820
ctaaaatgac ttacaaaatg agggcatgcc aagtgattgc tgaaaatcta atctcaaacg    14880
ggattggcaa atattttaag gacaatggga tggccaagga tgagcacgat ttgactaagg    14940
cactccacac tctagctgtc tcaggagtcc ccaaagatct caaagaaagt cacaggggg    15000
ggccagtctt aaaaacctac tcccgaagcc cagtccacac aagtaccagg aacgtgagag    15060
cagcaaaagg gtttataggg ttccctcaag taattcggca ggaccaagac actgatcatc    15120
cggagaatat ggaagcttac gagacagtca gtgcatttat cacgactgat ctcaagaagt    15180
actgccttaa ttggagatat gagaccatca gcttgtttgc acagaggcta aatgagattt    15240
acggattgcc ctcatttttc cagtggctgc ataagaggct tgagacctct gtcctgtatg    15300
taagtgaccc tcattgcccc cccgaccttg acgcccatat cccgttatat aaagtcccca    15360
atgatcaaat cttcattaag taccctatgg gaggtataga agggtattgt cagaagctgt    15420
ggaccatcag caccattccc tatctatacc tggctgctta tgagagcgga gtaaggattg    15480
cttcgttagt gcaaggggac aatcagacca tagccgtaac aaaaagggta cccagcacat    15540
ggcccctacaa ccttaagaaa cgggaagctg ctagagtaac tagagattac tttgtaattc    15600
ttaggcaaag gctacatgat attggccatc acctcaaggc aaatgagaca attgtttcat    15660
cacatttttt tgtctattca aaaggaatat attatgatgg gctacttgtg tcccaatcac    15720
tcaagagcat cgcaagatgt gtattctggt cagagactat agttgatgaa caagggcag    15780
catgcagtaa tattgctaca acaatggcta aaagcatcga gagaggttat gaccgttacc    15840
ttgcatattc cctgaacgtc ctaaaagtga tacagcaaat tctgatctct cttggcttca    15900
caatcaattc aaccatgacc cgggatgtag tcatacccct cctcacgaac aacgacctct    15960
taataaggat ggcactgttg cccgctccta ttggggggat gaattatctg aatatgagca    16020
ggctgttttgt cagaaacatc ggtgatccag taacatcatc aattgctgat ctcaagagaa    16080
tgattctcgc ctcactaatg cctgaagaga ccctccatca agtaatgaca caacaaccgg    16140
gggactcttc attcctagac tgggctagcg acccttactc agcaaatctt gtatgtgtcc    16200
agagcatcac tagactcctc aagaacataa ctgcaaggtt tgtcctgatc catagtccaa    16260
acccaatgtt aaaaggatta ttccatgatg acagtaaaga gaggacgag ggactggcgg    16320
cattcctcat ggacaggcat attatagtac ctagggcagc tcatgaaatc ctggatcata    16380
gtgtcacagg ggcaagagag tctattgcag gcatgctgga taccacaaaa ggcctgattc    16440
gagccagcat gaggaagggg gggttaacct ctcgagtgat aaccagattg tccaattatg    16500
actatgaaca attcagagca gggatggtgc tattgacagg aagaaagaga aatgtcctca    16560
ttgacaaaga gtcatgttca gtgcagctgg cgagagctct aagaagccat atgtgggcga    16620
```

```
ggctagctcg aggacggcct atttacggcc ttgaggtccc tgatgtacta gaatctatgc    16680
gaggccacct tattcggcgt catgagacat gtgtcatctg cgagtgtgga tcagtcaact    16740
acggatggtt ttttgtcccc tcgggttgcc aactggatga tattgacaag gaaacatcat    16800
ccttgagagt cccatatatt ggttctacca ctgatgagaa acagacatg  aagcttgcct    16860 tcgtaagagc cccaagtcga tccttgcgat ctgctgttag aatagcaaca gtgtactcat    16920
gggcttacgg tgatgatgat agctcttgga acgaagcctg gttgttggct aggcaaaggg    16980
ccaatgtgag cctggaggag ctaagggtga tcactcccat ctcaacttcg actaatttag    17040
cgcataggtt gagggatcgt agcactcaag tgaaatactc aggtacatcc cttgtccgag    17100
tggcgaggta taccacaatc tccaacgaca atctctcatt tgtcatatca gataagaagg    17160
ttgatactaa ctttatatac caacaaggaa tgcttctagg gttgggtgtt ttagaaacat    17220
tgtttcgact cgagaaagat accggatcat ctaacacggt attacatctt cacgtcgaaa    17280
cagattgttg cgtgatcccg atgatagatc atcccaggat acccagctcc cgcaagctag    17340
agctgagggc agagctatgt accaacccat tgatatatga taatgcacct ttaattgaca    17400
gagatacaac aaggctatac acccagagcc ataggaggca ccttgtggaa tttgttacat    17460
ggtccacacc ccaactatat cacatttag ctaagtccac agcactatct atgattgacc     17520
tggtaacaaa atttgagaag gaccatatga atgaaatttc agctctcata ggggatgacg    17580
atatcaatag tttcataact gagtttctgc tcatagagcc aagattattc actatctact    17640
tgggccagtg tgcggccatc aattgggcat ttgatgtaca ttatcataga ccatcaggga    17700
aatatcagat gggtgagctg ttgtcatcgt tcctttctag aatgagcaaa ggagtgttta    17760
aggtgcttgt caatgctcta agccacccaa agatctacaa gaaattctgg cattgtggta    17820
ttatagagcc tatccatggt ccttcacttg atgctcaaaa cttgcacaca actgtgtgca    17880
acatggttta cacatgctat atgacctacc tcgacctgtt gttgaatgaa gagttagaag    17940
agttcacatt tctcttgtgt gaaagcgacg aggatgtagt accggacaga ttcgacaaca    18000
tccaggcaaa acacttatgt gttctggcag atttgtactg tcaaccaggg acctgcccac    18060
caattcgagg tctaagaccg gtagagaaat gtgcagttct aaccgaccat atcaaggcag    18120
aggctaggtt atctccagca ggatcttcgt ggaacataaa tccaattatt gtagaccatt    18180
actcatgctc tctgacttat ctccggcgag atcgatcaa  acagataaga ttgagagttg    18240
atccaggatt cattttcgac gccctcgctg aggtaaatgt cagtcagcca aagatcggca    18300
gcaacaacat ctcaaatatg agcatcaagg ctttcagacc cccacacgat gatgttgcaa    18360
aattgctcaa agatatcaac acaagcaagc acaatcttcc catttcaggg ggcaatctcg    18420
ccaattatga aatccatgct ttccgcagaa tcgggttgaa ctcatctgct tgctacaaag    18480
ctgttgagat atcaacatta attaggagat gccttgagcc aggggaggac ggcttgttct    18540
tgggtgaggt atcgggttcc atgttgatca cttataagga gatacttaaa ctaaacaagt    18600
gcttctataa tagtgggggtt tccgccaatt ctagatctgg tcaaagggaa ttagcaccct    18660
atccctccga agttggcctt gtcgaacaca gaatgggagt aggtaatatt gtcaaagtgc    18720
tctttaacgg gaggcccgaa gtcacgtggg taggcagtgt agattgcttc aatttcatag    18780
ttagtaatat ccctacctct agtgtggggt ttatccattc agatatagag accttgccta    18840
acaaagatac tatagagaag ctagaggaat tggcagccat cttatcgatg gctctgctcc    18900
tgggcaaaat aggatcaata ctggtgatta agcttatgcc tttcagcggg gattttgttc    18960
```

```
agggatttat aagttatgta gggtcccatt atagagaagt gaaccttgta tacccctagat    19020
acagcaactt catatctact gaatcttatt tggttatgac agatctcaag gctaaccggc    19080
taatgaatcc tgaaaagatt aagcagcaga taattgaatc atctgtgagg acttcacctg    19140
gacttatagg tcacatccta tccattaagc aactaagctg catacaagca attgtgggag    19200
acgcagttag tagaggtgat atcaatccta ctctgaaaaa acttacacct atagagcagg    19260
tgctgatcaa ttgcgggttg gcaattaacg gacctaagct gtgcaaagaa ttgatccacc    19320
atgatgttgc ctcagggcaa gatggattgc ttaattctat actcatcctc tacagggagt    19380
tggcaagatt caaagacaac caaagaagtc aacaagggat gttccacgct taccccgtat    19440
tggtaagtag caggcaacga gaacttatat ctaggatcac ccgcaaattt tgggggcaca    19500
ttcttcttta ctccgggaac agaaagttga taaataagtt tatccagaat ctcaagtccg    19560
gctatctgat actagactta caccagaata tcttcgttaa gaatctatcc aagtcagaga    19620
aacagattat tatgacgggg ggtttgaaac gtgagtgggt ttttaaggta acagtcaagg    19680
agaccaaaga atggtataag ttagtcggat acagtgccct gattaaggac taattggttg    19740
aactccggaa ccctaatcct gccctaggtg gttaggcatt atttgcaata gattaaagaa    19800
aactttgaaa atacgaagtt tctattccca gctttgtctg gtggccggca tggtcccagc    19860
ctcctcgctg gcgccggctg gcaacattc cgagggacc gtcccctcgg taatggcgaa    19920
tgggacgcgg ccgatccggc tgctaacaaa gcccgaaagg aagctgagtt ggctgctgcc    19980
accgctgagc aataactagc ataacccctt ggggcctcta aacgggtctt gagggggtttt    20040
ttgctgaaag gaggaactat atccggatgc ggccgatccg gctgctaaca aagcccgaaa    20100
ggaagctgag ttggctgctg ccaccgctga gcaataacta gcataacccc ttggggcctc    20160
taaacgggtc ttgagggggtt ttttgctgaa aggaggaact atatccggat ggccgccacc    20220
ggccggtggg ccttgcagca catcccctt tcgccagctg gcgtaatagc gaagaggccc    20280
gcaccgatcg cccttcccaa cagttgcgca gcctgaatgg cgaatgggac gcgccctgta    20340
gcggcgcatt aagcgcggcg ggtgtggtgg ttacgcgcag cgtgaccgct acacttgcca    20400
gcgccctagc gcccgctcct ttcgctttct tcccttcctt tctcgccacg ttcgccggct    20460
ttccccgtca gctctaaat cggggggctcc ctttagggtt ccgatttagt gctttacggc    20520
acctcgaccc caaaaaactt gattagggtg atggttcacg tgggccatcg ccctgataga    20580
cggttttcg ccctttgacg ttggagtcca cgttctttaa tagtggactc ttgttccaaa    20640
ctggaacaac actcaaccct atctcggtct attctttga tttataaggg attttgccga    20700
tttcggccta ttggttaaaa atgagctga tttaacaaaa atttaacgcg aattttaaca    20760
aaatattaac gcttacaatt taggtggcac ttttcgggga aatgtgcgcg aacccctat    20820
ttgtttattt ttctaaatac attcaaatat gtatccgctc atgagacaat aaccctgata    20880
aatgcttcaa taatattgaa aaaggaagag tatgagtatt caacatttcc gtgtcgccct    20940
tattcccttt tttgcggcat tttgccttcc tgtttttgct cacccagaaa cgctggtgaa    21000
agtaaaagat gctgaagatc agttgggtgc acgagtgggt tacatcgaac tggatctcaa    21060
cagcggtaag atccttgaga gttttcgccc cgaagaacgt tttccaatga tgagcactt    21120
taaagttctg ctatgtggcg cggtattatc ccgtattgac gccgggcaag agcaactcgg    21180
tcgccgcata cactattctc agaatgactt ggttgagtac tcaccagtca cagaaaagca    21240
tcttacggat ggcatgacag taagagaatt atgcagtgct gccataacca tgagtgataa    21300
cactgcggcc aacttacttc tgacaacgat cggaggaccg aaggagctaa ccgcttttttt    21360
```

```
gcacaacatg ggggatcatg taactcgcct tgatcgttgg gaaccggagc tgaatgaagc   21420
cataccaaac gacgagcgtg acaccacgat gcctgtagca atggcaacaa cgttgcgcaa   21480
actattaact ggcgaactac ttacactagc ttcccggcaa caattaatag actggatgga   21540
ggcggataaa gttgcaggac cacttctgcg ctcggccctt ccggctggct ggtttattgc   21600
tgataaatct ggagccggtg agcgtgggtc tcgcggtatc attgcagcac tggggccaga   21660
tggtaagccc tcccgtatcg tagttatcta cacgacgggg agtcaggcaa ctatggatga   21720
acgaaataga cagatcgctg agataggtgc ctcactgatt aagcattggt aactgtcaga   21780
ccaagtttac tcatatatac tttagattga tttaaaactt catttttaat ttaaaaggat   21840
ctaggtgaag atcctttttg ataatctcat gaccaaaatc ccttaacgtg agttttcgtt   21900
ccactgagcg tcagacccccg tagaaaagat caaaggatct tcttgagatc ctttttttct   21960
gcgcgtaatc tgctgcttgc aaacaaaaaa accaccgcta ccagcggtgg tttgtttgcc   22020
ggatcaagag ctaccaactc tttttccgaa ggtaactggc ttcagcagag cgcagatacc   22080
aaatactgtt cttctagtgt agccgtagtt aggccaccac ttcaagaact ctgtagcacc   22140
gcctacatac ctcgctctgc taatcctgtt accagtggct gctgccagtg gcgataagtc   22200
gtgtcttacc gggttggact caagacgata gttaccggat aaggcgcagc ggtcgggctg   22260
aacggggggt tcgtgcacac agcccagctt ggagcgaacg acctacaccg aactgagata   22320
cctacagcgt gagctatgag aaagcgccac gcttcccgaa gggagaaagg cggacaggta   22380
tccggtaagc ggcagggtcg gaacaggaga gcgcacgagg gagcttccag ggggaaacgc   22440
ctggtatctt tatagtcctg tcgggtttcg ccacctctga cttgagcgtc gatttttgtg   22500
atgctcgtca gggggggcgga gcctatggaa aaacgccagc aacgcggcct ttttacggtt   22560
cctggccttt tgctggcctt tgctcacat gttctttcct gcgttatccc ctgattctgt   22620
ggataaccgt attaccgcct ttgagtgagc tgataccgct cgccgcagcc gaacgaccga   22680
gcgcagcgag tcagtgagcg aggaagcgga agagcgccca atacgcaaac cgcctctccc   22740
cgcgcgttgg ccgattcatt aatgcagctg gcacgacagg tttcccgact ggaaagcggg   22800
cagtgagcgc aacgcaatta atgtgagtta gctcactcat taggcacccc aggctttaca   22860
ctttatgctt ccggctcgta tgttgtgtgg aattgtgagc ggacaacaat ttcacacagg   22920
aaacagctat gaccatgatt acgccaagct cgggcggccg cttgtaatac gactcactat   22980
a                                                                  22981
```

<210> SEQ ID NO 19
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S-CO-AA-PP

<400> SEQUENCE: 19

```
accaaacaaa gttgggtaag gatagttcaa tcaatgatca ttttctagtg cacttaggat    60
tcaagatcct attatcaggg acaagagcag gattaaggat atccgagatg ccacacttt    120
taaggagctt agcattgttc aaaagaaaca aggacaaacc acccattaca tcaggatccg   180
gtggagccat cagaggaatc aaacacatta ttatagtacc aatccctgga gattcctcaa   240
```

```
ttaccactcg atccagactt ctggaccggt tggtcaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcga gaacaaggaa atctcagata ttgaagtgca agaccctgag ggattcaaca    600
tgattctggg taccatccta gctcaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc atacccctctg ctctggagct atgccatggg agtaggagtg gaacttgaaa   1140
actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttgggggggca aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc atcggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag gaccagaaca acatccgcct acctccatc attgttataa   1740
aaaacttagg aaccaggtcc acacagccgc cagcccatca accatccact cccacgattg   1800
gagccgatgg cagaagagca ggcacgccat gtcaaaaacg gactgaaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa cttttgggaat cccccccaaga   2100
aatctccagg catcaagcac tgggttacag tgttattatg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc tccggacccc   2460
ggtagggcca gcacttccgg gacacccatt aaaaagggca cagacgcgag attagcctca   2520
tttgaacgag agatcgcgtc tttattgaca ggtggtgcaa cccaatgtgc tcgaaagtca   2580
ccctcggaac catcagggcc aggtgcacct gcggggaatg tccccgagtg tgtgagcaat   2640
```

```
gccgcactga tacaggagtg gacacccgaa tctggtacca caatctcccc gagatcccag    2700
aataatgaag aaggggaga ctattatgat gatgagctgt tctctgatgt ccaagatatt    2760
aaaacagcct tggccaaaat acacgaggat aatcagaaga taatctccaa gctagaatca    2820
ctgctgttat tgaagggaga agttgagtca attaagaagc agatcaacag gcaaaatatc    2880
agcatatcca ccctggaagg acacctctca agcatcatga tcgccattcc tggacttggg    2940
aaggatccca acgaccccac tgcagatgtc gaaatcaatc ccgacttgaa acccatcata    3000
ggcagagatt caggccgagc actggccgaa gttctcaaga acccgttgc cagccgacaa    3060 ctccaaggaa tgacaaatgg acggaccagt tccagaggac agctgctgaa ggaatttcag    3120
ctaaagccga tcgggaaaaa gatgagctca gccgtcgggt tgttcctga caccggccct    3180 gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc caaccccatg    3360
ccagtcgacc caactagtac aacctaaatc cattataaaa aacttaggag caaagtgatt    3420
gcctcccaag ttccacaggc gcgccatgtt cgtcttcctg gtcctgctgc ctctggtctc    3480
ctcacagtgc gtcaatctga caactcggac tcagctgcca cctgcttata ctaatagctt    3540
caccagaggc gtgtactatc ctgacaaggt gtttagaagc tccgtgctgc actctacaca    3600
ggatctgttt ctgccattct ttagcaacgt gacctggttc cacgccatcc acgtgagcgg    3660
caccaatggc acaaagcggt tcgacaatcc cgtgctgcct tttaacgatg gcgtgtactt    3720
cgcctctacc gagaagagca acatcatcag aggctggatc tttggcacca cactggactc    3780
caagacacag tctctgctga tcgtgaacaa tgccaccaac gtggtcatca aggtgtgcga    3840
gttccagttt tgtaatgatc ccttcctggg cgtgtactat cacaagaaca ataagagctg    3900
gatggagtcc gagtttagag tgtattctag cgccaacaac tgcacatttg agtacgtgag    3960
ccagcctttc ctgatggacc tggagggcaa gcagggcaat ttcaagaacc tgagggagtt    4020
cgtgtttaag aatatcgacg gctacttcaa aatctactct aagcacaccc ccatcaacct    4080
ggtgcgcgac ctgcctcagg gcttcagcgc cctggagccc ctggtggatc tgcctatcgg    4140
catcaacatc acccggtttc agacactgct ggccctgcac agaagctacc tgacacccgg    4200
cgactcctct agcggatgga ccgccggcgc tgccgcctac tatgtgggct acctccagcc    4260
ccggaccttc ctgctgaagt acaacgagaa tggcaccatc acagacgcag tggattgcgc    4320 cctggaccc ctgagcgaga caaagtgtac actgaagtcc tttaccgtgg agaagggcat    4380
ctatcagaca tccaatttca gggtgcagcc aaccgagtct atcgtgcgct ttcctaatat    4440
cacaaacctg tgcccatttg gcgaggtgtt caacgcaacc cgcttcgcca gcgtgtacgc    4500
ctggaatagg aagcggatca gcaactgcgt ggccgactat agcgtgctgt acaactccgc    4560
ctctttcagc acctttaagt gctatggcgt gtcccccaca aagctgaatg acctgtgctt    4620
taccaacgtc tacgccgatt cttttcgtgat caggggcgac gaggtgcgcc agatcgcccc    4680
cggccagaca ggcaagatcg cagactacaa ttataagctg ccagacgatt tcaccggctg    4740
cgtgatcgcc tggaacagca acaatctgga ttccaaagtg gcggcaact acaattatct    4800 gtaccggctg tttagaaaga gcaatctgaa gcccttcgag agggacatct ctacagaaat    4860
ctaccaggcc ggcagcaccc cttgcaatgg cgtggagggc tttaactgtt atttcccact    4920
ccagtcctac ggcttccagc ccacaaacgg cgtgggctat cagccttacc gcgtggtggt    4980
```

```
gctgagctttgagctgctgcacgccccagcaacagtgtgcggccccaagaagtccaccaa      5040
tctggtgaagaacaagtgcgtgaacttcaacttcaacggcctgaccggcacaggcgtgct      5100
gaccgagtccaacaagaagttcctgccattcagcagttcggcagggacatcgcagatac      5160
cacagacgccgtgcgcgaccacagacccctggagatcctggacatcacaccctgctcttt      5220
cggcggcgtgagcgtgatcacacccggcaccaatacaagcaaccaggtggccgtgctgta      5280
tcaggacgtgaattgtaccgaggtgcccgtggctatccacgccgatcagctgaccccaac      5340
atggcgggtgtacagcaccggctccaacgtcttccagacaagagccggatgcctgatcgg      5400
agcagagcacgtgaacaattcctatgagtgcgacatcccaatcggcgccggcatctgtgc      5460
ctcttaccagacccagacaaactctcccagaagagcccggagcgtggcctcccagtctat      5520
catcgcctataccatgtccctgggcgccgaaacagcgtggcctactctaacaatagcat      5580
cgccatcccaaccaacttcaatctctgtgaccacagagatcctgcccgtgtccatgac      5640
caagacatctgtggactgcaatgtatatctgtggcgatctaccgagtgcagcaacct      5700
gctgctccagtacggcagcttttgtacccagctgaatagagccctgacaggcatcgccgt      5760
ggagcaggataagaacacacaggaggtgttcgcccaggtgaagcaaatctacaagacccc      5820
ccctatcaagactttggcggcttcaattttccccagatcctgcctgatccatccaagcc      5880
ttctaagcggagctttatcgaggacctgctgttcaacaaggtgaccctggccgatgccgg      5940
cttcatcaagcagtatggcgattgcctgggcgacatcgcagccagggacctgatctgcgc      6000
ccagaagtttaatggcctgaccgtgctgcccccctgctgacagatgagatgatcgcaca      6060
gtacacaagcgccctgctggccggcaccatcacatccggatggaccttcgcgcaggagc      6120
cgccctccagatccccttttgccatgcagatggcctataggttcaacggcatcggcgtgac      6180
ccagaatgtgctgtacgagaaccagaagctgatcgccaatcagtttaactccgccatcgg      6240
caagatccagacagcctgtcctctacagccagcgccctggcaagctccaggatgtggt      6300
gaatcagaacgcccaggccctgaatacccctggtgaagcagctgagcagcaacttcggcgc      6360
catctctagcgtgctgaatgacatcctgagccggctggaccctcctgaggcagaggtgca      6420
gatcgaccgctgatcaccgccggctccagagcctccagacctatgtgacacagcagct      6480
gatcagggccgccgagatcagggccagcgccaatctggcagcaaccaagatgtccgagtg      6540
cgtgctgggccagtctaagagagtggactttgtgcaaggctatcacctgatgtccttt      6600
ccctcagtctgccccacacgcgtggtgttctgcacgtgacctacgtgccgcccagga      6660
gaagaacttcaccacagcccctgccatctgccacgatggcaaggcccacttccaaggga      6720
gggcgtgttcgtgtccaacgggcacccactgtttgtgacacagcgcaattttctacgagcc      6780
ccagatcatcaccacagacaacaccttcgtgagcggcaactgtgacgtggtcatcggcat      6840
cgtgaacaataccgtgtatgatccactccagcccgagctgacagctttaaggaggagct      6900
ggataagtatttcaagaatcacacctccccctgacgtggatctgggcgacatcagcggcat      6960
caatgcctccgtggtgaacatccagaaggagatcgaccgcctgaacgaggtggctaagaa      7020
tctgaacgagagcctgatcgaacctccaggagctgggcaagtatgagcagtacatcaagtg      7080
gccctggtacatctggctgggcttcatcgccggcctgatcgccatcgtgatggtgaccat      7140
catgctgtgctgtatgacatcctgctgttcttgcctgaaggctgctgtagctgtggctc      7200
ctgctgtaagtttgacgaggatgactctgaacctgtgctgaagggcgtggcgctggctta      7260
cacctaacgcgcgacgtcctacagctcaacttacctgccaaccccatgccagtcgaccca      7320
actagtacaacctaaatccattataaaaaacttaggagcaaagtgattgcctcccaagtt      7380
```

```
ccacaatgac agagatctac gacttcgaca agtcggcatg ggacatcaaa gggttgatcg   7440
ctccgataca acccaccacc tacagtgatg gcaggctggt gccccaggtc agagtcatag   7500
atcctggtct aggcgacagg aaggatgaat gctttatgta catgtttctg ctgggggttg   7560
ttgaggacag cgatccccta gggcctccaa tcgggcgagc atttgggtcc ctgcccttag   7620
gtgttggcag atccacagca aagcccgaaa aactcctcaa agaggccact gagcttgaca   7680
tagttgttag acgtacagca gggctcaatg aaaaactggt gttctacaac aacaccccac   7740
taactctcct cacaccttgg agaaaggtcc taacaacagg gagtgtcttc aacgcaaacc   7800
aagtgtgcaa tgcggttaat ctgataccgc tcgataccc gcagaggttc cgtgttgttt   7860
atatgagcat cacccgtctt tcggataacg ggtattacac cgttcctaga agaatgctgg   7920
aattcagatc ggtcaatgca gtggccttca acctgctggt gacccttagg attgacaagg   7980
cgataggccc tgggaagatc atcgacaata cagagcaact tcctgaggca acatttatgg   8040
tccacatcgg gaacttcagg agaaagaaga gtgaagtcta ctctgccgat tattgcaaaa   8100
tgaaaatcga aagatgggc ctggtttttg cacttggtgg gatagggggc accagtcttc   8160
acattagaag cacaggcaaa atgagcaaga ctctccatgc acaactcggg ttcaagaaga   8220
ccttatgtta cccgctgata gatatcaatg aagaccttaa tcgattactc tggaggagca   8280
gatgcaagat agtaagaatc caggcagttt tgcagccatc agttcctcaa gaattccgca   8340
tttacgacga cgtgatcata aatgatgacc aaggactatt caaagttctg tagaccgtag   8400
tgcccagcaa tgcccgaaaa cgaccccct cacaatgaca gccagaaggc ccggacaaaa   8460 aagcccctc cgaaagactc cacggaccaa gcgagaggcc agccagcagc cgacggcaag   8520
cgcgaacacc aggcggcccc agcacagaac agccctgata caaggccacc accagccacc   8580
ccaatctgca tcctcctcgt gggacccccg aggaccaacc cccaaggctg ccccgatcc   8640 aaaccaccaa ccgcatcccc accaccccg ggaaagaaac cccagcaat tggaaggccc   8700 ctcccctct tcctcaacac aagaactcca caaccgaacc gcacaagcga ccgaggtgac   8760
ccaaccgcag gcatccgact ccctagacag atcctctc cccggcaaac taaacaaaac   8820
ttagggccaa ggaacataca cacccaacag aacccagacc ccggcccacg gcgccgcgcc   8880
cccaaccccc gacaaccaga gggagccccc aaccaatccc gccggctccc ccggtgccca   8940
caggcaggga caccaacccc gaacagacc cagcacccaa ccatcgacaa tccaagacgg   9000
gggggccccc ccaaaaaaag gccccaggg gccgacagcc agcaccgcga ggaagcccac   9060
ccaccccaca cacgaccacg gcaaccaaac cagaacccag accaccctgg gccaccagct   9120
cccagactcg gccatcaccc cgcagaaagg aaaggccaca acccgcgcac cccagccccg   9180
atccggcggg gagccaccca acccgaacca gcacccaaga gcgatcccg aaggacccc   9240 gaaccgcaaa ggacatcagt atcccacagc ctctccaagt ccccggtct cctcccttc    9300 tcgaagggac caaagatca atccaccaca cccgacgaca ctcaactccc cacccctaaa   9360
ggagacaccg ggaatcccag aatcaagact catccaatgt ccatcatggg tctcaaggtg   9420
aacgtctctg ccatattcat ggcagtactt ttaactctcc aaacacccac cggtcaaatc   9480 cattgggca atctctctaa gataggggtg gtaggaatag gaagtgcaag ctacaaagtt   9540
atgactcgtt ccagccatca atcattagtc ataaaattaa tgcccaatat aactctcctc   9600
aataactgca cgagggtaga gattgcagaa tacaggagac tactgagaac agttttggaa   9660
ccaattagag atgcacttaa tgcaatgacc cagaatataa gaccggttca gagtgtagct   9720
```

```
tcaagtagga gacacaagag atttgcggga gtagtcctgg caggtgcggc cctaggcgtc    9780
gccacagctg ctcagataac agccggcatt gcacttcacc agtccatgct gaactctcaa    9840
gccatcgaca atctgagagc gagcctggaa actactaatc aggcaattga ggcaatcaga    9900
caagcagggc aggagatgat attggctgtt cagggtgtcc aagactacat caataatgag    9960
ctgataccgt ctatgaacca actatcttgt gatttaatcg gccagaagct cgggctcaaa   10020
ttgctcagat actatacaga aatcctgtca ttatttggcc ccagcttacg ggaccccata   10080
tctgcggaga tatctatcca ggctttgagc tatgcgcttg gaggagacat caataaggtg   10140
ttagaaaagc tcggatacag tggaggtgat ttactgggca tcttagagag cagaggaata   10200
aaggcccgga taactcacgt cgacacagag tcctacttca ttgtcctcag tatagcctat   10260
ccgacgctgt ccgagattaa gggggtgatt gtccaccggc tagaggggt ctcgtacaac   10320
ataggctctc aagagtggta taccactgtg cccaagtatg ttgcaaccca agggtacctt   10380
atctcgaatt ttgatgagtc atcgtgtact ttcatgccag aggggactgt gtgcagccaa   10440
aatgccttgt acccgatgag tcctctgctc caagaatgcc tccggggtc caccaagtcc   10500
tgtgctcgta cactcgtatc cgggtctttt gggaaccggt tcattttatc acaagggaac   10560
ctaatagcca attgtgcatc aatcctttgc aagtgttaca caacaggaac gatcattaat   10620
caagaccctg acaagatcct aacatacatt gctgccgatc actgcccggt agtcgaggtg   10680
aacggcgtga ccatccaagt cgggagcagg aggtatccag atgctgtgta cttgcacaga   10740
attgacctcg gtcctcccat atcattggag aggttggacg tagggacaaa tctggggaat   10800
gcaattgcta agttggagga tgccaaggaa ttgttggagt catcggacca gatattgagg   10860
agtatgaaag gtttatcgag cactagcata gtctacatcc tgattgcagt gtgtcttgga   10920
gggttgatag ggatccccgc tttaatatgt tgctgcaggg ggcgttgtaa caaaaaggga   10980
gaacaagttg gtatgtcaag accaggccta agcctgatc ttacgggaac atcaaaatcc   11040
tatgtaaggt cgctctgatc ctctacaact cttgaaacac aaatgtccca caagtctcct   11100
cttcgtcatc aagcaaccac cgcacccagc atcaagccca cctgaaatta tctccggctt   11160
ccctctggcc gaacaatatc ggtagttaat taaaacttag ggtgcaagat catccacaat   11220
gtcaccacaa cgagaccgga taaatgcctt ctacaaagat aaccccatc ccaagggaag   11280
taggatagtc attaacagag aacatcttat gattgataga ccttatgttt tgctggctgt   11340
tctgtttgtc atgtttctga gcttgatcgg gttgctagcc attgcaggca ttagacttca   11400
tcgggcagcc atctacaccg cagagatcca taaaagcctc agcaccaatc tagatgtaac   11460
taactcaatc gagcatcagg tcaaggacgt gctgacacca ctcttcaaaa tcatcggtga   11520
tgaagtgggc ctgaggacac ctcagagatt cactgaccta gtgaaattca tctctgacaa   11580
gattaaattc cttaatccgg atagggagta cgacttcaga gatctcactt ggtgtatcaa   11640
cccgccagag agaatcaaat tggattatga tcaatactgt gcagatgtgg ctgctgaaga   11700
gctcatgaat gcattggtga actcaactct actggagacc agaacaacca atcagttcct   11760
agctgtctca aagggaaact gctcagggcc cactacaatc agaggtcaat tctcaaacat   11820
gtcgctgtcc ctgttagact tgtatttagg tcgaggttac aatgtgtcat ctatagtcac   11880
tatgacatcc cagggaatgt atgggggaac ttacctagtg gaaaagccta atctgagcag   11940
caaaaggtca gagttgtcac aactgagcat gtaccgagtg tttgaagtag gtgttatcag   12000
aaatccgggt ttgggggctc cggtgttcca tatgacaaac tatcttgagc aaccagccag   12060
taatgatctc agcaactgta tggtggcttt ggggggagctc aaactcgcag ccctttgtca   12120
```

```
cggggaagat tctatcacaa ttccctatca gggatcaggg aaaggtgtca gcttccagct  12180
cgtcaagcta ggtgtctgga aatccccaac cgacatgcaa tcctgggtcc ccttatcaac  12240
ggatgatcca gtgatagaca ggctttacct ctcatctcac agaggtgtta tcgctgacaa  12300
tcaagcaaaa tgggctgtcc cgacaacacg aacagatgac aagttgcgaa tggagacatg  12360
cttccaacag gcgtgtaagg gtaaaatcca agcactctgc gagaatcccg agtgggcacc  12420
attgaaggat aacaggattc cttcatacgg ggtcttgtct gttgatctga gtctgacagt  12480
tgagcttaaa atcaaaattg cttcgggatt cgggccattg atcacacacg gttcagggat  12540
ggacctatac aaatccaacc acaacaatgt gtattggctg actatcccgc caatgaagaa  12600
cctagcctta ggtgtaatca acacattgga gtggataccg agattcaagg ttagtcccta  12660
cctcttcaat gtcccaatta aggaagcagg cgaagactgc catgcccaa catacctacc  12720 tgcggaggtg gatggtgatg tcaaactcag ttccaatctg gtgattctac ctggtcaaga  12780
tctccaatat gttttggcaa cctacgatac ttccagggtt gaacatgctg tggtttatta  12840
cgtttacagc ccaggccgct cattttctta cttttatcct tttaggttgc ctataaaggg  12900
ggtccccatc gaattacaag tggaatgctt cacatgggac caaaaactct ggtgccgtca  12960
cttctgtgtg cttgcggact cagaatctgg tggacatatc actcactctg ggatggtggg  13020
catgggagtc agctgcacag tcacccggga agatggaacc aatcgcagat agggctgcta  13080
gtgaaccaat ctcatgatgt cacccagaca tcaggcatac ccactagtgt gaaatagaca  13140
tcagaattaa gaaaaacgta gggtccaagt ggttccccgt tatggactcg ctatctgtca  13200
accagatctt ataccctgaa gttcacctag atagcccgat agttaccaat aagatagtag  13260
ccatcctgga gtatgctcga gtccctcacg cttacagcct ggaggaccct acactgtgtc  13320
agaacatcaa gcaccgccta aaaaacggat tttccaacca aatgattata aacaatgtgg  13380
aagttgggaa tgtcatcaag tccaagctta ggagttatcc ggcccactct catattccat  13440
atccaaattg taatcaggat ttatttaaca tagaagacaa agagtcaacg aggaagatcc  13500
gtgaactcct caaaagggg aattcgctgt actccaaagt cagtgataag gttttccaat  13560
gcttaaggga cactaactca cggcttggcc taggctccga attgagggag gacatcaagg  13620
agaaagttat taacttggga gtttacatgc acagctccca gtggtttgag ccctttctgt  13680
tttggtttac agtcaagact gagatgaggt cagtgattaa atcacaaacc catacttgcc  13740
ataggaggag acacacacct gtattcttca ctggtagttc agttgagttg ctaatctctc  13800
gtgaccttgt tgctataatc agtaaagagt ctcaacatgt atattacctg acatttgaac  13860
tggttttgat gtattgtgat gtcatagagg ggaggttaat gacagagacc gctatgacta  13920
ttgatgctag gtatacagag cttctaggaa gagtcagata catgtggaaa ctgatagatg  13980
gtttcttccc tgcactcggg aatccaactt atcaaattgt agccatgctg gagcctcttt  14040
cacttgctta cctgcagctg agggatataa cagtagaact cagaggtgct ttccttaacc  14100
actgctttac tgaaatacat gatgttcttg accaaaacgg gttttctgat gaaggtactt  14160
atcatgagtt aattgaagct ctagattaca ttttcataac tgatgacata catctgacag  14220
gggagatttt ctcattttc agaagtttcg gccacccccag acttgaagca gtaacggctg  14280
ctgaaaatgt taggaaatac atgaatcagc taaagtcat tgtgtatgag actctgatga  14340
aaggtcatgc catattttgt ggaatcataa tcaacggcta tcgtgacagg cacgaggca  14400 gttggccacc gctgaccctc cccctgcatg ctgcagacac aatccggaat gctcaagctt  14460
```

```
caggtgaagg gttaacacat gagcagtgcg ttgataactg gagatctttt gctggagtga   14520
aatttggctg ctttatgcct cttagcctgg atagtgatct gacaatgtac ctaaaggaca   14580
aggcacttgc tgctctccaa agggaatggg attcagttta cccgaaagag ttcctgcgtt   14640
acgaccctcc caagggaacc gggtcacgga ggcttgtaga tgttttcctt aatgattcga   14700
gctttgaccc atatgatgtg ataatgtatg ttgtaagtgg agcttacctc catgaccctg   14760
agttcaacct gtcttacagc ctgaaagaaa aggagatcaa ggaaacaggt agactttttg   14820
ctaaaatgac ttacaaaatg agggcatgcc aagtgattgc tgaaaatcta atctcaaacg   14880
ggattggcaa atattttaag gacaatggga tggccaagga tgagcacgat ttgactaagg   14940
cactccacac tctagctgtc tcaggagtcc ccaaagatct caaagaaagt cacaggggg    15000
ggccagtctt aaaaacctac tcccgaagcc cagtccacac aagtaccagg aacgtgagag   15060
cagcaaaagg gtttataggg ttccctcaag taattcggca ggaccaagac actgatcatc   15120
cggagaatat ggaagcttac gagacagtca gtgcatttat cacgactgat ctcaagaagt   15180
actgccttaa ttggagatat gagaccatca gcttgtttgc acagaggcta aatgagattt   15240
acggattgcc ctcattttc cagtggctgc ataagaggct tgagacctct gtcctgtatg    15300
taagtgaccc tcattgcccc cccgaccttg acgcccatat cccgttatat aaagtcccca   15360
atgatcaaat cttcattaag taccctatgg gaggtataga agggtattgt cagaagctgt   15420
ggaccatcag caccattccc tatctatacc tggctgctta tgagagcgga gtaaggattg   15480
cttcgttagt gcaaggggac aatcagacca tagccgtaac aaaaagggta cccagcacat   15540
ggccctacaa ccttaagaaa cgggaagctg ctagagtaac tagagattac tttgtaattc   15600
ttaggcaaag gctacatgat attggccatc acctcaaggc aaatgagaca attgtttcat   15660
cacattttt tgtctattca aaaggaatat attatgatgg gctacttgtg tcccaatcac    15720
tcaagagcat cgcaagatgt gtattctggt cagagactat agttgatgaa caagggcag    15780
catgcagtaa tattgctaca acaatggcta aaagcatcga gagaggttat gaccgttacc   15840
ttgcatattc cctgaacgtc ctaaaagtga tacagcaaat tctgatctct cttggcttca   15900
caatcaattc aaccatgacc cgggatgtag tcatacccct cctcacgaac aacgacctct   15960
taataaggat ggcactgttg cccgctccta ttgggggat gaattatctg aatatgagca    16020
ggctgtttgt cagaaacatc ggtgatccag taacatcatc aattgctgat ctcaagagaa   16080
tgattctcgc ctcactaatg cctgaagaga ccctccatca agtaatgaca caacaaccgg   16140
gggactcttc attcctagac tgggctagcg acccttactc agcaaatctt gtatgtgtcc   16200
agagcatcac tagactcctc aagaacataa ctgcaaggtt tgtcctgatc catagtccaa   16260
acccaatgtt aaaaggatta ttccatgatg acagtaaaga agaggacgag ggactggcgg   16320
cattcctcat ggacaggcat attatagtac ctaggcagc tcatgaaatc ctggatcata    16380
gtgtcacagg ggcaagagag tctattgcag gcatgctgga taccacaaaa ggcctgattc   16440
gagccagcat gaggaagggg gggttaacct ctcgagtgat aaccagattg tccaattatg   16500
actatgaaca attcagagca gggatggtgc tattgacagg aagaaagaga aatgtcctca   16560
ttgacaaaga gtcatgttca gtgcagctgg cgagagctct aagaagccat atgtgggcga   16620
ggctagctcg aggacggcct atttacggcc ttgaggtccc tgatgtacta gaatctatgc   16680
gaggccacct tattcggcgt catgagacat gtgtcatctg cgagtgtgga tcagtcaact   16740
acggatggtt ttttgtcccc tcgggttgcc aactggatga tattgacaag gaaacatcat   16800
ccttgagagt cccatatatt ggttctacca ctgatgagag aacagacatg aagcttgcct   16860
```

```
tcgtaagagc cccaagtcga tccttgcgat ctgctgttag aatagcaaca gtgtactcat    16920
gggcttacgg tgatgatgat agctcttgga acgaagcctg gttgttggct aggcaaaggg    16980
ccaatgtgag cctggaggag ctaagggtga tcactcccat ctcaacttcg actaatttag    17040
cgcataggtt gagggatcgt agcactcaag tgaaatactc aggtacatcc cttgtccgag    17100
tggcgaggta taccacaatc tccaacgaca atctctcatt tgtcatatca gataagaagg    17160
ttgatactaa ctttatatac caacaaggaa tgcttctagg gttgggtgtt ttagaaacat    17220
tgtttcgact cgagaaagat accggatcat ctaacacggt attacatctt cacgtcgaaa    17280
cagattgttg cgtgatcccg atgatagatc atcccaggat acccagctcc cgcaagctag    17340
agctgagggc agagctatgt accaacccat tgatatatga taatgcaccT ttaattgaca    17400
gagatacaac aaggctatac acccagagcc ataggaggca ccttgtggaa tttgttacat    17460
ggtccacacc ccaactatat cacattttag ctaagtccac agcactatct atgattgacc    17520
tggtaacaaa atttgagaag gaccatatga atgaaatttc agctctcata ggggatgacg    17580
atatcaatag tttcataact gagtttctgc tcatagagcc aagattattc actatctact    17640
tgggccagtg tgcggccatc aattgggcat ttgatgtaca ttatcataga ccatcaggga    17700
aatatcagat gggtgagctg ttgtcatcgt tcctttctag aatgagcaaa ggagtgttta    17760
aggtgcttgt caatgctcta agccacccaa agatctacaa gaaattctgg cattgtggta    17820
ttatagagcc tatccatggt ccttcacttg atgctcaaaa cttgcacaca actgtgtgca    17880
acatggttta cacatgctat atgacctacc tcgacctgtt gttgaatgaa gagttagaag    17940
agttcacatt tctcttgtgt gaaagcgacg aggatgtagt accggacaga ttcgacaaca    18000
tccaggcaaa acacttatgt gttctggcag atttgtactg tcaaccaggg acctgcccac    18060
caattcgagg tctaagaccg gtagagaaat gtgcagttct aaccgaccat atcaaggcag    18120
aggctaggtt atctccagca ggatcttcgt ggaacataaa tccaattatt gtagaccatt    18180
actcatgctc tctgacttat ctccggcgag gatcgatcaa acagataaga ttgagagttg    18240
atccaggatt cattttcgac gccctcgctg aggtaaatgt cagtcagcca aagatcggca    18300
gcaacaacat ctcaaatatg agcatcaagg cttTcagacc cccacacgat gatgttgcaa    18360
aattgctcaa agatatcaac acaagcaagc acaatcttcc catttcaggg ggcaatctcg    18420
ccaattatga aatccatgct ttccgcagaa tcgggttgaa ctcatctgct tgctacaaag    18480
ctgttgagat atcaacatta attaggagat gccttgagcc agggaggac ggcttgttct    18540 tgggtgaggg atcgggttcc atgttgatca cttataagga gatacttaaa ctaaacaagt    18600
gcttctataa tagtgggtt tccgccaatt ctagatctgg tcaaagggaa ttagcaccct    18660
atccctccga agttggcctt gtcgaacaca gaatgggagt aggtaatatt gtcaaagtgc    18720
tctttaacgg gaggcccgaa gtcacgtggg taggcagtgt agattgcttc aatttcatag    18780
ttagtaatat ccctacctct agtgtggggt ttatccattc agatatagag accttgccta    18840
acaaagatac tatagagaag ctagaggaat tggcagccat cttatcgatg gctctgctcc    18900
tgggcaaaat aggatcaata ctggtgatta agcttatgcc tttcagcggg gattttgttc    18960
agggatttat aagttatgta gggtcccatt atagagaagt gaaccttgta tacccctagat    19020 acagcaactt catatctact gaatcttatt tggttatgac agatctcaag gctaaccggc    19080
taatgaatcc tgaaaagatt aagcagcaga taattgaatc atctgtgagg acttcacctg    19140
gacttatagg tcacatccta tccattaagc aactaagctg catacaagca attgtgggag    19200
```

```
acgcagttag tagaggtgat atcaatccta ctctgaaaaa acttacacct atagagcagg   19260
tgctgatcaa ttgcgggttg gcaattaacg gacctaagct gtgcaaagaa ttgatccacc   19320
atgatgttgc ctcagggcaa gatggattgc ttaattctat actcatcctc tacagggagt   19380
tggcaagatt caaagacaac caaagaagtc aacaagggag gttccacgct taccccgtat   19440
tggtaagtag caggcaacga gaacttatat ctaggatcac ccgcaaattt tgggggcaca   19500
ttcttcttta ctccgggaac agaaagttga taaataagtt tatccagaat ctcaagtccg   19560
gctatctgat actagactta caccagaata tcttcgttaa gaatctatcc aagtcagaga   19620
aacagattat tatgacgggg ggtttgaaac gtgagtgggt ttttaaggta acagtcaagg   19680
agaccaaaga atggtataag ttagtcggat acagtgccct gattaaggac taattggttg   19740
aactccggaa ccctaatcct gccctaggtg gttaggcatt atttgcaata gattaaagaa   19800
aactttgaaa atacgaagtt tctattccca gctttgtctg gtggccggca tggtcccagc   19860
ctcctcgctg gcgccggctg ggcaacattc cgagggacc gtcccctcgg taatggcgaa    19920
tgggacgcgg ccgatccggc tgctaacaaa gcccgaaagg aagctgagtt ggctgctgcc   19980
accgctgagc aataactagc ataacccctt ggggcctcta acgggtctt gaggggtttt     20040 ttgctgaaag gaggaactat atccggatgc ggccgatccg gctgctaaca aagcccgaaa   20100
ggaagctgag ttggctgctg ccaccgctga gcaataacta gcataacccc ttggggcctc    20160
taaacgggtc ttgaggggtt ttttgctgaa aggaggaact atatccggat ggccgccacc   20220
ggccggtggg ccttgcagca catccccctt tcgccagctg gcgtaatagc gaagaggccc   20280
gcaccgatcg cccttcccaa cagttgcgca gcctgaatgg cgaatgggac gcgccctgta    20340
gcggcgcatt aagcgcggcg ggtgtggtgg ttacgcgcag cgtgaccgct acacttgcca    20400
gcgccctagc gcccgctcct ttcgctttct tcccttcctt tctcgccacg ttcgccggct    20460
ttccccgtca gctctaaat cggggctcc ctttagggtt ccgatttagt gctttacggc      20520
acctcgaccc caaaaaactt gattagggtg atggttcacg tgggccatcg ccctgataga   20580 cggttttcg ccctttgacg ttggagtcca cgttctttaa tagtggactc ttgttccaaa     20640
ctggaacaac actcaaccct atctcggtct attcttttga tttataaggg attttgccga    20700
tttcggccta ttggttaaaa aatgagctga tttaacaaaa atttaacgcg aattttaaca   20760
aaatattaac gcttacaatt taggtggcac ttttcgggga aatgtgcgcg gaaccccta t   20820 ttgtttattt ttctaaatac attcaaatat gtatccgctc atgagacaat aaccctgata   20880
aatgcttcaa taatattgaa aaaggaagag tatgagtatt caacatttcc gtgtcgccct   20940
tattcccttt tttgcggcat tttgccttcc tgttttgct cacccagaaa cgctggtgaa     21000
agtaaaagat gctgaagatc agttgggtgc acgagtgggt tacatcgaac tggatctcaa   21060
cagcggtaag atccttgaga gttttcgccc cgaagaacgt tttccaatga tgagcacttt   21120
taaagttctg ctatgtggcg cggtattatc ccgtattgac gccgggcaag agcaactcgg   21180
tcgccgcata cactattctc agaatgactt ggttgagtac tcaccagtca cagaaaagca   21240
tcttacggat ggcatgacag taagagaatt atgcagtgct gccataacca tgagtgataa   21300
cactgcggcc aacttacttc tgacaacgat cggaggaccg aaggagctaa ccgcttttt t   21360 gcacaacatg ggggatcatg taactcgcct tgatcgttgg gaaccggagc tgaatgaagc   21420
cataccaaac gacgagcgtg acaccacgat gcctgtagca atggcaacaa cgttgcgcaa   21480
actattaact ggcgaactac ttacactagc ttcccggcaa caattaatag actggatgga   21540
ggcggataaa gttgcaggac cacttctgcg ctcggccctt ccggctggct ggtttattgc   21600
```

```
tgataaatct ggagccggtg agcgtgggtc tcgcggtatc attgcagcac tggggccaga   21660
tggtaagccc tcccgtatcg tagttatcta cacgacgggg agtcaggcaa ctatggatga   21720
acgaaataga cagatcgctg agataggtgc ctcactgatt aagcattggt aactgtcaga   21780
ccaagtttac tcatatatac tttagattga tttaaaactt catttttaat ttaaaaggat   21840
ctaggtgaag atccttttg ataatctcat gaccaaaatc ccttaacgtg agttttcgtt    21900
ccactgagcg tcagacccg tagaaaagat caaaggatct tcttgagatc ctttttttct    21960
gcgcgtaatc tgctgcttgc aaacaaaaaa accaccgcta ccagcggtgg tttgtttgcc   22020
ggatcaagag ctaccaactc tttttccgaa ggtaactggc ttcagcagag cgcagatacc   22080
aaatactgtt cttctagtgt agccgtagtt aggccaccac ttcaagaact ctgtagcacc   22140
gcctacatac ctcgctctgc taatcctgtt accagtggct gctgccagtg gcgataagtc   22200
gtgtcttacc gggttggact caagacgata gttaccggat aaggcgcagc ggtcgggctg   22260
aacggggggt tcgtgcacac agcccagctt ggagcgaacg acctacaccg aactgagata   22320
cctacagcgt gagctatgag aaagcgccac gcttcccgaa gggagaaagg cggacaggta   22380
tccggtaagc ggcagggtcg gaacaggaga gcgcacgagg gagcttccag ggggaaacgc   22440
ctggtatctt tatagtcctg tcgggtttcg ccacctctga cttgagcgtc gatttttgtg   22500
atgctcgtca gggggggcgga gcctatggaa aaacgccagc aacgcggcct ttttacggtt   22560
cctggccttt tgctggcctt ttgctcacat gttctttcct gcgttatccc ctgattctgt   22620
ggataaccgt attaccgcct ttgagtgagc tgataccgct cgccgcagcc gaacgaccga   22680
gcgcagcgag tcagtgagcg aggaagcgga agagcgccca atacgcaaac cgcctctccc   22740
cgcgcgttgg ccgattcatt aatgcagctg gcacgacagg tttcccgact ggaaagcggg   22800
cagtgagcgc aacgcaatta atgtgagtta gctcactcat taggcacccc aggctttaca   22860
ctttatgctt ccggctcgta tgttgtgtgg aattgtgagc ggacaacaat ttcacacagg   22920
aaacagctat gaccatgatt acgccaagct cgggcggccg cttgtaatac gactcactat   22980
a                                                                   22981
```

<210> SEQ ID NO 20
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S-CO-AA-fneg-PP

<400> SEQUENCE: 20

```
accaaacaaa gttgggtaag gatagttcaa tcaatgatca ttttctagtg cacttaggat     60
tcaagatcct attatcaggg acaagagcag gattaaggat atccgagatg gccacacttt    120
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtcaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
```

```
atgaggcgga ccaatacttt tcacatgatg atccaattag tagtgatcaa tccaggttcg    540
gatggttcga gaacaaggaa atctcagata ttgaagtgca agaccctgag ggattcaaca    600
tgattctggg taccatccta gctcaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc ataccctctg ctctggagct atgccatggg agtaggagtg aacttgaaa    1140
actccatggg aggtttgaac tttggccgat cttactttga tccagcatat tttagattag   1200
ggcaagagat ggtaaggagg tcagctgaaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttgggggca aggaagatag gagggtcaaa cagagtcgag   1440
gagaagccag ggagagctac agagaaaccg ggcccagcag agcaagtgat gcgagagctg   1500
cccatcttcc aaccggcaca ccctagaca ttgacactgc atcggagtcc agccaagatc   1560
cgcaggacag tcgaaggtca gctgacgccc tgcttaggct gcaagccatg caggaatct    1620
cggaagaaca aggctcagac acggacaccc ctatagtgta caatgacaga atcttctag    1680
actaggtgcg agaggccgag gaccagaaca acatccgcct accctccatc attgttataa   1740
aaaacttagg aaccaggtcc acacagccgc cagcccatca accatccact cccacgattg   1800
gagccgatgg cagaagagca ggcacgccat gtcaaaaacg gactgaatg catccgggct    1860
ctcaaggccg agcccatcgg ctcactggcc atcgaggaag ctatggcagc atggtcagaa   1920
atatcagaca cccaggaca ggagcgagcc acctgcaggg aagagaaggc aggcagttcg    1980
ggtctcagca aaccatgcct ctcagcaatt ggatcaactg aaggcggtgc acctcgcatc   2040
cgcggtcagg gacctggaga gagcgatgac gacgctgaaa cttttgggaat ccccccaaga   2100
aatctccagg catcaagcac tgggttacag tgttattatg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc tccgaccccc   2460
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aagggggaga ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
```

| | |
|---|---|
| agcatatcca ccctggaagg acacctctca agcatcatga tcgccattcc tggacttggg | 2940 |
| aaggatccca acgaccccac tgcagatgtc gaaatcaatc ccgacttgaa acccatcata | 3000 |
| ggcagagatt caggccgagc actggccgaa gttctcaaga aacccgttgc cagccgacaa | 3060 |
| ctccaaggaa tgacaaatgg acggaccagt tccagaggac agctgctgaa ggaatttcag | 3120 |
| ctaaagccga tcgggaaaaa gatgagctca gccgtcgggt tgttcctga caccggccct | 3180 |
| gcatcacgca gtgtaatccg ctccattata aaatccagcc ggctagagga ggatcggaag | 3240 |
| cgttacctga tgactctcct tgatgatatc aaaggagcca atgatcttgc caagttccac | 3300 |
| cagatgctga tgaagataat aatgaagtag ctacagctca acttacctgc caaccccatg | 3360 |
| ccagtcgacc caactagtac aacctaaatc cattataaaa aacttaggag caaagtgatt | 3420 |
| gcctcccaag ttccacaggc gcgccatgtt cgtcttcctg gtcctgctgc ctctggtctc | 3480 |
| ctcacagtgc gtcaatctga caactcggac tcagctgcca cctgcttata ctaatagctt | 3540 |
| caccagaggc gtgtactatc ctgacaaggt gtttagaagc tccgtgctgc actctacaca | 3600 |
| ggatctgttt ctgccattct ttagcaacgt gacctggttc cacgccatcc acgtgagcgg | 3660 |
| caccaatggc acaaagcggt tcgacaatcc cgtgctgcct tttaacgatg gcgtgtactt | 3720 |
| cgcctctacc gagaagagca acatcatcag aggctggatc tttggcacca cactggactc | 3780 |
| caagacacag tctctgctga tcgtgaacaa tgccaccaac gtggtcatca aggtgtgcga | 3840 |
| gttccagttt tgtaatgatc ccttcctggg cgtgtactat cacaagaaca ataagagctg | 3900 |
| gatggagtcc gagtttagag tgtattctag cgccaacaac tgcacatttg agtacgtgag | 3960 |
| ccagcctttc ctgatggacc tggagggcaa gcagggcaat ttcaagaacc tgagggagtt | 4020 |
| cgtgtttaag aatatcgacg gctacttcaa aatctactct aagcacaccc ccatcaacct | 4080 |
| ggtgcgcgac ctgcctcagg gcttcagcgc cctggagccc ctggtggatc tgcctatcgg | 4140 |
| catcaacatc acccggtttc agacactgct ggccctgcac agaagctacc tgacacccgg | 4200 |
| cgactcctct agcggatgga ccgccggcgc tgccgcctac tatgtgggct acctccagcc | 4260 |
| ccggaccttc ctgctgaagt acaacgagaa tggcaccatc acagacgcag tggattgcgc | 4320 |
| cctggaccc ctgagcgaga caaagtgtac actgaagtcc tttaccgtgg agaagggcat | 4380 |
| ctatcagaca tccaatttca gggtgcagcc aaccgagtct atcgtgcgct ttcctaatat | 4440 |
| cacaaacctg tgcccatttg gcgaggtgtt caacgcaacc cgcttcgcca gcgtgtacgc | 4500 |
| ctggaatagg aagcggatca gcaactgcgt ggccgactat agcgtgctgt acaactccgc | 4560 |
| ctctttcagc acctttaagt gctatggcgt gtcccccaca aagctgaatg acctgtgctt | 4620 |
| taccaacgtc tacgccgatt ctttcgtgat caggggcgac gaggtgcgcc agatcgcccc | 4680 |
| cggccagaca ggcaagatcg cagactacaa ttataagctg ccagacgatt tcaccggctg | 4740 |
| cgtgatcgcc tggaacagca caatctggga ttccaaagtg ggcggcaact acaattatct | 4800 |
| gtaccggctg tttagaaaga gcaatctgaa gcccttcgag agggacatct ctacagaaat | 4860 |
| ctaccaggcc ggcagcaccc cttgcaatgg cgtggagggc tttaactgtt atttcccact | 4920 |
| ccagtcctac ggcttccagc ccacaaacgg cgtgggctat cagccttacc gcgtggtggt | 4980 |
| gctgagcttt gagctgctgc acgccccagc aacagtgtgc ggccccaaga agtccaccaa | 5040 |
| tctggtgaag aacaagtgcg tgaacttcaa cttcaacggc ctgaccggca caggcgtgct | 5100 |
| gaccgagtcc aacaagaagt tcctgccatt tcagcagttc ggcagggaca tcgcagatac | 5160 |
| cacagacgcc gtgcgcgacc cacagaccct ggagatcctg gacatcacac cctgctcttt | 5220 |

```
cggcggcgtg agcgtgatca cacccggcac caatacaagc aaccaggtgg ccgtgctgta    5280
tcaggacgtg aattgtaccg aggtgcccgt ggctatccac gccgatcagc tgaccccaac    5340
atggcgggtg tacagcaccg gctccaacgt cttccagaca agagccggat gcctgatcgg    5400
agcagagcac gtgaacaatt cctatgagtg cgacatccca atcggcgccg gcatctgtgc    5460
ctcttaccag acccagacaa actctcccgc atctgtgggc agcgtggcct cccagtctat    5520
catcgcctat accatgtccc tgggcgccga gaacagcgtg gcctactcta acaatagcat    5580
cgccatccca accaacttca caatctctgt gaccacagag atcctgcccg tgtccatgac    5640
caagacatct gtggactgca caatgtatat ctgtggcgat tctaccgagt gcagcaacct    5700
gctgctccag tacggcagct tttgtaccca gctgaataga gccctgacag gcatcgccgt    5760
ggagcaggat aagaacacac aggaggtgtt cgcccaggtg aagcaaatct acaagacccc    5820
ccctatcaag gactttggcg gcttcaattt ttcccagatc ctgcctgatc catccaagcc    5880
ttctaagcgg agctttatcg aggacctgct gttcaacaag gtgacctggc ccgatgccgg    5940
cttcatcaag cagtatggcg attgcctggg cgacatcgca gccagggacc tgatctgcgc    6000
ccagaagttt aatggcctga ccgtgctgcc acccctgctg acagatgaga tgatcgcaca    6060
gtacacaagc gccctgctgg ccggcaccat cacatccgga tggaccttcg gcgcaggagc    6120
cgccctccag atccccttty ccatgcagat ggcctatagg ttcaacggca tcggcgtgac    6180
ccagaatgtg ctgtacgaga accagaagct gatcgccaat cagtttaact ccgccatcgg    6240
caagatccag gacagcctgt cctctacagc cagcgccctg ggcaagctcc aggatgtggt    6300
gaatcagaac gcccaggccc tgaataccct ggtgaagcag ctgagcagca acttcggcgc    6360
catctctagc gtgctgaatg acatcctgag ccggctggac cctcctgagg cagaggtgca    6420
gatcgaccgg ctgatcaccg gccggctcca gagcctccag acctatgtga cacagcagct    6480
gatcagggcc gccgagatca gggccagcgc caatctggca gcaaccaaga tgtccgagtg    6540
cgtgctgggc cagtctaaga gagtggactt ttgtggcaag ggctatcacc tgatgtcctt    6600
ccctcagtct gccccacacg gcgtggtgtt tctgcacgtg acctacgtgc cgcccaggga    6660
gaagaacttc accacagccc ctgccatctg ccacgatggc aaggcccact tccaagggga    6720
gggcgtgttc gtgtccaacg gcacccactg gtttgtgaca cagcgcaatt tctacgagcc    6780
ccagatcatc accacagaca cacccttcgt gagcggcaac tgtgacgtgg tcatcggcat    6840
cgtgaacaat accgtgtatg atccactcca gcccgagctg gacagcttta aggaggagct    6900
ggataagtat ttcaagaatc acacctcccc tgacgtggat ctgggcgaca tcagcggcat    6960
caatgcctcc gtggtgaaca tccagaagga gatcgaccgc ctgaacgagg tggctaagaa    7020
tctgaacgag agcctgatcg acctccagga gctgggcaag tatgagcagt acatcaagtg    7080
gccctggtac atctggctgg gcttcatcgc cggcctgatc gccatcgtga tggtgaccat    7140
catgctgtgc tgtatgacat cctgctgttc ttgcctgaag ggctgctgta gctgtggctc    7200
ctgctgtaag tttgacgagg atgactctga acctgtgctg aagggcgtgg cgctggctta    7260
cacctaacgc gcgacgtcct acagctcaac ttacctgcca accccatgcc agtcgaccca    7320
actagtacaa cctaaatcca ttataaaaaa cttaggagca aagtgattgc ctcccaagtt    7380
ccacaatgac agagatctac gacttcgaca gtcggcatgg gacatcaaa ggggttgatcg    7440
ctccgataca acccaccacc tacagtgatg gcaggctggt gccccaggtc agagtcatag    7500
atcctggtct aggcgacagg aaggatgaat gctttatgta catgtttctg ctggggttg    7560
ttgaggacag cgatccccta gggcctccaa tcgggcgagc atttgggtcc ctgcccttag    7620
```

```
gtgttggcag atccacagca aagcccgaaa aactcctcaa agaggccact gagcttgaca      7680
tagttgttag acgtacagca gggctcaatg aaaaactggt gttctacaac aacaccccac      7740
taactctcct cacaccttgg agaaaggtcc taacaacagg gagtgtcttc aacgcaaacc      7800
aagtgtgcaa tgcggttaat ctgataccgc tcgataccccc gcagaggttc cgtgttgttt      7860
atatgagcat cacccgtctt tcggataacg ggtattacac cgttcctaga agaatgctgg      7920
aattcagatc ggtcaatgca gtggccttca acctgctggt gacccttagg attgacaagg      7980
cgataggccc tgggaagatc atcgacaata cagagcaact tcctgaggca acatttatgg      8040
tccacatcgg gaacttcagg agaaagaaga gtgaagtcta ctctgccgat tattgcaaaa      8100
tgaaaatcga aagatgggc ctggtttttg cacttggtgg datagggggc accagtcttc       8160
acattagaag cacaggcaaa atgagcaaga ctctccatgc acaactcggg ttcaagaaga      8220
ccttatgtta cccgctgata gatatcaatg aagaccttaa tcgattactc tggaggagca      8280
gatgcaagat agtaagaatc caggcagttt tgcagccatc agttcctcaa gaattccgca      8340
tttacgacga cgtgatcata aatgatgacc aaggactatt caaagttctg tagaccgtag      8400
tgcccagcaa tgcccgaaaa cgacccccct cacaatgaca gccagaaggc ccggacaaaa      8460 aagcccctc cgaaagactc cacggaccaa gcgagaggcc agccagcagc cgacggcaag       8520
cgcgaacacc aggcggcccc agcacagaac agccctgata caaggccacc accagccacc      8580
ccaatctgca tcctcctcgt gggacccccg aggaccaacc cccaaggctg cccccgatcc      8640
aaaccaccaa ccgcatcccc accaccccg ggaaagaaac cccagcaat tggaaggccc        8700 ctcccctct tcctcaacac aagaactcca caaccgaacc gcacaagcga ccgaggtgac       8760
ccaaccgcag gcatccgact ccctagacag atcctctctc cccggcaaac taaacaaaac      8820
ttagggccaa ggaacataca cacccaacag aacccagacc ccggcccacg cgccgcgcc      8880 cccaaccccc gacaaccaga gggagccccc aaccaatccc gccggctccc ccggtgccca      8940
caggcaggga caccaacccc cgaacagacc cagcacccaa ccatcgacaa tccaagacgg      9000 gggggcccccc ccaaaaaaag gccccagggg gccgacagcc agcaccgcga ggaagcccac     9060
ccaccccaca cacgaccacg gcaaccaaac cagaaccccag accaccctgg gccaccagct    9120
cccagactcg gccatcaccc cgcagaaagg aaaggccaca acccgcgcac cccagccccg     9180
atccggcggg gagccaccca acccgaacca gcacccaaga gcgatcccccg aaggaccccc    9240 gaaccgcaaa ggacatcagt atcccacagc ctctccaagt cccccggtct cctccccttc     9300
tcgaagggac caaaagatca atccaccaca cccgacgaca ctcaactccc caccccctaaa    9360 ggagacaccg ggaatcccag aatcaagact catccaatgt ccatcatggg tctcaaggtg     9420
aacgtctctg ccatattcat ggcagtactg ttaactctcc aaacacccac cggtcaaatc     9480 cattgggggca atctctctaa gatagggggtg gtaggaatag gaagtgcaag ctacaaagtt    9540
atgactcgtt ccagccatca atcattagtc ataaaattaa tgcccaatat aactctcctc     9600
aataactgca cgagggtaga gattgcagaa tacaggagac tactgagaac agttttggaa      9660
ccaattagag atgcacttaa tgcaatgacc cagaatataa gaccggttca gagtgtagct      9720
tcaagtagga gacacaagag atttgcggga gtagtcctgg caggtgcggc cctaggcgtc      9780
gccacagctg ctcagataac agccggcatt gcacttcacc agtccatgct gaactctcaa     9840
gccatcgaca atctgagagc gagcctggaa actactaatc aggcaattga ggcaatcaga      9900
caagcagggc aggagatgat attggctgtt caggtgtcc aagactacat caataatgag       9960
```

```
ctgataccgt ctatgaacca actatcttgt gatttaatcg gccagaagct cgggctcaaa   10020
ttgctcagat actatacaga aatcctgtca ttatttggcc ccagcttacg ggaccccata   10080
tctgcggaga tatctatcca ggctttgagc tatgcgcttg gaggagacat caataaggtg   10140
ttagaaaagc tcggatacag tggaggtgat ttactgggca tcttagagag cagaggaata   10200
aaggcccgga taactcacgt cgacacagag tcctacttca ttgtcctcag tatagcctat   10260
ccgacgctgt ccgagattaa gggggtgatt gtccaccggc tagaggggt ctcgtacaac    10320 ataggctctc aagagtggta taccactgtg cccaagtatg ttgcaaccca agggtacctt   10380
atctcgaatt ttgatgagtc atcgtgtact ttcatgccag aggggactgt gtgcagccaa   10440
aatgccttgt acccgatgag tcctctgctc aagaatgcc tccggggggtc caccaagtcc    10500 tgtgctcgta cactcgtatc cgggtctttt gggaaccggt tcattttatc acaagggaac   10560
ctaatagcca attgtgcatc aatcctttgc aagtgttaca acacaggaac gatcattaat   10620
caagaccctg acaagatcct aacatacatt gctgccgatc actgcccggt agtcgaggtg   10680
aacggcgtga ccatccaagt cgggagcagg aggtatccag atgctgtgta cttgcacaga   10740
attgacctcg gtcctcccat atcattggag aggttggacg tagggacaaa tctggggaat   10800
gcaattgcta agttggagga tgccaaggaa ttgttggagt catcggacca gatattgagg   10860
agtatgaaag gtttatcgag cactagcata gtctacatcc tgattgcagt gtgtcttgga   10920
gggttgatag ggatccccgc tttaatatgt tgctgcaggg ggcgttgtaa caaaaaggga   10980
gaacaagttg gtatgtcaag accaggccta aagcctgatc ttacgggaac atcaaaatcc   11040
tatgtaaggt cgctctgatc ctctacaact cttgaaacac aaatgtccca caagtctcct   11100
cttcgtcatc aagcaaccac cgcacccagc atcaagccca cctgaaatta tctccggctt   11160
ccctctggcc gaacaatatc ggtagttaat taaaacttag ggtgcaagat catccacaat   11220
gtcaccacaa cgagaccgga taaatgcctt ctacaaagat aaccccatc ccaagggaag    11280 taggatagtc attaacagag aacatcttat gattgataga ccttatgttt tgctggctgt   11340
tctgtttgtc atgtttctga gcttgatcgg gttgctagcc attgcaggca ttagacttca   11400
tcgggcagcc atctacaccg cagagatcca taaaagcctc agcaccaatc tagatgtaac   11460
taactcaatc gagcatcagg tcaaggacgt gctgacacca ctcttcaaaa tcatcggtga   11520
tgaagtgggc ctgaggacac ctcagagatt cactgaccta gtgaaattca tctctgacaa   11580
gattaaattc cttaatccgg atagggagta cgacttcaga gatctcactt ggtgtatcaa   11640
cccgccagag agaatcaaat tggattatga tcaatactgt gcagatgtgg ctgctgaaga   11700
gctcatgaat gcattggtga actcaactct actggagacc agaacaacca atcagttcct   11760
agctgtctca aagggaaact gctcaggggcc cactacaatc agaggtcaat tctcaaacat   11820
gtcgctgtcc ctgttagact tgtatttagg tcgaggttac aatgtgtcat ctatagtcac   11880
tatgacatcc cagggaatgt atgggggaac ttacctagtg gaaaagccta atctgagcag   11940
caaaaggtca gagttgtcac aactgagcat gtaccgagtg tttgaagtag gtgttatcag   12000
aaatccgggt ttgggggctc cggtgttcca tatgacaaac tatcttgagc aaccagccag   12060
taatgatctc agcaactgta tggtggcttt ggggagctc aaactcgcag ccctttgtca    12120
cggggaagat tctatcacaa ttccctatca gggatcaggg aaaggtgtca gcttccagct   12180
cgtcaagcta ggtgtctgga atccccaac cgacatgcaa tcctgggtcc ccttatcaac    12240
ggatgatcca gtgatagaca caggctttac ctctcatctc acagaggtgtta tcgctgacaa   12300 tcaagcaaaa tgggctgtcc cgacaacacg aacagatgac aagttgcgaa tggagacatg   12360
```

```
cttccaacag gcgtgtaagg gtaaaatcca agcactctgc gagaatcccg agtgggcacc   12420
attgaaggat aacaggattc cttcatacgg ggtcttgtct gttgatctga gtctgacagt   12480
tgagcttaaa atcaaaattg cttcgggatt cgggccattg atcacacacg gttcagggat   12540
ggacctatac aaatccaacc acaacaatgt gtattggctg actatcccgc caatgaagaa   12600
cctagcctta ggtgtaatca acacattgga gtggataccg agattcaagg ttagtcccta   12660
cctcttcaat gtcccaatta aggaagcagg cgaagactgc catgcccaa catacctacc    12720 tgcggaggtg gatggtgatg tcaaactcag ttccaatctg gtgattctac ctggtcaaga   12780
tctccaatat gttttggcaa cctacgatac ttccagggtt gaacatgctg tggtttatta   12840
cgtttacagc ccaggccgct cattttctta cttttatcct tttaggttgc ctataaaggg   12900
ggtccccatc gaattacaag tggaatgctt cacatgggac caaaaactct ggtgccgtca   12960
cttctgtgtg cttgcggact cagaatctgg tggacatatc actcactctg ggatggtggg   13020
catgggagtc agctgcacag tcacccggga agatggaacc aatcgcagat agggctgcta   13080
gtgaaccaat ctcatgatgt cacccagaca tcaggcatac ccactagtgt gaaatagaca   13140
tcagaattaa gaaaaacgta gggtccaagt ggttccccgt tatggactcg ctatctgtca   13200
accagatctt ataccctgaa gttcacctag atagcccgat agttaccaat aagatagtag   13260
ccatcctgga gtatgctcga gtccctcacg cttacagcct ggaggaccct acactgtgtc   13320
agaacatcaa gcaccgccta aaaaacggat tttccaacca aatgattata acaatgtgg    13380 aagttgggaa tgtcatcaag tccaagctta ggagttatcc ggcccactct catattccat   13440
atccaaattg taatcaggat ttatttaaca tagaagacaa agagtcaacg aggaagatcc   13500
gtgaactcct caaaaagggg aattcgctgt actccaaagt cagtgataag gttttccaat   13560
gcttaaggga cactaactca cggcttggcc taggctccga attgagggag gacatcaagg   13620
agaaagttat taacttggga gtttacatgc acagctccca gtggtttgag cccttctctgt  13680 tttggtttac agtcaagact gagatgaggt cagtgattaa atcacaaacc catacttgcc   13740
ataggaggag acacacacct gtattcttca ctggtagttc agttgagttg ctaatctctc   13800
gtgaccttgt tgctataatc agtaaagagt ctcaacatgt atattacctg acatttgaac   13860
tggttttgat gtattgtgat gtcatagagg ggaggttaat gacagagacc gctatgacta   13920
ttgatgctag gtatacagag cttctaggaa gagtcagata catgtggaaa ctgatagatg   13980
gtttcttccc tgcactcggg aatccaactt atcaaattgt agccatgctg gagcctcttt   14040
cacttgctta cctgcagctg agggatataa cagtagaact cagaggtgct ttccttaacc   14100
actgctttac tgaaatacat gatgttcttg accaaaacgg gttttctgat gaaggtactt   14160
atcatgagtt aattgaagct ctagattaca ttttcataac tgatgacata catctgacag   14220
gggagatttt ctcatttttc agaagtttcg gccaccccag acttgaagca gtaacggctg   14280
ctgaaaatgt taggaaatac atgaatcagc ctaaagtcat tgtgtatgag actctgatga   14340
aaggtcatgc catattttgt ggaatcataa tcaacggcta tcgtgacagg cacggaggca   14400
gttggccacc gctgaccctc cccctgcatg ctgcagacac aatccggaat gctcaagctt   14460
caggtgaagg gttaacacat gagcagtgcg ttgataactg gagatctttt gctggagtga   14520
aatttggctg ctttatgcct cttagcctgg atagtgatct gacaatgtac ctaaaggaca   14580
aggcacttgc tgctctccaa agggaatggg attcagttta cccgaaagag ttcctgcgtt   14640
acgaccctcc caagggaacc gggtcacgga ggcttgtaga tgttttcctt aatgattcga   14700
```

```
gctttgaccc atatgatgtg ataatgtatg ttgtaagtgg agcttacctc catgaccctg    14760
agttcaacct gtcttacagc ctgaaagaaa aggagatcaa ggaaacaggt agactttttg    14820
ctaaaatgac ttacaaaatg agggcatgcc aagtgattgc tgaaaatcta atctcaaacg    14880
ggattggcaa atattttaag gacaatggga tggccaagga tgagcacgat ttgactaagg    14940
cactccacac tctagctgtc tcaggagtcc ccaaagatct caaagaaagt cacagggggg    15000
ggccagtctt aaaaacctac tcccgaagcc cagtccacac aagtaccagg aacgtgagag    15060
cagcaaaagg gtttataggg ttccctcaag taattcggca ggaccaagac actgatcatc    15120
cggagaatat ggaagcttac gagacagtca gtgcatttat cacgactgat ctcaagaagt    15180
actgccttaa ttggagatat gagaccatca gcttgtttgc acagaggcta aatgagattt    15240
acggattgcc ctcattttc cagtggctgc ataagaggct tgagacctct gtcctgtatg    15300
taagtgaccc tcattgcccc cccgaccttg acgcccatat cccgttatat aaagtcccca    15360
atgatcaaat cttcattaag taccctatgg gaggtataga agggtattgt cagaagctgt    15420
ggaccatcag caccattccc tatctatacc tggctgctta tgagagcgga gtaaggattg    15480
cttcgttagt gcaaggggac aatcagacca tagccgtaac aaaaagggta cccagcacat    15540
ggccctacaa ccttaagaaa cgggaagctg ctagagtaac tagagattac tttgtaattc    15600
ttaggcaaag gctacatgat attggccatc acctcaaggc aaatgagaca attgtttcat    15660
cacatttttt tgtctattca aaaggaatat attatgatgg gctacttgtg tcccaatcac    15720
tcaagagcat cgcaagatgt gtattctggt cagagactat agttgatgaa acaagggcag    15780
catgcagtaa tattgctaca acaatggcta aaagcatcga gagaggttat gaccgttacc    15840
ttgcatattc cctgaacgtc ctaaaagtga tacagcaaat tctgatctct cttggcttca    15900
caatcaattc aaccatgacc cgggatgtag tcataccccct cctcacgaac aacgacctct    15960
taataaggat ggcactgttg cccgctccta ttgggggggat gaattatctg aatatgagca    16020
ggctgtttgt cagaaacatc ggtgatccag taacatcatc aattgctgat ctcaagagaa    16080
tgattctcgc ctcactaatg cctgaagaga ccctccatca agtaatgaca caacaaccgg    16140
gggactcttc attcctagac tgggctagcg acccttactc agcaaatctt gtatgtgtcc    16200
agagcatcac tagactcctc aagaacataa ctgcaaggtt tgtcctgatc catagtccaa    16260
acccaatgtt aaaaggatta ttccatgatg acagtaaaga agaggacgag ggactggcgg    16320
cattcctcat ggacaggcat attatagtac ctagggcagc tcatgaaatc ctggatcata    16380
gtgtcacagg ggcaagagag tctattgcag gcatgctgga taccacaaaa ggcctgattc    16440
gagccagcat gaggaagggg gggttaacct ctcgagtgat aaccagattg tccaattatg    16500
actatgaaca attcagagca gggatggtgc tattgacagg aagaaagaga atgtccctca    16560
ttgacaaaga gtcatgttca gtgcagctgg cgagagctct aagaagccat atgtgggcga    16620
ggctagctcg aggacggcct atttacggcc ttgaggtccc tgatgtacta gaatctatgc    16680
gaggccacct tattcggcgt catgagacat gtgtcatctg cgagtgtgga tcagtcaact    16740
acggatggtt ttttgtcccc tcgggttgcc aactggatga tattgacaag gaaacatcat    16800
ccttgagagt cccatatatt ggttctacca ctgatgagag aacagacatg aagcttgcct    16860
tcgtaagagc cccaagtcga tccttgcgat ctgctgttag aatagcaaca gtgtactcat    16920
gggcttacgg tgatgatgat agctcttgga acgaagcctg ttgttggcct aggcaaaggg    16980
ccaatgtgag cctggaggag ctaagggtga tcactcccat ctcaacttcg actaatttag    17040
cgcataggtt gagggatcgt agcactcaag tgaaatactc aggtacatcc cttgtccgag    17100
```

```
tggcgaggta taccacaatc tccaacgaca atctctcatt tgtcatatca gataagaagg   17160
ttgatactaa ctttatatac caacaaggaa tgcttctagg gttgggtgtt ttagaaacat   17220
tgtttcgact cgagaaagat accggatcat ctaacacggt attacatctt cacgtcgaaa   17280
cagattgttg cgtgatcccg atgatagatc atcccaggat acccagctcc cgcaagctag   17340
agctgagggc agagctatgt accaacccat tgatatatga taatgcacct ttaattgaca   17400
gagatacaac aaggctatac acccagagcc ataggaggca ccttgtggaa tttgttacat   17460
ggtccacacc ccaactatat cacattttag ctaagtccac agcactatct atgattgacc   17520
tggtaacaaa atttgagaag gaccatatga atgaaatttc agctctcata ggggatgacg   17580
atatcaatag tttcataact gagtttctgc tcatagagcc aagattattc actatctact   17640
tgggccagtg tgcggccatc aattgggcat ttgatgtaca ttatcataga ccatcaggga   17700
aatatcagat gggtgagctg ttgtcatcgt tcctttctag aatgagcaaa ggagtgttta   17760
aggtgcttgt caatgctcta agccacccaa agatctacaa gaaattctgg cattgtggta   17820
ttatagagcc tatccatggt ccttcacttg atgctcaaaa cttgcacaca actgtgtgca   17880
acatggttta cacatgctat atgacctacc tcgacctgtt gttgaatgaa gagttagaag   17940
agttcacatt tctcttgtgt gaaagcgacg aggatgtagt accggacaga ttcgacaaca   18000
tccaggcaaa acactatgt gttctggcag atttgtactg tcaaccaggg acctgcccac   18060
caattcgagg tctaagaccg gtagagaaat gtgcagttct aaccgaccat atcaaggcag   18120
aggctaggtt atctccagca ggatcttcgt ggaacataaa tccaattatt gtagaccatt   18180
actcatgctc tctgacttat ctccggcgag gatcgatcaa acagataaga ttgagagttg   18240
atccaggatt cattttcgac gccctcgctg aggtaaatgt cagtcagcca agatcggca   18300 gcaacaacat ctcaaatatg agcatcaagg cttttcagacc cccacacgat gatgttgcaa   18360
aattgctcaa agatatcaac acaagcaagc acaatcttcc catttcaggg ggcaatctcg   18420
ccaattatga aatccatgct ttccgcagaa tcgggttgaa ctcatctgct tgctacaaag   18480
ctgttgagat atcaacatta attaggagat gccttgagcc aggggaggac ggcttgttct   18540
tgggtgaggg atcgggttcc atgttgatca cttataagga gatacttaaa ctaaacaagt   18600
gcttctataa tagtgggggtt tccgccaatt ctagatctgg tcaaaggaa ttagcaccct   18660 atccctccga agttggcctt gtcgaacaca gaatgggagt aggtaatatt gtcaaagtgc   18720 tcttttaacgg gaggcccgaa gtcacgtggg taggcagtgt agattgcttc aatttcatag   18780
ttagtaatat ccctacctct agtgtggggt ttatccattc agatatagag ccttgccta   18840 acaaagatac tatagagaag ctagaggaat tggcagccat cttatcgatg gctctgctcc   18900
tgggcaaaat aggatcaata ctggtgatta agcttatgcc tttcagcggg gattttgttc   18960
agggatttat aagttatgta gggtcccatt atagagaagt gaaccttgta taccctagat   19020
acagcaactt catatctact gaatcttatt tggttatgac agatctcaag gctaaccggc   19080
taatgaatcc tgaaaagatt aagcagcaga taattgaatc atctgtgagg acttcacctg   19140
gacttatagg tcacatccta tccattaagc aactaagctg catacaagca attgtgggag   19200
acgcagttag tagaggtgat atcaatccta ctctgaaaaa acttacacct atagagcagg   19260
tgctgatcaa ttgcgggttg gcaattaacg gacctaagct gtgcaaagaa ttgatccacc   19320
atgatgttgc ctcagggcaa gatggattgc ttaattctat actcatcctc tacagggagt   19380
tggcaagatt caaagacaac caaagaagtc aacaagggat gttccacgct tacccgtat   19440
```

```
tggtaagtag caggcaacga gaacttatat ctaggatcac ccgcaaattt tgggggcaca   19500
ttcttcttta ctccgggaac agaaagttga taaataagtt tatccagaat ctcaagtccg   19560
gctatctgat actagactta caccagaata tcttcgttaa gaatctatcc aagtcagaga   19620
aacagattat tatgacgggg ggtttgaaac gtgagtgggt ttttaaggta acagtcaagg   19680
agaccaaaga atggtataag ttagtcggat acagtgccct gattaaggac taattggttg   19740
aactccggaa ccctaatcct gccctaggtg gttaggcatt atttgcaata gattaaagaa   19800
aactttgaaa atacgaagtt tctattccca gctttgtctg gtggccggca tggtcccagc   19860
ctcctcgctg gcgccggctg ggcaacattc cgagggacc gtcccctcgg taatggcgaa    19920
tgggacgcgg ccgatccggc tgctaacaaa gcccgaaagg aagctgagtt ggctgctgcc   19980
accgctgagc aataactagc ataacccctt ggggcctcta aacgggtctt gaggggtttt   20040
ttgctgaaag gaggaactat atccggatgc ggccgatccg gctgctaaca aagcccgaaa   20100
ggaagctgag ttggctgctg ccaccgctga gcaataacta gcataacccc ttggggcctc   20160
taaacgggtc ttgaggggtt ttttgctgaa aggaggaact atatccggat ggccgccacc   20220
ggccggtggg ccttgcagca catcccccTT tcgccagctg gcgtaatagc gaagaggccc   20280
gcaccgatcg cccttcccaa cagttgcgca gcctgaatgg cgaatgggac gcgccctgta   20340
gcggcgcatt aagcgcggcg ggtgtggtgg ttacgcgcag cgtgaccgct acacttgcca   20400
gcgccctagc gcccgctcct ttcgctttct tcccttcctt tctcgccacg ttcgccggct   20460
ttccccgtca gctctaaatc gggggctcc ctttagggtt ccgatttagt gctttacggc    20520
acctcgaccc caaaaaactt gattagggtg atggttcacg tgggccatcg ccctgataga   20580 cggttttttcg ccctttgacg ttggagtcca cgttctttaa tagtggactc ttgttccaaa   20640
ctggaacaac actcaaccct atctcggtct attcttttga tttataaggg attttgccga   20700
tttcggccta ttggttaaaa aatgagctga tttaacaaaa atttaacgcg aattttaaca   20760
aaatattaac gcttacaatt taggtggcac ttttcgggga aatgtgcgcg gaaccccctat   20820 ttgtttattt ttctaaatac attcaaatat gtatccgctc atgagacaat aaccctgata   20880
aatgcttcaa taatattgaa aaaggaagag tatgagtatt caacatttcc gtgtcgccct   20940
tattcccttt tttgcggcat tttgccttcc tgttttTgct cacccagaaa cgctggtgaa   21000
agtaaaagat gctgaagatc agttgggtgc acgagtgggt tacatcgaac tggatctcaa   21060
cagcggtaag atccttgaga gttttcgccc cgaagaacgt tttccaatga tgagcacttt   21120
taaagttctg ctatgtggcg cggtattatc ccgtattgac gccgggcaag agcaactcgg   21180
tcgccgcata cactattctc agaatgactt ggttgagtac tcaccagtca cagaaaagca   21240
tcttacggat ggcatgacag taagagaatt atgcagtgct gccataacca tgagtgataa   21300
cactgcggcc aacttacttc tgacaacgat cggaggaccg aaggagctaa ccgcttttTt   21360
gcacaacatg ggggatcatg taactcgcct tgatcgttgg gaaccggagc tgaatgaagc   21420
cataccaaac gacgagcgtg acaccacgat gcctgtagca atggcaacaa cgttgcgcaa   21480
actattaact ggcgaactac ttacactagc ttcccggcaa caattaatag actggatgga   21540
ggcggataaa gttgcaggac cacttctgcg ctcggccctt ccggctggct ggtttattgc   21600
tgataaatct ggagccggtg agcgtgggtc tcgcggtatc attgcagcac tggggccaga   21660
tggtaagccc tcccgtatcg tagttatcta cacgacgggg agtcaggcaa ctatggatga   21720
acgaaataga cagatcgctg agataggtgc ctcactgatt aagcattggt aactgtcaga   21780
ccaagtttac tcatatatac tttagattga tttaaaactt catttttaat ttaaaaggat   21840
```

```
ctaggtgaag atccttttg ataatctcat gaccaaaatc ccttaacgtg agttttcgtt    21900
ccactgagcg tcagacccg tagaaaagat caaaggatct tcttgagatc cttttttct    21960
gcgcgtaatc tgctgcttgc aaacaaaaaa accaccgcta ccagcggtgg tttgtttgcc    22020
ggatcaagag ctaccaactc tttttccgaa ggtaactggc ttcagcagag cgcagatacc    22080
aaatactgtt cttctagtgt agccgtagtt aggccaccac ttcaagaact ctgtagcacc    22140
gcctacatac ctcgctctgc taatcctgtt accagtggct gctgccagtg gcgataagtc    22200
gtgtcttacc gggttggact caagacgata gttaccggat aaggcgcagc ggtcgggctg    22260
aacgggggt tcgtgcacac agcccagctt ggagcgaacg acctacaccg aactgagata    22320
cctacagcgt gagctatgag aaagcgccac gcttcccgaa gggagaaagg cggacaggta    22380
tccggtaagc ggcagggtcg gaacaggaga gcgcacgagg gagcttccag ggggaaacgc    22440
ctggtatctt tatagtcctg tcgggtttcg ccacctctga cttgagcgtc gatttttgtg    22500
atgctcgtca gggggcgga gcctatggaa aaacgccagc aacgcggcct ttttacggtt    22560
cctggccttt tgctggcctt tgctcacat gttctttcct gcgttatccc ctgattctgt    22620
ggataaccgt attaccgcct ttgagtgagc tgataccgct cgccgcagcc gaacgaccga    22680
gcgcagcgag tcagtgagcg aggaagcgga agagcgccca atacgcaaac cgcctctccc    22740
cgcgcgttgg ccgattcatt aatgcagctg gcacgacagg tttcccgact ggaaagcggg    22800
cagtgagcgc aacgcaatta atgtgagtta gctcactcat taggcacccc aggctttaca    22860
ctttatgctt ccggctcgta tgttgtgtgg aattgtgagc ggacaacaat ttcacacagg    22920
aaacagctat gaccatgatt acgccaagct cgggcggccg cttgtaatac gactcactat    22980
a                                                                   22981

<210> SEQ ID NO 21
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S-CO-AA-fneg

<400> SEQUENCE: 21
accaaacaaa gttgggtaag gatagttcaa tcaatgatca ttttctagtg cacttaggat      60
tcaagatcct attatcaggg acaagagcag gattaaggat atccgagatg gccacacttt     120
taaggagctt agcattgttc aaaagaaaca aggacaaacc acccattaca tcaggatccg     180
gtggagccat cagaggaatc aaacacatta ttatagtacc aatccctgga gattcctcaa     240
ttaccactcg atccagactt ctggaccggt tggtcaggtt aattggaaac ccggatgtga     300
gcgggcccaa actaacaggg gcactaatag gtatattatc cttatttgtg gagtctccag     360
gtcaattgat tcagaggatc accgatgacc ctgacgttag cataaggctg ttagaggttg     420
tccagagtga ccagtcacaa tctggcctta ccttcgcatc aagaggtacc aacatggagg     480
atgaggcgga ccaatacttt tcacatgatg atccaattag tagtgatcaa tccaggttcg     540
gatggttcga gaacaaggaa atctcagata ttgaagtgca agaccctgag ggattcaaca     600
tgattctggg taccatccta gctcaaattt gggtcttgct cgcaaaggcg ttacggccc      660
cagacacggc agctgattcg gagctaagaa ggtggataaa gtacacccaa caagaaggg     720
```

```
tagttggtga atttagattg agagaaaat  ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatgggga  aactgcaccc tacatggtaa tcctggagaa ctcaattcag aacaagttca   1080
gtgcaggatc ataccctctg ctctggagct atgccatggg agtaggagtg aacttgaaa    1140
actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttgggggca  aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc atcggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag gaccagaaca acatccgcct accctccatc attgttataa   1740
aaaacttagg aaccaggtcc acacagccgc cagcccatca accatccact cccacgattg   1800
gagccgatgg cagaagagca ggcacgccat gtcaaaaacg gactgaaatg catccgggct   1860
ctcaaggccg agcccatcgg ctcactggcc atcgaggaag ctatggcagc atggtcagaa   1920
atatcagaca cccaggaca  ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa cttTgggaat cccccaaga    2100
aatctccagg catcaagcac tgggttacag tgttattatg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc tccgacccc    2460
ggtagggcca gcacttccgg gacacccatt aaaaagggca cagacgcgag attagcctca   2520
tttgaacgg  agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aaggggaga  ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg cacctctca  agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
```

```
ctaaagccga tcgggaaaaa gatgagctca gccgtcgggt tgttcctga caccggccct    3180 gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc caaccccatg    3360
ccagtcgacc caactagtac aacctaaatc cattataaaa aacttaggag caaagtgatt    3420
gcctcccaag ttccacaggc gcgccatgtt cgtcttcctg gtcctgctgc ctctggtctc    3480
ctcacagtgc gtcaatctga caactcggac tcagctgcca cctgcttata ctaatagctt    3540
caccagaggc gtgtactatc ctgacaaggt gtttagaagc tccgtgctgc actctacaca    3600
ggatctgttt ctgccattct ttagcaacgt gacctggttc cacgccatcc acgtgagcgg    3660
caccaatggc acaaagcggt tcgacaatcc cgtgctgcct tttaacgatg gcgtgtactt    3720
cgcctctacc gagaagagca acatcatcag aggctggatc tttggcacca cactggactc    3780
caagacacag tctctgctga tcgtgaacaa tgccaccaac gtggtcatca aggtgtgcga    3840
gttccagttt tgtaatgatc ccttcctggg cgtgtactat cacaagaaca ataagagctg    3900
gatggagtcc gagtttagag tgtattctag cgccaacaac tgcacatttg agtacgtgag    3960
ccagcctttc ctgatggacc tggagggcaa gcagggcaat ttcaagaacc tgagggagtt    4020
cgtgtttaag aatatcgacg gctacttcaa aatctactct aagcacaccc ccatcaacct    4080
ggtgcgcgac ctgcctcagg gcttcagcgc cctggagccc ctggtggatc tgcctatcgg    4140
catcaacatc acccggtttc agacactgct ggccctgcac agaagctacc tgacacccgg    4200
cgactcctct agcggatgga ccgccggcgc tgccgcctac tatgtgggct acctccagcc    4260
ccggaccttc ctgctgaagt acaacgagaa tggcaccatc acagacgcag tggattgcgc    4320
cctggacccc ctgagcgaga caaagtgtac actgaagtcc tttaccgtgg agaagggcat    4380
ctatcagaca tccaatttca gggtgcagcc aaccgagtct atcgtgcgct ttcctaatat    4440
cacaaacctg tgcccatttg gcgaggtgtt caacgcaacc cgcttcgcca gcgtgtacgc    4500
ctggaatagg aagcggatca gcaactgcgt ggccgactat agcgtgctgt acaactccgc    4560
ctctttcagc acctttaagt gctatggcgt gtcccccaca aagctgaatg acctgtgctt    4620
taccaacgtc tacgccgatt cttttcgtgat caggggcgac gaggtgcgcc agatcgcccc    4680
cggccagaca ggcaagatcg cagactacaa ttataagctg ccagacgatt tcaccggctg    4740
cgtgatcgcc tggaacagca acaatctgga ttccaaagtg ggcggcaact acaattatct    4800
gtaccggctg tttagaaaga gcaatctgaa gcccttcgag agggacatct ctacagaaat    4860
ctaccaggcc ggcagcaccc cttgcaatgg cgtggagggc tttaactgtt atttcccact    4920
ccagtcctac ggcttccagc ccacaaacgg cgtgggctat cagccttacc gcgtggtggt    4980
gctgagcttt gagctgctgc acgccccagc aacagtgtgc ggccccaaga agtccaccaa    5040
tctggtgaag aacaagtgcg tgaacttcaa cttcaacggc ctgaccggca caggcgtgct    5100
gaccgagtcc aacaagaagt tcctgccatt tcagcagttc ggcagggaca tcgcagatac    5160
cacagacgcc gtgcgcgacc cacagaccct ggagatcctg gacatcacac cctgctcttt    5220
cggcggcgtg agcgtgatca cacccggcac caatacaagc aaccaggtgg ccgtgctgta    5280
tcaggacgtg aattgtaccg aggtgcccgt ggctatccac gccgatcagc tgaccccaac    5340
atggcgggtg tacagcaccg gctccaacgt cttccagaca agagccggat gcctgatcgg    5400
agcagagcac gtgaacaatt cctatgagtg cgacatccca atcggcgccg gcatctgtgc    5460
```

```
ctcttaccag acccagacaa actctcccgc atctgtgggc agcgtggcct cccagtctat    5520
catcgcctat accatgtccc tgggcgccga gaacagcgtg gcctactcta acaatagcat    5580
cgccatccca accaacttca caatctctgt gaccacagag atcctgcccg tgtccatgac    5640
caagacatct gtggactgca caatgtatat ctgtggcgat tctaccgagt gcagcaacct    5700
gctgctccag tacggcagct tttgtaccca gctgaataga gccctgacag gcatcgccgt    5760
ggagcaggat aagaacacac aggaggtgtt cgcccaggtg aagcaaatct acaagacccc    5820
ccctatcaag gactttggcg gcttcaattt ttcccagatc ctgcctgatc catccaagcc    5880
ttctaagcgg agctttatcg aggacctgct gttcaacaag gtgaccctgg ccgatgccgg    5940
cttcatcaag cagtatggcg attgcctggg cgacatcgca gccagggacc tgatctgcgc    6000
ccagaagttt aatggcctga ccgtgctgcc acccctgctg acagatgaga tgatcgcaca    6060
gtacacaagc gccctgctgg ccggcaccat cacatccgga tggaccttcg gcgcaggagc    6120
cgccctccag atcccctttg ccatgcagat ggcctatagg ttcaacggca tcggcgtgac    6180
ccagaatgtg ctgtacgaga accagaagct gatcgccaat cagtttaact ccgccatcgg    6240
caagatccag gacagcctgt cctctacagc cagcgccctg ggcaagctcc aggatgtggt    6300
gaatcagaac gcccaggccc tgaataccct ggtgaagcag ctgagcagca cttcggcgc    6360 catctctagc gtgctgaatg acatcctgag ccggctggac aaggtggagg cagaggtgca    6420
gatcgaccgg ctgatcaccg gccggctcca gagcctccag acctatgtga cacagcagct    6480
gatcagggcc gccgagatca gggccagcgc caatctggca gcaaccaaga tgtccgagtg    6540
cgtgctgggc cagtctaaga gagtggactt ttgtggcaag ggctatcacc tgatgtcctt    6600
ccctcagtct gccccacacg gcgtggtgtt tctgcacgtg acctacgtgc cgcccagga    6660 gaagaacttc accacagccc ctgccatctg ccacgatggc aaggcccact ttccaaggga    6720
gggcgtgttc gtgtccaacg gcacccactg gtttgtgaca cagcgcaatt tctacgagcc    6780
ccagatcatc accacagaca cacccttcgt gagcggcaac tgtgacgtgg tcatcggcat    6840
cgtgaacaat accgtgtatg atccactcca gcccgagctg gacagctta aggaggagct    6900 ggataagtat ttcaagaatc acacctcccc tgacgtggat ctgggcgaca tcagcggcat    6960
caatgcctcc gtggtgaaca tccagaagga gatcgaccgc tgaacgagg tggctaagaa    7020 tctgaacgag agcctgatcg acctccagga gctgggcaag tatgagcagt acatcaagtg    7080
gccctggtac atctggctgg gcttcatcgc cggcctgatc gccatcgtga tggtgaccat    7140
catgctgtgc tgtatgacat cctgctgttc ttgcctgaag gctgctgta gctgtggctc    7200 ctgctgtaag tttgacgagg atgactctga acctgtgctg aagggcgtgg cgctggctta    7260
cacctaacgc gcgacgtcct acagctcaac ttacctgcca accccatgcc agtcgaccca    7320
actagtacaa cctaaatcca ttataaaaaa cttaggagca aagtgattgc ctcccaagtt    7380
ccacaatgac agagatctac gacttcgaca agtcggcatg ggacatcaaa gggttgatcg    7440
ctccgataca acccaccacc tacagtgatg gcaggctggt gccccaggtc agagtcatag    7500
atcctggtct aggcgacagg aaggatgaat gctttatgta catgtttctg ctgggggttg    7560
ttgaggacag cgatccccta gggcctccaa tcgggcgagc atttgggtcc ctgcccttag    7620
gtgttggcag atccacagca aagcccgaaa aactcctcaa agaggccact gagcttgaca    7680
tagttgttag acgtacagca gggctcaatg aaaaactggt gttctacaac aacccccac    7740 taactctcct cacaccttgg agaaaggtcc taacaacagg gagtgtcttc aacgcaaacc    7800
aagtgtgcaa tgcggttaat ctgataccgc tcgataccc gcagaggttc cgtgttgttt    7860
```

```
atatgagcat cacccgtctt tcggataacg ggtattacac cgttcctaga agaatgctgg    7920
aattcagatc ggtcaatgca gtggccttca acctgctggt gacccttagg attgacaagg    7980
cgataggccc tgggaagatc atcgacaata cagagcaact tcctgaggca acatttatgg    8040
tccacatcgg gaacttcagg agaaagaaga gtgaagtcta ctctgccgat tattgcaaaa    8100
tgaaaatcga aaagatgggc ctggtttttg cacttggtgg gatagggggc accagtcttc    8160
acattagaag cacaggcaaa atgagcaaga ctctccatgc acaactcggg ttcaagaaga    8220
ccttatgtta cccgctgata gatatcaatg aagaccttaa tcgattactc tggaggagca    8280
gatgcaagat agtaagaatc caggcagttt tgcagccatc agttcctcaa gaattccgca    8340
tttacgacga cgtgatcata aatgatgacc aaggactatt caaagttctg tagaccgtag    8400
tgcccagcaa tgcccgaaaa cgaccccccct cacaatgaca gccagaaggc ccggacaaaa    8460 aagcccccte cgaaagactc cacggaccaa gcgagaggcc agccagcagc cgacggcaag    8520
cgcgaacacc aggcggcccc agcacagaac agccctgata caaggccacc accagccacc    8580
ccaatctgca tcctcctcgt gggaccccccg aggaccaacc cccaaggctg cccccgatcc    8640
aaaccaccaa ccgcatcccc accaccccg ggaaagaaac cccagcaat tggaaggccc    8700 ctccccctct tcctcaacac aagaactcca caaccgaacc gcacaagcga ccgaggtgac    8760
ccaaccgcag gcatccgact ccctagacag atcctctctc cccggcaaac taaacaaaac    8820
ttagggccaa ggaacataca cacccaacag aaccagacc ccggcccacg gcgccgcgcc    8880
cccaaccccc gacaaccaga gggagcccccc aaccaatccc gccggctccc ccggtgccca    8940
caggcaggga caccaacccc cgaacagacc cagcacccaa ccatcgacaa tccaagacgg    9000
ggggggcccc ccaaaaaaag gcccccaggg gccgacagcc agcaccgcga ggaagcccac    9060
ccaccccaca cacgaccacg gcaaccaaac cagaacccag accaccctgg gccaccagct    9120
cccagactcg gccatcaccc cgcagaaagg aaaggccaca acccgcgcac cccagccccg    9180
atccggcggg gagccacccca acccgaacca gcacccaaga gcgatccccg aaggacccccc    9240 gaaccgcaaa ggacatcagt atcccacagc ctctccaagt ccccccggtct cctccccttc    9300 tcgaagggac caaaagatca atccaccaca cccgacgaca ctcaactccc cacccctaaa    9360
ggagacaccg ggaatcccag aatcaagact catccaatgt ccatcatggg tctcaaggtg    9420
aacgtctctg ccatattcat ggcagtactg ttaactctcc aaacacccac cggtcaaatc    9480
cattggggca atctctctaa gataggggtg gtaggaatag gaagtgcaag ctacaaagtt    9540
atgactcgtt ccagccatca atcattagtc ataaaattaa tgcccaatat aactctcctc    9600
aataactgca cgagggtaga gattgcagaa tacaggagac tactgagaac agttttggaa    9660
ccaattagag atgcacttaa tgcaatgacc cagaatataa gaccggttca gagtgtagct    9720
tcaagtagga gacacaagag attttgcggga gtagtcctgg caggtgcggc cctaggcgtc    9780
gccacagctg ctcagataac agccggcatt gcacttcacc agtccatgct gaactctcaa    9840
gccatcgaca atctgagagc gagcctggaa actactaatc aggcaattga ggcaatcaga    9900
caagcagggc aggagatgat attggctgtt caggtgtcc aagactacat caataatgag    9960
ctgataccgt ctatgaacca actatcttgt gatttaatcg gccagaagct cgggctcaaa    10020
ttgctcagat actatacaga aatcctgtca ttatttggcc ccagcttacg ggaccccata    10080
tctgcggaga tatctatcca ggctttgagc tatgcgcttg gaggagacat caataaggtg    10140
ttagaaaagc tcggatacag tggaggtgat ttactgggca tcttagagag cagaggaata    10200
```

-continued

```
aaggcccgga taactcacgt cgacacagag tcctacttca ttgtcctcag tatagcctat   10260
ccgacgctgt ccgagattaa gggggtgatt gtccaccggc tagaggggt ctcgtacaac    10320
ataggctctc aagagtggta taccactgtg cccaagtatg ttgcaaccca agggtacctt   10380
atctcgaatt ttgatgagtc atcgtgtact ttcatgccag aggggactgt gtgcagccaa   10440
aatgccttgt acccgatgag tcctctgctc caagaatgcc tccgggggtc caccaagtcc   10500
tgtgctcgta cactcgtatc cgggtctttt gggaaccggt tcattttatc acaagggaac   10560
ctaatagcca attgtgcatc aatcctttgc aagtgttaca caacaggaac gatcattaat   10620
caagaccctg acaagatcct aacatacatt gctgccgatc actgcccggt agtcgaggtg   10680
aacggcgtga ccatccaagt cgggagcagg aggtatccag atgctgtgta cttgcacaga   10740
attgacctcg gtcctcccat atcattggag aggttggacg tagggacaaa tctggggaat   10800
gcaattgcta agttggagga tgccaaggaa ttgttggagt catcggacca gatattgagg   10860
agtatgaaag gtttatcgag cactagcata gtctacatcc tgattgcagt gtgtcttgga   10920
gggttgatag ggatccccgc tttaatatgt tgctgcaggg ggcgttgtaa caaaaaggga   10980
gaacaagttg gtatgtcaag accaggccta agcctgatc ttacgggaac atcaaaatcc    11040
tatgtaaggt cgctctgatc ctctacaact cttgaaacac aaatgtccca caagtctcct   11100
cttcgtcatc aagcaaccac cgcacccagc atcaagccca cctgaaatta tctccggctt   11160
ccctctggcc gaacaatatc ggtagttaat taaaacttag ggtgcaagat catccacaat   11220
gtcaccacaa cgagaccgga taatgccctt ctacaaagat aaccccccatc ccaagggaag  11280
taggatagtc attaacagag aacatcttat gattgataga ccttatgttt tgctggctgt   11340
tctgttttgtc atgtttctga gcttgatcgg gttgctagcc attgcaggca ttagacttca  11400
tcgggcagcc atctacaccg cagagatcca taaaagcctc agcaccaatc tagatgtaac   11460
taactcaatc gagcatcagg tcaaggacgt gctgacacca ctcttcaaaa tcatcggtga   11520
tgaagtgggc ctgaggacac ctcagagatt cactgaccta gtgaaattca tctctgacaa   11580
gattaaattc cttaatccgg ataggagta cgacttcaga gatctcactt ggtgtatcaa    11640
cccgccagag agaatcaaat tggattatga tcaatactgt gcagatgtgg ctgctgaaga   11700
gctcatgaat gcattggtga actcaactct actggagacc agaacaacca atcagttcct   11760
agctgtctca aagggaaact gctcagggcc cactacaatc agaggtcaat tctcaaacat   11820
gtcgctgtcc ctgttagact tgtatttagg tcgaggttac aatgtgtcat ctatagtcac   11880
tatgacatcc cagggaatgt atgggggaac ttacctagtg gaaaagccta atctgagcag   11940
caaaaggtca gagttgtcac aactgagcat gtaccgagtg tttgaagtag gtgttatcag   12000
aaatccgggt ttgggggctc cggtgttcca tatgacaaac tatcttgagc aaccagccag   12060
taatgatctc agcaactgta tggtggcttt gggggagctc aaactcgcag ccctttgtca   12120
cggggaagat tctatcacaa ttccctatca gggatcaggg aaaggtgtca gcttccagct   12180
cgtcaagcta ggtgtctgga atccccaac cgacatgcaa tcctgggtcc ccttatcaac    12240
ggatgatcca gtgatagaca ggctttacct ctcatctcac agaggtgtta cgctgacaa    12300
tcaagcaaaa tggctgtcc cgacaacacg aacagatgac aagttgcgaa tggagacatg    12360
cttccaacag gcgtgtaagg gtaaaatcca agcactctgc gagaatcccg agtgggcacc   12420
attgaaggat aacaggattc cttcatacgg ggtcttgtct gttgatctga gtctgacagt   12480
tgagcttaaa atcaaaattg cttcgggatt cgggccattg atcacacacg ttcagggat    12540
ggacctatac aaatccaacc acaacaatgt gtattggctg actatcccgc caatgaagaa   12600
```

```
cctagcctta ggtgtaatca acacattgga gtggataccg agattcaagg ttagtcccta    12660
cctcttcaat gtcccaatta aggaagcagg cgaagactgc catgccccaa catacctacc    12720
tgcggaggtg gatggtgatg tcaaactcag ttccaatctg gtgattctac ctggtcaaga    12780
tctccaatat gttttggcaa cctacgatac ttccagggtt gaacatgctg tggtttatta    12840
cgtttacagc ccaggccgct cattttctta cttttatcct tttaggttgc ctataaaggg    12900
ggtccccatc gaattacaag tggaatgctt cacatgggac caaaaactct ggtgccgtca    12960
cttctgtgtg cttgcggact cagaatctgg tggacatatc actcactctg ggatggtggg    13020
catgggagtc agctgcacag tcacccggga agatggaacc aatcgcagat agggctgcta    13080
gtgaaccaat ctcatgatgt cacccagaca tcaggcatac ccactagtgt gaaatagaca    13140
tcagaattaa gaaaaacgta gggtccaagt ggttccccgt tatggactcg ctatctgtca    13200
accagatctt ataccctgaa gttcacctag atagcccgat agttaccaat aagatagtag    13260
ccatcctgga gtatgctcga gtccctcacg cttacagcct ggaggaccct acactgtgtc    13320
agaacatcaa gcaccgccta aaaaacggat tttccaacca aatgattata acaatgtgg    13380 aagttgggaa tgtcatcaag tccaagctta ggagttatcc ggcccactct catattccat    13440
atccaaattg taatcaggat ttatttaaca tagaagacaa agagtcaacg aggaagatcc    13500
gtgaactcct caaaaagggg aattcgctgt actccaaagt cagtgataag gttttccaat    13560
gcttaaggga cactaactca cggcttggcc taggctccga attgagggag gacatcaagg    13620
agaaagttat taacttggga gtttacatgc acagctccca gtggtttgag cccttttctgt   13680 tttggtttac agtcaagact gagatgaggt cagtgattaa atcacaaacc catacttgcc    13740
ataggaggag acacacacct gtattcttca ctggtagttc agttgagttg ctaatctctc    13800
gtgaccttgt tgctataatc agtaaagagt ctcaacatgt atattacctg acatttgaac    13860
tggttttgat gtattgtgat gtcatagagg ggaggttaat gacagagacc gctatgacta    13920
ttgatgctag gtatacagag cttctaggaa gagtcagata catgtggaaa ctgatagatg    13980
gtttcttccc tgcactcggg aatccaactt atcaaattgt agccatgctg gagcctcttt    14040
cacttgctta cctgcagctg agggatataa cagtagaact cagaggtgct ttccttaacc    14100
actgctttac tgaaatacat gatgttcttg accaaaacgg gttttctgat gaaggtactt    14160
atcatgagtt aattgaagct ctagattaca ttttcataac tgatgacata catctgacag    14220
gggagatttt ctcattttc agaagtttcg gccaccccag acttgaagca gtaacggctg    14280
ctgaaaatgt taggaaatac atgaatcagc ctaaagtcat tgtgtatgag actctgatga    14340
aaggtcatgc catattttgt ggaatcataa tcaacggcta tcgtgacagg cacggaggca    14400
gttggccacc gctgaccctc cccctgcatg ctgcagacac aatccggaat gctcaagctt    14460
caggtgaagg gttaacacat gagcagtgcg ttgataactg gagatctttt gctggagtga    14520
aatttggctg cttatgcct cttagcctgg atagtgatct gacaatgtac ctaaaggaca    14580
aggcacttgc tgctctccaa agggaatggg attcagttta cccgaaagag ttcctgcgtt    14640
acgaccctcc caagggaacc gggtcacgga ggcttgtaga tgttttcctt aatgattcga    14700
gctttgaccc atatgatgtg ataatgtatg ttgtaagtgg agcttacctc catgaccctg    14760
agttcaacct gtcttacagc ctgaaagaaa aggagatcaa ggaaacaggt agacttttg    14820 ctaaaatgac ttcaaaaatg agggcatgcc aagtgattgc tgaaaatcta atctcaaacg    14880
ggattggcaa atattttaag gacaatggga tggccaagga tgagcacgat ttgactaagg    14940
```

```
cactccacac tctagctgtc tcaggagtcc ccaaagatct caaagaaagt cacagggggg   15000
ggccagtctt aaaaacctac tcccgaagcc cagtccacac aagtaccagg aacgtgagag   15060
cagcaaaagg gtttataggg ttccctcaag taattcggca ggaccaagac actgatcatc   15120
cggagaatat ggaagcttac gagacagtca gtgcatttat cacgactgat ctcaagaagt   15180
actgccttaa ttggagatat gagaccatca gcttgtttgc acagaggcta aatgagattt   15240
acggattgcc ctcattttc cagtggctgc ataagaggct tgagacctct gtcctgtatg   15300
taagtgaccc tcattgcccc cccgaccttg acgcccatat cccgttatat aaagtcccca   15360
atgatcaaat cttcattaag taccctatgg gaggtataga agggtattgt cagaagctgt   15420
ggaccatcag caccattccc tatctatacc tggctgctta tgagagcgga gtaaggattg   15480
cttcgttagt gcaaggggac aatcagacca tagccgtaac aaaaagggta cccagcacat   15540
ggccctacaa ccttaagaaa cgggaagctg ctagagtaac tagagattac tttgtaattc   15600
ttaggcaaag gctacatgat attggccatc acctcaaggc aaatgagaca attgtttcat   15660 cacattttt tgtctattca aaaggaatat attatgatgg gctacttgtg tcccaatcac   15720
tcaagagcat cgcaagatgt gtattctggt cagagactat agttgatgaa acaagggcag   15780
catgcagtaa tattgctaca acaatggcta aaagcatcga gagaggttat gaccgttacc   15840
ttgcatattc cctgaacgtc ctaaaagtga tacagcaaat tctgatctct cttggcttca   15900
caatcaattc aaccatgacc cgggatgtag tcataccct cctcacgaac aacgacctct   15960
taataaggat ggcactgttg cccgctccta ttgggggat gaattatctg aatatgagca   16020
ggctgtttgt cagaaacatc ggtgatccag taacatcatc aattgctgat ctcaagagaa   16080
tgattctcgc ctcactaatg cctgaagaga ccctccatca agtaatgaca caacaaccgg   16140
gggactcttc attcctagac tgggctagcg acccttactc agcaaatctt gtatgtgtcc   16200
agagcatcac tagactcctc aagaacataa ctgcaaggtt tgtcctgatc catagtccaa   16260
acccaatgtt aaaaggatta ttccatgatg acagtaaaga agaggacgag ggactggcgg   16320
cattcctcat ggacaggcat attatagtac ctagggcagc tcatgaaatc ctggatcata   16380
gtgtcacagg ggcaagagag tctattgcag gcatgctgga taccacaaaa ggcctgattc   16440
gagccagcat gaggaagggg gggttaacct ctcgagtgat aaccagattg tccaattatg   16500
actatgaaca attcagagca gggatggtgc tattgacagg aagaaagaga atgtccctca   16560
ttgacaaaga gtcatgttca gtgcagctgg cgagagctct aagaagccat atgtgggcga   16620
ggctagctcg aggacggcct atttacggcc ttgaggtccc tgatgtacta gaatctatgc   16680
gaggccacct tattcggcgt catgagacat gtgtcatctg cgagtgtgga tcagtcaact   16740
acggatggtt ttttgtcccc tcgggttgcc aactggatga tattgacaag gaaacatcat   16800
ccttgagagt cccatatatt ggttctacca ctgatgagag aacagacatg aagcttgcct   16860
tcgtaagagc cccaagtcga tccttgcgat ctgctgttag aatagcaaca gtgtactcat   16920
gggcttacgg tgatgatgat agctcttgga cgaagcctg gttgttggct aggcaaaggg   16980
ccaatgtgag cctggaggag ctaagggtga tcactcccat ctcaacttcg actaatttag   17040
cgcataggtt gagggatcgt agcactcaag tgaaatactc aggtacatcc cttgtccgag   17100
tggcgaggta taccacaatc tccaacgaca atctctcatt tgtcatatca gataagaagg   17160
ttgatactaa ctttatatac caacaaggaa tgcttctagg gttgggtgtt ttagaaacat   17220
tgtttcgact cgagaaagat accggatcat ctaacacggt attacatctt cacgtcgaaa   17280
cagattgttg cgtgatcccg atgatagatc atcccaggat acccagctcc cgcaagctag   17340
```

```
agctgagggc agagctatgt accaacccat tgatatatga taatgcacct ttaattgaca    17400
gagatacaac aaggctatac acccagagcc ataggaggca ccttgtggaa tttgttacat    17460
ggtccacacc ccaactatat cacattttag ctaagtccac agcactatct atgattgacc    17520
tggtaacaaa atttgagaag gaccatatga atgaaatttc agctctcata ggggatgacg    17580
atatcaatag tttcataact gagtttctgc tcatagagcc aagattattc actatctact    17640
tgggccagtg tgcggccatc aattgggcat ttgatgtaca ttatcataga ccatcaggga    17700
aatatcagat gggtgagctg ttgtcatcgt tcctttctag aatgagcaaa ggagtgttta    17760
aggtgcttgt caatgctcta agccacccaa agatctacaa gaaattctgg cattgtggta    17820
ttatagagcc tatccatggt ccttcacttg atgctcaaaa cttgcacaca actgtgtgca    17880
acatggttta cacatgctat atgacctacc tcgacctgtt gttgaatgaa gagttagaag    17940
agttcacatt tctcttgtgt gaaagcgacg aggatgtagt accggacaga ttcgacaaca    18000
tccaggcaaa acactatgt gttctggcag atttgtactg tcaaccaggg acctgcccac    18060
caattcgagg tctaagaccg gtagagaaat gtgcagttct aaccgaccat atcaaggcag    18120
aggctaggtt atctccagca ggatcttcgt ggaacataaa tccaattatt gtagaccatt    18180
actcatgctc tctgacttat ctccggcgag gatcgatcaa acagataaga ttgagagttg    18240
atccaggatt cattttcgac gccctcgctg aggtaaatgt cagtcagcca agatcggca    18300 gcaacaacat ctcaaatatg agcatcaagg ctttcagacc cccacacgat gatgttgcaa    18360
aattgctcaa agatatcaac acaagcaagc acaatcttcc catttcaggg ggcaatctcg    18420
ccaattatga aatccatgct ttccgcagaa tcgggttgaa ctcatctgct tgctacaaag    18480
ctgttgagat atcaacatta attaggagat gccttgagcc aggggaggac ggcttgttct    18540
tgggtgaggg atcgggttcc atgttgatca cttataagga gatacttaaa ctaaacaagt    18600
gcttctataa tagtgggggtt tccgccaatt ctagatctgg tcaaagggaa ttagcaccct    18660
atccctccga agttggcctt gtcgaacaca gaatgggagt aggtaatatt gtcaaagtgc    18720
tctttaacgg gaggcccgaa gtcacgtggg taggcagtgt agattgcttc aatttcatag    18780
ttagtaatat ccctacctct agtgtgggg ttatccattc agatatagag accttgccta    18840
acaaagatac tatagagaag ctagaggaat tggcagccat cttatcgatg gctctgctcc    18900
tgggcaaaat aggatcaata ctggtgatta agcttatgcc tttcagcggg gattttgttc    18960
agggatttat aagttatgta gggtcccatt atagagaagt gaaccttgta taccctagat    19020
acagcaactt catatctact gaatcttatt tggttatgac agatctcaag gctaaccggc    19080
taatgaatcc tgaaaagatt aagcagcaga taattgaatc atctgtgagg acttcacctg    19140
gacttatagg tcacatccta tccattaagc aactaagctg catacaagca attgtgggag    19200
acgcagttag tagaggtgat atcaatccta ctctgaaaaa acttacacct atagagcagg    19260
tgctgatcaa ttgcgggttg gcaattaacg gacctaagct gtgcaaagaa ttgatccacc    19320
atgatgttgc ctcagggcaa gatggattgc ttaattctat actcatcctc tacaggggagt    19380 tggcaagatt caaagacaac caaagaagtc aacaagggat gttccacgct taccccgtat    19440
tggtaagtag caggcaacga gaacttatat ctaggatcac ccgcaaattt tggggggcaca    19500 ttcttcttta ctccgggaac agaaagttga taaataagtt tatccagaat ctcaagtccg    19560
gctatctgat actagactta caccagaata tcttcgttaa gaatctatcc aagtcagaga    19620
aacagattat tatgacgggg ggtttgaaac gtgagtgggt ttttaaggta acagtcaagg    19680
```

```
agaccaaaga atggtataag ttagtcggat acagtgccct gattaaggac taattggttg   19740
aactccggaa ccctaatcct gccctaggtg gttaggcatt atttgcaata gattaaagaa   19800
aactttgaaa atacgaagtt tctattccca gctttgtctg gtggccggca tggtcccagc   19860
ctcctcgctg gcgccggctg ggcaacattc cgagggggacc gtcccctcgg taatggcgaa   19920
tgggacgcgg ccgatccggc tgctaacaaa gcccgaaagg aagctgagtt ggctgctgcc   19980
accgctgagc aataactagc ataaccccctt ggggcctcta acgggtctt gaggggtttt   20040
ttgctgaaag gaggaactat atccggatgc ggccgatccg gctgctaaca agcccgaaa    20100
ggaagctgag ttggctgctg ccaccgctga gcaataacta gcataacccc ttggggcctc   20160
taaacgggtc ttgaggggtt ttttgctgaa aggaggaact atatccggat ggccgccacc   20220
ggccggtggg ccttgcagca catccccctt tcgccagctg gcgtaatagc gaagaggccc   20280
gcaccgatcg ccccttcccaa cagttgcgca gcctgaatgg cgaatgggac gcgccctgta   20340
gcggcgcatt aagcgcggcg ggtgtggtgg ttacgcgcag cgtgaccgct acacttgcca   20400
gcgccctagc gcccgctcct ttcgctttct tcccttcctt tctcgccacg ttcgccggct   20460
ttccccgtca gctctaaat cggggggctcc ctttagggtt ccgatttagt gctttacggc   20520
acctcgaccc caaaaaactt gattagggtg atggttcacg tgggccatcg ccctgataga   20580
cggtttttcg ccctttgacg ttggagtcca cgttctttaa tagtggactc ttgttccaaa   20640
ctggaacaac actcaaccct atctcggtct attcttttga ttttataaggg attttgccga   20700
tttcggccta ttggttaaaa aatgagctga tttaacaaaa atttaacgcg aattttaaca   20760
aaatattaac gcttacaatt taggtggcac ttttcgggga aatgtgcgcg gaaccccctat   20820
ttgttttattt ttctaaatac attcaaatat gtatccgctc atgagacaat aaccctgata   20880
aatgcttcaa taatattgaa aaaggaagag tatgagtatt caacatttcc gtgtcgccct   20940
tattcccttt tttgcggcat tttgccttcc tgtttttgct cacccagaaa cgctggtgaa   21000
agtaaaagat gctgaagatc agttgggtgc acgagtgggt tacatcgaac tggatctcaa   21060
cagcggtaag atccttgaga gttttcgccc cgaagaacgt tttccaatga tgagcacttt   21120
taaagttctg ctatgtggcg cggtattatc ccgtattgac gccgggcaag agcaactcgg   21180
tcgccgcata cactattctc agaatgactt ggttgagtac tcaccagtca cagaaaagca   21240
tcttacggat ggcatgacag taagagaatt atgcagtgct gccataacca tgagtgataa   21300
cactgcggcc aacttacttc tgacaacgat cggaggaccg aaggagctaa ccgcttttt    21360
gcacaacatg ggggatcatg taactcgcct tgatcgttgg gaaccggagc tgaatgaagc   21420
cataccaaac gacgagcgtg acaccacgat gcctgtagca atggcaacaa cgttgcgcaa   21480
actattaact ggcgaactac ttacactagc ttcccggcaa caattaatag actggatgga   21540
ggcggataaa gttgcaggac cacttctgcg ctcggccctt ccggctggct ggtttattgc   21600
tgataaatct ggagccggtg agcgtgggtc tcgcggtatc attgcagcac tggggccaga   21660
tggtaagccc tcccgtatcg tagttatcta cacgacgggg agtcaggcaa ctatggatga   21720
acgaaataga cagatcgctg agataggtgc ctcactgatt aagcattggt aactgtcaga   21780
ccaagtttac tcatatatac tttagattga tttaaaactt catttttaat ttaaaaggat   21840
ctaggtgaag atcctttttg ataatctcat gaccaaaatc ccttaacgtg agttttcgtt   21900
ccactgagcg tcagaccccg tagaaaagat caaaggatct tcttgagatc cttttttct    21960
gcgcgtaatc tgctgcttgc aaacaaaaaa accaccgcta ccagcggtgg tttgtttgcc   22020
ggatcaagag ctaccaactc tttttccgaa ggtaactggc ttcagcagag cgcagatacc   22080
```

```
aaatactgtt cttctagtgt agccgtagtt aggccaccac ttcaagaact ctgtagcacc    22140
gcctacatac ctcgctctgc taatcctgtt accagtggct gctgccagtg gcgataagtc    22200
gtgtcttacc gggttggact caagacgata gttaccggat aaggcgcagc ggtcgggctg    22260 aacgggggt tcgtgcacac agcccagctt ggagcgaacg acctacaccg aactgagata    22320
cctacagcgt gagctatgag aaagcgccac gcttcccgaa gggagaaagg cggacaggta    22380
tccggtaagc ggcagggtcg gaacaggaga gcgcacgagg gagcttccag ggggaaacgc    22440
ctggtatctt tatagtcctg tcgggtttcg ccacctctga cttgagcgtc gattttgtg     22500 atgctcgtca gggggcgga gcctatggaa aaacgccagc aacgcggcct ttttacggtt     22560
cctggccttt tgctggcctt ttgctcacat gttctttcct gcgttatccc ctgattctgt    22620
ggataaccgt attaccgcct ttgagtgagc tgataccgct cgccgcagcc gaacgaccga    22680
gcgcagcgag tcagtgagcg aggaagcgga agagcgccca atacgcaaac cgcctctccc    22740
cgcgcgttgg ccgattcatt aatgcagctg gcacgacagg tttcccgact ggaaagcggg    22800
cagtgagcgc aacgcaatta atgtgagtta gctcactcat taggcacccc aggctttaca    22860
ctttatgctt ccggctcgta tgttgtgtgg aattgtgagc ggacaacaat ttcacacagg    22920
aaacagctat gaccatgatt acgccaagct cgggcggccg cttgtaatac gactcactat    22980
a                                                                    22981
```

<210> SEQ ID NO 22
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3822)
<223> OTHER INFORMATION: Non-codon optimized SARS-CoV-2 Spike from rMV-EZ-SARS-CoV-2-S clone 3
<220> FEATURE:
<221> NAME/KEY: misc_feature
<222> LOCATION: (3713)..(3713)
<223> OTHER INFORMATION: mutation that arose during cloning
<220> FEATURE:
<221> NAME/KEY: misc_feature
<222> LOCATION: (3805)..(3807)
<223> OTHER INFORMATION: mutation that disrupts ER retention signal
<220> FEATURE:
<221> NAME/KEY: misc_feature
<222> LOCATION: (3811)..(3813)
<223> OTHER INFORMATION: mutation that disrupts ER retention signal

<400> SEQUENCE: 22

```
atgtttgttt ttcttgtttt attgccacta gtctctagtc agtgtgttaa tcttacaacc      60
agaactcaat taccccctgc atacactaat tctttcacac gtggtgttta ttaccctgac     120
aaagttttca gatcctcagt tttacattca actcaggact tgttcttacc tttcttttcc    180
aatgttactt ggttccatgc tatacatgtc tctgggacca atggtactaa gaggtttgat    240
aaccctgtcc taccatttaa tgatggtgtt tattttgctt ccactgagaa gtctaacata    300
ataagaggct ggattttggt actactttta gattcgaaga cccagtccct acttattgtt    360
aataacgcta ctaatgttgt tattaaagtc tgtgaatttc aattttgtaa tgatccattt    420
ttgggtgttt attaccacaa aaacaacaaa agttggatgg aaagtgagtt cagagtttat    480
tctagtgcga ataattgcac ttttgaatat gtctctcagc ctttttcttat ggaccttgaa    540 ggaaaacagg gtaatttcaa aaatcttagg gaatttgtgt ttaagaatat tgatggttat    600
```

```
tttaaaatat attctaagca cacgcctatt aatttagtgc gtgatctccc tcagggtttt    660
tcggctttag aaccattggt agatttgcca ataggtatta acatcactag gtttcaaact    720
ttacttgctt tacatagaag ttatttgact cctggtgatt cttcttcagg ttggacagct    780
ggtgctgcag cttattatgt gggttatctt caacctagga cttttctatt aaaatataat    840
gaaaatggaa ccattacaga tgctgtagac tgtgcacttg accctctctc agaaacaaag    900
tgtacgttga atccttcac tgtagaaaaa ggaatctatc aaacttctaa ctttagagtc    960
caaccaacag aatctattgt tagatttcct aatattacaa acttgtgccc ttttggtgaa   1020 gttttttaacg ccaccagatt tgcatctgtt tatgcttgga acaggaagag aatcagcaac   1080
tgtgttgctg attattctgt cctatataat tccgcatcat tttccacttt taagtgttat   1140
ggagtgtctc ctactaaatt aaatgatctc tgctttacta atgtctatgc agattcattt   1200
gtaattagag gtgatgaagt cagacaaatc gctccagggc aaactggaaa gattgctgat   1260
tataattata aattaccaga tgattttaca ggctgcgtta tagcttggaa ttctaacaat   1320
cttgattcta aggttggtgg taattataat tacctgtata gattgtttag aagtctaat    1380 ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg atgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
cctcggcggg cacgtagtgt agctagtcaa tccatcattg cctacactat gtcacttggt   2100
gcagaaaatt cagttgctta ctctaataac tctattgcca tacccacaaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagtttttgt   2280
acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400 aattttctcac aaatattacc agatccatca aaaccaagca gaggtcatt tattgaagat   2460 ctacttttca acaaagtgac acttgcagat gctggcttca tcaaacaata tggtgattgc   2520
cttggtgata ttgctgctag agacctcatt tgtgcacaaa agtttaacgg ccttactgtt   2580 ttgccaccttt tgctcacaga tgaaatgatt gctcaataca cttctgcact gttagcgggt   2640
acaatcactt ctggttggac ctttggtgca ggtgctgcat tacaaatacc atttgctatg   2700
caaatggctt ataggtttaa tggtattgga gttacacaga atgttctcta tgagaaccaa   2760
aaattgattg ccaaccaatt taatagtgct attggcaaaa ttcaagactc actttcttcc   2820
acagcaagtg cacttggaaa acttcaagat gtggtcaacc aaaatgcaca agctttaaac   2880
acgcttgtta aacaacttag ctccaatttt ggtgcaattt caagtgtttt aaatgatatc   2940
```

```
ctttcacgtc ttgacaaagt tgaggctgaa gtgcaaattg ataggttgat cacaggcaga    3000
cttcaaagtt tgcagacata tgtgactcaa caattaatta gagctgcaga aatcagagct    3060
tctgctaatc ttgctgctac taaaatgtca gagtgtgtac ttggacaatc aaaaagagtt    3120
gatttttgtg gaaagggcta tcatcttatg tccttccctc agtcagcacc tcatggtgta    3180
gtcttcttgc atgtgactta tgtccctgca caagaaaaga acttcacaac tgctcctgcc    3240
atttgtcatg atggaaaagc acactttcct cgtgaaggtg tctttgtttc aaatggcaca    3300
cactggtttg taacacaaag gaattttat gaaccacaaa tcattactac agacaacaca    3360
tttgtgtctg gtaactgtga tgttgtaata ggaattgtca acaacacagt ttatgatcct    3420
ttgcaacctg aattagactc attcaaggag gagttagata aatattttaa gaatcataca    3480
tcaccagatg ttgatttagg tgacatctct ggcattaatg cttcagttgt aaacattcaa    3540
aaagaaattg accgcctcaa tgaggttgcc aagaatttaa atgaatctct catcgatctc    3600
caagaacttg gaaagtatga gcagtatata aaatggccat ggtacatttg gctaggtttt    3660
atagctggct tgattgccat agtaatggtg acaattatgc tttgctgtat gaacagttgc    3720
tgtagttgtc tcaagggctg ttgttcttgt ggatcctgct gcaaatttga tgaagacgac    3780
tctgagccag tgctcaaagg agtcgcatta gcttacacat aa                       3822
```

<210> SEQ ID NO 23
<211> LENGTH: 4
<212> TYPE: PRT
<213> ORGANISM: Artificial Sequence
<220> FEATURE:
<223> OTHER INFORMATION: Synthetic

<400> SEQUENCE: 23

Ala Ser Val Gly
1

<210> SEQ ID NO 24
<211> LENGTH: 53
<212> TYPE: DNA
<213> ORGANISM: Artificial Sequence
<220> FEATURE:
<223> OTHER INFORMATION: Synthetic

<400> SEQUENCE: 24
caaagtgatt gcctcccaag ttccacaggc gcgccatgtt cgtcttcctg gtc          53

<210> SEQ ID NO 25
<211> LENGTH: 56
<212> TYPE: DNA
<213> ORGANISM: Artificial Sequence
<220> FEATURE:
<223> OTHER INFORMATION: Synthetic

<400> SEQUENCE: 25
gttggcaggt aagttgagct gtaggacgtc gcgcgttagg tgtaatgcag cttcac       56

<210> SEQ ID NO 26
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (47)..(48)
<223> OTHER INFORMATION: mutation that disrupts the ER retention signal
<220> FEATURE:

```
<221> NAME/KEY: misc_feature
<222> LOCATION: (53)..(54)
<223> OTHER INFORMATION: mutation that disrupts the ER retention signal

<400> SEQUENCE: 26
ggttggcagg taagttgagc tgtaggacgt cgcgcgttag gtgtaagcca gcgccacgcc    60
```